(12) United States Patent
Manoharan et al.

(10) Patent No.: US 8,575,123 B2
(45) Date of Patent: Nov. 5, 2013

(54) SITE-SPECIFIC DELIVERY OF NUCLEIC ACIDS BY COMBINING TARGETING LIGANDS WITH ENDOSOMOLYTIC COMPONENTS

(75) Inventors: Muthiah Manoharan, Cambridge, MA (US); Kallanthottathil G. Rajeev, Cambridge, MA (US); David Butler, Cambridge, MA (US); Muthusamy Jayaraman, Cambridge, MA (US)

(73) Assignee: Tekmira Pharmaceuticals Corporation, Burnaby, BC (CA)

( * ) Notice: Subject to any disclaimer, the term of this patent is extended or adjusted under 35 U.S.C. 154(b) by 110 days.

(21) Appl. No.: 12/936,961

(22) PCT Filed: Apr. 10, 2009

(86) PCT No.: PCT/US2009/040274
§ 371 (c)(1),
(2), (4) Date: Dec. 28, 2010

(87) PCT Pub. No.: WO2009/126933
PCT Pub. Date: Oct. 15, 2009

(65) Prior Publication Data
US 2011/0123520 A1    May 26, 2011

Related U.S. Application Data

(60) Provisional application No. 61/044,186, filed on Apr. 11, 2008.

(51) Int. Cl.
*A61K 48/00* (2006.01)
*C12N 15/11* (2006.01)
*C12N 15/00* (2006.01)
*A01N 63/00* (2006.01)
*A01N 65/00* (2009.01)

(52) U.S. Cl.
USPC ............. 514/44 R; 424/93.1; 435/320.1

(58) Field of Classification Search
None
See application file for complete search history.

(56) References Cited

U.S. PATENT DOCUMENTS

| | | | |
|---|---|---|---|
| 5,994,517 | A | 11/1999 | Ts'o et al. |
| 6,906,182 | B2 | 6/2005 | Ts'o et al. |
| 7,109,165 | B2 | 9/2006 | Matulic-Adamic et al. |
| 7,491,805 | B2 | 2/2009 | Vargeese et al. |
| 2002/0086356 | A1 | 7/2002 | Tuschl et al. |
| 2003/0148928 | A1 | 8/2003 | Beigelman et al. |
| 2004/0110296 | A1 | 6/2004 | Vargeese et al. |
| 2006/0148740 | A1 | 7/2006 | Platenburg |

FOREIGN PATENT DOCUMENTS

| | | |
|---|---|---|
| EP | 0 957 107 A | 11/1999 |
| WO | WO 90/12096 | 10/1990 |
| WO | WO 99/52932 A | 10/1999 |
| WO | WO 00/44914 | 8/2000 |
| WO | WO 02/085908 A | 10/2002 |
| WO | 02094185 | 11/2002 |
| WO | WO 2004/080406 A3 | 9/2004 |
| WO | WO 2004/090108 A2 | 10/2004 |
| WO | WO 2006/020768 A | 2/2006 |
| WO | 2006052649 A2 | 5/2006 |
| WO | WO 2006/078278 A | 7/2006 |
| WO | 2008022309 A2 | 2/2008 |
| WO | 2009073809 A2 | 6/2009 |
| WO | 2009082606 A2 | 7/2009 |

OTHER PUBLICATIONS

Biessen, E.A., et al.: "The Cholesterol Derivative of a Triantennary Galactoside with High Affinity for Hepatic Asialoglycoprotein Receptor: A Potent Cholesterol Lowering Agent", Journal of Medicinal Chemistry, vol. 38(11), 1995, pp. 1846-1852.
Biessen, Erik A. L., et al.: "Synthesis of Cluster Galactosides with High Affinity for the Hepatic Asialoglycoprotein Receptor", Journal of Medicinal Chemistry, vol. 38(9), 1995, pp. 1538-1546.
Choi, Youngseon, et al.: "Targeting Cancer Cells with DNA-Assembled Dendrimers: A Mix and Match Strategy for Cancer", Cell Cycle, vol. 4(5), 2005, pp. 669-671.
Crossman, Arthur Jr., et al.: "Synthesis of Some Second-Generation Substrate Analogues of Early Intermediates in the Biosynthetic Pathway of Glycosylphosphatidylinositol Membrane Anchors", Carbohydrate Research, vol. 321(1-2), 1999, pp. 42-51.
Dubber, Michael, et al.: "Solid-Phase Synthesis of Multivalent Glycoconjugates on a DNA Synthesizer", Bioconjugate Chemistry, vol. 14(1), 2003, pp. 239-246.
Guo, S., et al.: "Construction of Folate-Conjugated pRNA of Bateriophase phi29 DNA Packaging Motor for Delivery of Chimeric siRNA to Nasopharyngeal Carcinoma Cells", Gene Therapy, vol. 13(10), 2006, pp. 814-820.
Ikeda, Yutaka, et al.: "Ligand-Targeted Delivery of Therapeutic siRNA", Pharmaceutical Research, vol. 23(8), 2006, pp. 1631-1640.
Karskela, Marika, et al.: "Synthesis and Cellular Uptake of Fluorescently Labeled Multivalent Hyaluronan Disaccharide Conjugates of Oligonucleotide Phosphorothioates", Bioconjugate Chemistry, vol. 19(12), 2008, pp. 2549-2558.
Katajisto, Johanna, et al.: "An Aminooxy-Functionalized Non-Nucleosidic Phosphoramidite for the Construction of Multiantennary Oligonucleotide Glycoconjugates on a Solid Support", Current Protocols in Nucleic Acid Chemistry, 2005, pp. 4.26.1-4.26.16.
Katajisto, Johanna, et al.: "Solid-Phase Synthesis of Oligonucleotide Glycoconjugates Bearing Three Different Glycosyl Groups: Orthoganally Protected Bis (Hydroxymethyl)-N, N'-bis(3-Hydroxyproply)Malondiamide Phosphoramidite as Key Building Block", Journal of Organic Chemistry, vol. 69(22), 2004 , pp. 7609-7615.
Katajisto, Johanna, et al.: "Solid-Phase Synthesis of Multiantennary Oligonucleotide Glycoconjugates Utilizing On-Support Oximation", Bioconjugate chemistry, vol. 15(4), 2004, pp. 890-896.

(Continued)

*Primary Examiner* — Robert M Kelly
(74) *Attorney, Agent, or Firm* — Viksnins Harris & Padys PLLP

(57) ABSTRACT

The invention relates to compositions and methods for site-specific delivery of nucleic acids by combining them with targeting ligands and endosomolytic components.

39 Claims, 10 Drawing Sheets

(56) References Cited

OTHER PUBLICATIONS

Li, Song, et al.: "Folate-Mediated Targeting of Antisense Oligodeoxynucleotides to Ovarian Cancer Cells", Pharmaceutical Research, vol. 15(10), 1998, pp. 1540-1545.

Liu, J., et al.: "Targeted Drug Delivery to Chemoresistant Cells: Folic Acid Derivatization of FdUMP [10] Enhances Cytotoxicity Toward 5-FU-Resistant Human Colorector Tumor Cells", Journal of Organic Chemistry, vol. 66(17), 2001, pp. 5655-5663.

Mahato, R. I., et al.: "Modulation of Gene Expression by Antisense and Antigen Oligodeoxynucleotides and Small Interfering RNA", Expert Opinion on Drug Delivery, 2005, vol. 2(1), pp. 3-28.

Murata, J. et al.: "Design of Quaternary Chitosan Conjugate Having Antennary Galactose Residues as a Gene Delivery Tool", Carbohydrate Polymers, vol. 32(2), 1997, pp. 105-109.

Rensen, Patrick, C. N., et al.: "Design and Synthesis of Novel N-Acetylgalactosamine-Terminated Glycolipids for Targeting of Lipoproteins to the Hepatic Asialoglycoprotein Receptor", Journal of Medicinal Chemistry, vol. 47(23), 2004, pp. 5798-5808.

Sioud, M.: "On the Delivery of Small Interfering RNAs into Mammalian Cells", Expert Opinion on Drug Delivery, vol. 2(4), 2005, pp. 639-651.

Six, L., et al.: "An Efficient and Stereoselective Synthesis of 1, 2-0-Dialkyl-3-0-Beta-D-Glycosyl-SN-Glycerols", Tetrahedron Letters, vol. 24(12), 1983, pp. 1229-1232.

Six, L., et al.: "Influence of Carbohydrate Moities on Monolayer Properties of Dialkylglycerylletherglycosides, Simple Model Compounds of the Glycolipids of Halophilic Bacteria", Journal of Colloid and Interface Science, vol. 93(1), 1983, pp. 109-114.

Sliedregt, Leo A. J. M., et al.: "Design and Synthesis of Novel Amphiphilic Dendritic Galactosides for Selective Targeting of Liposomes to the Hepatic Asialoglycoprotein Receptor", Journal of Medicinal Chemistry, vol. 42(4), 1999, pp. 609-618.

Vaino, A. R., et al.: "Synthesis of a D-Lactosyl Cluster-Nucleoside Conjugate", Chemical Communications, No. 19, 1997, pp. 1871-1872.

Wong, A., et al.: "Lipid, Sugar and Liposaccharide Based Delivery Systems", Current Medicinal Chemistry, vol. 8(9), 2001, pp. 1123-1136.

Zatsepin, Timofei S., et al.: "Synthesis and Applications of Oligonucleotide-Carbohydrate Conjugates", Chemistry & Biodiversity, vol. 1(10), 2004, pp. 1401-1417.

Zimmerman, T. S., et al.: "RNAi-Mediated Gene Silencing in Non-Human Primates", Nature, vol. 441(7089), 2006, pp. 111-114.

A. Paul Krapcho et al., "Mono-Protected Diamines. N-tert-Butoxycarbonyl-α,β-Alkanediamines from-α,β-Alkanediamines", Synthetic Communications, 1990, pp. 2559-2564.

Ya-Lin Chiu et al., "RNAi in Human Cells: Basic Structural and Functional Features of Small Interfering RNA", Molecular Cell, 2002, vol. 10, pp. 549-561.

Daniel T. Connolly et al., "Binding and Endocytosis of Cluster Glycosides by Rabbit Hepatocytes", The Journal of Biological Chemistry, 1982, vol. 257, No. 2, pp. 939-645.

Manoharan Muthiah: "Oligonucleotide conjugates as potential antisense drugs with improved uptake, biodistribution, targeted delivery, and mechanisms of action" Antisense and Nucleic Acid Drug Development, vol. 12, No. 2, Apr. 2002, pp. 103-128.

Turk M J et al.: "Characterization of a novel pH-sensitive peptide that enhances drug release from folate-targeted liposomes at endosomal pHs" Biochimica Et Biophysica Acta. Biomembranes, vol. 1559, No. 1, Feb. 10, 2002, pp. 56-68.

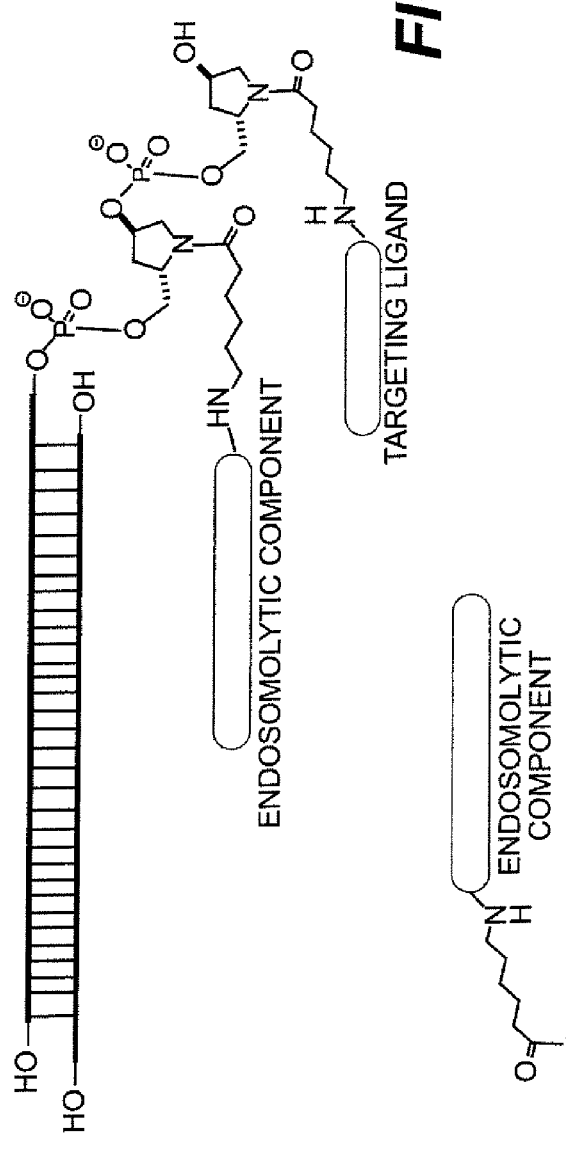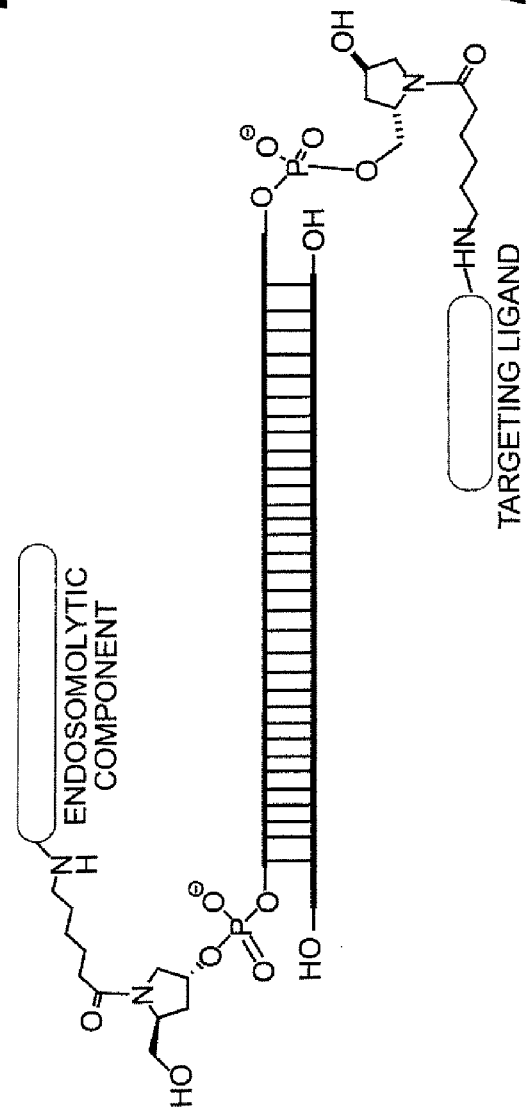

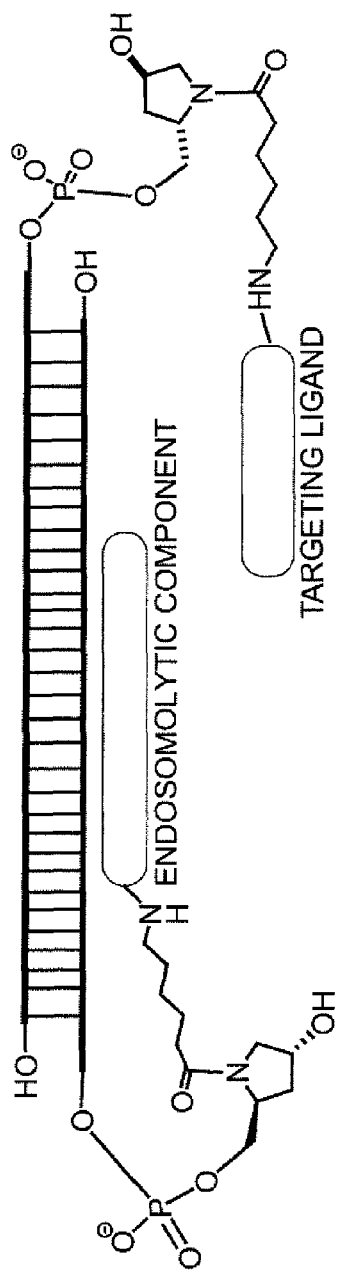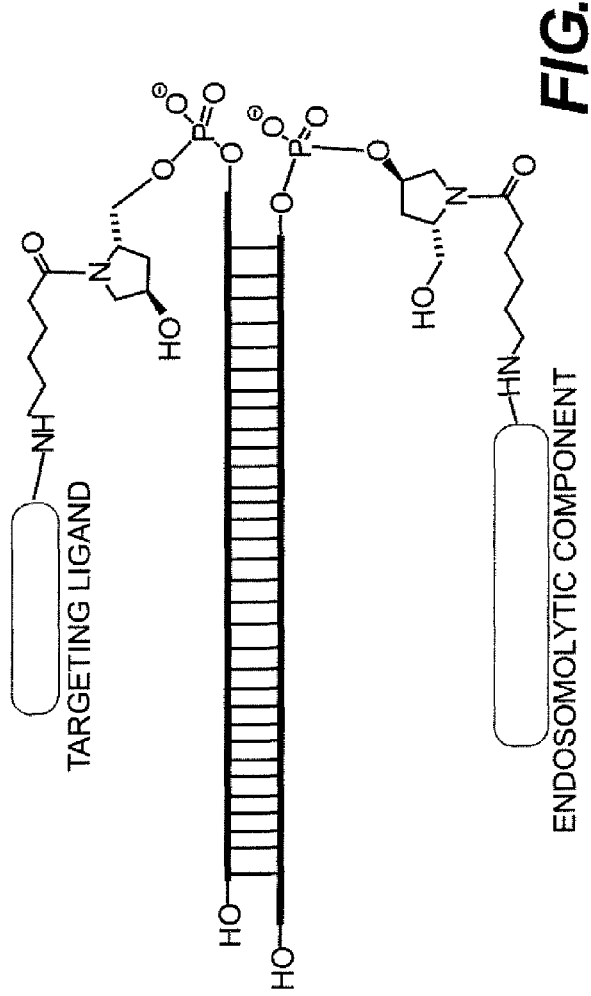
FIG. 1(C)
FIG. 1(D)

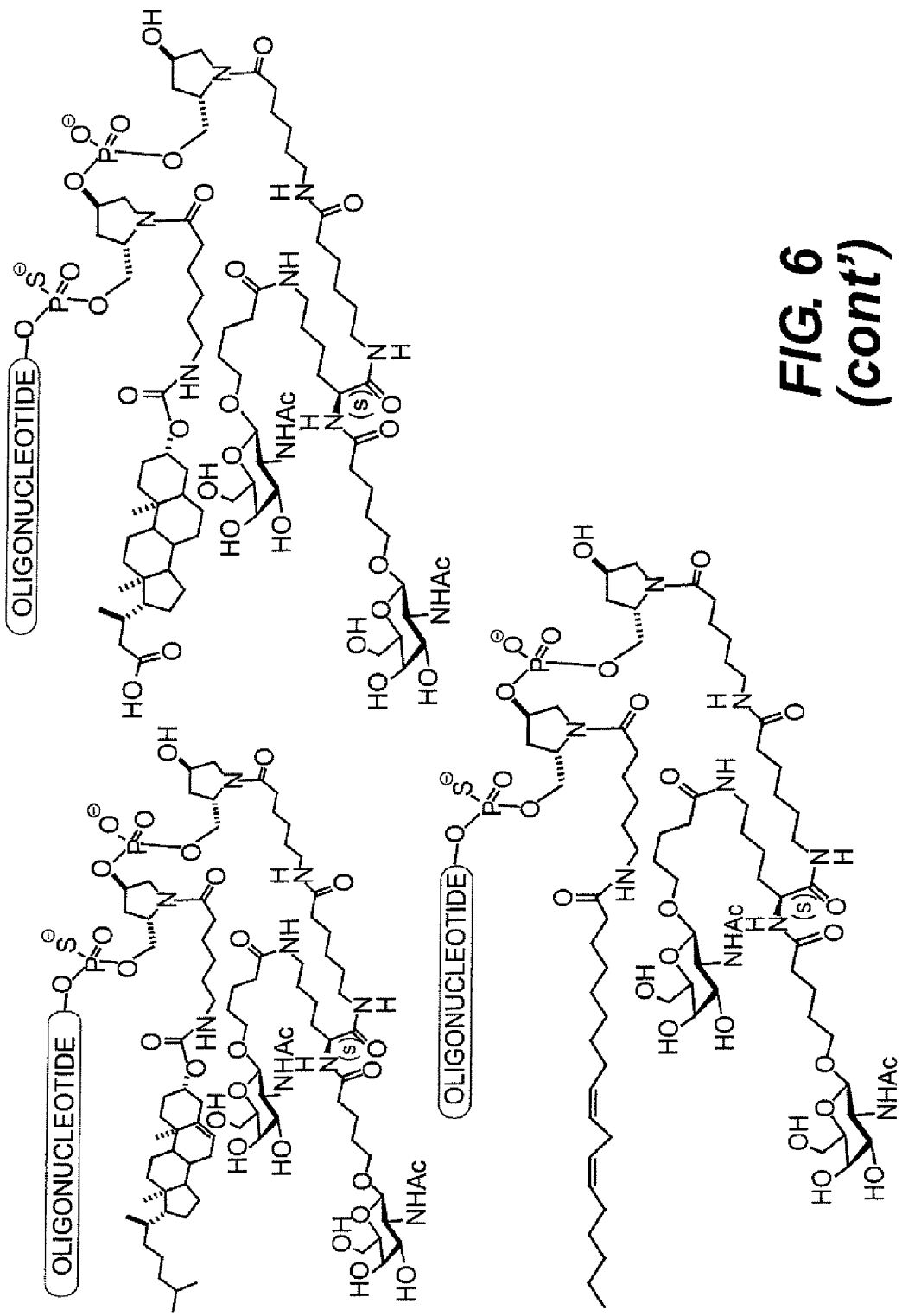
FIG. 6 (cont')

SITE-SPECIFIC DELIVERY OF NUCLEIC ACIDS BY COMBINING TARGETING LIGANDS WITH ENDOSOMOLYTIC COMPONENTS

RELATED APPLICATIONS

This application claims the benefit of priority to PCT Application No. PCT/US09/40274, filed Apr. 10, 2009, which claim priority to U.S. Provisional Patent Application Ser. No. 61/044,186, filed Apr. 11, 2008, both of which are herein incorporated by reference in their entirety.

BACKGROUND

RNA interference or "RNAi" is a term initially coined by Fire and co-workers to describe the observation that certain double-stranded RNA (dsRNA) can block gene expression when it is introduced into worms (Fire et al. (1998) Nature 391, 806-811). Short double-stranded interfering RNA (dsiRNA) directs gene-specific, post-transcriptional silencing in many organisms, including vertebrates, and has provided a new tool for studying gene function. RNAi may involve mRNA degradation.

Work in this field is typified by comparatively cumbersome approaches to delivery of dsiRNA to live mammals. E.g., McCaffrey et al. (Nature 418:38-39, 2002) demonstrated the use of dsiRNA to inhibit the expression of a luciferase reporter gene in mice. The dsiRNAs were administered by the method of hydrodynamic tail vein injections (in addition, inhibition appeared to depend on the injection of greater than 2 mg/kg dsiRNA). The inventors have discovered, inter alia, that the unwieldy methods typical of some reported work are not needed to provide effective amounts of dsiRNA to mammals and in particular not needed to provide therapeutic amounts of dsiRNA to human subjects. The advantages of the current invention include practical, uncomplicated methods of administration and therapeutic applications.

SUMMARY

The invention relates to compositions and methods for delivery of an iRNA agent, (e.g., an iRNA agent or siRNA agent) or other nucleic acid. In some embodiments, the nucleic acids which may be used in the modular composition and methods of the invention include iRNAs, siRNAs, single-stranded iRNAs, antagomirs, aptamers, antisense nucleic acids, decoy oligonucleotides, microRNAs (miRNAs), miRNA mimics, antimir, activating RNAs (RNAa), ribozymes, supermirs, U1 adaptor and the like. Derivatives of these nucleic acids may also be used.

Accordingly, in one aspect, the invention features a modular composition, comprising a nucleic acid (e.g., an iRNA agent or siRNA agent), an endosomolytic component, and a targeting ligand.

The endosomolytic component may be a polyanionic peptide or peptidomimetic which shows pH-dependent membrane activity and fusogenicity. In certain embodiments, the endosomolytic component assumes its active conformation at endosomal pH. The "active" conformation is that conformation in which the endosomolytic component promotes lysis of the endosome and/or transport of the modular composition of the invention, or its components, from the endosome to the cytoplasm of the cell.

Also provided are methods for screening libraries of compounds for their differential membrane activity at endosomal pH (e.g., pH 5-6) versus neutral pH. In certain embodiments, these method may utilize a hemolysis assay. Promising candidates isolated by this method may be useful as components of the modular compositions of the invention.

The targeting ligand may be any moiety that, for example, alters the pharmacokinetics, biodistribution, or cellular uptake of the modular composition of the invention. Exemplary targeting ligands include, for example, those which influence binding to proteins in the blood and those that target specific organs, tissues, or cell types. Targeting may be active or passive. Active targeting may be achieved, for example, by using an antibody or a binding partner for a cell-surface antigen, as the targeting ligand. Passive targeting may be achieved, for example, by altering the physicochemical properties (e.g., molecular weight) of the modular composition of the invention to influence biodistribution. One example of passive targeting is the enhanced permeability and retention (EPR) effect.

The endosomolytic component and the targeting ligand of the present invention may be linked to the nucleic acid in a number of different manners, which will be more fully described in the Detailed Description. In certain embodiments, a linker may be used covalently couple the endosomolytic component or targeting ligand to another component of the modular composition of the invention. The nature of this linker (e.g., cleavable or non-cleavable) will depend on the application.

In a certain embodiments, the modular composition may be used to deliver an iRNA agent, or other nucleic acid, to a subject in need thereof, e.g., to deliver an iRNA agent to a subject having a disorder, e.g., a disorder described herein.

In certain embodiments, the modular composition may be kept, maintained or stored at a pH greater than that typically found inside an endosome (e.g., greater than pH 6.5, greater than pH 6.8, greater than pH 7.0, greater than pH 7.5, greater than pH 8.0, or higher).

In another aspect, the invention includes a method of delivering an iRNA agent, or other nucleic acid, to a cell. The method includes (a) providing or obtaining a modular composition of the invention; (b) contacting a cell with the modular composition; and (c) allowing the cell to internalize the modular composition.

The method can be performed in vitro, ex vivo or in vivo, e.g., to treat a subject identified as being in need of an iRNA agent or other nucleic acid. A subject in need of a said agent is a subject, e.g., a human, in need of having the expression of a gene or genes, e.g., a gene related to a disorder, downregulated or silenced.

In a certain embodiments, the modular composition may be internalized by the cell into an endosome, e.g., by endocytosis. In such embodiments, the modular composition can disrupt the endosome, e.g., resulting in the release of the modular composition, or any of its components (e.g., the iRNA agent), into the cytoplasm of the cell.

In one aspect, the invention provides a method for inhibiting the expression of one or more genes. The method comprising contacting one or more cells with an effective amount of an oligonucleotide of the invention, wherein the effective amount is an amount that suppresses the expression of the one or more genes. The method can be performed in vitro, ex vivo or in vivo.

In another aspect, the invention features a kit. The kit may include (a) an endosomolytic component; (b) a targeting ligand; and (c) instructions for attaching an iRNA agent or other nucleic acid to the endosomolytic component and targeting ligand. In some embodiments, the kit may include an iRNA agent or other nucleic acid. In some other embodiments, the kit may include the modular composition of the invention, with instructions for in vitro, ex vivo, or in vivo administration.

The methods and compositions of the invention, e.g., the modular composition described herein, can be used with any of the iRNA agents or nucleic acids described herein. The methods and compositions of the invention may also be used with any of the iRNA agents or nucleic acids known in the art. In addition, the methods and compositions of the invention can be used for the treatment of any disease or disorder described herein, and for the treatment of any subject, e.g., any animal, any mammal, such as any human. One of ordinary skill in the art will also recognize that the methods and compositions of the invention may be used for the treatment of any disease that would benefit from downregulating or silencing a gene or genes.

The methods and compositions of the invention, e.g., the modular composition described herein, may be used with any dosage and/or formulation described herein, or any dosage or formulation known in the art. In addition to the routes of administration described herein, an ordinarily skilled artisan will also appreciate that other routes of administration may be used to administer the modular composition of the invention.

An "RNA agent" as used herein, is an unmodified RNA, modified RNA, or nucleoside surrogate, all of which are defined herein, see the section herein entitled RNA Agents. While numerous modified RNAs and nucleoside surrogates are described herein, examples include those which have greater resistance to nuclease degradation than do unmodified RNAs. Further examples include those which have a 2' sugar modification, a modification in a single strand overhang, for example a 3' single strand overhang, or, particularly if single stranded, a 5' modification which includes one or more phosphate groups or one or more analogs of a phosphate group.

An "iRNA agent", as used herein, is an RNA agent which can, or which can be cleaved into an RNA agent which can, downregulate the expression of a target gene, for example an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it may include a 5' modification which includes one or more phosphate groups or one or more analogs of a phosphate group.

In one aspect, the modular composition of the invention can modulate the expression of a target gene. By "modulate" is meant that the expression of the gene, or level of RNA molecule or equivalent of RNA molecules encoding one or more proteins or protein subunits, or activity of one or more proteins or protein subunits is up-regulated or down-regulated, such that expression, level, or activity is greater than or less than that observed in the absence of the modulator. For example, the term "modulate" can mean "inhibit" but use of the word "modulate" is not limited to this definition.

The details of one or more embodiments of the invention are set forth in the accompanying drawings and the description below. Other features, objects, and advantages of the invention will be apparent from this description, and from the claims. A person of ordinary skill in the art will readily recognize that additional embodiments of the invention exist.

This application incorporates all cited references, patents, and patent applications by reference in their entirety.

BRIEF DESCRIPTION OF THE DRAWINGS

FIG. 1. Schematic representation of some exemplary modular compositions comprising a nucleic acid (e.g., iRNA), a targeting ligand, and endosomolytic component: A) conjugation of the targeting ligand and endosomolytic component to the same terminal side on the nucleic acid (same strand and terminus); B) conjugation of the targeting ligand and endosomolytic component to the same strand but opposite termini; C) conjugation of the targeting ligand and endosomolytic component to opposite strands but same termini; D) conjugation of targeting ligand and endosomolytic component to opposite strands and opposite termini. In this embodiment, cholesterol is used as a targeting ligand. The targeting ligand may also be conjugated to the endosomolytic component as shown schematically in FIG. 2.

DETAILED DESCRIPTION

Figure 2:
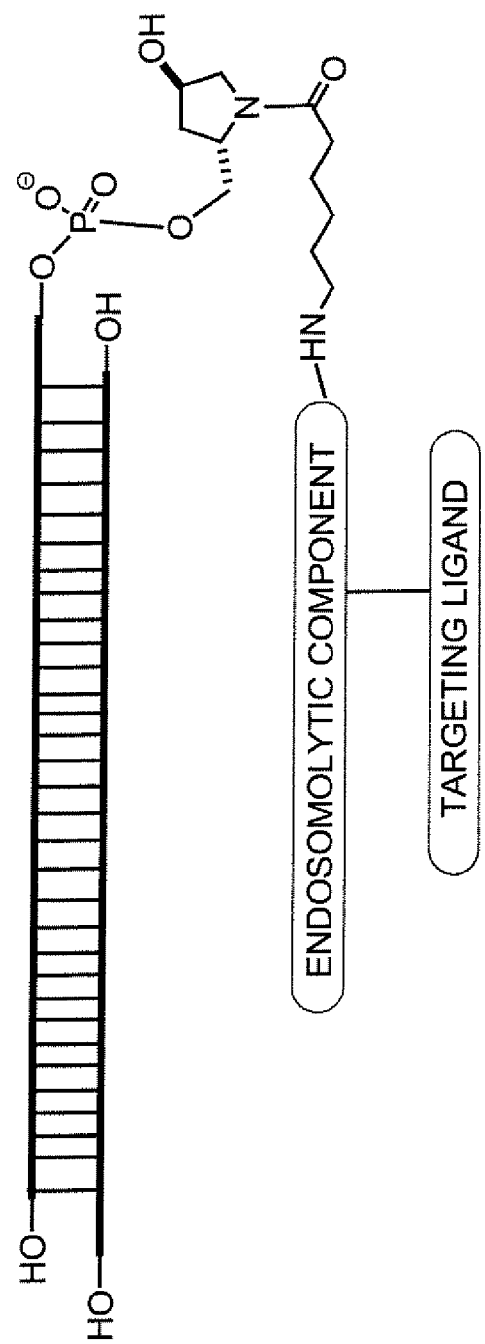
FIG. 2. Nucleic acid (e.g., iRNA) conjugate in which the targeting ligand is covalently attached to the endosomolytic component (nucleic acid-endosomolytic component-targeting ligand). The arrangement nucleic acid-targeting ligand-endosomolytic component is also contemplated.
Figure 3:
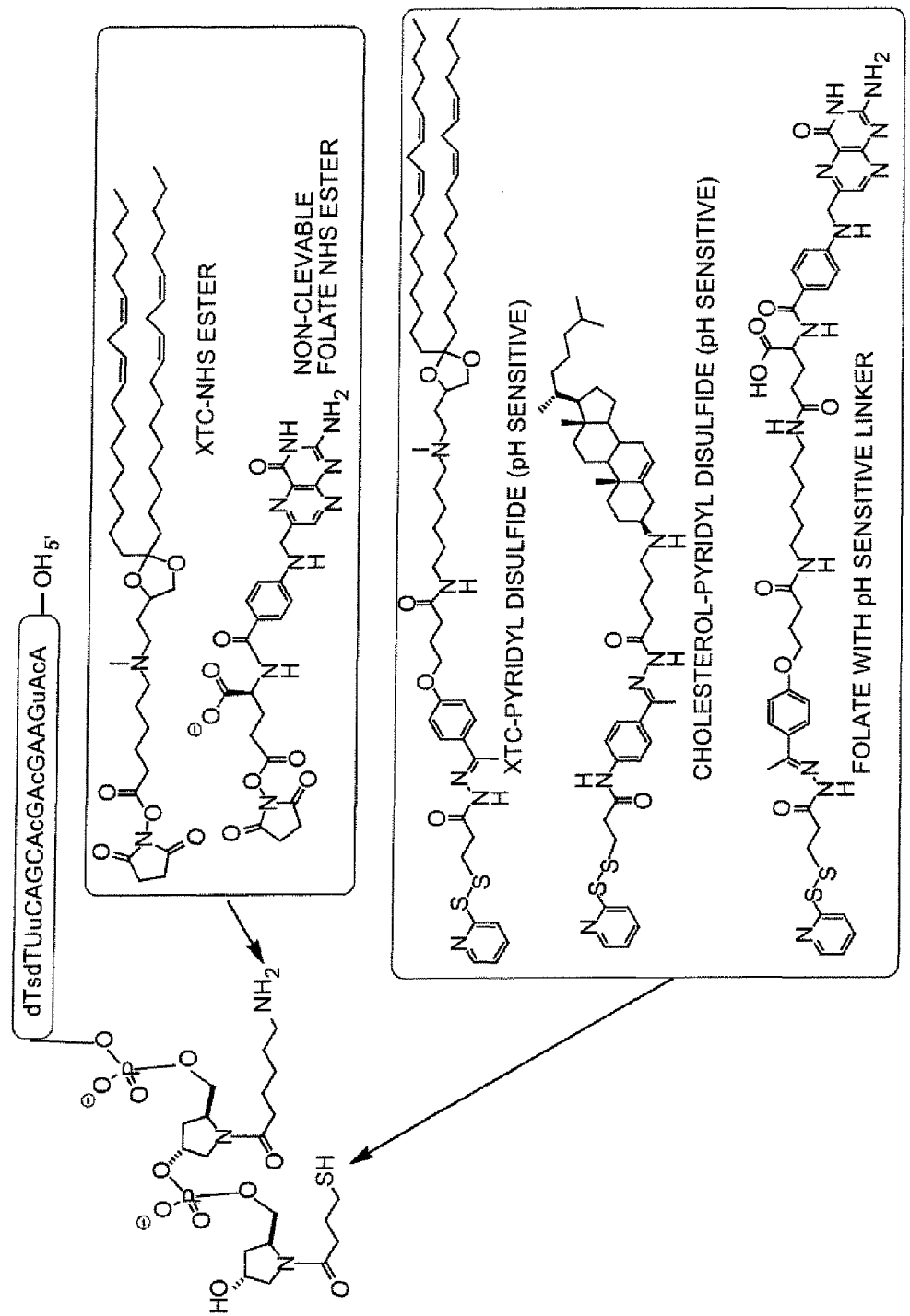
FIG. 3. Some exemplary strategies for conjugating targeting ligands and endsmolytic agents to oligonucleotides (e.g., SEQ ID NO: 189) with pH sensitive linkers.
Figure 4:
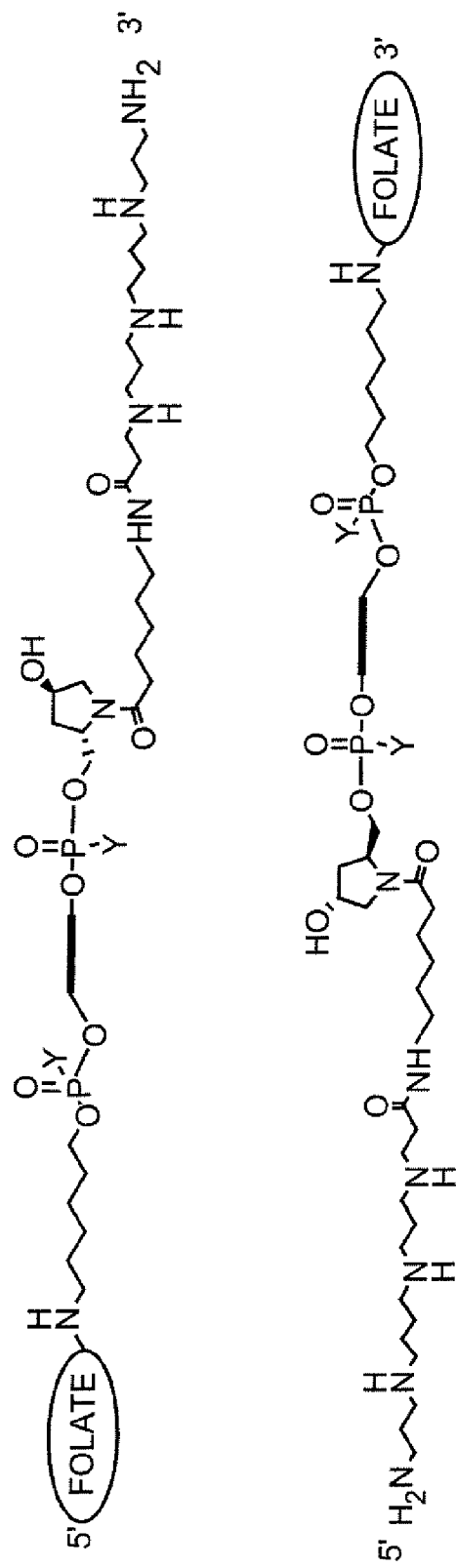
FIG. 4. Schematic representation of targeting ligand (folate) and endosomolytic agent (spermine) conjugated to an oligonucleotide.
Figure 5:
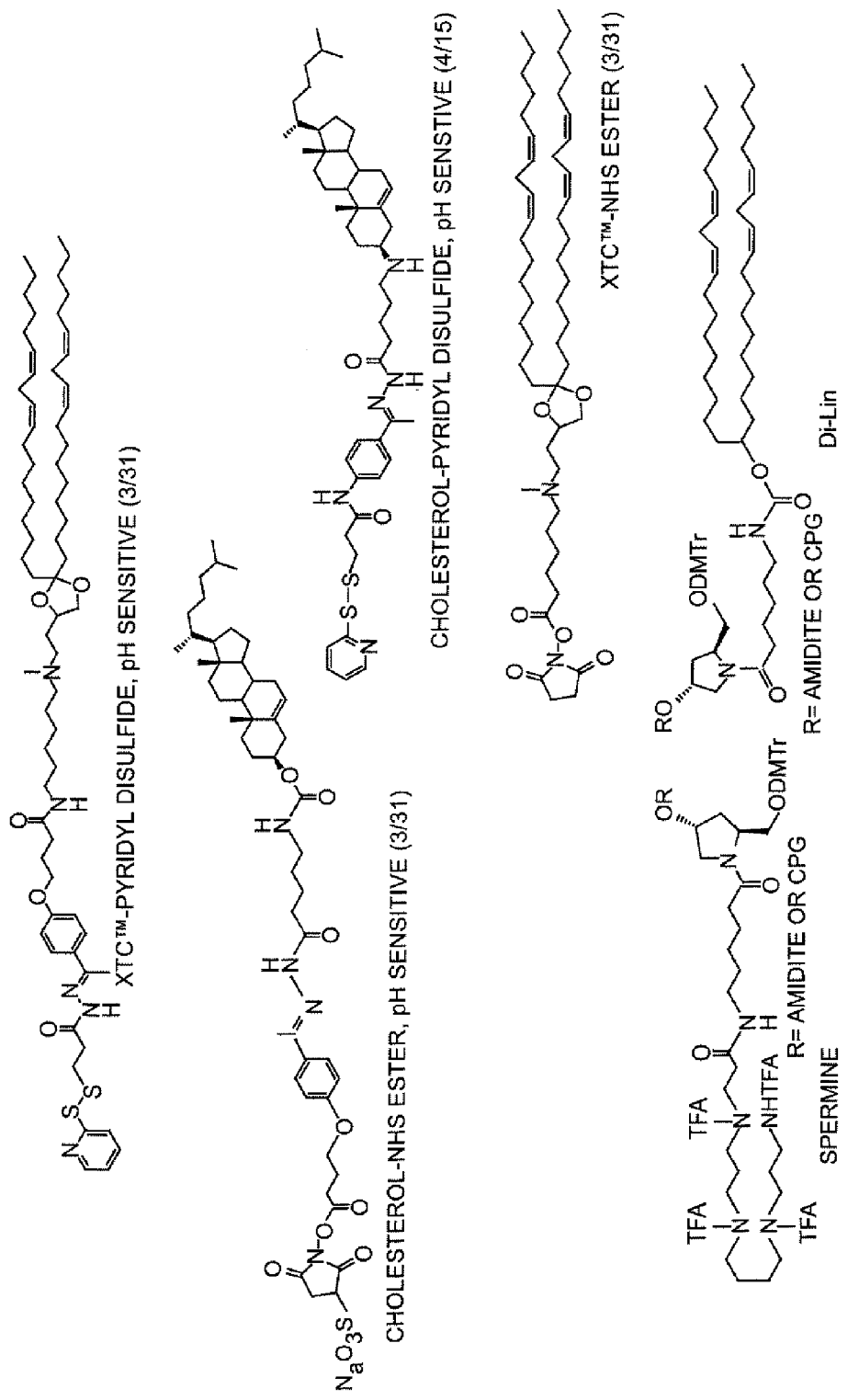
FIG. 5. Some exemplary synthetic monomers for conjugating endosomolytic agents and targeting ligands with oligonucleotides.
Figure 6:
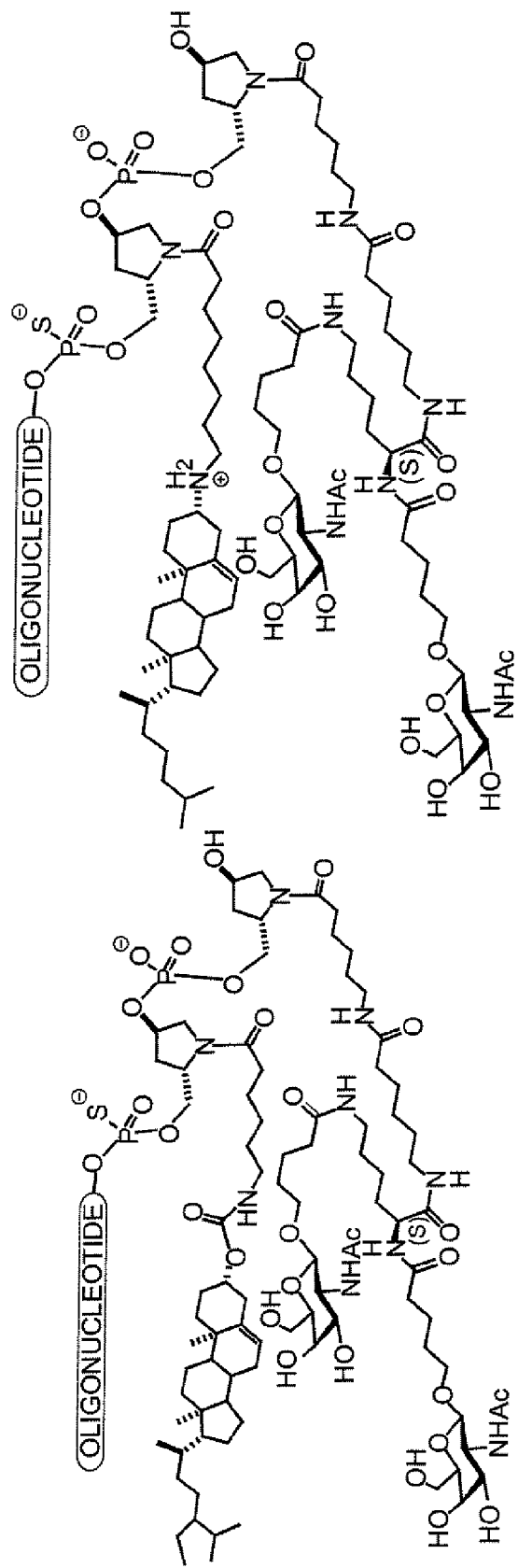
FIG. 6. Exemplary modular compositions having different endosomolytic agents using GalNAc2 as the targeting ligand.
Figure 7:
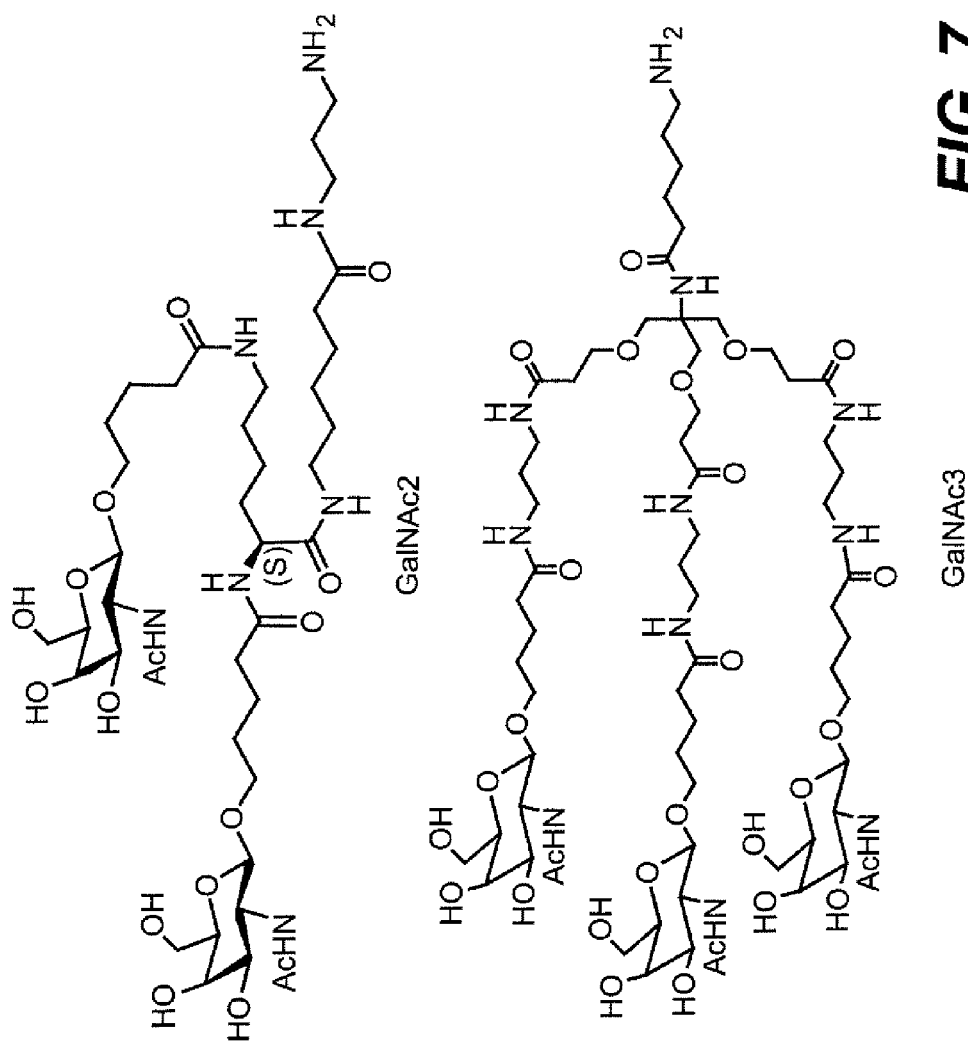
FIG. 7. Depicts the chemical structures of GalNAc2 and GalNAc3.
Figure 8:
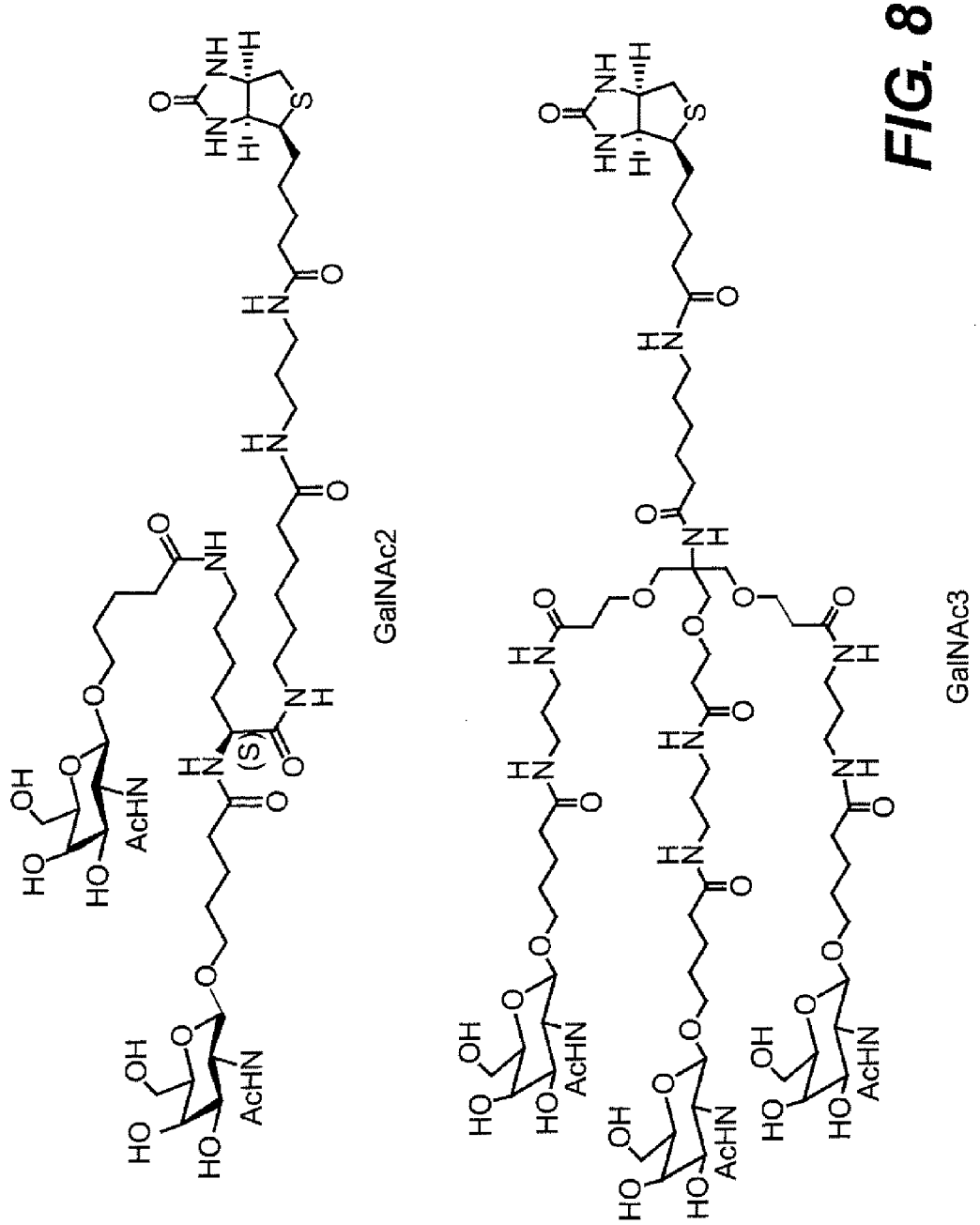
FIG. 8. Depicts biotinylated GalNAc2 and GalNAc3.

In one aspect, the invention features a modular composition, comprising a nucleic acid, at least one endosomolytic component, and at least one targeting ligand. The endosomolytic component is also referred to as endosomolytic ligand and endosomolytic agent herein.

The modular composition may have the formula:

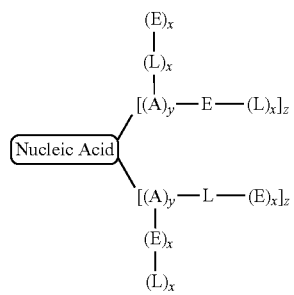

wherein

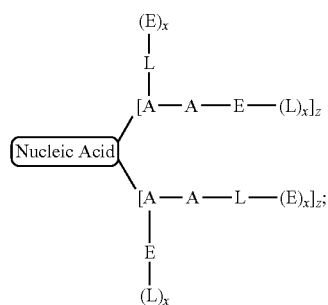

is the nucleic acid; E is the endosomolytic component; L is the targeting ligand; x represents independently for each occurrence 0 or 1; y represents independently for each occurrence 1, 2, 3, 4, 5, or 6; z represents independently for each occurrence 0, 1, 2, 3, 4, 5, or 6. In the modular composition, E and L are each present at least once.

Preferred modular compositions include a modular composition having the formula:

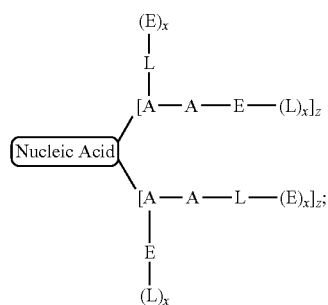

a modular composition having the formula:

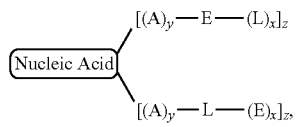

wherein each z is independently 1, 2, 3, 4, 5, or 6; and a modular composition having the formula:

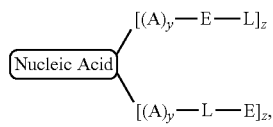

wherein z is 1, 2, 3, 4, 5, or 6 in one instance, and z is 0, 1, 2, 3, 4, 5, or 6 in the other instance.

The A moiety is a linking moiety. Any moiety known in the art may be used to attach the endosomolytic component and/or the targeting ligand to the nucleic acid. Preferably, A is a linking moiety selected from the group consisting of:

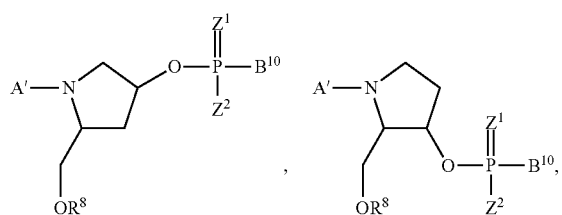

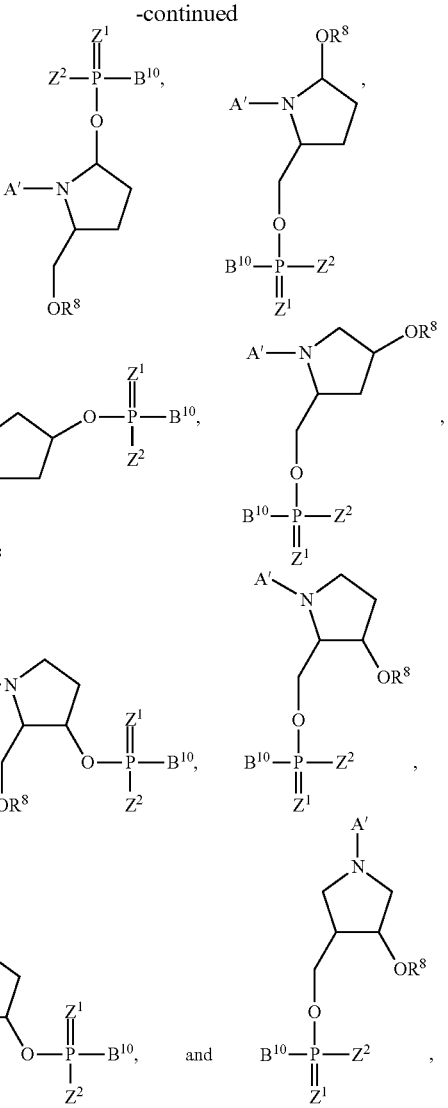

wherein $Z^1$ represents independently for each occurrence O or S;

$Z^2$ represents independently for each occurrence —OH, —OM, —Oalkyl, —Oaryl, —Oaralkyl, —SH, —SM, —Salkyl, —Saryl, -aralkyl, —N($R^3$)$R^4$, —C($R^{11}$)$_2$)$_m$N($R^{11}$)$_2$, —N($R^{11}$)(C($R^{11}$)$_2$)$_m$N($R^{11}$)$_2$, or alkyl;

$R^3$ and $R^4$ represent independently H or alkyl; or $R^3$ and $R^4$ taken together form a 3-, 4-, 5-, 6-, or 7-membered ring;

$R^{11}$ represents independently for each occurrence hydrogen or alkyl;

M represents independently for each occurrence an alkali metal or a transition metal with an overall charge of +1;

$R^8$ represents independently for each occurrence hydrogen, alkyl, aryl, aralkyl, acyl, silyl, a bond to the nucleic acid, or, when combined with $B^{10}$, a bond between linking moieties;

$B^{10}$ represents a bond between A and the nucleic acid or, when combined with $R^8$, is a bond between linking moieties.

Because A can be more than one, the linking moieties may be bonded to each other, and then bonded to an endosomolytic component and/or targeting ligand. In a preferred embodiment, at least two A linking moieties are bonded together and then bonded to the nucleic acid. The endosomolytic component and targeting ligand may both be bonded together through the same linking moiety, or the endosomolytic component may be bonded to one linking moiety and the targeting ligand to another linking moiety.

The linking may moiety may contain a tether (A') between the linking moiety and the endosomolytic component and/or targeting ligand. Thus, A' is a direct bond or a tether having the formula: —[(P-Q-R)$_q$—X—(P'-Q'-R')$_{q'}$]$_{q''}$-T-, wherein:

P, R, T, P' and R' are each independently absent, CO, NH, O, S, OC(O), NHC(O), CH$_2$, CH$_2$NH, CH$_2$O; NHCH(R$^a$)C (O), —C(O)—CH(R$^a$)—NH—, C(O)-(optionally substituted alkyl)-NH—, CH=N—O,

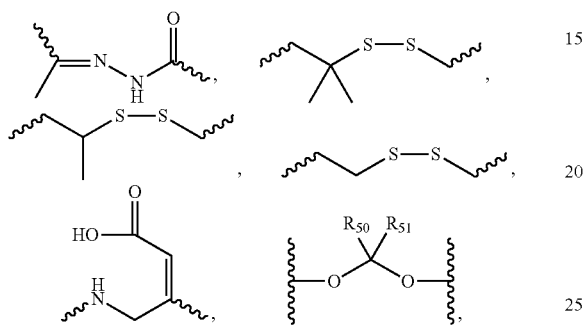

cyclyl, heterocyclyl, aryl or heteroaryl; where R$_{50}$ and R$_{51}$ are independently alkyl, substituted alkyl, or R$_{50}$ and R$_{51}$ taken together form a cyclic ring;

Q and Q' are each independently for each occurrence absent, —(CH$_2$)$_n$—, —C(R$^{40}$)(R$^{41}$)(CH$_2$)$_n$—, —(CH$_2$)$_n$C (R$^{40}$)(R$^{41}$)—, —(CH$_2$CH$_2$O)$_m$CH$_2$CH$_2$—, —(CH$_2$CH$_2$O)$_m$ CH$_2$CH$_2$NH—, aryl, heteroaryl, cyclyl, or heterocyclyl;

X is absent or a cleavable linking group;

R$^a$ is H or an amino acid side chain;

R$^{40}$ and R$^{41}$ are each independently H, CH$_3$, OH, SH or N(R$^X$)$_2$;

R$^X$ is, for each occurrence, H, methyl, ethyl, propyl, isopropyl, butyl or benzyl;

q, q' and q" are each independently 0-30;

n is, for each occurrence, an integer from 1-20; and m is, for each occurrence, an integer from 0-50.

In preferred embodiments, the tether contains a redox cleavable linking group, a pH sensitive component, or a combination thereof. Preferred tethers include an alkyl diradical, heteroalkyl diradical, alkenyl diradical, alkynyl diradical, alkylalkynyl diradical, aminoalkyl diradical, thioether, —C(O)—, —S(O)—, —S(O)$_2$—, —C(R)$_2$—, or a tether having the formula:

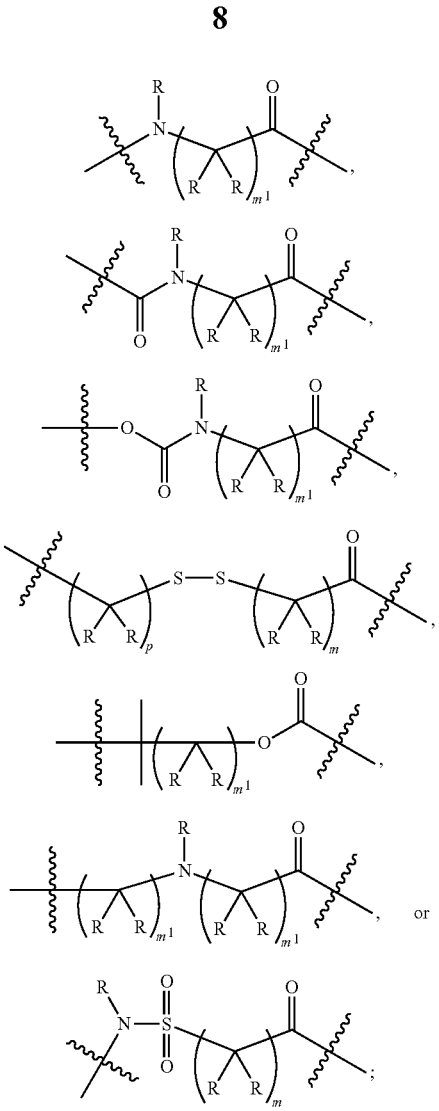

wherein m represents independently for each occurrence 1, 2, 3, 4, 5, 6, 7, or 8; m$^1$ represents independently for each occurrence 0, 1, 2, 3, 4, 5, 6, 7, or 8; p represents independently for each occurrence 1, 2, 3, or 4; and R represents independently for each occurrence hydrogen or alkyl.

More preferred tethers include

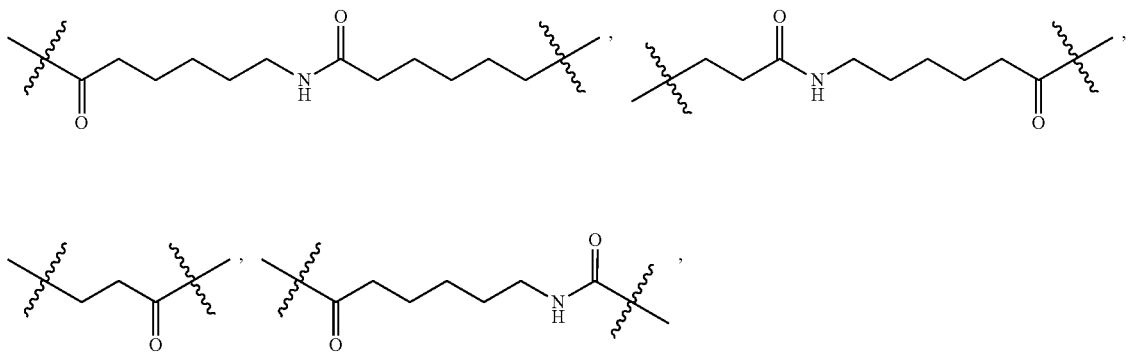

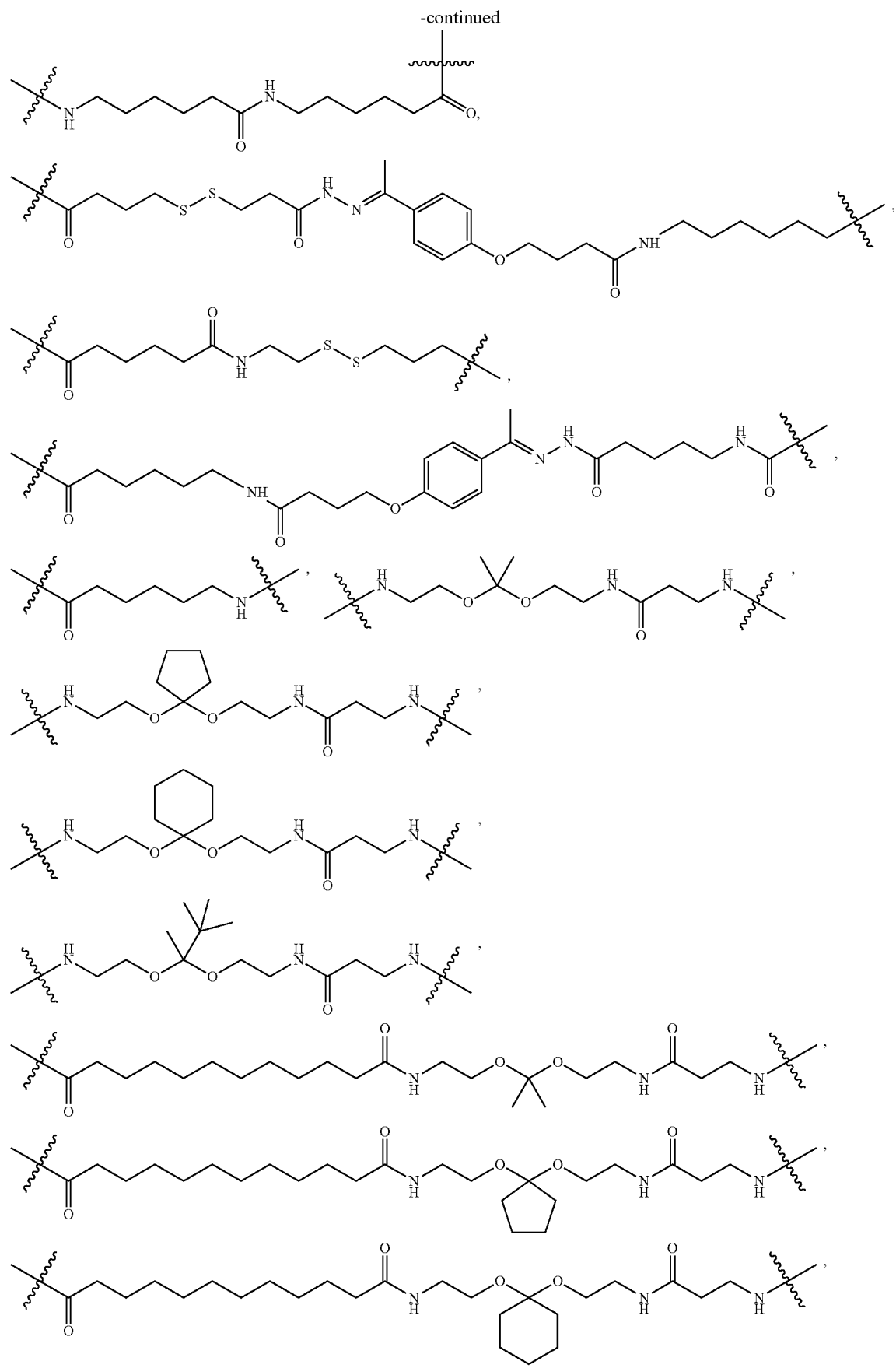

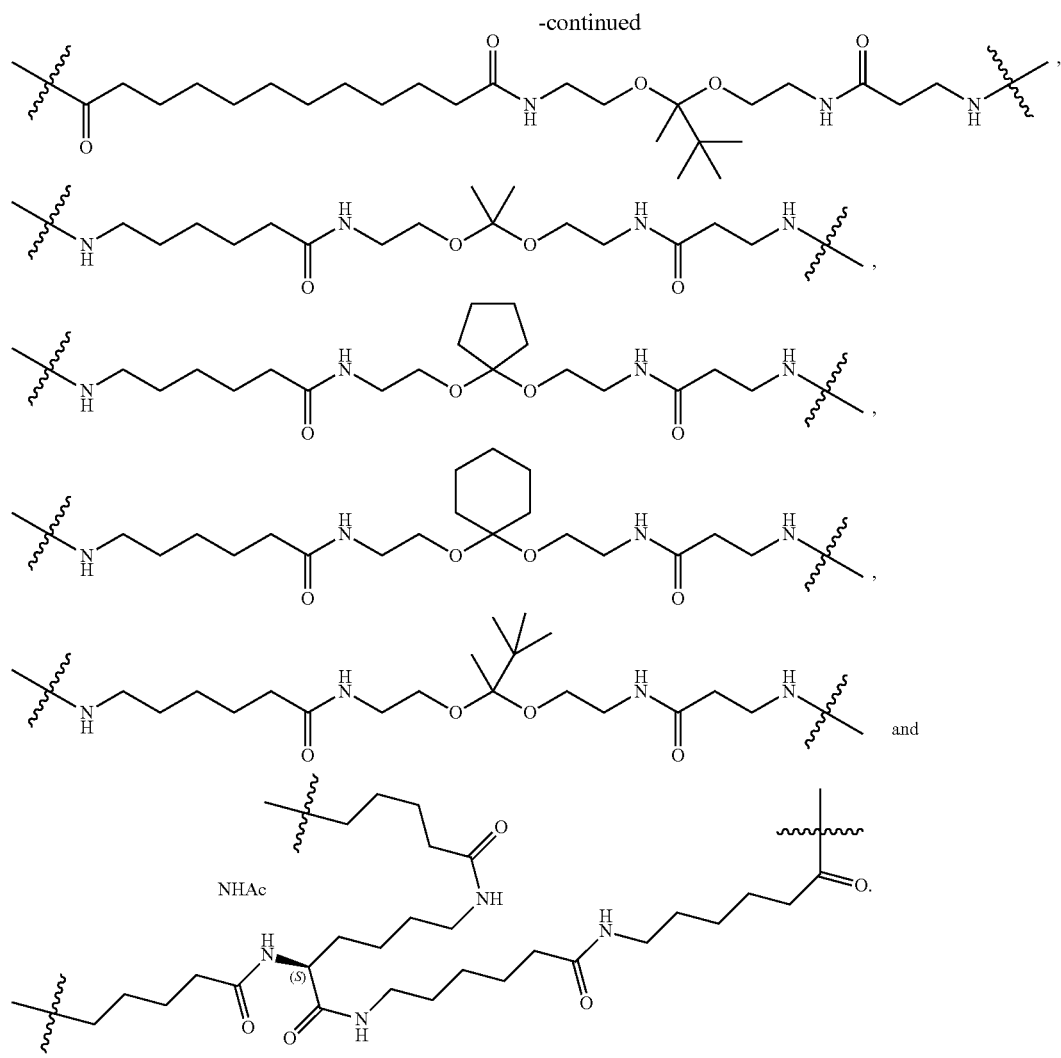

The endosomolytic component of this invention is a cellular compartmental release component, and may be any compound capable of releasing from any of the cellular compartments known in the art, such as the endosome, lysosome, endoplasmic reticulum (ER), golgi apparatus, microtubule, peroxisome, or other vesicular bodies with the cell.

The endosomolytic ligand and the targeting ligand can be located anywhere in the nucleic acid. Exemplary locations are the 5'-terminal end, the 3'-terminal end and/or internal non-terminal positions. The term "terminal end" includes the first 5 nucleotides from the end of the oligonucleotide. Thus the first 5 nucleotides from the end are considered to be in the terminal end.

For instance, the 5'-terminal end may contain both the endosomolytic ligand and targeting ligand on one or both strands of the nucleic acid; the 3'-terminal end may contain both the endosomolytic ligand and the targeting ligand on one or both strands of the nucleic acid; the endosomolytic ligand and the targeting ligand may both be present on an internal non-terminus position on the nucleic acid; or any combination of the above. The endosomolytic ligand and the targeting ligand may be attached through one another and/or through linking moieties. While the modular composition contains at least one endosomolytic component and targeting ligand, it can contain six or more endosomolytic components and six or more targeting ligands. A different number of endosomolytic components and targeting ligands may be present on the modular composition depending on the desired functionality of the composition.

In some embodiments, both the endosomolytic ligand and the targeting ligand are on the same terminal end of the oligonucleotide.

In some embodiments, both the endosomolytic ligand and the targeting ligand are on the 5'-terminal end of the oligonucleotide.

In some embodiments, both the endosomolytic ligand and the targeting ligand are on the 3'-terminal end of the oligonucleotide.

When both the endosomolytic ligand and the targeting ligand are on the same terminal end, one of them may be linked In some embodiments, the endosomolytic ligand and the targeting ligand are on opposite terminal ends of the oligonucleotide.

In some embodiments, the endosomolytic ligand is on the 5'-terminal end of the oligonucleotide and the targeting ligand is on the 3'-terminal end of the oligonucleotide.

In some embodiments, the endosomolytic ligand is on the 3'-terminal end of the oligonucleotide and the targeting ligand is on the 5'-terminal end of the oligonucleotide.

In some embodiments, one of the endosomolytic ligand and the targeting ligand is on the terminal while the other is located at an internal non-terminal part of the oligonucleotide.

In some embodiments, the endosomolytic ligand is on the terminal end and the targeting ligand is located at an internal position.

In some embodiments, the endosomolytic ligand is on the 5'-terminal end and the targeting ligand is located at an internal position.

In some embodiments, the endosomolytic ligand is on the 3'-terminal end and the targeting ligand is located at an internal position.

In some embodiments, the targeting ligand is on the terminal end and the endosomolytic ligand is located at an internal position.

In some embodiments, the targeting ligand is on the 5'-terminal end and the endosomolytic ligand is located at an internal position.

In some embodiments, the targeting ligand is on the 3'-terminal end and the endosomolytic ligand is located at an internal position.

In some embodiments, both the endosomolytic ligand and the targeting ligand are located at internal non-terminal positions.

When the oligonucleotide is a double-stranded oligonucleotide the endosomolytic ligand and the targeting ligand may both be located on the same strand or on different strands.

In some embodiments, the endosomolytic ligand and the targeting ligand are both on the same strand.

In some embodiments, the endosomolytic ligand and the targeting ligand are both on the sense strand.

In some embodiments, the endosomolytic ligand and the targeting ligand are both on the antisense strand.

In some embodiments, the endosomolytic ligand and the targeting ligand are located on different strands.

In some embodiments, the endosomolytic ligand is on the sense strand while the targeting ligand is on the antisense strand.

In some embodiments, the endosomolytic ligand is on the sense strand while the targeting ligand is on the antisense strand.

In some embodiments, the endosomolytic ligand and the targeting ligand are on different strands but on the same terminal end of the double-stranded oligonucleotide.

In some embodiments, the endosomolytic ligand and the targeting ligand are on different strands and on the opposite terminal ends of the double-stranded oligonucleotide.

In some embodiments, the endosomolytic ligand and the targeting ligand are on different strands and one of them is on the terminal end and the other is located at an internal non-terminal position of the double stranded oligonucleotide.

In some embodiments, the endosomolytic ligand and/or the targeting ligand is attached to the oligonucleotides via an intervening tether/linker. In some embodiments, the endosomolytic ligand and/or the targeting ligand is linked to a monomer before conjugation to the oligonucleotide. The endosomolytic ligand and/or the targeting ligand may be linked directly or through a linker to the monomer. The endosomolytic ligand and/or the targeting ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., $X-(CH_2)_nNH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

In some embodiments, the endosomolytic agents and/or targeting ligands can be conjugated to nucleobases, sugar moieties, or internucleosidic linkages of nucleic acid molecules, either directly or through a linker. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2',3',4' and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

In some embodiments, one endosomolytic ligand and two or more targeting ligands are present in the oligonucleotide.

In some embodiments, one targeting ligand and two or more targeting ligands are present in the oligonucleotide.

In some embodiments, two or more endosomolytic ligands and two or more targeting ligands are present.

When the oligonucleotide is a double-stranded oligonucleotide and multiple endosomolytic ligands and/or targeting ligands are present, such multiple endosomolytic ligands and/or targeting ligands may all be present in one strand or both strands of the double stranded oligonucleotide.

When multiple endosomolytic ligands and/or targeting ligands are present, they may all be the same or different.

In some embodiments, the ligands, e.g. endosomolytic ligands and/or targeting ligands, are linked to a monomer which is then incorporated into the growing oligonucleotide strand. Such monomers are also referred to as carrier monomers herein.

In some embodiments, oligonucleotide comprises at least one carrier monomer of formula (I)

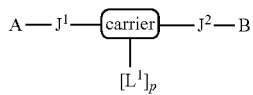

Formula (I)

wherein:

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—, or —P($Z^1$)($Z^2$)—;

$Z^1$ and $Z^2$ are each independently for each occurrence O, S, N(alkyl) or optionally substituted alkyl;

$J^1$ and $J^2$ are independently O, S, $NR^N$, optionally substituted alkyl, OC(O)NH, NHC(O)O, C(O)NH, NHC(O), OC(O), C(O)O, OC(O)O, NHC(O)NH, NHC(S)NH, OC(S)NH, OP(N($R^P$)$_2$)O, or OP(N($R^P$)$_2$);

[carrier]

is cyclic group or acyclic group;

$L^1$ is -$L^2$ or -$L^2$-linker-$L^3$;

$L^2$ and $L^3$ are each independently an endosomolytic agent or a targeting ligand; and p is 1-3.

In some embodiments, p is 1.

In some embodiments, carrier monomer is cyclic and

[carrier]

is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin.

In some embodiments, carrier monomer is acyclic and

[carrier]

is selected from serinol backbone or diethanolamine backbone.

In some embodiment, $L^1$ is -$L^2$.

In some embodiments, the carrier monomer is based on the pyrroline ring system as shown in formula (II)

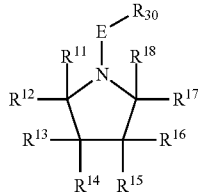

Formula (II)

wherein E is absent or C(O), C(O)O, C(O)NH, C(S), C(S)NH, SO, $SO_2$, or $SO_2$NH;

$R^{11}$, $R^{12}$, $R^{13}$, $R^{14}$, $R^{15}$, $R^{16}$, $R^{17}$, and $R^{18}$ are each independently for each occurrence H, —$CH_2OR^a$, or $OR^b$, $R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)— or —P($Z^1$)(O-linker-$R^L$)—;

$R^{30}$ is independently for each occurrence -linker-$R^L$;

$R^L$ is hydrogen, -$L^2$ or -$L^2$-linker-$L^3$;

$L^2$ and $L^3$ are each independently an endosomolytic agent or a targeting ligand; and $Z^1$ and $Z^2$ are each independently for each occurrence O, S, N(alkyl) or optionally substituted alkyl;

provided that $R^L$ is -$L^2$ or -$L^2$-linker-$L^3$ at least once.

In some embodiments, the oligonucleotide comprises at least one monomer of formula (II).

In some embodiment, $R^L$ is -$L^2$.

For the pyrroline-based monomers, $R^{11}$ is —$CH_2OR^a$ and $R1^3$ is $OR^b$; or $R^{11}$ is —$CH_2OR^a$ and $R^9$ is $OR^b$; or $R^{11}$ is —$CH_2OR^a$ and $R^{17}$ is $OR^b$; or $R^{13}$ is —$CH_2OR^a$ and $R^{11}$ is $OR^b$; or $R^{13}$ is —$CH_2OR^a$ and $R^{15}$ is $OR^b$; or $R^{13}$ is —$CH_2OR^a$ and $R^{17}$ is $OR^b$. In certain embodiments, $CH_2OR^a$ and $OR^b$ may be geminally substituted. For the 4-hydroxyproline-based monomers, $R^{11}$ is —$CH_2OR^a$ and $R^{17}$ is $OR^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, $CH_2OR^a$ and $OR^b$ may be cis or trans with respect to one another in any of the pairings delineated above Accordingly, all cis/trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing $CH_2OR^a$ and $OR^b$ can both have the R configuration; or both have the S configuration; or one center can have the R configuration and the other center can have the S configuration and vice versa).

In some embodiments, $R^{11}$ is $CH_2OR^a$ and $R^{15}$ is $OR^b$.

In some embodiments, $R^b$ is a solid support.

In one embodiment, carrier of formula (II) is a phosphoramidite, i.e., one of $R^a$ or $R^b$ is —P(O-alkyl)N(alkyl)$_2$, e.g., —P(OCH$_2$CH$_2$CN)N(i-propyl)$_2$. In one embodiment, $R^b$ is —P(O-alkyl)N(alkyl)$_2$.

In some embodiments, the carrier monomer is based on the ribose ring system as shown in formula (III).

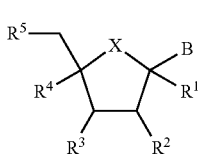

Formula (III)

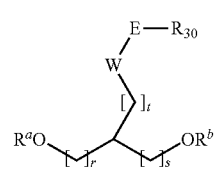

Formula (IV)

wherein:

X is O, S, $NR^N$ or $CR^P_2$;

B is independently for each occurrence hydrogen, optionally substituted natural or non-natural nucleobase, optionally substituted natural nucleobase conjugated with -linker-$R^L$ or optionally substituted non-natural nucleobase conjugated with -linker-$R^L$;

$R^1$, $R^2$, $R^3$, $R^4$ and $R^5$ are each independently for each occurrence H, $OR^6$, F, $N(R^N)_2$, or -J-linker-$R^L$;

J is absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, $OP(N(R^P)_2)O$, or $OP(N(R^P)_2)$;

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —$P(Z^1)(Z^2)$— or —$P(Z^1)$(O-linker-$R^L$)—;

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

$R^L$ is hydrogen, -$L^2$ or -$L^2$-linker-$L^3$;

$L^2$ and $L^3$ are each independently an endosomolytic agent or a targeting ligand; and $Z^1$ and $Z^2$ are each independently for each occurrence O, S N(alkyl) or optionally substituted alkyl;

provided that $R^L$ is present at least once and further provided that $R^L$ is -$L^2$ or -$L^2$-linker-$L^3$ at least once.

In some embodiments, the oligonucleotide comprises at least one monomer of formula (III).

In some embodiment, $R^L$ is -$L^2$.

In some embodiments, the carrier monomer is based on an acyclic group and is termed an "acyclic carrier". Preferred acyclic carriers can have the structure shown in formula (IV) or formula (V) below.

In some embodiments, the acyclic carrier has the structure shown in formula (IV).

wherein:

W is absent, O, S and $N(R^N)$, where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, $SO_2$, or $SO_2NH$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —$P(Z^1)(Z^2)$— or —$P(Z^1)$(O-linker-$R^L$)—;

$R^{30}$ is independently for each occurrence -linker-$R^L$;

$R^L$ is hydrogen, -$L^2$ or -$L^2$-linker-$L^3$;

$L^2$ and $L^3$ are each independently an endosomolytic agent or a targeting ligand;

$Z^1$ and $Z^2$ are each independently for each occurrence O, S, N(alkyl) or optionally substituted alkyl; and r, s and t are each independently for each occurrence 0, 1, 2 or 3;

provided that $R^L$ is -$L^2$ or -$L^2$-linker-$L^3$ at least once.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In one embodiment, the oligonucleotide comprises at least one monomer of formula (IV).

In some embodiment, $R^L$ is -$L^2$

In some embodiments, the acyclic carrier has the structure shown in formula (V)

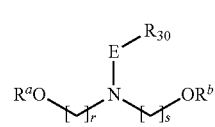

Formula (V)

wherein E is absent or C(O), C(O)O, C(O)NH, C(S), C(S)NH, SO, $SO_2$, or $SO_2NH$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)— or —P($Z^1$)(O-linker-$R^L$)—;

$R^{30}$ is independently for each occurrence -linker-$R^L$;

$R^L$ is hydrogen, -$L^2$ or -$L^2$-linker-$L^3$;

$L^2$ and $L^3$ are each independently an endosomolytic agent or a targeting ligand;

$Z^1$ and $Z^2$ are each independently for each occurrence O, S, N(alkyl) or optionally substituted alkyl; and r and s are each independently for each occurrence 0, 1, 2 or 3;

provided that $R^L$ is -$L^2$ or -$L^2$-linker-$L^3$ at least once.

In some embodiments, the oligonucleotide comprises at least one monomer of formula (V).

In some embodiment, $R^L$ is -$L^2$.

In some embodiments, the oligonucleotide comprises at least two different monomers selected from formula (I)-formula (V).

Interfering RNA

Double-stranded interfering RNA (dsiRNA) directs the sequence-specific silencing of mRNA through a process known as RNA interference (RNAi). The process occurs in a wide variety of organisms, including mammals and other vertebrates.

It has been demonstrated that 21-23 nt fragments of dsiRNA are sequence-specific mediators of RNA silencing, e.g., by causing RNA degradation. While not wishing to be bound by theory, it may be that a molecular signal, which may be merely the specific length of the fragments, present in these 21-23 nt fragments recruits cellular factors that mediate RNAi. Described herein are methods for preparing and administering these 21-23 nt fragments, and other iRNAs agents, and their use for specifically inactivating gene function. The use of iRNA agents (or recombinantly produced or chemically synthesized oligonucleotides of the same or similar nature) enables the targeting of specific mRNAs for silencing in mammalian cells. In addition, longer dsiRNA agent fragments can also be used, e.g., as described below.

Although, in mammalian cells, long dsiRNAs can induce the interferon response which is frequently deleterious, siRNAs do not trigger the interferon response, at least not to an extent that is deleterious to the cell and host. In particular, the length of the iRNA agent strands in an siRNA agent can be less than 31, 30, 28, 25, or 23 nt, e.g., sufficiently short to avoid inducing a deleterious interferon response. Thus, the administration of a composition of siRNA agent (e.g., formulated as described herein) to a mammalian cell can be used to silence expression of a target gene while circumventing the interferon response. Further, use of a discrete species of iRNA agent can be used to selectively target one allele of a target gene, e.g., in a subject heterozygous for the allele.

Moreover, in one embodiment, a mammalian cell is treated with an iRNA agent that disrupts a component of the interferon response, e.g., dsRNA-activated protein kinase PKR. Such a cell can be treated with a second iRNA agent that includes a sequence complementary to a target RNA and that has a length that might otherwise trigger the interferon response.

In a typical embodiment, the subject is a mammal such as a cow, horse, mouse, rat, dog, pig, goat, or a primate. The subject can be a dairy mammal (e.g., a cow, or goat) or other farmed animal (e.g., a chicken, turkey, sheep, pig, fish, shrimp). In certain embodiments, the subject is a human, e.g., a normal individual or an individual that has, is diagnosed with, or is predicted to have a disease or disorder.

Further, because iRNA agent mediated silencing persists for several days after administering the iRNA agent composition, in many instances, it is possible to administer the composition with a frequency of less than once per day, or, for some instances, only once for the entire therapeutic regimen. For example, treatment of some cancer cells may be mediated by a single bolus administration, whereas a chronic viral infection may require regular administration, e.g., once per week or once per month.

A number of exemplary routes of delivery are described that can be used to administer an iRNA agent to a subject. In addition, the iRNA agent can be formulated according to any exemplary method described herein.

The present invention relates to modular compositions and methods for delivery of a nucleic acid (e.g., an iRNA or siRNA). One aspect of the invention relates to a modular composition comprising an endosomolytic component, a targeting ligand, and a nucleic acid (e.g., an iRNA agent or siRNA agent).

For ease of exposition, certain formulations, compositions and methods in this application are discussed largely with regard to unmodified nucleic acids or iRNAs. It may be understood, however, that these formulations, compositions and methods can be practiced with modified nucleic acids, and that such practices are within the scope of the invention.

Endosomolytic Components

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation has been the most common approach (Singh, R. S., Goncalves, C. et al. (2004). On the Gene Delivery Efficacies of pH-Sensitive Cationic Lipids via Endosomal Protonation. A Chemical Biology Investigation. *Chem. Biol.* 11, 713-723). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. *Polymers Adv. Technol.* 13, 992-999; Kakudo, Chaki, T., S. et al. (2004). Transferrin-Modified Liposomes Equipped with a pH-Sensitive Fusogenic Peptide: An Artificial Viral-like Delivery System. *Biochemistry* 436, 5618-5628; Yessine, M. A. and Leroux, J. C. (2004). Membrane-destabilizing polyanions: interaction with lipid bilayers and endosomal escape of biomacromolecules. *Adv. Drug Deliv. Rev.* 56, 999-1021; Oliveira, S., van Rooy, I. et al. (2007). Fusogenic peptides enhance endosomal escape improving siRNA-induced silencing of oncogenes. *Int. J. Pharm.* 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs. *Biochim. Biophys. Acta* 1559, 56-68).

In certain embodiments, the endosomolytic components of the present invention may be polyanionic peptides or peptidomimetics which show pH-dependent membrane activity and/or fusogenicity. A peptidomimetic may be a small protein-like chain designed to mimic a peptide. A peptidomimetic may arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Libraries of compounds may be screened for their differential membrane activity at endosomal pH versus neutral pH using a hemolysis assay. Promising candidates isolated by this method may be used as components of the modular compositions of the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of endosomolytic components include $H_2N$-(AALEALAEALEALAEALEALAE-AAAAGGC)-$CO_2H$ (SEQ ID NO: 1); $H_2N$-(AALAE-ALAEALAEALAEALAEALAAAAGGC)-$CO_2H$ (SEQ ID NO: 2); and $H_2N$-(ALEALAEALEALAEA)-$CONH_2$ (SEQ ID NO: 3).

Further examples of endosomolytic components include those in Table 1:

TABLE 1

Exemplary Endosomolytic Components

| Name | Sequence (N to C) | SEQ ID NO |
|---|---|---|
| GALA | AALEALAEALEALAEALEALAEAAAAGGC | 1 |
| EALA | AALAEALAEALAEALAEALAEALAAAAGGC | 2 |
|  | ALEALAEALEALAEA | 3 |
| INF-7 | GLFEAIEGFIENGWEGMIWDYG | 4 |
| Inf HA-2 | GLFGAIAGFIENGWEGMIDGWYG | 5 |
| diINF-7 | GLF EAI EGFI ENGW EGMI DGWYGC<br>GLF EAI EGFI ENGW EGMI DGWYGC | 6 |
| diINF3 | GLF EAI EGFI ENGW EGMI DGGC<br>GLF EAI EGFI ENGW EGMI DGGC | 7 |
| GLF | GLFGALAEALAEALAEHLAEALAEALEALAAGGSC | 8 |
| GALA-INF3 | GLFEAIEGFIENGWEGLAEALAEALEALAAGGSC | 9 |

TABLE 1-continued

Exemplary Endosomolytic Components

| Name | Sequence (N to C) | SEQ ID NO |
|---|---|---|
| INF-5 | GLF EAI EGFI ENGW EGnI DG K<br>GLF EAI EGFI ENGW EGnI DG | 10 |
| JTS-1 | GLFEALLELLESLWELLLEA | 11 |
| ppTG1 | GLFKALLKLLKSLWKLLLKA | 12 |
| ppTG20 | GLFRALLRLLRSLWRLLLRA | 13 |
| KALA | WEAKLAKALAKALAKHLAKALAKALKACEA | 14 |
| HA | GLFFEAIAEFIEGGWEGLIEGC | 15 |
| Melittin | GIGAVLKVLTTGLPALISWIKRKRQQ | 16 |
| Histidine rich | $CHK_6HC$ | 17 | n, norleucine

In some embodiments, endosomolytic ligands can include imidazoles, poly or oligoimidazoles, linear or branched polyethyleneimines (PEIs), linear and brached polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Preferred synthetic polymers with endosomolytic activity, are described in the following United States Patent Application Publications Nos. 2009/0048410; 20090023890; 2008/0287630; 20080287628; 2008/0281044; 2008/0281041; 2008/0269450; 2007/0105804; 20070036865; and 2004/0198687, contents of which are hereby incorporated by reference in their entirety.

In some embodiments, the membrane active functionality of the endosomolytic agent is masked when said endosomolytic agent is conjugated with the oligonucleotide. When the oligonucleotide reaches the endosome, the membrane active functionality is unmasked and the agent becomes active. The unmasking may be carried out more readily under the conditions found in the endosome than outside the endosome. For example, the membrane active functionality can be masked with a molecule through a cleavable linker that under goes cleavage in the endosome. Without wishing to be bound by theory, it is envisioned that upon entry into the endosome, such a linkage will be cleaved and the masking agent released from the endosomolytic agent.

In some embodiments, the masking agent has a cleavable linker that upon cleavage release a functional group that can cleave the linkage between the masking agent and the active functional group of the endosomolytic agent. One example is a masking agent linked to the endosomolytic agent through a amide type linkage, and having a S—S bond. Upon entry into the endosome, the S—S bond can be cleaved releasing free thiols that can then cleave the amide linkage between the masking agent and the endosomolytic agents either inter or intra molecularly. United States Patent Application Publication No. 2008/0281041 describes some masked endosomolytic polymers that are amenable to the present invention.

Lipids having membrane activity are also amenable to the present invention as endosomolytic agents. Such lipids are also described as fusogenic lipids. These fusogenic lipids are thought to fuse with and consequently destabilize a membrane. Fusogenic lipids usually have small head groups and unsaturated acyl chains. Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

The histidine-rich peptide H5WYG (SEQ ID NO: 18) is a derivative of the N-terminal sequence of the HA-2 subunit of the influenza virus hemagglutinin in which 5 of the amino acids have been replaced with histidine residues. H5WYG is able to selectively destabilize membranes at a slightly acidic pH as the histidine residues are protonated.

In some embodiments, the endosomolytic ligand is a cell-permeation agent, preferably a helical cell-permeation agent. Preferably, the agent is amphipathic. The helical agent is preferably an alpha-helical agent, which preferably has a lipophilic and a lipophobic phase. A cell-permeation agent can be, for example, a cell permeation peptide, cationic peptide, amphipathic peptide or hydrophobic peptide, e.g. consisting primarily of Tyr, Trp and Phe, dendrimer peptide, constrained peptide or crosslinked peptide. In some embodiments, the cell permeation peptide can include a hydrophobic membrane translocation sequence (MTS). An exemplary hydrophobic MTS-containing peptide is RFGF having the amino acid sequence AAVALLPAVLLALLAP(SEQ ID NO: 19). An RFGF analogue (e.g., amino acid sequence AALLPVLLAAP (SEQ ID NO: 20)) containing a hydrophobic MTS can also be a targeting ligand. The cell permeation peptide can be a "delivery" peptide, which can carry large polar molecules including peptides, oligonucleotides, and protein across cell membranes. Some exemplary cell-permeation peptides are shown in Table 2.

TABLE 2

Exemplary Cell Permeation Peptides.

| Cell Permeation Peptide | Amino acid Sequence | Reference |
|---|---|---|
| Penetratin | RQIKIWFQNRRMKWKK (SEQ ID NO: 21) | Derossi et al., J. Biol. Chem. 269: 10444, 1994 |
| Tat fragment (48-60) | GRKKRRQRRRPPQC (SEQ ID NO: 22) | Vives et al., J. Biol. Chem., 272: 16010, 1997 |
| Signal Sequence-based peptide | GALFLGWLGAAGSTM GAWSQPKKKRKV (SEQ ID NO: 23) | Chaloin et al., Biochem. Biophys. Res. Commun., 243: 601, 1998 |
| PVEC | LLIILRRRIRKQAHA HSK (SEQ ID NO: 24) | Elmquist et al., Exp. Cell Res., 269: 237, 2001 |
| Transportan | GWTLNSAGYLLKINL KALAALAKKIL (SEQ ID NO: 25) | Pooga et al., FASEB J., 12: 67, 1998 |
| Amphiphilic model peptide | KLALKLALKALKAA LKLA (SEQ ID NO: 26) | Oehlke et al., Mol. Ther., 2: 339, 2000 |

TABLE 2-continued

Exemplary Cell Permeation Peptides.

| Cell Permeation Peptide | Amino acid Sequence | Reference |
|---|---|---|
| $Arg_9$ | RRRRRRRRR (SEQ ID NO: 27) | Mitchell et al., J. Pept. Res., 56: 318, 2000 |
| Bacterial cell wall permeating | KFFKFFKFFK (SEQ ID NO: 28) | |
| LL-37 | LLGDFFRKSKEKIGKE FKRIVQRIKDFLRNLV PRTES (SEQ ID NO: 29) | |
| Cecropin P1 | SWLSKTAKKLENSAKK RISEGIAIAIQGGPR (SEQ ID NO: 30) | |
| α-defensin | ACYCRIPACIAGERRY GTCIYQGRLWAFCC (SEQ ID NO: 31) | |
| b-defensin | DHYNCVSSGGQCLYSA CPIFTKIQGTCYRGKA KCCK (SEQ ID NO: 32) | |
| Bactenecin | RKCRIVVIRVCR (SEQ ID NO: 33) | |
| PR-3 | RRRPRPPYLPRPRPPP FFPPRLPPRIPPGFPP RFPPRFPGKR-NH2 (SEQ ID NO: 34) | |
| Indolicidin | ILPWKWPWWPWRR-NH2 (SEQ ID NO: 35) | |

Cell-permeation peptides can be linear or cyclic, and include D-amino acids, non-peptide or pseudo-peptide linkages, peptidyl mimics. In addition the peptide and peptide mimics can be modified, e.g. glycosylated or methylated. Synthetic mimics of targeting peptides are also included.

In certain embodiments, more than one endosomolytic component may be incorporated in the modular composition of the invention. In some embodiments, this will entail incorporating more than one of the same endosomolytic component into the modular composition. In other embodiments, this will entail incorporating two or more different endosomolytic components into the modular composition.

These endosomolytic components may mediate endosomal escape by, for example, changing conformation at endosomal pH. In certain embodiments, the endosomolytic components may exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4). Fusogenic activity is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

In addition to the hemolysis assay described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, a modular composition described herein is constructed using one or more test or putative fusogenic agents. The modular composition can be constructed using a labeled nucleic acid. The ability of the endosomolytic component to promote endosomal escape, once the modular composition is taken up by the cell, can be evaluated, e.g., by preparation of an endosome preparation, or by microscopy techniques, which enable visualization of the labeled nucleic acid in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition.

A two-step assay can also be performed, wherein a first assay evaluates the ability of a test compound alone to respond to changes in pH, and a second assay evaluates the ability of a modular composition that includes the test compound to respond to changes in pH.

Targeting Ligands

The modular compositions of the present invention comprise a targeting ligand. In some embodiments, this targeting ligand may direct the modular composition to a particular cell. For example, the targeting ligand may specifically or non-specifically bind with a molecule on the surface of a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. For example, the targeting moiety can recognize a cancer-specific antigen (e.g., CA 15-3, CA 19-9, CEA, or HER2/neu) or a viral antigen, thus delivering the iRNA to a cancer cell or a virus-infected cell. Exemplary targeting moieties include antibodies (such as IgM, IgG, IgA, IgD, and the like, or a functional portions thereof), ligands for cell surface receptors (e.g., ectodomains thereof).

Table 3 provides examples of a number of antigens which can be used to target selected cells.

TABLE 3

Exemplary antigens for targeting specific cells

| ANTIGEN | Exemplary tumor tissue |
| --- | --- |
| CEA (carcinoembryonic antigen) | colon, breast, lung |
| PSA (prostate specific antigen) | prostate cancer |
| CA-125 | ovarian cancer |
| CA 15-3 | breast cancer |
| CA 19-9 | breast cancer |
| HER2/neu | breast cancer |
| α-feto protein | testicular cancer, hepatic cancer |
| β-HCG (human chorionic gonadotropin) | testicular cancer, choriocarcinoma |
| MUC-1 | breast cancer |
| Estrogen receptor | breast cancer, uterine cancer |
| Progesterone receptor | breast cancer, uterine cancer |
| EGFr (epidermal growth factor receptor) | bladder cancer |

Ligand-mediated targeting to specific tissues through binding to their respective receptors on the cell surface offers an attractive approach to improve the tissue-specific delivery of drugs. Specific targeting to disease-relevant cell types and tissues may help to lower the effective dose, reduce side effects and consequently maximize the therapeutic index. Carbohydrates and carbohydrate clusters with multiple carbohydrate motifs represent an important class of targeting ligands, which allow the targeting of drugs to a wide variety of tissues and cell types. For examples, see Hashida, M., Nishikawa, M. et al. (2001) Cell-specific delivery of genes with glycosylated carriers. Adv. Drug Deliv. Rev. 52, 187-9; Monsigny, M., Roche, A.-C. et al. (1994). Glycoconjugates as carriers for specific delivery of therapeutic drugs and genes. Adv. Drug Deliv. Rev. 14, 1-24; Gabius, S., Kayser, K. et al. (1996). Endogenous lectins and neoglycoconjugates. A sweet approach to tumor diagnosis and targeted drug delivery. Eur. J. Pharm. and Biopharm. 42, 250-261; Wadhwa, M. S., and Rice, K. G. (1995) Receptor mediated glycotargeting. J. Drug Target. 3, 111-127.

One of the best characterized receptor-ligand pairs is the asialoglycoprotein receptor (ASGP-R), which is highly expressed on hepatocytes and which has a high affinity for D-galactose as well as N-acetyl-D-galactose (GalNAc). Those carbohydrate ligands have been successfully used to target a wide variety of drugs and even liposomes or polymeric carrier systems to the liver parenchyma. For examples, see Wu, G. Y., and Wu, C. H. (1987) Receptor-mediated in vitro gene transformation by a soluble DNA carrier system. J. Biol. Chem. 262, 4429-4432; Biessen, E. A. L., Vietsch, H., Rump, E. T., Flutter, K., Bijsterbosch, M. K., and Van Berkel, T. J. C. (2000) Targeted delivery of antisense oligonucleotides to parenchymal liver cells in vivo. Methods Enzymol. 313, 324-342; Zanta, M.-A., Boussif, O., Adib, A., and Behr, J.-P. (1997) In Vitro Gene Delivery to Hepatocytes with Galactosylated Polyethylenimine. Bioconjugate Chem. 8, 839-844; Managit, C., Kawakami, S. et al. (2003). Targeted and sustained drug delivery using PEGylated galactosylated liposomes. Int. J. Pharm. 266, 77-84; Sato, A., Takagi, M. et al. (2007). Small interfering RNA delivery to the liver by intravenous administration of galactosylated cationic liposomes in mice. Biomaterials 28; 1434-42.

The Mannose receptor, with its high affinity to D-mannose represents another important carbohydrate-based ligand-receptor pair. The mannose receptor is highly expressed on specific cell types such as macrophages and possibly dendritic cells Mannose conjugates as well as mannosylated drug carriers have been successfully used to target drug molecules to those cells. For examples, see Biessen, E. A. L., Noorman, F. et al. (1996). Lysine-based cluster mannosides that inhibit ligand binding to the human mannose receptor at nanomolar concentration. *J. Biol. Chem.* 271, 28024-28030; Kinzel, O., Fattori, D. et al. (2003). Synthesis of a functionalized high affinity mannose receptor ligand and its application in the construction of peptide-, polyamide- and PNA-conjugates. *J. Peptide Sci.* 9, 375-385; Barratt, G., Tenu, J. P. et al. (1986). Preparation and characterization of liposomes containing mannosylated phospholipids capable of targeting drugs to macrophages. *Biochim. Biophys. Acta* 862, 153-64; Diebold, S. S., Plank, C. et al. (2002). Mannose Receptor-Mediated Gene Delivery into Antigen Presenting Dendritic Cells. *Somat. Cell Mol. Genetics.* 27, 65-74.

Carbohydrate based targeting ligands include, but are not limited to, D-galactose, multivalent galactose, N-acetyl-D-galactose (GalNAc), multivalent GalNAc, e.g. GalNAC2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits may be linked to each other through glycosidic linkages or linked to a scaffold molecule.

Lipophilic moieties, such as cholesterol or fatty acids, when attached to highly hydrophilic molecules such as nucleic acids can substantially enhance plasma protein binding and consequently circulation half life. In addition, binding to certain plasma proteins, such as lipoproteins, has been shown to increase uptake in specific tissues expressing the corresponding lipoprotein receptors (e.g., LDL-receptor or the scavenger receptor SR-B1). For examples, see Bijsterbosch, M. K., Rump, E. T. et al. (2000). Modulation of plasma protein binding and in vivo liver cell uptake of phosphorothioate oligodeoxynucleotides by cholesterol conjugation. *Nucleic Acids Res.* 28, 2717-25; Wolfrum, C., Shi, S. et al. (2007). Mechanisms and optimization of in vivo delivery of lipophilic siRNAs. *Nat. Biotechnol.* 25, 1149-57. Lipophilic conjugates can therefore also be considered as a targeted delivery approach and their intracellular trafficking could potentially be further improved by the combination with endosomolytic agents.

Exemplary lipophilic moieties that enhance plasma protein binding include, but are not limited to, sterols, cholesterol, fatty acids, cholic acid, lithocholic acid, dialkylglycerides, diacylglyceride, phospholipids, sphingolipids, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, phenoxazine, aspirin, naproxen, ibuprofen, vitamin E and biotin etc.

Folates represent another class of ligands which has been widely used for targeted drug delivery via the folate receptor. This receptor is highly expressed on a wide variety of tumor cells, as well as other cells types, such as activated macrophages. For examples, see Matherly, L. H. and Goldman, I. D. (2003). Membrane transport of folates. *Vitamins Hormones* 66, 403-456; Sudimack, J. and Lee, R. J. (2000). Targeted drug delivery via the folate receptor. *Adv. Drug Delivery Rev.* 41, 147-162. Similar to carbohydrate-based ligands, folates have been shown to be capable of delivering a wide variety of drugs, including nucleic acids and even liposomal carriers. For examples, see Reddy, J. A., Dean, D. et al. (1999). Optimization of Folate-Conjugated Liposomal Vectors for Folate Receptor-Mediated Gene Therapy. *J. Pharm. Sci.* 88, 1112-1118; Lu, Y. and Low P. S. (2002). Folate-mediated delivery of macromolecular anticancer therapeutic agents. *Adv. Drug Delivery Rev.* 54, 675-693; Zhao, X. B. and Lee, R. J. (2004). Tumor-selective targeted delivery of genes and antisense oligodeoxyribonucleotides via the folate receptor; Leamon, C. P., Cooper, S. R. et al. (2003). Folate-Liposome-Mediated Antisense Oligodeoxynucleotide Targeting to Cancer Cells: Evaluation in Vitro and in Vivo. *Bioconj. Chem.* 14, 738-747.

U.S. patent application Ser. No. 12/328,537, filed Dec. 4, 2008 and 12/328,528, filed Dec. 4, 2008 describe a number of folate and carbohydrate targeting ligands that are amenable to the modular compositions of the present invention. Contents of these patent applications are herein incorporated by reference in their entirety.

The targeting ligands also include proteins, peptides and peptidomimmetics that can target cell markers, e.g. markers enriched in proliferating cells. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long Such peptides include, but are not limited to, RGD containing peptides and peptidomimmetics that can target cancer cells, in particular cells that exhibit $\alpha_v\beta_3$ (alpha.v.beta.3) integrin. Targeting peptides can be linear or cyclic, and include D-amino acids, non-peptide or pseudo-peptide linkages, peptidyl mimics. In addition the peptide and peptide mimics can be modified, e.g. glycosylated or methylated. Synthetic mimics of targeting peptides are also included.

The targeting ligands can also include other receptor binding ligands such as hormones and hormone receptor binding ligands. A targeting ligand can be a thyrotropin, melanotropin, lectin, glycoprotein, surfactant protein A, mucin, glycosylated polyaminoacids, transferrin, bisphosphonate, polyglutamate, polyaspartate, a lipid, folate, vitamin B12, biotin, or an aptamer. Table 4 shows some examples of targeting ligands and their associated receptors.

TABLE 4

| Liver Targeting Ligands and their associated receptors | | |
|---|---|---|
| Liver Cells | Ligand | Receptor |
| 1) Parenchymal Cell (PC) (Hepatocytes) | Galactose | ASGP-R (Asiologlycoprotein receptor) |
| | Gal NAc (n-acetyl-galactosamine) | ASPG-R Gal NAc Receptor |
| | Lactose | |
| | Asialofetuin | ASPG-r |
| 2) Sinusoidal Endothelial Cell (SEC) | Hyaluronan | Hyaluronan receptor |
| | Procollagen | Procollagen receptor |

TABLE 4-continued

Liver Targeting Ligands and their associated receptors

| Liver Cells | Ligand | Receptor |
|---|---|---|
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Sugar-Albumin conjugates | |
| | Mannose-6-phosphate | Mannose-6-phosphate receptor |
| 3) Kupffer Cell (KC) | Mannose | Mannose receptors |
| | Fucose | Fucose receptors |
| | Albumins | Non-specific |
| | Mannose-albumin conjugates | |

When two or more targeting ligands are present, such targeting ligands may all be the same or different targeting ligands that target the same cell/tissue/organ.

In addition to the endosomolytic ligand and the targeting ligand, the modular composition may comprise one or more other moieties/ligands that may enhance circulation half life and/or cellular uptake. These can include naturally occurring substances, such as a protein (e.g., human serum albumin (HSA), low-density lipoprotein (LDL), high-density lipoprotein (HDL), or globulin); or a carbohydrate (e.g., a dextran, pullulan, chitin, chitosan, inulin, cyclodextrin or hyaluronic acid). These moieties may also be a recombinant or synthetic molecule, such as a synthetic polymer or synthetic polyamino acids. Examples include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG, e.g., PEG-5K, PEG-10K, PEG-12K, PEG-15K, PEG-20K, PEG-40K), methyl-PEG (mPEG), [mPEG]$_2$, polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Oligonucleotides and oligomeric compounds that comprise a number of phosphorothioate linkages are known in the art to bind to serum protein, thus short oligonucleotides, e.g. oligonucleotides of about 5 bases, 10 bases, 15 bases or 20 bases, and non-nucleosidic oligomeric compounds comprising multiple phosphorothioate linkages can be used to enhance the circulation half life of the modular composition of the invention. In addition, oligonucleotides, e.g. aptamers, that bind serum ligands (e.g. serum proteins) can also be used to enhance the circulation half life of the modular composition of the invention. These oligonucleotides and aptamers may comprise any nucleic acid modification, e.g. sugar modification, backbone modification or nucleobase modification, described in this application.

Ligands that increase the cellular uptake of the modular composition, may also be present in addition to the endosomolytic ligand and the targeting ligand. Exemplary ligands that enhance cellular uptake include vitamins. These are particularly useful for targeting cells/tissues/organs characterized by unwanted cell proliferation, e.g., of the malignant or non-malignant type, e.g., cancer cells. Exemplary vitamins include vitamin A, E, and K. Other exemplary vitamins include B vitamin, e.g., folic acid, B12, riboflavin, biotin, pyridoxal or other vitamins or nutrients taken up by cancer cells.

The ligand can be a substance, e.g, a drug, which can increase the uptake of the modular composition into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the modular composition into the cell by activating an inflammatory response, for example. Exemplary ligands that would have such an effect include tumor necrosis factor alpha (TNFalpha), interleukin-1 beta, or gamma interferon.

In some embodiments, such a ligand is a cell-permeation agent, preferably a helical cell-permeation agent. Preferably, the agent is amphipathic. The helical agent is preferably an alpha-helical agent, which preferably has a lipophilic and a lipophobic phase.

Other ligands that can be present in the modular composition of the invention include, dyes and reporter groups for monitoring distribution, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, mercapto, amino, polyamino, alkyl, substituted alkyl, radiolabeled markers, enzymes, haptens (e.g. biotin), synthetic ribonucleases (e.g., imidazole, bisimidazole, histamine, imidazole clusters, acridine-imidazole conjugates, Eu3+ complexes of tetraazamacrocycles, dinitrophenyl, HRP and AP.

In some embodiments, a single ligand may have more than one property, e.g. ligand has both endosomolytic and targeting properties.

Enhanced Permeability and Retention

In certain embodiments, the modular composition of the invention may be targeted to a site via the enhanced permeability and retention (EPR) effect. The EPR effect is the property by which certain sizes of molecules, typically macromolecules, tend to accumulate in, for example, tumor tissue to a greater extent than in normal tissue. Without being bound by theory, the general explanation for this phenomenon is that the blood vessels supplying a tumor are typically abnormal in their architecture, containing wide fenestrations which permit the diffusion of macromolecules from the blood. Moreover, tumors typically lack effective lymphatic drainage, leading to the accumulation of molecules that diffuse from the blood. A person of ordinary skill in the art will recognize that such methods of targeting may also be useful for other conditions in which abnormal vasculature enable access to a specific site, with or without compromised lymphatic drainage.

Representative United States patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; each of which is herein incorporated by reference.

Linkers

In certain embodiments, the covalent linkages between any of the three components of the modular composition of the invention may be mediated by a linker. This linker may be cleavable or non-cleavable, depending on the application. In certain embodiments, a cleavable linker may be used to release the nucleic acid after transport from the endosome to the cytoplasm. The intended nature of the conjugation or coupling interaction, or the desired biological effect, will determine the choice of linker group.

Linker groups may be connected to the oligonucleotide strand(s) at a linker group attachment point (LAP) and may include any $C_1$-$C_{100}$ carbon-containing moiety, (e.g., $C_1$-$C_{75}$, $C_1$-$C_{50}$, $C_1$-$C_{20}$, $C_1$-$C_{10}$; $C_1$, $C_2$, $C_3$, $C_4$, $C_5$, $C_6$, $C_7$, $C_8$, $C_9$, or $C_{10}$), in some embodiments having at least one oxygen atom, at least one phosphorous atom, and/or at least one nitrogen atom. In some embodiments, the phosphorous atom forms part of a terminal phosphate, or phosphorothioate, group on the linker group, which may serve as a connection point for the nucleic acid strand. In certain embodiments, the nitrogen atom forms part of a terminal ether, ester, amino or amido (NHC(O)—) group on the linker group, which may serve as a connection point for the endosomolytic component or targeting ligand. Preferred linker groups (underlined) include LAP-X—$(CH_2)_n$NH—; LAP-X—C(O)$(CH_2)_n$NH—; LAP-X—NR""$(CH_2)_n$NH—, LAP-X—C(O)—$(CH_2)_3$C(O)—; LAP-X—C(O)—$(CH_7)_2$—C(O)O—; LAP-X—C(O)—O—; LAP-X—C(O)—$(CH_2)_n$—NH—C(O)—; LAP-X—C(O)—$(CH_2)_n$—; LAP-X—C(O)—NH—; LAP-X—C(O)—; LAP-X—$(CH_2)_n$—C(O)—; LAP-X—$(CH_2)_n$—C(O)O—; LAP-X—$(CH_2)_n$—; or LAP-X—$(CH_2)_n$—NH—C(O)—; in which —X is (—O—(R""O)P(O)—O—$)_m$, (—O—(R""O)P(S)—O—$)_m$, (—O—(R""S)P(O)—O—$)_m$, (—O—(R""S)P(S)—O—$)_m$, (—O—(R""O)P(O)—S—$)_m$, (—S—(R""O)P(O)—O—$)_m$, or nothing, n is 1-20 (e.g., 1, 2, 3, 4, 5, 6, 7, 8, 9, 10, 11, 12, 13, 14, 15, 16, 17, 18, 19, or 20), m is 1 to 3, and R"" is H or $C_1$-$C_6$ alkyl. Preferably, n is 5, 6, or 11. In other embodiments, the nitrogen may form part of a terminal oxyamino group, e.g., —$ONH_2$, or hydrazino group, —$NHNH_2$. The linker group may optionally be substituted, e.g., with hydroxy, alkoxy, perhaloalkyl, and/or optionally inserted with one or more additional heteroatoms, e.g., N, O, or S. Certain linker groups may include, e.g., LAP-X—$(CH_2)_n$NH—; LAP-X—C(O)$(CH_2)_n$NH—; LAP-X—NR""$(CH_2)_n$NH—; LAP-X—$(CH_2)_n$ONH—; LAP-X—C(O)$(CH_2)_n$ONH—; LAP-X—NR""$(CH_2)_n$ONH—; LAP-X—$(CH_2)_n$NHNH_2—; LAP-X—C(O)$(CH_2)_n$—C(O)C—; LAP-X—NR""$(CH_2)_n$NHNH_2—; LAP-X—C(O)—$(CH_2)_n$—C(O)—; LAP-X—C(O)—$(CH_2)_n$—C(O)O—; LAP-X—C(O)—O—; LAP-X—C(O)—$(CH_2)_n$—NH—C(O)—; LAP-X—C(O)—$(CH_2)_n$—; LAP-X—C(O)—NH—; LAP-X—C(O)—; LAP-X—$(CH_2)_n$—C(O)—; LAP-X—$(CH_2)_n$—C(O)O—; or LAP-X—$(CH_2)_n$—; or LAP-X—$(CH_2)_n$—NH—C(O)—. In some embodiments, amino terminated linker groups (e.g., $NH_2$, $ONH_2$, $NH_2NH_2$) can form an imino bond (i.e., C=N) with the ligand. In some embodiments, amino terminated linker groups (e.g., $NH_2$, $ONH_2$, $NH_2NH_2$) can be acylated, e.g., with $C(O)CF_3$.

In some embodiments, the linker group can terminate with a mercapto group (i.e., SH) or an olefin (e.g., CH=$CH_2$). For example, the linker group can be LAP-X—$(CH_2)_n$—SH, LAP-X—C(O)$(CH_2)_n$SH, LAP-X—$(CH_2)_n$—(CH=$CH_2$), or LAP-X—C(O)$(CH_2)_n$(CH=$CH_2$), in which X and n can be as described for the linker groups above. In certain embodiments, the olefin can be a Diels-Alder diene or dienophile. The linker group may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the linker group may include an electrophilic moiety, preferably at the terminal position of the linker group. Certain electrophilic moieties include, e.g., an aldehyde, alkyl halide, mesylate, tosylate, nosylate, or brosylate, or an activated carboxylic acid ester, e.g., an NHS ester, or a pentafluorophenyl ester. Other linker groups (underlined) include LAP-X—$(CH_2)_n$CHO; LAP-X—C(O)$(CH_2)_n$CHO; or LAP-X—NR""$(CH_2)_n$CHO, in which n is 1-6 and R"" is $C_1$-$C_6$ alkyl; or LAP-X—$(CH_2)_n$C(O)ONHS; LAP-X—C(O)$(CH_2)_n$C(O)ONHS; or LAP-X—NR""$(CH_2)_n$C(O)ONHS, in which n is 1-6 and R"" is $C_1$-$C_6$ alkyl; LAP-X—$(CH_2)_n$C(O)O$C_6F_5$; LAP-X—C(O)$(CH_2)_n$C(O)O$C_6F_5$; or LAP-X—NR""$(CH_2)_n$C(O)O$C_6F_5$, in which n is 1-11 and R"" is $C_1$-$C_6$ alkyl; or —$(CH_2)_n$CH_2LG; LAP-X—C(O)$(CH_2)_n$CH_2LG; or LAP-X—NR""$(CH_2)_n$CH_2LG, in which X, R"" and n can be as described for the linker groups above (LG can be a leaving group, e.g., halide, mesylate, tosylate, nosylate, brosylate). In some embodiments, coupling the -linker group to the endosomolytic component or targeting ligand can be carried out by coupling a nucleophilic group of the endosomolytic component or targeting ligand with an electrophilic group on the linker group.

In other embodiments, other protected amino groups can be at the terminal position of the linker group, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

In any of the above linker groups, in addition, one, more than one, or all, of the n-$CH_2$— groups may be replaced by one or a combination of, e.g., X, as defined above, —Y—$(CH_2)_m$—, —Y—C(C($CH_3$)H)$_m$—, —Y—C(($CH_2)_p$$CH_3$)H)$_m$—, —Y—($CH_2$—C($CH_3$)H)$_m$—, —Y—($CH_2$—C(($CH_2)_p$$CH_3$)H)$_m$—, —CH=CH—, or —C≡C—, wherein Y is O, S, Se, S—S, S(O), S(O)$_2$, m is 1-4 and p is 0-4.

Where more than one endosomolytic component or targeting ligand is present on the same modular composition, the more than one endosomolytic component or targeting ligand may be linked to the oligonucleotide strand or an endosomolytic component or targeting ligand in a linear fashion, or by a branched linker group.

In some embodiments, the linker group is a branched linker group, and more in ceratin cases a symmetric branched linker group. The branch point may be an at least trivalent, but may be a tetravalent, pentavalent, or hexavalent atom, or a group presenting such multiple valencies. In some embodiments, the branch point is a glycerol, or glycerol triphosphate, group.

In some embodiments, the branchpoint is, —N—, —N(Q)-C, —O—C—, —S—C—, —SS—C—, —C(O)N(Q)-C—, —OC(O)N(Q)-C—, —N(Q)C(O)—C, or —N(Q)C(O)O—C; wherein Q is independently for each occurrence H or optionally substituted alkyl. In other embodiments, the branchpoint is a glycerol derivative.

In one embodiment, the linker is —[(P-Q-R)$_q$—X—(P'-Q'-R')$_{q'}$]$_{q''}$-T-, wherein:

P, R, T, P' and R¹ are each independently for each occurrence absent, CO, NH, O, S, OC(O), NHC(O), CH$_2$, CH$_2$NH, CH$_2$O; NHCH(R$^a$)C(O), —C(O)—CH(R$^a$)—NH—, C(O)—(optionally substituted alkyl)-NH—, CH═N—O,

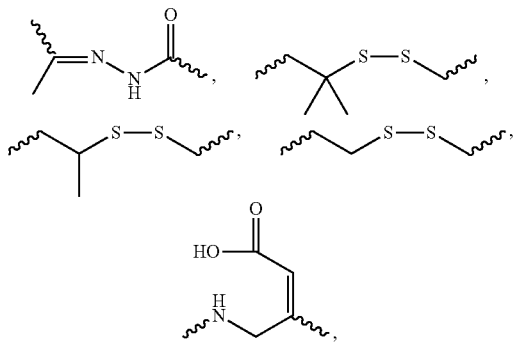

cyclyl, heterocycyclyl, aryl or heteroaryl;

Q and Q' are each independently for each occurrence absent, —(CH$_2$)$_n$—, —C(R$^{100}$)(R$^{200}$)(CH$_2$)$_n$—, —(CH$_2$)$_n$C(R$^{100}$)(R$^{200}$)—, —(CH$_2$CH$_2$O)$_m$CH$_2$CH$_2$—, —(CH$_2$CH$_2$O)$_m$ CH$_2$CH$_2$NH—, aryl, heteroaryl, cyclyl, or heterocyclyl;

X is absent or a cleavable linking group;

R$^a$ is H or an amino acid side chain;

R$^{100}$ and R$^{200}$ are each independently for each occurrence H, CH$_3$, OH, SH or N(R$^X$)$_2$;

R$^X$ is independently for each occurrence H, methyl, ethyl, propyl, isopropyl, butyl or benzyl;

q, q' and q'' are each independently for each occurrence 0-30 and wherein the repeating unit can be the same or different;

n is independently for each occurrence 1-20; and m is independently for each occurrence 0-50.

In some embodiments, a carrier monomer is also considered a linker. In those instances the term linker comprises the carrier monomer and the linker between the monomer and the ligand, e.g. endosomolytic ligand and targeting ligand.

In some embodiments, the linker comprises at least one cleavable linking group.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)—O—, —O—P(S)(ORk)—O—, —O—P(S)(SRk)—O—, —S—P(O)(ORk)—O—, —O—P(O)(ORk)-S—, —S—P(O)(ORk)-S—, —O—P(S)(ORk)-S—, —S—P(S)(ORk)—O—, —O—P(O)(Rk)—O—, —O—P(S)(Rk)—O—, —S—P(O)(Rk)—O—, —S—P(S)(Rk)—O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Cleavable Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Linking Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above.

Where, more than one endosomolytic ligand or targeting ligand is present on the same modular composition, the more than one endosomolytic ligand or targeting ligand may be linked to the oligonucleotide strand or an endosomolytic ligand or targeting ligand in a linear fashion, or by a branched linker group.

iRNA Agents

The iRNA agent should include a region of sufficient homology to the target gene, and be of sufficient length in terms of nucleotides, such that the iRNA agent, or a fragment thereof, can mediate downregulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more, or for example, 6, 5, 4, 3, 2, or fewer mismatches (with respect to the target RNA). The mismatches, particularly in the antisense strand, are most tolerated in the terminal regions and if present may be in a terminal region or regions, e.g., within 6, 5, 4, or 3 nucleotides of the 5' and/or 3' termini. The sense strand need only be sufficiently complementary with the antisense strand to maintain the over all double stranded character of the molecule.

As discussed elsewhere herein, and in the material incorporated by reference in its entirety, an iRNA agent will often be modified or include nucleoside surrogates. Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-termini of an iRNA agent, e.g., against exonucleases, or to favor the antisense siRNA agent to enter into RISC are also envisioned. Modifications can include C3 (or C6, C7, C12) amino linkers, thiol linkers, carboxyl linkers, non-nucleotide spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

iRNA agents include: molecules that are long enough to trigger the interferon response (which can be cleaved by Dicer (Bernstein et al. 2001. Nature, 409:363-366) and enter a RISC(RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60, 50, 40, or 30 nucleotide pairs. The siRNA agent, or a cleavage product thereof, can down regulate a target gene, e.g., by inducing RNAi with respect to a target RNA, wherein the target may comprise an endogenous or pathogen target RNA.

Each strand of an siRNA agent can be equal to or less than 30, 25, 24, 23, 22, 21, or 20 nucleotides in length. The strand may be at least 19 nucleotides in length. For example, each strand can be between 21 and 25 nucleotides in length. siRNA agents may have a duplex region of 17, 18, 19, 29, 21, 22, 23, 24, or 25 nucleotide pairs, and one or more overhangs, or one or two 3' overhangs, of 2-3 nucleotides.

In addition to homology to target RNA and the ability to down regulate a target gene, an iRNA agent may have one or more of the following properties:

(1) it may be of the Formula VI set out in the RNA Agent section below;
(2) if single stranded it may have a 5' modification which includes one or more phosphate groups or one or more analogs of a phosphate group;
(3) it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;
(4) it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. A modified moiety at the 2' sugar position may be able to enter into H bonding which is more characteristic of the OH moiety of a ribonucleotide than the H moiety of a deoxyribonucleotide. Certain iRNA agents will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to the RNA-characteristic A-family-type helix; will have no more than 20, 10, 5, 4, 3, 2, or 1 sugar which is not a $C_{3'}$-endo pucker structure. Regardless of the nature of the modification, and even though the RNA agent can contain deoxynucleotides or modified deoxynucleotides, particularly in overhang or other single strand regions, it is certain DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents may be antisense with regard to the target molecule. In certain embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(H0)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)2(O)P-5'-CH2-), 5'-alkyletherphosphonates (R=alkylether=methoxymethyl (MeOCH2-), ethoxymethyl, etc., e.g., RP(OH)(O)—O-5'-). (These modifications can also be used with the antisense strand of a double stranded iRNA.)

A single strand iRNA agent may be sufficiently long that it can enter the RISC and participate in RISC mediated cleavage of a target mRNA. A single strand iRNA agent is at least 14, and in other embodiments at least 15, 20, 25, 29, 35, 40, or 50 nucleotides in length. In certain embodiments, it is less than 200, 100, or 60 nucleotides in length.

Hairpin iRNA agents will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region, in some embodiments at the 3', and in certain embodiments on the antisense side of the hairpin. In some embodiments, the overhangs are 2-3 nucleotides in length.

A "double stranded (ds) iRNA agent" as used herein, is an iRNA agent which includes more than one, and in some cases two, strands in which interchain hybridization can form a region of duplex structure.

The antisense strand of a double stranded iRNA agent may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The sense strand of a double stranded iRNA agent may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded iRNA agent may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the ds iRNA agent is sufficiently large that it can be cleaved by an endogenous molecule, e.g., by Dicer, to produce smaller ds iRNA agents, e.g., siRNAs agents.

The present invention further includes iRNA agents that target within the sequence targeted by one of the mRNA agents of the present invention. As used herein a second iRNA agent is said to target within the sequence of a first iRNA agent if the second iRNA agent cleaves the message anywhere within the mRNA that is complementary to the antisense strand of the first iRNA agent. Such a second agent will generally consist of at least 15 contiguous nucleotides coupled to additional nucleotide sequences taken from the region contiguous to the selected sequence in the target gene.

The dsiRNAs of the invention can contain one or more mismatches to the target sequence. In a preferred embodiment, the dsiRNA of the invention contains no more than 3 mismatches. If the antisense strand of the dsiRNA contains mismatches to a target sequence, it is preferable that the area of mismatch not be located in the center of the region of complementarity. If the antisense strand of the dsiRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsiRNA strand which is complementary to a region of the target gene, the dsRNA generally does not contain any mismatch within the central 13 nucleotides. The methods described within the invention can be used to determine whether a dsiRNA containing a mismatch to a target sequence is effective in inhibiting the expression of the target gene. Consideration of the efficacy of dsiRNAs with mismatches in inhibiting expression of the target gene may be important, especially if the particular region of complementarity in the target gene is known to have polymorphic sequence variation within the population.

In some embodiments, the sense-strand comprises a mismatch to the antisense strand. In some embodiments, the mismatch is at the 5 nucleotides from the 3'-end, for example 5, 4, 3, 2, or 1 nucleotide from the end of the region of complementarity. In some embodiments, the mismatch is located in the target cleavage site region. In one embodiment, the sense strand comprises no more than 1, 2, 3, 4 or 5 mismatches to the antisense strand. In preferred embodiments, the sense strand comprises no more than 3 mismatches to the antisense strand.

In certain embodiments, the sense strand comprises a nucleobase modification, e.g. an optionally substituted natural or non-natural nucleobase, a universal nucleobase, in the target cleavage site region.

The "target cleavage site" herein means the backbone linkage in the target gene, e.g. target mRNA, or the sense strand that is cleaved by the RISC mechanism by utilizing the iRNA agent. And the "target cleavage site region" comprises at least one or at least two nucleotides on both side of the cleavage site. For the sense strand, the target cleavage site is the backbone linkage in the sense strand that would get cleaved if the sense strand itself was the target to be cleaved by the RNAi mechanism. The target cleavage site can be determined using methods known in the art, for example the 5'-RACE assay as detailed in Soutschek et al., *Nature* (2004) 432, 173-178. As is well understood in the art, the cleavage site region for a conical double stranded RNAi agent comprising two 21-nucleotides long strands (wherein the strands form a double stranded region of 19 consective basepairs having 2-nucleotide single stranded overhangs at the 3'-ends), the cleavage site region corresponds to positions 9-12 from the 5'-end of the sense strand.

The present invention also includes nucleic acids which are chimeric compounds. "Chimeric" nucleic acid compounds or "chimeras," in the context of this invention, are nucleic acid compounds, which contain two or more chemically distinct regions, each made up of at least one monomer unit, i.e., a nucleotide in the case of a nucleic acid compound. These nucleic acids typically contain at least one region wherein the nucleic acid is modified so as to confer upon the it increased resistance to nuclease degradation, increased cellular uptake, and/or increased binding affinity for the target nucleic acid. An additional region of the nucleic acid may serve as a substrate for enzymes capable of cleaving RNA:DNA or RNA:RNA hybrids. By way of example, RNase H is a cellular endonuclease which cleaves the RNA strand of an RNA:DNAduplex. Activation of RNase H, therefore, results in cleavage of the RNA target, thereby greatly enhancing the efficiency of dsRNA inhibition of gene expression.

The present invention also includes ds iRNAs wherein the two strands are linked together. The two strands can be linked together by a polynucleotide linker such as $(dT)_n$; wherein n is 4-10, and thus forming a hairpin. The two strands can also be linked together by a non-nucleosidic linker, e.g. a linker described herein. It will be appreciated by one of skill in the art that any oligonucleotide chemical modifications or variations describe herein can be used in the polynucleotide linker.

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5' end of the antisense strand. While not wishing to be bound by theory, the effect may be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5 Me-thio-U:A, are preferred over U:A, G-clamp (an analog of C having 4 hydrogen bonds):G is preferred over C:G, guanadinium-G-clamp:G is preferred over C:G, psuedo uridine:A, is preferred over U:A, sugar modifications, e.g., 2' modifications, e.g., 2'F, ENA, or LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, psuedo uridine:A, a pair in which one or both subunits has a sugar modification, e.g., a 2' modification, e.g., 2'F, ENA, or LNA, which enhance binding. In some embodiments, at least one, at least, at least 2, or at least 3, of the base pairs promote duplex stability.

In a preferred embodiment at least one, at least 2, or at least 3, of the base pairs are a pair in which one or both subunits has a sugar modification, e.g., a 2' modification, e.g., 2'-O-methyl, 2'-O-Me (2'-O-methyl), 2'-O-MOE (2'-O-methoxyethyl), 2'-F, 2'-O—CH$_2$-(4'-C) (LNA) and 2'-O—CH$_2$CH$_2$-(4'-C) (ENA), which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

As is discussed above, ds iRNA can be modified to both decrease the stability of the antisense 5' end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active siRNA/protein or RISC. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional siRNA 5'-end. Antisense strand modifications include 5' phosphorylation as well as any of the other 5' modifications discussed herein, particularly the 5' modifications discussed above in the section on single stranded iRNA molecules.

The sense and antisense strands may be chosen such that the ds iRNA agent includes a single strand or unpaired region at one or both ends of the molecule. Thus, a ds iRNA agent may contain sense and antisense strands, paired to contain an overhang, e.g., one or two 5' or 3' overhangs, or a 3' overhang of 2-3 nucleotides. Many embodiments will have a 3' overhang. Certain siRNA agents will have single-stranded overhangs, in some embodiments 3' overhangs, of 1 or 2 or 3 nucleotides in length at each end. The overhangs can be the result of one strand being longer than the other, or the result of two strands of the same length being staggered. 5' ends may be phosphorylated.

In one embodiment, the single-stranded overhang has the sequence 5'-GCNN-3', wherein N is independently for each occurrence, A, G, C, U, dT, dU or absent. Double-stranded iRNA having only one overhang has proven particularly stable and effective in vivo, as well as in a variety of cells, cell culture mediums, blood, and serum. The dsRNA may also have a blunt end, generally located at the 5'-end of the antisense strand.

In one embodiment, the antisense strand of the ds iRNA has 1-10 nucleotides overhangs each at the 3' end and the 5' end over the sense strand. In one embodiment, the sense strand of the ds iRNA has 1-10 nucleotides overhangs each at the 3' end and the 5' end over the antisense strand.

In some embodiments, the length for the duplexed region is between 15 and 30, or 18, 19, 20, 21, 22, and 23 nucleotides in length, e.g., in the siRNA agent range discussed above. siRNA agents can resemble in length and structure the natural Dicer processed products from long dsiRNAs. Embodiments in which the two strands of the siRNA agent are linked, e.g., covalently linked are also included. Hairpin, or other single strand structures which provide the required double stranded region, and a 3' overhang are also within the invention.

In some embodiments, the length for the duplexed region is between 10-15, e.g. 10, 11, 12, 13, 14 and 15 nucleotides in length and the antisense strand has 1-10 nucleotides single-strand overhangs each at the 3' end and the 5' end over the sense strand.

The isolated iRNA agents described herein, including ds iRNA agents and siRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, an iRNA agent is "sufficiently complementary" to a target RNA, e.g., a target mRNA, such that the iRNA agent silences production of protein encoded by the target mRNA. In another embodiment, the iRNA agent is "exactly complementary" to a target RNA, e.g., the target RNA and the iRNA agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA: Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

RNA agents discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The art has often referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA refers to a molecule in which one or more of the components of the nucleic acid, namely sugars, bases, and phosphate moieties, are different from that which occur in nature, for example, different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a double stranded iRNA agent, e.g., a partially double stranded iRNA agent, is envisioned. Thus, it is understood that that double stranded structures (e.g., where two separate molecules are contacted to form the double stranded region or where the double stranded region is formed by intramolecular pairing (e.g., a hairpin structure)) made of the single stranded structures described below are within the invention. Lengths are described elsewhere herein.

As nucleic acids are polymers of subunits, many of the modifications described below occur at a position which is repeated within a nucleic acid, e.g., a modification of a base, or a phosphate moiety, or the a non-linking 0 of a phosphate moiety. In some cases the modification will occur at all of the subject positions in the nucleic acid but in many cases it will not. By way of example, a modification may only occur at a 3' or 5' terminal position, may only occur in a terminal regions, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

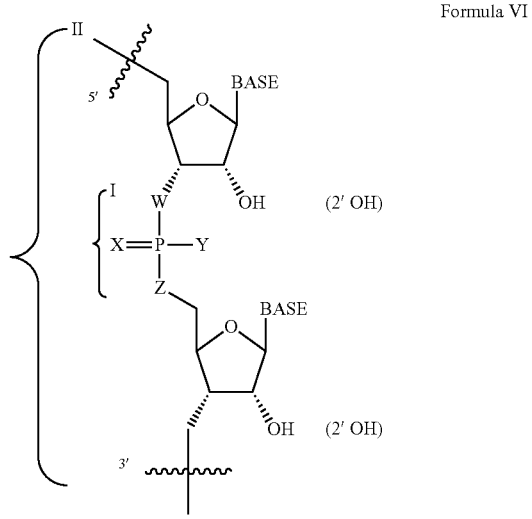

Formula VI

The scaffold presented above in Formula VI represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula VI represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases.

Modified nucleic acids and nucleotide surrogates can include one or more of:

(i) alteration, e.g., replacement, of one or both of the non-linking (X and Y) to phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e., Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula VI above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, $BR_3$ (R is hydrogen, alkyl, aryl), C (i.e. an alkyl group, an aryl group, etc. . . . ), H, $NR_2$ (R is hydrogen, alkyl, aryl, etc.), or OR (R is alkyl or aryl). Thus Y can be any one of S, Se, B, $BR_3$ (R is hydrogen, alkyl, aryl), C (i.e. an alkyl group, an aryl group, etc. . . . ), H, $NR_2$ (R is hydrogen, alkyl, aryl, etc. . . . ), or OR (R is alkyl or aryl). Replacement of X and/or Y with sulfur is possible.

When the modification of the phosphate leads to phosphorous atom becoming stereogenic, such chiral phosphate can posses either the "R" configuration (herein Rp) or the "S" configuration (herein Sp).

The phosphate linker can also be modified by replacement of a linking oxygen (i.e., W or Z in Formula VI) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is possible. When the bridging oxygen is 3'-oxygen of a nucleoside, replacement with carbon is preferred. When the bridging oxygen is the 5'-oxygen of a nucleoside, replacement with nitrogen is preferred.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; ENA in which the 2' hydroxyl is connected by a ethylene bridge, to the 4' carbon of the same ribose sugar; O-AMINE (AMINE=$NH_2$,alkylamino, dialkylamino, heterocyclyl, arylamino, diaryl amino, heteroaryl amino, diheteroaryl amino, ethylene diamine, polyamino and aminoalkoxy), $O(CH_2)_n$AMINE, (e.g., AMINE=$NH_2$, alkylamino, dialkylamino, heterocyclyl, arylamino, diaryl amino, heteroaryl amino, diheteroaryl amino, ethylene diamine, polyamino and aminoalkoxy). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O) R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino; heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido. Other substituents of certain embodiments include 2'-methoxyethyl, 2'-OCH3, 2'-O-allyl, 2'-C-allyl, and 2'-fluoro.

Other preferred substituents are 2'-O-[2-(methylamino)-2-oxoethyl] (2'-O-NMA), 2'-$NH_2$, 2'-O-amine, 2'-SH, 2'-S-alkyl, 2'-S-allyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-β-dimethylaminopropyl (2'-O-DMAP) and 2'-O-dimethylaminoethyloxyethyl (2'-O-DMAEOE).

In some embodiments, the 2'- and the 4'-carbons of the same ribose sugar may be linked together by a linker described herein.

The sugar group can also contain one or more carbons that possess the opposite stereochemical configuration than that of the corresponding carbon in ribose. Thus, a modified RNA can include nucleotides containing e.g., arabinose, as the sugar.

The sugar group can also have an alpha linkage at the 1' position on the sugar, e.g., alpha-nucleosides.

The sugar group can also be a L-sugar, e.g. L-nucleosides.

Modified RNA's can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

Candidate modifications can be evaluated as described below.

Replacement of the Phosphate Group

The phosphate group can be replaced by non-phosphorus containing connectors (cf. Bracket I in Formula VI above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

In certain embodiments, replacements may include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula I above). While not wishing to be bound by theory, it is believed that the absence of a repetitively charged backbone diminishes binding to proteins that recognize polyanions (e.g., nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. In certain embodiments, PNA surrogates may be used.

Modified phosphate linkages where at least one of the oxygens linked to the phosphate has been replaced or the phosphate group has been replaced by a non-phosphorous group, are also referred to as "non-phosphodiester backbone linkage."

Preferred backbone modifications are phsophorothioate, phosphorodithioate, phosphoramidate, phosphonate, alkylphosphonate, siloxane, carbonate, carboxymethyl, carbamate, amide, thioether, ethylene oxide linker, sulfonate, sulfonamide, thioformacetal, formacetal, oxime, methyleneimino, methyleneaminocarbonyl, methylenemethylimino (MMI), methylenehydrazo, methylenedimethylhydrazo (MDH) and methyleneoxymethylimino.

Candidate modifications can be evaluated as described below.

Types of Backbone Linkages

The canonical 3'-5' backbone linkage can also be replaced with linkage between other positions on the nucleosides. In some embodiments, the oligonucleotide comprises at least one of 5'-5', 3'-3', 3'-2', 2'-3', 2'-3' or 2'-5' backbone linkage.

In some embodiments, the last nucleotide on the end of the oligonucleotide is linked via a 5'-5', 3'-3',3'-2', 2'-3' or 2'-3' backbone linkage to the rest of the oligonucleotide.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., $-(CH_2)_n-$, $-(CH_2)_nN-$, $-(CH_2)_nO-$, $-(CH_2)_nS-$, $O(CH_2CH_2O)_n CH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in certain embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P-β-(HO)(O)P—O—P(HO)(O)—O-5'); 5'-guanosine cap (7-methylated or non-methylated) (7m-G-O-5'-(H0)(O)P—O—(HO)(O)P—O—P(HO)(O)—O-5'); 5'-adenosine cap (Appp), and any modified or unmodified nucleotide cap structure (N—O-5'-(H0)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)2(O)P-5'-CH2-), 5'-alkyletherphosphonates (R=alkylether=methoxymethyl (MeOCH2-), ethoxymethyl, etc., e.g., RP(OH)(O)—O-5'-).

Terminal modifications can also be useful for monitoring distribution, and in such cases the groups to be added may include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are not used for promoting stability, but they can be useful for other reasons, e.g., some, e.g., 2,6-diaminopurine and 2 amino purine, are fluorescent. Modified bases can reduce target specificity. This may be taken into consideration in the design of iRNA agents.

In some embodiments, nucleobase is chosen from a group consisting of inosine, thymine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil,5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl) uracil, 5-(dialkylaminoalkyl)uracil, 5-(dimethylaminoalkyl) uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl) uracil, 5-(trifluoromethyl)uracil, 6-(azo)uracil, dihydrouracil, $N^3$-(methyl)uracil, 5-uracil (i.e., pseudouracil), 2-(thio) pseudouracil,4-(thio)pseudouracil,2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio) pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio) pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza) indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo)thymine, 2-pyridinone, 5-nitroindole, 3-nitropyrrole, 6-(azo)pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, and any O-alkylated or N-alkylated derivatives thereof.

Candidate modifications can be evaluated as described below.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

Placement of Modifications within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 3'-2',5'-5', 2'-2' or 2'-3' linkages.

An oligonucleotide may comprise at least one 5'-pyrimidine-purine-3' (5'-PyPu-3') dinucleotide wherein the pyrimidine is modified with a modification chosen independently from a group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA).

In one embodiment, the 5'-most pyrimidines in all occurrences of sequence motif 5'-pyrimidine-purine-3' (5'-PyPu-3') dinucleotide in the oligonucleotide are modified with a modification chosen from a group consisting of 2''-O-Me (2'-O-methyl), 2'-O-MOE (2'-β-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA).

A double-stranded oligonucleotide may include at least one 5'-uridine-adenine-3' (5'-UA-3') dinucleotide wherein the uridine is a 2'-modified nucleotide, or a 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

Evaluation of Candidate RNAs

One can evaluate a candidate RNA agent, e.g., a modified RNA, for a selected property by exposing the agent or modified molecule and a control molecule to the appropriate conditions and evaluating for the presence of the selected property. For example, resistance to a degradant can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dsiRNA agents.

In an alternative functional assay, a candidate dsiRNA agent homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dsiRNA agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

RNA Structure References

The disclosure of all publications, patents, and published patent applications listed herein are hereby incorporated by reference.

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F.

Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 11972, 1991. Carbamate replacements are described in Stirchak, E. P. *Nucleic Acids Res.* 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Base References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Terminal Modification References

Terminal modifications are described in Manoharan, M. et al. *Antisense and Nucleic Acid Drug Development* 12, 103-128 (2002) and references therein.

Definitions

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, aryl, heterocyclyl, or heteroaryl group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Palindromes

The iRNA agents of the invention can target more than one RNA region. For example, an iRNA agent can include a first and second sequence that are sufficiently complementary to each other to hybridize. The first sequence can be complementary to a first target RNA region and the second sequence can be complementary to a second target RNA region. The first and second sequences of the iRNA agent can be on different RNA strands, and the mismatch between the first and second sequences can be less than 50%, 40%, 30%, 20%, 10%, 5%, or 1%. The first and second sequences of the iRNA agent are on the same RNA strand, and in a related embodiment more than 50%, 60%, 70%, 80%, 90%, 95%, or 1% of the iRNA agent can be in bimolecular form. The first and second sequences of the iRNA agent can be fully complementary to each other.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The compositions of the invention can include mixtures of iRNA agent molecules. For example, one iRNA agent can contain a first sequence and a second sequence sufficiently complementary to each other to hybridize, and in addition the first sequence is complementary to a first target RNA region and the second sequence is complementary to a second target RNA region. The mixture can also include at least one additional iRNA agent variety that includes a third sequence and a fourth sequence sufficiently complementary to each other to hybridize, and where the third sequence is complementary to a third target RNA region and the fourth sequence is complementary to a fourth target RNA region. In addition, the first or second sequence can be sufficiently complementary to the third or fourth sequence to be capable of hybridizing to each other. The first and second sequences can be on the same or different RNA strands, and the third and fourth sequences can be on the same or different RNA strands.

The target RNA regions can be variant sequences of a viral or human RNA, and in certain embodiments, at least two of the target RNA regions can be on variant transcripts of an oncogene or tumor suppressor gene. The target RNA regions can correspond to genetic hot-spots.

Methods of making an iRNA agent composition can include obtaining or providing information about a region of an RNA of a target gene (e.g., a viral or human gene, or an oncogene or tumor suppressor, e.g., p53), where the region has high variability or mutational frequency (e.g., in humans). In addition, information about a plurality of RNA targets within the region can be obtained or provided, where each RNA target corresponds to a different variant or mutant of the gene (e.g., a region including the codon encoding p53 248Q and/or p53 249S). The iRNA agent can be constructed such that a first sequence is complementary to a first of the plurality of variant RNA targets (e.g., encoding 249Q) and a second sequence is complementary to a second of the plurality of variant RNA targets (e.g., encoding 249S), and the first and second sequences can be sufficiently complementary to hybridize.

Sequence analysis, e.g., to identify common mutants in the target gene, can be used to identify a region of the target gene that has high variability or mutational frequency. A region of the target gene having high variability or mutational frequency can be identified by obtaining or providing genotype information about the target gene from a population.

Expression of a target gene can be modulated, e.g., downregulated or silenced, by providing an iRNA agent that has a first sequence and a second sequence sufficiently complementary to each other to hybridize. In addition, the first sequence can be complementary to a first target RNA region and the second sequence can be complementary to a second target RNA region.

An iRNA agent can include a first sequence complementary to a first variant RNA target region and a second sequence complementary to a second variant RNA target region. The first and second variant RNA target regions can correspond to first and second variants or mutants of a target gene, e.g., viral gene, tumor suppressor or oncogene. The first and second variant target RNA regions can include allelic variants, mutations (e.g., point mutations), or polymorphisms of the target gene. The first and second variant RNA target regions can correspond to genetic hot-spots.

A plurality of iRNA agents (e.g., a panel or bank) can be provided.

Other Embodiments

In yet another embodiment, iRNAs agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a iRNA agent and one that produces a transcript that includes the bottom strand of a iRNA agent. When the templates are transcribed, the iRNA agent is produced, and processed into siRNA agent fragments that mediate gene silencing.

In certain embodiments, the nucleic acid may be modified with a 2'-OMe modification (Kraynack & Baker, RNA, 12: 163-176, 2006). In other embodiments, the nucleic acid may comprise an ethylene-bridged nucleic acid (ENA) (Morita et al., Nucleic Acids Res., 2001, Suppl. 1, 241-242; Surono A et al., Human Gene Therapy, 15: 749-757, 2004).

MicroRNAs

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock R J, van Dongen S, Bateman A, Enright A J, NAR, 2006, 34, Database Issue, D140-D144; "The microRNA Registry" Griffiths-Jones S, NAR, 2004, 32, Database Issue, D109-D111.

Single-stranded oligonucleotides, including those described and/or identified as microRNAs or mirs which may be used as targets or may serve as a template for the design of oligonucleotides of the invention are taught in, for example, Esau, et al. US Publication No. 20050261218 (USSN: 10/909,125) entitled "Oligomeric compounds and compositions for use in modulation small non-coding RNAs" the entire contents of which is incorporated herein by reference. It will be appreciated by one of skill in the art that any oligonucleotide chemical modifications or variations describe herein also apply to single stranded oligonucleotides.

miRNA Mimics miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). miRNA mimics can be comprised of nucleic acid (Modified or modified nucleic acids) including oligonucleotides comprising, without limitation, RNA, modified RNA, DNA, modified DNA, locked nucleic acids, or 2'-O,4'-C-ethylene-bridged nucleic acids (ENA); or any combination of the above (including DNA-RNA hybrids). In addition, miRNA mimics can comprise conjugates that can affect delivery, intracellular compartmentalization, stability, specificity, functionality, strand usage, and/or potency. In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-0 methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality. In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. This term includes oligonucleotides composed of naturally-occurring nucleobases, sugars and covalent internucleoside (backbone) linkages and which contain at least one non-naturally-occurring portion which functions similarly. Such modified or substituted oligonucleotides are preferred over native forms because of desirable properties such as, for example, enhanced cellular uptake, enhanced affinity for nucleic acid target and increased stability in the presence of nucleases. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. An supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or n nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimir or miRNA Inhibitor

The terms "antimir" "microRNA inhibitor", "miR inhibitor", or "inhibitor" are synonymous and refer to oligonucleotides or modified oligonucleotides that interfere with the ability of specific miRNAs. In general, the inhibitors are nucleic acid or modified nucleic acids in nature including oligonucleotides comprising RNA, modified RNA, DNA, modified DNA, locked nucleic acids (LNAs), or any combination of the above. Modifications include 2' modifications (including 2'-0 alkyl modifications and 2' F modifications) and internucleotide modifications (e.g. phosphorothioate modifications) that can affect delivery, stability, specificity, intracellular compartmentalization, or potency. In addition, miRNA inhibitors can comprise conjugates that can affect delivery, intracellular compartmentalization, stability, and/or potency. Inhibitors can adopt a variety of configurations including single stranded, double stranded (RNA/RNA or RNA/DNA duplexes), and hairpin designs, in general, microRNA inhibitors comprise contain one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl) methoxy)-3 hydroxypentylcarbamate) which allows passive uptake of a micro-RNA inhibitor into a cell. Micro-RNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

U1 Adaptors

U1 adaptors inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5' end of U1 snRNA base pair bind with the 5' ss of the pre mRNA. In one embodiment, oligonucleotides of the invention are U1 adaptors. In one embodiment, the U1 adaptor can be administered in combination with at least one other iRNA agent.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein, in its entirety. Antagomir RNAs may be synthesized using standard solid phase oligonucleotide synthesis protocols. See U.S. patent application Ser. No. 11/502,158 and 11/657,341 (the disclosure of each of which are incorporated herein by reference). An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Antagomirs may be single stranded, double stranded, partially double stranded or hairpin-structured, chemically modified oligonucleotides that target a microRNA. An antagomir may consist essentially of or comprise about 12 or more contiguous nucleotides substantially complementary to an endogenous miRNA, and more particularly, agents that include about 12 or more contiguous nucleotides substantially complementary to a target sequence of an miRNA or pre-miRNA nucleotide sequence. In certain embodiments, an antagomir featured in the invention includes a nucleotide sequence sufficiently complementary to hybridize to a miRNA target sequence of about 12 to 25 nucleotides, in some instances about 15 to 23 nucleotides.

Decoy Oligonucleotides

Because transcription factors can recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

An oligonucleotide agent featured in the invention can also be a decoy nucleic acid, e.g., a decoy RNA. A decoy nucleic acid resembles a natural nucleic acid, but may be modified in such a way as to inhibit or interrupt the activity of the natural nucleic acid. For example, a decoy RNA can mimic the natural binding domain for a ligand. The decoy RNA, therefore, competes with natural binding domain for the binding of a specific ligand. The natural binding target can be an endogenous nucleic acid, e.g., a pre-miRNA, miRNA, pre-mRNA, mRNA or DNA. For example, it has been shown that overexpression of HIV trans-activation response (TAR) RNA can act as a "decoy" and efficiently bind HIV tat protein, thereby preventing it from binding to TAR sequences encoded in the HIV RNA. In certain embodiments, a decoy RNA may include a modification that improves targeting, e.g., a targeting modification described herein.

Antisense Oligonucleotides

Antisense oligonucleotides are single strands of DNA or RNA that are at least partially complementary to a chosen sequence. In the case of antisense RNA, they prevent translation of complementary RNA strands by binding to it. Antisense DNA can also be used to target a specific, complementary (coding or non-coding) RNA. If binding takes place, the DNA/RNA hybrid can be degraded by the enzyme RNase H. Examples of the utilization of antisense oligonucleotides may be found in Dias et al., Mol. Cancer. Ther., 2002, 1: 347-355, which is expressly incorporated by reference herein, in its entirety.

The single-stranded oligonucleotide agents featured in the invention include antisense nucleic acids. An "antisense" nucleic acid includes a nucleotide sequence that is complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. Accordingly, an antisense nucleic acid may form hydrogen bonds with a sense nucleic acid target.

Given a coding strand sequence (e.g., the sequence of a sense strand of a cDNA molecule), antisense nucleic acids can be designed according to the rules of Watson and Crick base pairing. The antisense nucleic acid molecule can be complementary to a portion of the coding or noncoding region of an RNA, e.g., a pre-mRNA or mRNA. For example, the antisense oligonucleotide can be complementary to the region surrounding the translation start site of a pre-mRNA or mRNA, e.g., the 5' UTR. An antisense oligonucleotide can be, for example, about 10 to 25 nucleotides in length (e.g., about 11, 12, 13, 14, 15, 16, 18, 19, 20, 21, 22, 23, or 24 nucleotides in length). An antisense oligonucleotide can also be complementary to a miRNA or pre-miRNA.

In certain embodiments, an antisense nucleic acid can be constructed using chemical synthesis and/or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and target nucleic acids, e.g., phosphorothioate derivatives and acridine substituted nucleotides can be used. Other appropriate nucleic acid modifications are described herein. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense agent can include ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme, e.g., RNAse H. Degradation of the target RNA prevents translation. The flanking RNA sequences can include 2'-O-methylated nucleotides, and phosphorothioate linkages, and the internal DNA sequence can include phosphorothioate internucleotide linkages. In some embodiments, the internal DNA sequence may be at least five nucleotides in length when targeting by RNAseH activity is desired.

For increased nuclease resistance, an antisense agent can be further modified by inverting the nucleoside at the 3'-terminus with a 3'-3' linkage. In another alternative, the 3'-terminus can be blocked with an aminoalkyl group.

In other embodiments, an antisense oligonucleotide agent may include a modification that improves targeting, e.g., a targeting modification described herein.

Aptamers

Aptamers are nucleic acid molecules that bind a specific target molecule or molecules. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule.

An oligonucleotide agent featured in the invention can be an aptamer. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand. An aptamer can contain any of the modifications described herein.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

Increasing Cellular Uptake of dsiRNAs

A method of the invention that includes administering an iRNA agent and a drug that affects the uptake of the iRNA agent into the cell. The drug can be administered before, after, or at the same time that the mRNA agent is administered. The drug can be covalently linked to the iRNA agent. The drug can be, for example, a lipopolysaccharid, an activator of p38 MAP kinase, or an activator of NF-κB. The drug can have a transient effect on the cell.

The drug can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The drug can also increase the uptake of the iRNA agent into the cell by activating an inflammatory response, for example. Exemplary drug's that would have such an effect include tumor necrosis factor alpha (TNFalpha), interleukin-1 beta, or gamma interferon.

iRNA Conjugates

An iRNA agent can be coupled, e.g., covalently coupled, to a second agent. For example, an iRNA agent used to treat a particular disorder can be coupled to a second therapeutic agent, e.g., an agent other than the iRNA agent. The second therapeutic agent can be one which is directed to the treatment of the same disorder. For example, in the case of an iRNA used to treat a disorder characterized by unwanted cell proliferation, e.g., cancer, the iRNA agent can be coupled to a second agent which has an'anti-cancer effect. For example, it can be coupled to an agent which stimulates the immune system, e.g., a CpG motif, or more generally an agent that activates a toll-like receptor and/or increases the production of gamma interferon.

iRNA Production

An iRNA can be produced, e.g., in bulk, by a variety of methods. Exemplary methods include: organic synthesis and RNA cleavage, e.g., in vitro cleavage. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives.

Regardless of the method of synthesis, the oligonucleotide can be prepared in a solution (e.g., an aqueous and/or organic solution) that is appropriate for formulation. For example, the oligonucleotide preparation can be precipitated and, redissolved in pure double-distilled water, and lyophilized. The dried oligonucleotiode can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262, 241, and 5,459,255, drawn to, inter alia, methods of synthesizing 2'-fluoro-oligonucleotides.

Organic Synthesis

An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed, e.g., after release from the solid Support and deprotection.

Organic synthesis can be used to produce a discrete iRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsiRNA Cleavage iRNAs can also be made by cleaving a larger ds iRNA. The cleavage can be mediated in vitro or in vivo. For example, to produce iRNAs by cleavage in vitro, the following method can be used:

In vitro transcription. dsiRNA is produced by transcribing a nucleic acid (DNA) segment in both directions. For example, the HiScribe™ RNAi transcription kit (New England Biolabs) provides a vector and a method for producing a dsiRNA for a nucleic acid segment that is cloned into the vector at a position flanked on either side by a T7 promoter. Separate templates are generated for T7 transcription of the two complementary strands for the dsiRNA. The templates are transcribed in vitro by addition of T7 RNA polymerase and dsiRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsiRNA is cleaved in vitro into iRNAs, for example, using a Dicer or comparable RNAse III-based activity. For example, the dsiRNA can be incubated in an in vitro extract from *Drosophila* or using purified components, e.g., a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293(5532):1146-50.

dsiRNA cleavage generally produces a plurality of iRNA species, each being a particular 21 to 23 nt fragment of a source dsiRNA molecule. For example, iRNAs that include sequences complementary to overlapping regions and adjacent regions of a source dsiRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Formulation

The iRNA agents described herein can be formulated for administration to a subject For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration (see, below).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A iRNA preparation can be formulated in combination with another agent, e.g., another therapeutic agent or an agent that stabilizes a iRNA, e.g., a protein that complexes with mRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least 3, 5, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA). For example, a iRNA composition for the treatment of a viral disease, e.g., HIV, might include a known antiviral agent (e.g., a protease inhibitor or reverse transcriptase inhibitor). In another example, a iRNA composition for the treatment of a cancer might further comprise a chemotherapeutic agent.

Exemplary formulations are discussed below:

Liposomes

For ease of exposition the formulations, compositions and methods in this section are discussed largely with regard to unmodified iRNA agents. It may be understood, however, that these formulations, compositions and methods can be practiced with other iRNA agents, e.g., modified iRNA s agents, and such practice is within the invention. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a iRNA can be prepared by a variety of methods.

In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA preparation is then added to the micelles that include the lipid component. The cationic groups on the lipid interact with the iRNA and condense around the iRNA to form a liposome. After condensation, the detergent is removed, e.g., by dialysis, to yield a liposomal preparation of iRNA.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Feigner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA preparations into liposomes.

Liposomes that are pH-sensitive or negatively-charged, entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Feigner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNAs to macrophages.

Further advantages of liposomes include: liposomes obtained from natural phospholipids are biocompatible and biodegradable; liposomes can incorporate a wide range of water and lipid soluble drugs; liposomes can protect encapsulated iRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA (see, e.g., Feigner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194. Other cationic lipids suitable for liposome formation are described in U.S. Provisional applications No. 61/018,616 (filed Jan. 2, 2008), No. 61/039,748 (filed Mar. 26, 2008), No. 61/047,087 (filed Apr. 22, 2008) and No. 61/051,528 (filed May 21-2008), all of which are incorporated by reference in their entireties for all purposes.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA, into the skin. In some implementations, liposomes are used for delivering iRNA to epidermal cells and also to enhance the penetration of iRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149: 157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA can be delivered, for example, subcutaneously by infection in order to deliver iRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Surfactants

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. Surfactants find wide application in formulations such as emulsions (including microemulsions) and liposomes (see above). iRNA (or a precursor, e.g., a larger dsiRNA which can be processed into a iRNA, or a DNA which encodes a iRNA or precursor) compositions can include a surfactant. In one embodiment, the iRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and Other Membranous Formulations

For ease of exposition the micelles and other formulations, compositions and methods in this section are discussed largely with regard to unmodified iRNA agents. It may be understood, however, that these micelles and other formulations, compositions and methods can be practiced with other iRNA agents, e.g., modified iRNA agents, and such practice is within the invention. The iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the iRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linoleic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the iRNA composition and at least the alkali metal alkyl sulphate. The first micellar composition is then mixed with at least three micelle forming compounds to form a mixed micellar composition. In another method, the micellar composition is prepared by mixing the iRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles

For ease of exposition the particles, formulations, compositions and methods in this section are discussed largely with regard to unmodified iRNA agents. It may be understood, however, that these particles, formulations, compositions and methods can be practiced with other iRNA agents, e.g., modified iRNA agents, and such practice is within the invention. In another embodiment, an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques. See below for further description.

Sustained-Release Formulations. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) described herein can be formulated for controlled, e.g., slow release. Controlled release can be achieved by disposing the iRNA within a structure or substance which impedes its release. E.g., iRNA can be disposed within a porous matrix or in an erodable matrix, either of which allow release of the iRNA over a period of time.

Polymeric particles, e.g., polymeric in microparticles can be used as a sustained-release reservoir of iRNA that is taken up by cells only released from the microparticle through biodegradation. The polymeric particles in this embodiment should therefore be large enough to preclude phagocytosis (e.g., larger than 10 μm or larger than 20 μm). Such particles can be produced by the same methods to make smaller particles, but with less vigorous mixing of the first and second emulsions. That is to say, a lower homogenization speed, vortex mixing speed, or sonication setting can be used to obtain particles having a diameter around 100 μm rather than 10 μm. The time of mixing also can be altered.

Larger microparticles can be formulated as a suspension, a powder, or an implantable solid, to be delivered by intramuscular, subcutaneous, intradermal, intravenous, or intraperitoneal injection; via inhalation (intranasal or intrapulmonary); orally; or by implantation. These particles are useful for delivery of any iRNA when slow release over a relatively long term is desired. The rate of degradation, and consequently of release, varies with the polymeric formulation.

Microparticles may include pores, voids, hollows, defects or other interstitial spaces that allow the fluid suspension medium to freely permeate or perfuse the particulate boundary. For example, the perforated microstructures can be used to form hollow, porous spray dried microspheres.

Polymeric particles containing iRNA (e.g., a siRNA) can be made using a double emulsion technique, for instance. First, the polymer is dissolved in an organic solvent. A polymer may be polylactic-co-glycolic acid (PLGA), with a lactic/glycolic acid weight ratio of 65:35, 50:50, or 75:25. Next, a sample of nucleic acid suspended in aqueous solution is added to the polymer solution and the two solutions are mixed to form a first emulsion. The solutions can be mixed by vortexing or shaking, and in the mixture can be sonicated. Any method by which the nucleic acid receives the least amount of damage in the form of nicking, shearing, or degradation, while still allowing the formation of an appropriate emulsion is possible. For example, acceptable results can be obtained with a Vibra-cell model VC-250 sonicator with a ⅛" microtip probe, at setting #3.

Spray Drying

An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded mRNA agent, or siRNA agent, or precursor thereof)) can be prepared by spray drying. Spray dried iRNA can be administered to a subject or be subjected to further formulation. A pharmaceutical composition of iRNA can be prepared by spray drying a homogeneous aqueous mixture that includes a mRNA under conditions sufficient to provide a dispersible powdered composition, e.g., a pharmaceutical composition. The material for spray drying can also include one or more of: a pharmaceutically acceptable excipient, or a dispersibility-enhancing amount of a physiologically acceptable, water-soluble protein. The spray-dried product can be a dispersible powder that includes the iRNA.

Spray drying is a process that converts a liquid or slurry material to a dried particulate form. Spray drying can be used to provide powdered material for various administrative routes including inhalation. See, for example, M. Sacchetti and M. M. Van Oort in: Inhalation Aerosols Physical and Biological Basis for Therapy, A. J. Hickey, ed. Marcel Dekkar, New York, 1996.

Spray drying can include atomizing a solution, emulsion, or suspension to form a fine mist of droplets and drying the droplets. The mist can be projected into a drying chamber (e.g., a vessel, tank, tubing, or coil) where it contacts a drying gas. The mist can include solid or liquid pore forming agents. The solvent and pore forming agents evaporate from the droplets into the drying gas to solidify the droplets, simultaneously forming pores throughout the solid. The solid (typically in a powder, particulate form) then is separated from the drying gas and collected.

Spray drying includes bringing together a highly dispersed liquid, and a sufficient volume of air (e.g., hot air) to produce evaporation and drying of the liquid droplets. The preparation to be spray dried can be any solution, course suspension, slurry, colloidal dispersion, or paste that may be atomized using the selected spray drying apparatus. Typically, the feed is sprayed into a current of warm filtered air that evaporates the solvent and conveys the dried product to a collector. The spent air is then exhausted with the solvent. Several different types of apparatus may be used to provide the desired product. For example, commercial spray dryers manufactured by Buchi Ltd. or Niro Corp. can effectively produce particles of desired size.

Spray-dried powdered particles can be approximately spherical in shape, nearly uniform in size and frequently hollow. There may be some degree of irregularity in shape depending upon the incorporated medicament and the spray drying conditions. In many instances the dispersion stability of spray-dried microspheres appears to be more effective if an inflating agent (or blowing agent) is used in their production. Certain embodiments may comprise an emulsion with an inflating agent as the disperse or continuous phase (the other phase being aqueous in nature). An inflating agent may be dispersed with a surfactant solution, using, for instance, a commercially available microfluidizer at a pressure of about 5000 to 15,000 psi. This process forms an emulsion, which may be stabilized by an incorporated surfactant, typically comprising submicron droplets of water immiscible blowing agent dispersed in an aqueous continuous phase. The formation of such dispersions using this and other techniques are common and well known to those in the art. The blowing agent may be a fluorinated compound (e.g., perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable blowing agents include chloroform, freons, and hydrocarbons. Nitrogen gas and carbon dioxide are also contemplated as a suitable blowing agent.

Although the perforated microstructures may be formed using a blowing agent as described above, it will be appreciated that, in some instances, no blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties (e.g., high crystallinity, elevated melting temperature, surface activity, etc.) that make it particularly suitable for use in such techniques.

The perforated microstructures may optionally be associated with, or comprise, one or more surfactants. Moreover, miscible surfactants may optionally be combined with the suspension medium liquid phase. It will be appreciated by those skilled in the art that the use of surfactants may further increase dispersion stability, simplify formulation procedures or increase bioavailability upon administration. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

Surfactants suitable for use include any compound or composition that aids in the formation and maintenance of the stabilized respiratory dispersions by forming a layer at the interface between the structural matrix and the suspension medium. The surfactant may comprise a single compound or any combination of compounds, such as in the case of co-surfactants. Particularly certain surfactants are substantially insoluble in the propellant, nonfluorinated, and selected from the group consisting of saturated and unsaturated lipids, nonionic detergents, nonionic block copolymers, ionic surfactants, and combinations of such agents. It may be emphasized that, in addition to the aforementioned surfactants, suitable (i.e., biocompatible) fluorinated surfactants are compatible with the teachings herein and may be used to provide the desired stabilized preparations.

Lipids, including phospholipids, from both natural and synthetic sources may be used in varying concentrations to form a structural matrix. Generally, compatible lipids comprise those that have a gel to liquid crystal phase transition greater than about 40° C. In certain embodiments, the incorporated lipids are relatively long chain (i.e., $C_6$-$C_{22}$) saturated lipids and may comprise phospholipids. Exemplary phospholipids useful in the disclosed stabilized preparations comprise egg phosphatidylcholine, dilauroylphosphatidylcholine, dioleylphosphatidylcholine, dipalmitoylphosphatidyl-choline, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as, polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (Spans™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.). Certain block copolymers include diblock and triblock copolymers of polyoxyethylene and polyoxypropylene, including poloxamer 188 (Pluronic.RTM. F68), poloxamer 407 (Pluronic.RTM. F-127), and poloxamer 338. Ionic surfactants such as sodium sulfosuccinate, and fatty acid soaps may also be utilized. In certain embodiments, the microstructures may comprise oleic acid or its alkali salt.

In addition to the aforementioned surfactants, cationic surfactants or lipids may be used, especially in the case of delivery of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). Examples of suitable cationic lipids include: DOTMA, N-[-(2,3-dioleyloxy)propyl]-N,N,N-trimethylammonium-chloride; DOTAP,1,2-dioleyloxy-3-(trimethylammonio)propane; and DOTB, 1,2-dioleyl-3-(4'-trimethylammonio)butanoyl-sn-glycerol.
Polycationic amino acids such as polylysine, and polyarginine are also contemplated.

For the spraying process, such spraying methods as rotary atomization, pressure atomization and two-fluid atomization can be used. Examples of the devices used in these processes include "Parubisu [phonetic rendering] Mini-Spray GA-32" and "Parubisu Spray Drier DL-41", manufactured by Yamato Chemical Co., or "Spray Drier CL-8," "Spray Drier L-8," "Spray Drier FL-12," "Spray Drier FL-16" or "Spray Drier FL-20," manufactured by Okawara Kakoki Co., can be used for the method of spraying using rotary-disk atomizer.

While no particular restrictions are placed on the gas used to dry the sprayed material, it is recommended to use air, nitrogen gas or an inert gas. The temperature of the inlet of the gas used to dry the sprayed materials such that it does not cause heat deactivation of the sprayed material. The range of temperatures may vary between about 50° C. to about 200° C., for example, between about 50° C. and 100° C. The temperature of the outlet gas used to dry the sprayed material, may vary between about 0° C. and about 150° C., for example, between 0° C. and 90° C., and for example between 0° C. and 60° C.

The spray drying is done under conditions that result in substantially amorphous powder of homogeneous constitution having a particle size that is respirable, a low moisture content and flow characteristics that allow for ready aerosolization. In some cases, the particle size of the resulting powder is such that more than about 98% of the mass is in particles having a diameter of about 10 µm or less with about 90% of the mass being in particles having a diameter less than 5 µm. Alternatively, about 95% of the mass will have particles with a diameter of less than 10 µm with about 80% of the mass of the particles having a diameter of less than 5 µm.

The dispersible pharmaceutical-based dry powders that include the iRNA preparation may optionally be combined with pharmaceutical carriers or excipients which are suitable for respiratory and pulmonary administration. Such carriers may serve simply as bulking agents when it is desired to reduce the iRNA concentration in the powder which is being delivered to a patient, but may also serve to enhance the stability of the iRNA compositions and to improve the dispersibility of the powder within a powder dispersion device in order to provide more efficient and reproducible delivery of the iRNA and to improve handling characteristics of the iRNA such as flowability and consistency to facilitate manufacturing and powder filling.

Such carrier materials may be combined with the drug prior to spray drying, i.e., by adding the carrier material to the purified bulk solution. In that way, the carrier particles will be formed simultaneously with the drug particles to produce a homogeneous powder. Alternatively, the carriers may be separately prepared in a dry powder form and combined with the dry powder drug by blending. The powder carriers will usually be crystalline (to avoid water absorption), but might in some cases be amorphous or mixtures of crystalline and amorphous. The size of the carrier particles may be selected to improve the flowability of the drug powder, typically being in the range from 25 µm to 100 µm. A carrier material may be crystalline lactose having a size in the above-stated range.

Powders prepared by any of the above methods will be collected from the spray dryer in a conventional manner for subsequent use. For use as pharmaceuticals and other purposes, it will frequently be desirable to disrupt any agglomerates which may have formed by screening or other conventional techniques. For pharmaceutical uses, the dry powder formulations will usually be measured into a single dose, and the single dose sealed into a package. Such packages are particularly useful for dispersion in dry powder inhalers, as described in detail below. Alternatively, the powders may be packaged in multiple-dose containers.

Methods for spray drying hydrophobic and other drugs and components are described in U.S. Pat. Nos. 5,000,888; 5,026,550; 4,670,419, 4,540,602; and 4,486,435. Bloch and Speison (1983) Pharm. Acta Helv 58:14-22 teaches spray drying of hydrochlorothiazide and chlorthalidone (lipophilic drugs) and a hydrophilic adjuvant (pentaerythritol) in azeotropic solvents of dioxane-water and 2-ethoxyethanol-water. A number of Japanese Patent application Abstracts relate to spray drying of hydrophilic-hydrophobic product combinations, including JP 806766; JP 7242568; JP 7101884; JP 7101883; JP 71018982; JP 7101881; and JP 4036233. Other foreign patent publications relevant to spray drying hydrophilic-hydrophobic product combinations include FR 2594693; DE 2209477; and WO 88/07870.

Lyophilization

An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) preparation can be made by lyophilization. Lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of nucleic acids in perforated microstructures without compromising physiological activity. Methods for providing lyophilized particulates are known to those of skill in the art and it would clearly not require undue experimentation to provide dispersion compatible microstructures in accordance with the teachings herein. Accordingly, to the extent that lyophilization processes may be used to provide microstructures having the desired porosity and size, they are conformance with the teachings herein and are expressly contemplated as being within the scope of the instant invention.

Genes

In one aspect, the invention features, a method of treating a subject at risk for or afflicted with a disease that may benefit from the administration of the modular composition of the invention. The method comprises administering the modular composition of the invention to a subject in need thereof, thereby treating the subject. The nucleic acid that is administered will depend on the disease being treated.

In certain embodiments, the iRNA agent (e.g., the iRNA agent in a modular composition described herein) silences a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In some embodiments the iRNA agent (e.g., the iRNA agent in a modular composition described herein) silences the PDGF beta gene, and thus can be used to treat a subject having or at risk for a disorder characterized by unwanted PDGF beta expression, e.g., testicular and lung cancers.

In some embodiments the mRNA agent (e.g., the iRNA agent in a modular composition described herein) silences the Erb-B gene, and thus can be used to treat a subject having or at risk for a disorder characterized by unwanted Erb-B expression, e.g., breast cancer.

In some embodiments the iRNA agent (e.g., the iRNA agent in a modular composition described herein) silences the Src gene, and thus can be used to treat a subject having or at risk for a disorder characterized by unwanted Src expression, e.g., colon cancers.

In some embodiments the iRNA agent (e.g., the iRNA agent in a modular composition described herein) silences the CRK gene, and thus can be used to treat a subject having or at risk for a disorder characterized by unwanted CRK expression, e.g., colon and lung cancers.

In some embodiments the iRNA agent (e.g., the iRNA agent in a modular composition described herein) silences the GRB2 gene, and thus can be used to treat a subject having or at risk for a disorder characterized by unwanted GRB2 expression, e.g., squamous cell carcinoma.

In another embodiment the iRNA agent (e.g., the iRNA agent in a modular composition described herein) silences the RAS gene, and thus can be used to treat a subject having or at risk for a disorder characterized by unwanted RAS expression, e.g., pancreatic, colon and lung cancers, and chronic leukemia.

In another embodiment the iRNA agent (e.g., the iRNA agent in a modular composition described herein) silences the MEKK gene, and thus can be used to treat a subject having or at risk for a disorder characterized by unwanted MEKK expression, e.g., squamous cell carcinoma, melanoma or leukemia.

In another embodiment the iRNA agent (e.g., the iRNA agent in a modular composition described herein) silences the JNK gene, and thus can be used to treat a subject having or at risk for a disorder characterized by unwanted JNK expression, e.g., pancreatic or breast cancers.

In some embodiments the iRNA agent (e.g., the iRNA agent in a modular composition described herein) silences the RAF gene, and thus can be used to treat a subject having or at risk for a disorder characterized by unwanted RAF expression, e.g., lung cancer or leukemia.

In some embodiments the iRNA agent (e.g., the iRNA agent in a modular composition described herein) silences the Erk1/2 gene, and thus can be used to treat a subject having or at risk for a disorder characterized by unwanted Erk1/2 expression, e.g., lung cancer.

In another embodiment the iRNA agent (e.g., the iRNA agent in a modular composition described herein) silences the PCNA(p21) gene, and thus can be used to treat a subject having or at risk for a disorder characterized by unwanted PCNA expression, e.g., lung cancer.

In some embodiments the iRNA agent (e.g., the iRNA agent in a modular composition described herein) silences the MYB gene, and thus can be used to treat a subject having or at risk for a disorder characterized by unwanted MYB expression, e.g., colon cancer or chronic myelogenous leukemia.

In some embodiments the iRNA agent (e.g., the iRNA agent in a modular composition described herein) silences the c-MYC gene, and thus can be used to treat a subject having or at risk for a disorder characterized by unwanted c-MYC expression, e.g., Burkitt's lymphoma or neuroblastoma.

In another embodiment the iRNA agent (e.g., the iRNA agent in a modular composition described herein) silences the JUN gene, and thus can be used to treat a subject having or at risk for a disorder characterized by unwanted JUN expression, e.g., ovarian, prostate or breast cancers.

In another embodiment the iRNA agent (e.g., the iRNA agent in a modular composition described herein) silences the FOS gene, and thus can be used to treat a subject having or at risk for a disorder characterized by unwanted FOS expression, e.g., skin or prostate cancers.

In some embodiments the iRNA agent (e.g., the iRNA agent in a modular composition described herein) silences the BCL-2 gene, and thus can be used to treat a subject having or at risk for a disorder characterized by unwanted BCL-2 expression, e.g., lung or prostate cancers or Non-Hodgkin lymphoma.

In some embodiments the iRNA agent (e.g., the iRNA agent in a modular composition described herein) silences the Cyclin D gene, and thus can be used to treat a subject having or at risk for a disorder characterized by unwanted Cyclin D expression, e.g., esophageal and colon cancers.

In some embodiments the iRNA agent (e.g., the iRNA agent in a modular composition described herein) silences the VEGF gene, and thus can be used to treat a subject having or at risk for a disorder characterized by unwanted VEGF expression, e.g., esophageal and colon cancers.

In some embodiments the iRNA agent (e.g., the iRNA agent in a modular composition described herein) silences the EGFR gene, and thus can be used to treat a subject having or at risk for a disorder characterized by unwanted EGFR expression, e.g., breast cancer.

In another embodiment the iRNA agent (e.g., the iRNA agent in a modular composition described herein) silences the Cyclin A gene, and thus can be used to treat a subject having or at risk for a disorder characterized by unwanted Cyclin A expression, e.g., lung and cervical cancers.

In another embodiment the iRNA agent (e.g., the iRNA agent in a modular composition described herein) silences the Cyclin E gene, and thus can be used to treat a subject having or at risk for a disorder characterized by unwanted Cyclin E expression, e.g., lung and breast cancers.

In another embodiment the iRNA agent (e.g., the iRNA agent in a modular composition described herein) silences the WNT-1 gene, and thus can be used to treat a subject having or at risk for a disorder characterized by unwanted WNT-1 expression, e.g., basal cell carcinoma.

In another embodiment the iRNA agent (e.g., the iRNA agent in a modular composition described herein) silences the beta-catenin gene, and thus can be used to treat a subject having or at risk for a disorder characterized by unwanted beta-catenin expression, e.g., adenocarcinoma or hepatocellular carcinoma.

In another embodiment the iRNA agent (e.g., the iRNA agent in a modular composition described herein) silences the c-MET gene, and thus can be used to treat a subject having or at risk for a disorder characterized by unwanted c-MET expression, e.g., hepatocellular carcinoma.

In another embodiment the iRNA agent (e.g., the iRNA agent in a modular composition described herein) silences the PKC gene, and thus can be used to treat a subject having or at risk for a disorder characterized by unwanted PKC expression, e.g., breast cancer.

In some embodiments the iRNA agent (e.g., the iRNA agent in a modular composition described herein) silences the NFKB gene, and thus can be used to treat a subject having or at risk for a disorder characterized by unwanted NFKB expression, e.g., breast cancer.

In some embodiments the iRNA agent (e.g., the iRNA agent in a modular composition described herein) silences the STAT3 gene, and thus can be used to treat a subject having or at risk for a disorder characterized by unwanted STAT3 expression, e.g., prostate cancer.

In another embodiment the iRNA agent (e.g., the iRNA agent in a modular composition described herein) silences the survivin gene, and thus can be used to treat a subject having or at risk for a disorder characterized by unwanted survivin expression, e.g., cervical or pancreatic cancers.

In another embodiment the iRNA agent (e.g., the iRNA agent in a modular composition described herein) silences the Her2/Neu gene, and thus can be used to treat a subject having or at risk for a disorder characterized by unwanted Her2/Neu expression, e.g., breast cancer.

In another embodiment the iRNA agent (e.g., the iRNA agent in a modular composition described herein) silences the topoisomerase I gene, and thus can be used to treat a subject having or at risk for a disorder characterized by unwanted topoisomerase I expression, e.g., ovarian and colon cancers.

In some embodiments the iRNA agent (e.g., the iRNA agent in a modular composition described herein) silences the topoisomerase II alpha gene, and thus can be used to treat a subject having or at risk for a disorder characterized by unwanted topoisomerase II expression, e.g., breast and colon cancers.

In some embodiments the iRNA agent (e.g., the iRNA agent in a modular composition described herein) silences mutations in the p73 gene, and thus can be used to treat a subject having or at risk for a disorder characterized by unwanted p73 expression, e.g., colorectal adenocarcinoma.

In some embodiments the iRNA agent (e.g., the iRNA agent in a modular composition described herein) silences mutations in the p21(WAF1/CIP1) gene, and thus can be used to treat a subject having or at risk for a disorder characterized by unwanted p21(WAF1/CIP1) expression, e.g., liver cancer.

In some embodiments the iRNA agent (e.g., the iRNA agent in a modular composition described herein) silences mutations in the p27(KIP1) gene, and thus can be used to treat a subject having or at risk for a disorder characterized by unwanted p27(KIP1) expression, e.g., liver cancer.

In some embodiments the iRNA agent (e.g., the iRNA agent in a modular composition described herein) silences mutations in the PPM1D gene, and thus can be used to treat a subject having or at risk for a disorder characterized by unwanted PPM1D expression, e.g., breast cancer.

In some embodiments the iRNA agent (e.g., the iRNA agent in a modular composition described herein) silences mutations in the RAS gene, and thus can be used to treat a subject having or at risk for a disorder characterized by unwanted RAS expression, e.g., breast cancer.

In another embodiment the iRNA agent (e.g., the iRNA agent in a modular composition described herein) silences mutations in the caveolin I gene, and thus can be used to treat a subject having or at risk for a disorder characterized by unwanted caveolin I expression, e.g., esophageal squamous cell carcinoma.

In another embodiment the iRNA agent (e.g., the iRNA agent in a modular composition described herein) silences mutations in the MIB I gene, and thus can be used to treat a subject having or at risk for a disorder characterized by unwanted MIB I expression, e.g., male breast carcinoma (MBC).

In another embodiment the iRNA agent (e.g., the iRNA agent in a modular composition described herein) silences mutations in the MTAI gene, and thus can be used to treat a subject having or at risk for a disorder characterized by unwanted MTAI expression, e.g., ovarian carcinoma.

In another embodiment the iRNA agent (e.g., the iRNA agent in a modular composition described herein) silences mutations in the M68 gene, and thus can be used to treat a subject having or at risk for a disorder characterized by unwanted M68 expression, e.g., human adenocarcinomas of the esophagus, stomach, colon, and rectum.

In certain embodiments the iRNA agent (e.g., the iRNA agent in a modular composition described herein) silences mutations in tumor suppressor genes, and thus can be used as a method to promote apoptotic activity in combination with chemotherapeutics.

In some embodiments the iRNA agent (e.g., the iRNA agent in a modular composition described herein) silences mutations in the p53 tumor suppressor gene, and thus can be used to treat a subject having or at risk for a disorder characterized by unwanted p53 expression, e.g., gall bladder, pancreatic and lung cancers.

In some embodiments the iRNA agent (e.g., the iRNA agent in a modular composition described herein) silences mutations in the p53 family member DN-p63, and thus can be used to treat a subject having or at risk for a disorder characterized by unwanted DN-p63 expression, e.g., squamous cell carcinoma In some embodiments the iRNA agent (e.g., the iRNA agent in a modular composition described herein) silences mutations in the pRb tumor suppressor gene, and thus can be used to treat a subject having or at risk for a disorder characterized by unwanted pRb expression, e.g., oral squamous cell carcinoma In some embodiments the iRNA agent (e.g., the iRNA agent in a modular composition described herein) silences mutations in the APC1 tumor suppressor gene, and thus can be used to treat a subject having or at risk for a disorder characterized by unwanted APC1 expression, e.g., colon cancer.

In some embodiments the iRNA agent (e.g., the iRNA agent in a modular composition described herein) silences mutations in the BRCA1 tumor suppressor gene, and thus can be used to treat a subject having or at risk for a disorder characterized by unwanted BRCA1 expression, e.g., breast cancer.

In some embodiments the iRNA agent (e.g., the iRNA agent in a modular composition described herein) silences mutations in the PTEN tumor suppressor gene, and thus can be used to treat a subject having or at risk for a disorder characterized by unwanted PTEN expression, e.g., hamartomas, gliomas, and prostate and endometrial cancers.

In some embodiments the iRNA agent (e.g., the iRNA agent in a modular composition described herein) silences MLL fusion genes, e.g., MLL-AF9, and thus can be used to treat a subject having or at risk for a disorder characterized by unwanted MLL fusion gene expression, e.g., acute leukemias.

In another embodiment the iRNA agent (e.g., the iRNA agent in a modular composition described herein) silences the BCR/ABL fusion gene, and thus can be used to treat a subject having or at risk for a disorder characterized by unwanted BCR/ABL fusion gene expression, e.g., acute and chronic leukemias.

In another embodiment the iRNA agent (e.g., the iRNA agent in a modular composition described herein) silences the TEL/AML1 fusion gene, and thus can be used to treat a subject having or at risk for a disorder characterized by unwanted TEL/AML1 fusion gene expression, e.g., childhood acute leukemia.

In another embodiment the iRNA agent (e.g., the iRNA agent in a modular composition described herein) silences the EWS/FLI1 fusion gene, and thus can be used to treat a subject having or at risk for a disorder characterized by unwanted EWS/FLI1 fusion gene expression, e.g., Ewing Sarcoma.

In another embodiment the iRNA agent (e.g., the iRNA agent in a modular composition described herein) silences the TLS/FUS1 fusion gene, and thus can be used to treat a subject having or at risk for a disorder characterized by unwanted TLS/FUS1 fusion gene expression, e.g., Myxoid liposarcoma.

In another embodiment the iRNA agent (e.g., the iRNA agent in a modular composition described herein) silences the PAX3/FKHR fusion gene, and thus can be used to treat a subject having or at risk for a disorder characterized by unwanted PAX3/FKHR fusion gene expression, e.g., Myxoid liposarcoma.

In another embodiment the iRNA agent (e.g., the iRNA agent in a modular composition described herein) silences the AML1/ETO fusion gene, and thus can be used to treat a subject having or at risk for a disorder characterized by unwanted AML1/ETO fusion gene expression, e.g., acute leukemia.

Diseases

Angiogenesis

In another aspect, the invention features, a method of treating a subject, e.g., a human, at risk for or afflicted with a disease or disorder that may benefit by angiogenesis inhibition, e.g., cancer. The method comprises administering the modular composition of the invention to a subject in need thereof, thereby treating the subject. The nucleic acid that is administered will depend on the type of angiogenesis-related gene being treated.

In some embodiments the iRNA agent (e.g., the iRNA agent in a modular composition described herein) silences the alpha v-integrin gene, and thus can be used to treat a subject having or at risk for a disorder characterized by unwanted alpha V integrin, e.g., brain tumors or tumors of epithelial origin.

In some embodiments the iRNA agent (e.g., the iRNA agent in a modular composition described herein) silences the Flt-1 receptor gene, and thus can be used to treat a subject having or at risk for a disorder characterized by unwanted Flt-1 receptors, eg. cancer and rheumatoid arthritis.

In some embodiments the iRNA agent (e.g., the iRNA agent in a modular composition described herein) silences the tubulin gene, and thus can be used to treat a subject having or at risk for a disorder characterized by unwanted tubulin, eg. cancer and retinal neovascularization.

In some embodiments the iRNA agent (e.g., the iRNA agent in a modular composition described herein) silences the tubulin gene, and thus can be used to treat a subject having or at risk for a disorder characterized by unwanted tubulin, eg. cancer and retinal neovascularization.

Viral Diseases

In yet another aspect, the invention features a method of treating a subject infected with a virus or at risk for or afflicted with a disorder or disease associated with a viral infection. The method comprises administering the modular composition of the invention to a subject in need thereof, thereby treating the subject. The nucleic acid that is administered will depend on the type of viral disease being treated. In some embodiments, the nucleic acid may target a viral gene. In other embodiments, the nucleic acid may target a host gene.

Thus, the invention provides for a method of treating patients infected by the Human Papilloma Virus (HPV) or at risk for or afflicted with a disorder mediated by HPV, e.g., cervical cancer. HPV is linked to 95% of cervical carcinomas and thus an antiviral therapy is an attractive method to treat these cancers and other symptoms of viral infection. In some embodiments, the expression of a HPV gene is reduced. In another embodiment, the HPV gene is one of the group of E2, E6, or E7. In some embodiments the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In some embodiments, the expression of a HIV gene is reduced. In another embodiment, the HIV gene is CCR5, Gag, or Rev. In some embodiments the expression of a human gene that is required for HIV replication is reduced. In another embodiment, the gene is CD4 or Tsg101.

The invention also includes a method for treating patients infected by the Hepatitis B Virus (HBV) or at risk for or afflicted with a disorder mediated by HBV, e.g., cirrhosis and hepatocellular carcinoma. In some embodiments, the expression of a HBV gene is reduced. In another embodiment, the targeted HBV gene encodes one of the group of the tail region of the HBV core protein, the pre-cregious (pre-c) region, or the cregious (c) region. In another embodiment, a targeted HBV-RNA sequence is comprised of the poly(A) tail. In certain embodiment the expression of a human gene that is required for HBV replication is reduced.

The invention also provides for a method of treating patients infected by the Hepatitis A Virus (HAV), or at risk for or afflicted with a disorder mediated by HAV. In some embodiments the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In some embodiments, the expression of a HCV gene is reduced. In another embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In some embodiments, the expression of a Hepatitis, D, E, F, G, or H gene is reduced. In another embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In some embodiments, the expression of a RSV gene is reduced. In another embodiment, the targeted HBV gene encodes one of the group of genes N, L, or P. In some embodiments the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In some embodiments, the expression of a HSV gene is reduced. In another embodiment, the targeted HSV gene encodes DNA polymerase or the helicase-primase. In some embodiments the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In some embodiments, the expression of a CMV gene is reduced. In some embodiments the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In some embodiments, the expression of a EBV gene is reduced. In some embodiments the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In some embodiments, the expression of a KSHV gene is reduced. In some embodiments the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In some embodiments, the expression of a JCV gene is reduced. In certain embodiments the expression of a human gene that is required for JCV replication is reduced.

Methods of the invention also provide for treating patients infected by the myxovirus or at risk for or afflicted with a disorder mediated by myxovirus, e.g., influenza. In some embodiments, the expression of a myxovirus gene is reduced. In some embodiments the expression of a human gene that is required for myxovirus replication is reduced.

Methods of the invention also provide for treating patients infected by the rhinovirus or at risk for of afflicted with a disorder mediated by rhinovirus, e.g., the common cold. In some embodiments, the expression of a rhinovirus gene is reduced. In certain embodiments the expression of a human gene that is required for rhinovirus replication is reduced.

Methods of the invention also provide for treating patients infected by the coronavirus or at risk for of afflicted with a disorder mediated by coronavirus, e.g., the common cold. In some embodiments, the expression of a coronavirus gene is reduced. In certain embodiments the expression of a human gene that is required for coronavirus replication is reduced.

Methods of the invention also provide for treating patients infected by the flavivirus West Nile or at risk for or afflicted with a disorder mediated by West Nile Virus. In some embodiments, the expression of a West Nile Virus gene is reduced. In another embodiment, the West Nile Virus gene is one of the group comprising E, NS3, or NS5. In some embodiments the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In some embodiments, the expression of a St. Louis Encephalitis gene is reduced. In some embodiments the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In some embodiments, the expression of a Tick-borne encephalitis virus gene is reduced. In some embodiments the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In some embodiments, the expression of a Murray Valley encephalitis virus gene is reduced. In some embodiments the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In some embodiments, the expression of a dengue virus gene is reduced. In some embodiments the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In some embodiments, the expression of a SV40 gene is reduced. In some embodiments the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In some embodiments, the expression of a HTLV gene is reduced. In another embodiment the HTLV1 gene is the Tax transcriptional activator. In some embodiments the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In some embodiments, the expression of a Mo-MuLV gene is reduced. In some embodiments the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g., myocarditis. EMCV leads to myocarditis in mice and pigs and is capable of infecting human myocardial cells. This virus is therefore a concern for patients undergoing xenotransplantation. In some embodiments, the expression of a EMCV gene is reduced. In some embodiments the expression of a human gene that is required for EMCV replication is reduced.

The invention also includes a method for treating patients infected by the measles virus (MV) or at risk for or afflicted with a disorder mediated by MV, e.g., measles. In some embodiments, the expression of a MV gene is reduced. In some embodiments the expression of a human gene that is required for MV replication is reduced.

The invention also includes a method for treating patients infected by the Varicella zoster virus (VZV) or at risk for or afflicted with a disorder mediated by VZV, e.g., chicken pox or shingles (also called zoster). In some embodiments, the expression of a VZV gene is reduced. In some embodiments the expression of a human gene that is required for VZV replication is reduced.

The invention also includes a method for treating patients infected by an adenovirus or at risk for or afflicted with a disorder mediated by an adenovirus, e.g., respiratory tract infection. In some embodiments, the expression of an adenovirus gene is reduced. In some embodiments the expression of a human gene that is required for adenovirus replication is reduced.

The invention includes a method for treating patients infected by a yellow fever virus (YFV) or at risk for or afflicted with a disorder mediated by a YFV, e.g., respiratory tract infection. In some embodiments, the expression of a YFV gene is reduced. In another embodiment, the gene may be one of a group that includes the E, NS2A, or NS3 genes. In some embodiments the expression of a human gene that is required for YFV replication is reduced.

Methods of the invention also provide for treating patients infected by the poliovirus or at risk for or afflicted with a disorder mediated by poliovirus, e.g., polio. In some embodiments, the expression of a poliovirus gene is reduced. In some embodiments the expression of a human gene that is required for poliovirus replication is reduced.

Methods of the invention also provide for treating patients infected by a poxvirus or at risk for or afflicted with a disorder mediated by a poxvirus, e.g., smallpox. In some embodiments, the expression of a poxvirus gene is reduced. In some embodiments the expression of a human gene that is required for poxvirus replication is reduced.

Other Pathogens

In another, aspect the invention features methods of treating a subject infected with a pathogen, e.g., a bacterial, amoebic, parasitic, or fungal pathogen. The method comprises administering the modular composition of the invention to a subject in need thereof, thereby treating the subject. The nucleic acid that is administered will depend on the type of pathogen being treated. In some embodiments, the nucleic acid may target a pathogen gene. In other embodiments, the nucleic acid may target a host gene.

The target gene can be one involved in growth, cell wall synthesis, protein synthesis, transcription, energy metabolism, e.g., the Krebs cycle, or toxin production.

Thus, the present invention provides for a method of treating patients infected by a *plasmodium* that causes malaria. In some embodiments, the expression of a *plasmodium* gene is reduced. In another embodiment, the gene is apical membrane antigen 1 (AMA1). In some embodiments the expression of a human gene that is required for *plasmodium* replication is reduced.

The invention also includes methods for treating patients infected by the *Mycobacterium* ulcerans, or a disease or disorder associated with this pathogen, e.g., Buruli ulcers. In some embodiments, the expression of a *Mycobacterium* ulcerans gene is reduced. In some embodiments the expression of a human gene that is required for *Mycobacterium* ulcerans replication is reduced.

The invention also includes methods for treating patients infected by the *Mycobacterium tuberculosis*, or a disease or disorder associated with this pathogen, e.g., tuberculosis. In some embodiments, the expression of a *Mycobacterium tuberculosis* gene is reduced. In some embodiments the expression of a human gene that is required for *Mycobacterium tuberculosis* replication is reduced.

The invention also includes methods for treating patients infected by the *Mycobacterium leprae*, or a disease or disorder associated with this pathogen, e.g., leprosy. In some embodiments, the expression of a *Mycobacterium leprae* gene is reduced. In some embodiments the expression of a human gene that is required for *Mycobacterium leprae* replication is reduced.

The invention also includes methods for treating patients infected by the bacteria *Staphylococcus aureus*, or a disease or disorder associated with this pathogen, e.g., infections of the skin and muscous membranes. In some embodiments, the expression of a *Staphylococcus aureus* gene is reduced. In some embodiments the expression of a human gene that is required for *Staphylococcus aureus* replication is reduced.

The invention also includes methods for treating patients infected by the bacteria *Streptococcus pneumoniae*, or a disease or disorder associated with this pathogen, e.g., pneumonia or childhood lower respiratory tract infection. In some embodiments, the expression of a *Streptococcus pneumoniae* gene is reduced. In some embodiments the expression of a human gene that is required for *Streptococcus pneumoniae* replication is reduced.

The invention also includes methods for treating patients infected by the bacteria *Streptococcus pyogenes*, or a disease or disorder associated with this pathogen, e.g., Strep throat or Scarlet fever. In some embodiments, the expression of a *Streptococcus pyogenes* gene is reduced. In some embodiments the expression of a human gene that is required for *Streptococcus pyogenes* replication is reduced.

The invention also includes methods for treating patients infected by the bacteria *Chlamydia pneumoniae*, or a disease or disorder associated with this pathogen, e.g., pneumonia or childhood lower respiratory tract infection. In some embodiments, the expression of a *Chlamydia pneumoniae* gene is reduced. In some embodiments the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g., pneumonia or childhood lower respiratory tract infection. In some embodiments, the expression of a *Mycoplasma pneumoniae* gene is reduced. In some embodiments the expression of a human gene that is required for *Mycoplasma pneumoniae* replication is reduced.

Immune Disorders

In one aspect, the invention features, a method of treating a subject, e.g., a human, at risk for or afflicted with a disease or disorder characterized by an unwanted immune response, e.g., an inflammatory disease or disorder, or an autoimmune disease or disorder. The method comprises administering the modular composition of the invention to a subject in need thereof, thereby treating the subject. The nucleic acid that is administered will depend on the type of immune disorder being treated.

In some embodiments the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis.

In some embodiments the disease or disorder is restenosis, e.g., restenosis associated with surgical intervention e.g., angioplasty, e.g., percutaneous transluminal coronary angioplasty.

In certain embodiments the disease or disorder is Inflammatory Bowel Disease, e.g., Crohn's Disease or Ulcerative Colitis.

In certain embodiments the disease or disorder is inflammation associated with an infection or injury.

In certain embodiments the disease or disorder is asthma, lupus, multiple sclerosis, diabetes, e.g., type II diabetes, arthritis, e.g., rheumatoid or psoriatic.

In certain other embodiments the iRNA agent (e.g., the iRNA agent in a modular composition described herein) silences an integrin or co-ligand thereof, e.g., VLA4, VCAM, ICAM.

In certain other embodiments the iRNA agent (e.g., the iRNA agent in a modular composition described herein) silences a selectin or co-ligand thereof, e.g., P-selectin, E-selectin (ELAM), 1-selectin, P-selectin glycoprotein-1 (PSGL-1).

In certain other embodiments the iRNA agent (e.g., the iRNA agent in a modular composition described herein) silences a component of the complement system, e.g., C3, C5, C3aR, C5aR, C3 convertase, C5 convertase.

In certain other embodiments the iRNA agent (e.g., the iRNA agent in a modular composition described herein) silences a chemokine or receptor thereof, e.g., TNFI, TNFJ, IL-1I, IL-1J, 1L-2, IL-2R, IL-4, IL-4R, IL-5, IL-6, IL-8, TNFRI, TNFRII, IgE, SCYA11, CCR3.

In other embodiments the iRNA agent (e.g., the iRNA agent in a modular composition described herein) silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, I-309.

Pain

In one aspect, the invention features, a method of treating a subject, e.g., a human, at risk for or afflicted with acute pain or chronic pain. The method comprises administering the modular composition of the invention to a subject in need thereof, thereby treating the subject. The nucleic acid that is administered will depend on the type of pain being treated.

In certain other embodiments the iRNA agent (e.g., the iRNA agent in a modular composition described herein) silences a component of an ion channel.

In certain other embodiments the iRNA agent (e.g., the iRNA agent in a modular composition described herein) silences a neurotransmitter receptor or ligand.

In one aspect, the invention features, a method of treating a subject, e.g., a human, at risk for or afflicted with a neurological disease or disorder. The method includes:

providing an iRNA agent (e.g., the iRNA agent in a modular composition described herein) which iRNA is homologous to and can silence, e.g., by cleavage, a gene which mediates a neurological disease or disorder;

administering the to a subject, thereby treating the subject.

Neurological Disorders

In certain embodiments the disease or disorder is a neurological disorder, including Alzheimer's Disease or Parkinson Disease. The method comprises administering the modular composition of the invention to a subject in need thereof, thereby treating the subject. The nucleic acid that is administered will depend on the type of neurological disorder being treated.

In certain other embodiments the iRNA agent (e.g., the iRNA agent in a modular composition described herein) silences an amyloid-family gene, e.g., APP; a presenilin gene, e.g., PSEN1 and PSEN2, or I-synuclein.

In some embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In certain other embodiments the iRNA agent (e.g., the iRNA agent in a modular composition described herein) silences HD, DRPLA, SCA1, SCA2, MJD1, CACNL1A4, SCA7, SCA8.

Loss of Heterozygosity

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with an iRNA agent (e.g., the iRNA agent in a modular composition described herein) of the invention. The iRNA agent (e.g., the iRNA agent in a modular composition described herein) is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH.

One of ordinary skill in the art can identify essential genes which are in proximity to tumor suppressor genes, and which are within a LOH region which includes the tumor suppressor gene. The gene encoding the large subunit of human RNA polymerase H, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, the invention features, a method of treating a disorder characterized by LOH, e.g., cancer. The method comprises optionally, determining the genotype of the allele of a gene in the region of LOH and determining the genotype of both alleles of the gene in a normal cell; providing an iRNA agent (e.g., the iRNA agent in a modular composition described herein) which preferentially cleaves or silences the allele found in the LOH cells; and administering the iRNA to the subject, thereby treating the disorder.

The invention also includes a iRNA agent (e.g., the iRNA agent in a modular composition described herein) disclosed herein, e.g, an iRNA agent (e.g., the iRNA agent in a modular composition described herein) which can preferentially silence, e.g., cleave, one allele of a polymorphic gene.

In another aspect, the invention provides a method of cleaving or silencing more than one gene with an iRNA agent (e.g., the iRNA agent in a modular composition described herein). In these embodiments the iRNA agent (e.g., the iRNA agent in a modular composition described herein) is selected so that it has sufficient homology to a sequence found in more than one gene. For example, the sequence AAGCTGGCCCTG-GACATGGAGAT (SEQ ID NO:36) is conserved between mouse lamin B1, lamin B2, keratin complex 2-gene 1 and lamin A/C. Thus an iRNA agent (e.g., the iRNA agent in a modular composition described herein) targeted to this sequence would effectively silence the entire collection of genes.

The invention also includes an iRNA agent (e.g., the iRNA agent in a modular composition described herein) disclosed herein, which can silence more than one gene.

Routes of Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. A composition that includes a iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes may be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

Topical Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. In some embodiments, an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 µm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle. (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, erythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. A composition that includes an iRNA-agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can be administered to a subject by pulmonary delivery. Pulmonary delivery compositions can be delivered by inhalation by the patient of a dispersion so that the composition, for example, iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellar and dry powder-based formulations. Delivery can be achieved with liquid nebulizers, aerosol-based inhalers, and dry powder dispersion devices. Metered-dose devices are may be used. One of the benefits of using an atomizer or inhaler is that the potential for contamination is minimized because the devices are self contained. Dry powder dispersion devices, for example, deliver drugs that may be readily formulated as dry powders. A iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." For example, the average particle size is less than about 10 µm in diameter with a relatively uniform spheroidal shape distribution. In some embodiments, the diameter is less than about 7.5 µm and in some embodiments less than about 5.0 µm. Usually the particle size distribution is between about 0.1 µm and about 5 µm in diameter, sometimes about 0.3 µm to about 5 µm.

The term "dry" means that the composition has a moisture content below about 10% by weight (% w) water, usually below about 5% w and in some cases less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A group of carbohydrates may includes lactose, trehalose, raffinose maltodextrins, and mannitol. Suitable polypeptides include aspartame. Amino acids include alanine and glycine, with glycine being used in some embodiments.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate may be used in some embodiments.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery

For ease of exposition the formulations, compositions and methods in this section are discussed largely with regard to unmodified iRNA agents. It may be understood, however, that these formulations, compositions and methods can be practiced with other iRNA agents, e.g., modified iRNA agents, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Devices

For ease of exposition the devices, formulations, compositions and methods in this section are discussed largely with regard to unmodified iRNA agents. It may be understood, however, that these devices, formulations, compositions and methods can be practiced with other iRNA agents, e.g., modified iRNA agents, and such practice is within the invention. An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can be disposed on or in a device, e.g., a device which implanted or otherwise placed in a subject. Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a iRNA, e.g., a device can release insulin.

Other devices include artificial joints, e.g., hip joints, and other orthopedic implants.

In one embodiment, unit doses or measured doses of a composition that includes iRNA are dispensed by an implanted device. The device can include a sensor that monitors a parameter within a subject. For example, the device can include pump, e.g., and, optionally, associated electronics.

Tissue, e.g., cells or organs can be treated with An iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) ex vivo and then administered or implanted in a subject.

The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation.

Introduction of treated tissue, whether autologous or transplant, can be combined with other therapies.

In some implementations, the iRNA treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). Exemplary devices include condoms, diaphragms, IUD (implantable uterine devices, sponges, vaginal sheaths, and birth control devices. In one embodiment, the iRNA is chosen to inactive sperm or egg. In another embodiment, the iRNA is chosen to be complementary to a viral or pathogen RNA, e.g., an RNA of an STD. In some instances, the iRNA composition can include a spermicide.

Dosage

In one aspect, the invention features a method of administering an iRNA agent, e.g., a double-stranded iRNA agent, or siRNA agent, to a subject (e.g., a human subject). The method includes administering a unit dose of the iRNA agent, e.g., a siRNA agent, e.g., double stranded siRNA agent that (a) the double-stranded part is 19-25 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nanomole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nanomole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous or intramuscular), an inhaled dose, or a topical application. In some embodiments dosages may be less than 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than an iRNA agent, e.g., other than a double-stranded iRNA agent, or siRNA agent. In another embodiment, the subject has atherosclerosis and the effective dose of an iRNA agent, e.g., a double-stranded iRNA agent, or siRNA agent, is administered in combination with, e.g., after surgical intervention, e.g., angioplasty.

In one embodiment, a subject is administered an initial dose and one or more maintenance doses of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are, for example, administered no more than once every 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

In some cases, a patient is treated with a iRNA agent in conjunction with other therapeutic modalities. For example, a patient being treated for a viral disease, e.g., an HIV associated disease (e.g., AIDS), may be administered a iRNA agent specific for a target gene essential to the virus in conjunction with a known antiviral agent (e.g., a protease inhibitor or reverse transcriptase inhibitor). In another example, a patient being treated for cancer may be administered a iRNA agent specific for a target essential for tumor cell proliferation in conjunction with a chemotherapy.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g., nasal, buccal, pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) can include a single treatment or, for example, can include a series of treatments. It will also be appreciated that the effective dosage of a iRNA agent such as a siRNA agent used for treatment may increase or decrease over the course of a particular treatment. Changes in dosage may result and become apparent from the results of diagnostic assays as described herein. For example, the subject can be monitored after administering a iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA. The transgenic animal can be deficient for the corresponding endogenous RNA. In another embodiment, the composition for testing includes a iRNA agent that is complementary, at least in an internal region, to a sequence that is conserved between the target RNA in the animal model and the target RNA in a human.

The inventors have discovered that iRNA agents described herein can be administered to mammals, particularly large mammals such as nonhuman primates or humans in a number of ways.

In one embodiment, the administration of the iRNA agent, e.g., a double-stranded iRNA agent, or siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of iRNA agents described herein.

Accordingly, an iRNA agent, e.g., a double-stranded iRNA agent, or siRNA agent, (e.g., a precursor, e.g., a larger iRNA agent which can be processed into a siRNA agent, or a DNA which encodes a an iRNA agent, e.g., a double-stranded iRNA agent, or siRNA agent, or precursor thereof) described herein, e.g., a therapeutically effective amount of a iRNA agent described herein, e.g., a iRNA agent having a double stranded region of less than 40, and, for example, less than 30 nucleotides and having one or two 1-3 nucleotide single strand 3' overhangs can be administered rectally, e.g., introduced through the rectum into the lower or upper colon. This approach is particularly useful in the treatment of, inflammatory disorders, disorders characterized by unwanted cell proliferation, e.g., polyps, or colon cancer.

The medication can be delivered to a site in the colon by introducing a dispensing device, e.g., a flexible, camera-guided device similar to that used for inspection of the colon or removal of polyps, which includes means for delivery of the medication.

The rectal administration of the iRNA agent is by means of an enema. The iRNA agent of the enema can be dissolved in a saline or buffered solution. The rectal administration can also by means of a suppository, which can include other ingredients, e.g., an excipient, e.g., cocoa butter or hydroxypropylmethylcellulose.

Any of the iRNA agents described herein can be administered orally, e.g., in the form of tablets, capsules, gel capsules, lozenges, troches or liquid syrups. Further, the composition can be applied topically to a surface of the oral cavity.

Any of the iRNA agents described herein can be administered buccally. For example, the medication can be sprayed into the buccal cavity or applied directly, e.g., in a liquid, solid, or gel form to a surface in the buccal cavity. This administration is particularly desirable for the treatment of inflammations of the buccal cavity, e.g., the gums or tongue, e.g., in one embodiment, the buccal administration is by spraying into the cavity, e.g., without inhalation, from a dispenser, e.g., a metered dose spray dispenser that dispenses the pharmaceutical composition and a propellant.

Any of the iRNA agents described herein can be administered to ocular tissue. For example, the medications can be applied to the surface of the eye or nearby tissue, e.g., the inside of the eyelid. They can be applied topically, e.g., by spraying, in drops, as an eyewash, or an ointment. Administration can be provided by the subject or by another person, e.g., a health care provider. The medication can be provided in measured doses or in a dispenser which delivers a metered dose. The medication can also be administered to the interior of the eye, and can be introduced by a needle or other delivery device which can introduce it to a selected area or structure. Ocular treatment is particularly desirable for treating inflammation of the eye or nearby tissue.

Any of the iRNA agents described herein can be administered directly to the skin. For example, the medication can be applied topically or delivered in a layer of the skin, e.g., by the use of a microneedle or a battery of microneedles which penetrate into the skin, but, for example, not into the underlying muscle tissue. Administration of the iRNA agent composition can be topical. Topical applications can, for example, deliver the composition to the dermis or epidermis of a subject. Topical administration can be in the form of transdermal patches, ointments, lotions, creams, gels, drops, suppositories, sprays, liquids or powders. A composition for topical administration can be formulated as a liposome, micelle, emulsion, or other lipophilic molecular assembly. The transdermal administration can be applied with at least one penetration enhancer, such as iontophoresis, phonophoresis, and sonophoresis.

Any of the iRNA agents described herein can be administered to the pulmonary system. Pulmonary administration can be achieved by inhalation or by the introduction of a delivery device into the pulmonary system, e.g., by introducing a delivery device which can dispense the medication. Certain embodiments may use a method of pulmonary delivery by inhalation. The medication can be provided in a dispenser which delivers the medication, e.g., wet or dry, in a form sufficiently small such that it can be inhaled. The device can deliver a metered dose of medication. The subject, or another person, can administer the medication.

Pulmonary delivery is effective not only for disorders which directly affect pulmonary tissue, but also for disorders which affect other tissue.

iRNA agents can be formulated as a liquid or nonliquid, e.g., a powder, crystal, or aerosol for pulmonary delivery.

Any of the iRNA agents described herein can be administered nasally. Nasal administration can be achieved by introduction of a delivery device into the nose, e.g., by introducing a delivery device which can dispense the medication. Methods of nasal delivery include spray, aerosol, liquid, e.g., by drops, or by topical administration to a surface of the nasal cavity. The medication can be provided in a dispenser with delivery of the medication, e.g., wet or dry, in a form sufficiently small such that it can be inhaled. The device can deliver a metered dose of medication. The subject, or another person, can administer the medication.

Nasal delivery is effective not only for disorders which directly affect nasal tissue, but also for disorders which affect other tissue iRNA agents can be formulated as a liquid or nonliquid, e.g., a powder, crystal, or for nasal delivery.

An iRNA agent can be packaged in a viral natural capsid or in a chemically or enzymatically produced artificial capsid or structure derived therefrom.

The dosage of a pharmaceutical composition including a iRNA agent can be administered in order to alleviate the symptoms of a disease state, e.g., cancer or a cardiovascular disease. A subject can be treated with the pharmaceutical composition by any of the methods mentioned above.

Gene expression in a subject can be modulated by administering a pharmaceutical composition including an iRNA agent.

A subject can be treated by administering a defined amount of an iRNA agent, e.g., a double-stranded iRNA agent, or siRNA agent, (e.g., a precursor, e.g., a larger iRNA agent which can be processed into a siRNA agent) composition that is in a powdered form, e.g., a collection of microparticles, such as crystalline particles. The composition can include a plurality of iRNA agents, e.g., specific for one or more different endogenous target RNAs. The method can include other features described herein.

A subject can be treated by administering a defined amount of an iRNA agent composition that is prepared by a method that includes spray-drying, i.e., atomizing a liquid solution, emulsion, or suspension, immediately exposing the droplets to a drying gas, and collecting the resulting porous powder particles. The composition can include a plurality of iRNA agents, e.g., specific for one or more different endogenous target RNAs. The method can include other features described herein.

The iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), can be provided in a powdered, crystallized or other finely divided form, with or without a carrier, e.g., a micro- or nano-particle suitable for inhalation or other pulmonary delivery. This can include providing an aerosol preparation, e.g., an aerosolized spray-dried composition. The aerosol composition can be provided in and/or dispensed by a metered dose delivery device.

The subject can be treated for a condition treatable by inhalation, e.g., by aerosolizing a spray-dried iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) composition and inhaling the aerosolized composition. The iRNA agent can be an siRNA. The composition can include a plurality of iRNA agents, e.g., specific for one or more different endogenous target RNAs. The method can include other features described herein.

A subject can be treated by, for example, administering a composition including an effective/defined amount of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), wherein the composition is prepared by a method that includes spray-drying, lyophilization, vacuum drying, evaporation, fluid bed drying, or a combination of these techniques.

In another aspect, the invention features a method that includes: evaluating a parameter related to the abundance of a transcript in a cell of a subject; comparing the evaluated parameter to a reference value; and if the evaluated parameter has a preselected relationship to the reference value (e.g., it is greater), administering a iRNA agent (or a precursor, e.g., a larger iRNA agent which can be processed into a siRNA agent, or a DNA which encodes a iRNA agent or precursor thereof) to the subject. In one embodiment, the iRNA agent includes a sequence that is complementary to the evaluated transcript. For example, the parameter can be a direct measure of transcript levels, a measure of a protein level, a disease or disorder symptom or characterization (e.g., rate of cell proliferation and/or tumor mass, viral load).

In another aspect, the invention features a method that includes: administering a first amount of a composition that comprises an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) to a subject, wherein the iRNA agent includes a strand substantially complementary to a target nucleic acid; evaluating an activity associated with a protein encoded by the target nucleic acid; wherein the evaluation is used to determine if a second amount may be administered. In some embodiments the method includes administering a second amount of the composition, wherein the timing of administration or dosage of the second amount is a function of the evaluating. The method can include other features described herein.

In another aspect, the invention features a method of administering a source of a double-stranded iRNA agent (ds iRNA agent) to a subject. The method includes administering or implanting a source of a ds iRNA agent, e.g., a siRNA agent, that (a) includes a double-stranded region that is 19-25 nucleotides long, for example, 21-23 nucleotides, (b) is complementary to a target RNA (e.g., an endogenous RNA or a pathogen RNA), and, optionally, (c) includes at least one 3' overhang 1-5 nt long. In one embodiment, the source releases ds iRNA agent over time, e.g., the source is a controlled or a slow release source, e.g., a microparticle that gradually releases the ds iRNA agent. In another embodiment, the source is a pump, e.g., a pump that includes a sensor or a pump that can release one or more unit doses.

In one aspect, the invention features a pharmaceutical composition that includes an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) including a nucleotide sequence complementary to a target RNA, e.g., substantially and/or exactly complementary. The target RNA can be a transcript of an endogenous human gene. In one embodiment, the iRNA agent (a) is 19-25 nucleotides long, for example, 21-23 nucleotides, (b) is complementary to an endogenous target RNA, and, optionally, (c) includes at least one 3' overhang 1-5 nt long. In one embodiment, the pharmaceutical composition can be an emulsion, microemulsion, cream, jelly, or liposome.

In one example the pharmaceutical composition includes an iRNA agent mixed with a topical delivery agent. The topical delivery agent can be a plurality of microscopic vesicles. The microscopic vesicles can be liposomes. In some embodiments the liposomes are cationic liposomes.

In another aspect, the pharmaceutical composition includes an iRNA agent, e.g., a double-stranded iRNA agent, or siRNA agent (e.g., a precursor, e.g., a larger iRNA agent which can be processed into a siRNA agent, or a DNA which encodes an iRNA agent, e.g., a double-stranded iRNA agent, or siRNA agent, or precursor thereof) admixed with a topical penetration enhancer. In one embodiment, the topical penetration enhancer is a fatty acid. The fatty acid can be arachidonic acid, oleic acid, lauric acid, caprylic acid, capric acid, myristic acid, palmitic acid, stearic acid, linoleic acid, linolenic acid, dicaprate, tricaprate, monolein, dilaurin, glyceryl 1-monocaprate, 1-dodecylazacycloheptan-2-one, an acylcarnitine, an acylcholine, or a $C_{1-10}$ alkyl ester, monoglyceride, diglyceride or pharmaceutically acceptable salt thereof.

In another embodiment, the topical penetration enhancer is a bile salt. The bile salt can be cholic acid, dehydrocholic acid, deoxycholic acid, glucholic acid, glycholic acid, glycodeoxycholic acid, taurocholic acid, taurodeoxycholic acid, chenodeoxycholic acid, ursodeoxycholic acid, sodium tauro-24,25-dihydro-fusidate, sodium glycodihydrofusidate, polyoxyethylene-9-lauryl ether or a pharmaceutically acceptable salt thereof.

In another embodiment, the penetration enhancer is a chelating agent. The chelating agent can be EDTA, citric acid, a salicyclate, a N-acyl derivative of collagen, laureth-9, an N-amino acyl derivative of a beta-diketone or a mixture thereof.

In another embodiment, the penetration enhancer is a surfactant, e.g., an ionic or nonionic surfactant. The surfactant can be sodium lauryl sulfate, polyoxyethylene-9-lauryl ether, polyoxyethylene-20-cetyl ether, a perfluorchemical emulsion or mixture thereof.

In another embodiment, the penetration enhancer can be selected from a group consisting of unsaturated cyclic ureas, 1-alkyl-alkones, 1-alkenylazacyclo-alakanones, steroidal anti-inflammatory agents and mixtures thereof. In yet another embodiment the penetration enhancer can be a glycol, a pyrrol, an azone, or a terpenes.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a form suitable for oral delivery. In one embodiment, oral delivery can be used to deliver an iRNA agent composition to a cell or a region of the gastro-intestinal tract, e.g., small intestine, colon (e.g., to treat a colon cancer), and so forth. The oral delivery form can be tablets, capsules or gel capsules. In one embodiment, the iRNA agent of the pharmaceutical composition modulates expression of a cellular adhesion protein, modulates a rate of cellular proliferation, or has biological activity against eukaryotic pathogens or retroviruses. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methylcellulose phthalate or cellulose acetate phthalate.

In another embodiment, the oral dosage form of the pharmaceutical composition includes a penetration enhancer. The penetration enhancer can be a bile salt or a fatty acid. The bile salt can be ursodeoxycholic acid, chenodeoxycholic acid, and salts thereof. The fatty acid can be capric acid, lauric acid, and salts thereof.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an iRNA agent and a delivery vehicle. In one embodiment, the iRNA agent is (a) is 19-25 nucleotides long, for example, 21-23 nucleotides, (b) is complementary to an endogenous target RNA, and, optionally, (c) includes at least one 3' overhang 1-5 nucleotides long.

In one embodiment, the delivery vehicle can deliver an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) to a cell by a topical route of administration. The delivery vehicle can be microscopic vesicles. In one example the microscopic vesicles are liposomes. In some embodiments the liposomes are cationic liposomes. In another example the microscopic vesicles are micelles. In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in an injectable dosage form. In one embodiment, the injectable dosage form of the pharmaceutical composition includes sterile aqueous solutions or dispersions and sterile powders. In some embodiments the sterile solution can include a diluent such as water; saline solution; fixed oils, polyethylene glycols, glycerin, or propylene glycol.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in oral dosage form. In one embodiment, the oral dosage form is selected from the group consisting of tablets, capsules and gel capsules. In another embodiment, the pharmaceutical composition includes an enteric material that substantially prevents dissolution of the tablets, capsules or gel capsules in a mammalian stomach. In some embodiments the enteric material is a coating. The coating can be acetate phthalate, propylene glycol, sorbitan monoleate, cellulose acetate trimellitate, hydroxy propyl methyl cellulose phthalate or cellulose acetate phthalate. In one embodiment, the oral dosage form of the pharmaceutical composition includes a penetration enhancer, e.g., a penetration enhancer described herein.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a rectal dosage form. In one embodiment, the rectal dosage form is an enema. In another embodiment, the rectal dosage form is a suppository.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a vaginal dosage form. In one embodiment, the vaginal dosage form is a suppository. In another embodiment, the vaginal dosage form is a foam, cream, or gel.

In one aspect, the invention features a pharmaceutical composition including an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) in a pulmonary or nasal dosage form. In one embodiment, the iRNA agent is incorporated into a particle, e.g., a macroparticle, e.g., a microsphere. The particle can be produced by spray drying, lyophilization, evaporation, fluid bed drying, vacuum drying, or a combination thereof. The microsphere can be formulated as a suspension, a powder, or an implantable solid.

In one aspect, the invention features a spray-dried iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof) composition suitable for inhalation by a subject, including: (a) a therapeutically effective amount of a iRNA agent suitable for treating a condition in the subject by inhalation; (b) a pharmaceutically acceptable excipient selected from the group consisting of carbohydrates and amino acids; and (c) optionally, a dispersibility-enhancing amount of a physiologically-acceptable, water-soluble polypeptide.

In one embodiment, the excipient is a carbohydrate. The carbohydrate can be selected from the group consisting of monosaccharides, disaccharides, trisaccharides, and polysaccharides. In some embodiments the carbohydrate is a monosaccharide selected from the group consisting of dextrose, galactose, mannitol, D-mannose, sorbitol, and sorbose. In another embodiment the carbohydrate is a disaccharide selected from the group consisting of lactose, maltose, sucrose, and trehalose.

In another embodiment, the excipient is an amino acid. In one embodiment, the amino acid is a hydrophobic amino acid. In some embodiments the hydrophobic amino acid is selected from the group consisting of alanine, isoleucine, leucine, methionine, phenylalanine, proline, tryptophan, and valine. In yet another embodiment the amino acid is a polar amino acid. In some embodiments the amino acid is selected from the group consisting of arginine, histidine, lysine, cysteine, glycine, glutamine, serine, threonine, tyrosine, aspartic acid and glutamic acid.

In one embodiment, the dispersibility-enhancing polypeptide is selected from the group consisting of human serum albumin, α-lactalbumin, trypsinogen, and polyalanine.

In one embodiment, the spray-dried iRNA agent composition includes particles having a mass median diameter (MMD) of less than 10 microns. In another embodiment, the spray-dried iRNA agent composition includes particles having a mass median diameter of less than 5 microns. In yet another embodiment the spray-dried iRNA agent composition includes particles having a mass median aerodynamic diameter (MMAD) of less than 5 microns.

In certain other aspects, the invention provides kits that include a suitable container containing a pharmaceutical formulation of an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an iRNA agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In another aspect, the invention features a device, e.g., an implantable device, wherein the device can dispense or administer a composition that includes an iRNA agent, e.g., a double-stranded iRNA agent, or siRNA agent, (e.g., a precursor, e.g., a larger iRNA agent which can be processed into a siRNA agent, or a DNA which encodes an iRNA agent, e.g., a double-stranded iRNA agent, or siRNA agent, or precursor thereof), e.g., a iRNA agent that silences an endogenous transcript. In one embodiment, the device is coated with the composition. In another embodiment the iRNA agent is disposed within the device. In another embodiment, the device includes a mechanism to dispense a unit dose of the composition. In other embodiments the device releases the composition continuously, e.g., by diffusion. Exemplary devices include stents, catheters, pumps, artificial organs or organ components (e.g., artificial heart, a heart valve, etc.), and sutures.

As used herein, the term "crystalline" describes a solid having the structure or characteristics of a crystal, i.e., particles of three-dimensional structure in which the plane faces intersect at definite angles and in which there is a regular internal structure. The compositions of the invention may have different crystalline forms. Crystalline forms can be prepared by a variety of methods, including, for example, spray drying.

The invention is further illustrated by the following examples, which should not be construed as further limiting. The contents of all references, pending patent applications and published patents, cited throughout this application are hereby expressly incorporated by reference.

EXAMPLES

Example 1

Synthesis of a Modular Composition Comprising an iRNA, an Endosomolytic Component, and a Targeting Ligand An iRNA, or other nucleic acid (e.g., antagomir, aptamer, antisense oligonucleotide, decoy oligonucleotide) is provided. The endosomolytic component and the targeting ligand may be conjugated to the selected iRNA or nucleic acid in a variety of formats (FIGS. 1 and 2). In certain embodiments, a linker may be used between the nucleic acid and the endosomolytic component, the nucleic acid and the targeting ligand, and/or the targeting ligand and the endosomolytic component. This linker may be cleavable or non-cleavable, depending on the application.

Example 2

Oligonucleotide Synthesis and Purification

Step 1. Oligonucleotide Synthesis

All oligonucleotides were synthesized on an AKTAoligopilot synthesizer or on an ABI 394 DNA/RNA synthesizer. Commercially available controlled pore glass solid supports (rU-CPG, 2'-O-methly modified rA-CPG and 2'-O-methyl modified rG-CPG from Prime Synthesis) or the in-house synthesized solid support hydroxyprolinol-cholesterol-CPG were used for the synthesis. RNA phosphoramidites and 2'-O-methyl modified RNA phosphoramidites with standard protecting groups (5'-O-dimethoxytrityl-N6-benzoyl-2'-t-butyldimethylsilyl-adenosine-3'-O-N,N'-diisopropyl-2-cyanoethylphosphoramidite, 5'-O-dimethoxytrityl-N4-acetyl-2'-t-butyldimethylsilyl-cytidine-3'-O-N,N'-diisopropyl-2-cyanoethylphosphoramidite, 5'-O-dimethoxytrityl-N2-isobutryl-2'-t-butyldimethylsilylguanosine-3'-O-N,N'-diisopropyl-2-cyanoethylphosphoramidite, 5'-O-dimethoxytrityl-2'-t-butyldimethylsilyl-uridine-3'-O-N,N'-diisopropyl-2-cyanoethylphosphoramidite, 5'-O-dimethoxytrityl-N6-benzoyl-2'-O-methyl-adenosine-3'-O-N,N'-diisopropyl-2-cyanoethylphosphoramidite, 5'-O-dimethoxytrityl-N4-acetyl-2'-O-methyl-cytidine-3'-O-N,N'-diisopropyl-2-cyanoethylphosphoramidite, 5'-O-dimethoxytrityl-N2-isobutryl-2'-O-methyl-guanosine-3'-O-N,N'-diisopropyl-2-cyanoethylphosphoramidite, 5'-O-dimethoxytrityl-2'-O-methyl-uridine-3'-O-N,N'-diisopropyl-2-cyanoethylphosphoramidite and 5'-O-dimethoxytrityl-2'-deoxy-thymidine-3'-O-N,N'-diisopropyl-2-cyanoethylphosphoramidite) were obtained from Pierce Nucleic Acids Technologies and ChemGenes Research. The Quasar 570 phosphoramidite was obtained from Biosearch Technologies. The 5'-O-dimethoxytrityl-diisopropyl-2-cyanoethylphosphoramidite was obtained from ChemGenes Research. The 5% O-dimethoxytrityl-2'-t-butyldimethylsilyl-(2,4)-difluorotolyl-3'-O-N,N'-diisopropyl-2-cyanoethylphosphoramidite (DFT-phosphoramidite) and the 5'-O-dimethoxytrityl-2'-t-butyldimethylsilyl-9-(2-aminoethoxy)-phenoxazine-3'-O-N,N'-diisopropyl-2-cyanoethylphosphoramidite (G-clamp phosphoramidite) were synthesized in house.

For the syntheses on AKTAoligopilot synthesizer, all phosphoramidites were used at a concentration of 0.2 M in $CH_3CN$ except for guanosine and 2'-O-methyl-uridine, which were used at 0.2 M concentration in 10% $THF/CH_3CN$ (v/v). A coupling/recycling time of 16 minutes was used for all phosphoramidite couplings. The activator was 5-ethyl-thio-tetrazole (0.75 M, American International Chemicals). For the PO-oxidation, 50 mM iodine in water/pyridine (10:90 v/v) was used and for the PS-oxidation 2% PADS (GL Synthesis) in 2,6-lutidine/$CH_3CN$ (1:1 v/v) was used. For the syntheses on ABI 394 DNA/RNA synthesizer, all phosphoramidites, including DFT and G-clamp phosphoramidites were used at a concentration of 0.15 M in $CH_3CN$ except for 2'-O-methyl-uridine, which was used at 0.15 M concentration in 10% $THF/CH_3CN$ (v/v). A coupling time of 10 minutes was used for all phosphoramidite couplings. The activator was 5-ethyl-thio-tetrazole (0.25 M, Glen Research). For the PO-oxidation, 20 mM iodine in water/pyridine (Glen Research) was used and for the PS-oxidation 0.1M DDTT (AM Chemicals) in pyridine was used. Coupling of the Quasar 570 phosphoramidite was carried out on the ABI DNA/RNA synthesizer. The Quasar 570 phosphoramidite was used at a concentration of 0.1M in $CH_3CN$ with a coupling time of 10 mins. The activator was 5-ethyl-thio-tetrazole (0.25 M, Glen Research) and 0.1M DDTT (AM Chemicals) in pyridine was used for PS oxidation.

Step 2. Deprotection of Oligonucleotides

A. Sequences Synthesized on the AKTAoligopilot Synthesizer

After completion of synthesis, the support was transferred to a 100 mL glass bottle (VWR). The oligonucleotide was cleaved from the support with simultaneous deprotection of base and phosphate groups with 40 mL of a 40% aq. methyl amine (Aldrich) 90 mins at 45° C. The bottle was cooled briefly on ice and then the methylamine was filtered into a new 500 mL bottle. The CPG was washed three times with 40 mL portions of DMSO. The mixture was then cooled on dry ice.

In order to remove the tert-butyldimethylsilyl (TBDMS) groups at the 2' position, 60 mL triethylamine trihydrofluoride (Et3N-HF) was added to the above mixture. The mixture was heated at 40° C. for 60 minutes. The reaction was then quenched with 220 mL of 50 mM sodium acetate (pH 5.5) and stored in the freezer until purification.

B. Sequences Synthesized on the ABI DAN/RNA Synthesizer

After completion of synthesis, the support was transferred to a 15 mL tube (VWR). The oligonucleotide was cleaved from the support with simultaneous deprotection of base and phosphate groups with 7 mL of a 40% aq. methyl amine (Aldrich) 15 mins at 65° C. The bottle was cooled briefly on ice and then the methylamine was filtered into a 100 mL bottle (VWR). The CPG was washed three times with 7 mL portions of DMSO. The mixture was then cooled on dry ice.

In order to remove the tert-butyldimethylsilyl (TBDMS) groups at the 2' position, 10.5 mL triethylamine trihydrofluoride (Et3N-HF) was added to the above mixture. The mixture was heated at 60° C. for 15 minutes. The reaction was then quenched with 38.5 mL of 50 mM sodium acetate (pH 5.5) and stored in the freezer until purification.

Step 3. Quantitation of Crude Oligonucleotides

For all samples, a 10 μL aliquot was diluted with 990 μL of deionised nuclease free water (1.0 mL) and the absorbance reading at 260 nm was obtained.

Step 4. Purification of Oligonucleotides (a) Unconjugated Oligonucleotides

The unconjugated crude oligonucleotides were first analyzed by HPLC (Dionex PA 100). The buffers were 20 mM phosphate, pH 11 (buffer A); and 20 mM phosphate, 1.8 M NaBr, pH 11 (buffer B). The flow rate 1.0 mL/min and monitored wavelength was 260-280 nm. Injections of 5-15 μL were done for each sample.

The unconjugated samples were purified by HPLC on a TSK-Gel SuperQ-5PW (20) column packed in house (17.3×5 cm) or on a commercially available TSK-Gel SuperQ-5PW column (15×0.215 cm) available from TOSOH Bioscience. The buffers were 20 mM phosphate in 10% $CH_3CN$, pH 8.5 (buffer A) and 20 mM phosphate, 1.0 M NaBr in 10% $CH_3CN$, pH 8.5 (buffer B). The flow rate was 50.0 mL/min for the in house packed column and 10.0 ml/min for the commercially obtained column. Wavelengths of 260 and 294 nm were monitored. The fractions containing the full-length oligonucleotides were pooled together, evaporated, and reconstituted to ~100 mL with deionised water.

(b) Cholesterol-Conjugated Oligonucleotides

The cholesterol-conjugated crude oligonucleotides were first analyzed by LC/MS to determine purity. The cholesterol conjugated sequences were HPLC purified on RPC-Source15 reverse-phase columns packed in house (17.3×5 cm or 15×2 cm). The buffers were 20 mM NaOAc in 10% $CH_3CN$ (buffer A) and 20 mM NaOAc in 70% $CH_3CN$ (buffer B). The flow rate was 50.0 mL/min for the 17.3×5 cm column and 12.0 mL/min for the 15×2 cm column. Wavelengths of 260 and 284 nm were monitored. The fractions containing the full-length oligonucleotides were pooled, evaporated, and reconstituted to 100 mL with deionised water.

Step 5. Desalting of Purified Oligonucleotides

The purified oligonucleotides were desalted on either an AKTA Explorer or an AKTA Prime system (Amersham Biosciences) using a Sephadex G-25 column packed in house. First, the column was washed with water at a flow rate of 40 mL/min for 20-30 min. The sample was then applied in 40-60 mL fractions. The eluted salt-free fractions were combined, dried, and reconstituted in ~50 mL of RNase free water.

Step 6. Purity Analysis by Capillary Gel Electrophoresis (CGE), Ion-exchange HPLC (IEX), and Electrospray LC/Ms Approximately 0.3 OD of each of the desalted oligonucleotides were diluted in water to 300 μL and were analyzed by CGE, ion exchange HPLC, and LC/MS.

Step 7. Duplex Formation

For the fully double stranded duplexes, equimolar amounts of two strands were mixed together. The mixtures were frozen at −80° C. and dried under vacuum on a speed vac. Dried samples were then dissolved in 1×PBS to a final concentration of 40 mg/mL. The dissolved samples were heated to 95° C. for 5 min and slowly cooled to room temperature.

Step 8. Tm Determination

For the partial double stranded duplexes and hairpins melting temperatures were determined. For the duplexes, equimolar amounts of the two single stranded RNAs were mixed together. The mixtures were frozen at −80° C. and dried under vacuum on a speed vac. Dried samples were then dissolved in 1×PBS to a final concentration of 2.5 μm. The dissolved samples were heated to 95° C. for 5 min and slowly cooled to room temperature. Denaturation curves were acquired between 10-90° C. at 260 nm with temperature ramp of 0.5° C./min using a Beckman spectrophotometer fitted with a 6-sample thermostated cell block. The Tm was then determined using the 1st derivative method of the manufacturer's supplied program.

Example 3

2'-F Oligonucleotide Synthesis

1. Oligonucleotide Synthesis:

All oligonucleotides were synthesized on an AKTAoligopilot synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O-N,N'-diisopropyl-2-cyanoethylphosphoramidite, 5'-O-dimethoxytrityl-N4-acetyl-2'-t-butyldimethylsilyl-cytidine-3'-O-N,N'-diisopropyl-2-cyanoethylphosphoramidite, 5'-O-dimethoxytrityl-N2-isobutryl-2'-t-butyldimethylsilyl-guanosine-3'-O-N,N'-diisopropyl-2-cyanoethylphosphoramidite, and 5'-O-dimethoxytrityl-2'-t-butyldimethylsilyl-uridine-3'-O-N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluoro-cytidine-3'-O-N,N'-diisopropyl-2-cyanoethyl-phosphoramidite and 5'-O-dimethoxytrityl-2'-fluoro-uridine-3'-O-N,N'-diisopropyl-2-cyanoethyl-phosphoramidite were purchased from (Promega). All phosphoramidites were used at a concentration of 0.2M in acetonitrile ($CH_3CN$) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used. The cholesterol phosphoramidite was synthesized in house, and used at a concentration of 0.1 M in dichloromethane. Coupling time for the cholesterol phosphoramidite was 16 minutes.

2. Deprotection-I (Nucleobase Deprotection)

After completion of synthesis, the support was transferred to a 100 mL glass bottle (VWR). The oligonucleotide was cleaved from the support with simultaneous deprotection of base and phosphate groups with 80 mL of a mixture of ethanolic ammonia [ammonia:ethanol (3:1)] for 6.5 h at 55° C. The bottle was cooled briefly on ice and then the ethanolic ammonia mixture was filtered into a new 250 mL bottle. The CPG was washed with 2×40 mL portions of ethanol/water (1:1 v/v). The volume of the mixture was then reduced to ~30 mL by roto-vap. The mixture was then frozen on dyince and dried under vacuum on a speed vac.

3. Deprotection-II (Removal of 2' TBDMS Group)

The dried residue was resuspended in 26 mL of triethylamine, triethylamine trihydrofluoride (TEA.3HF) and DMSO (3:4:6) and heated at 60° C. for 90 minutes to remove the tert-butyldimethylsilyl (TBDMS) groups at the 2' position. The reaction was then quenched with 50 mL of 20 mM sodium acetate and pH adjusted to 6.5, and stored in freezer until purification.

4. Quantitation of Crude Oligomer or Raw Analysis

For all samples, a 10 μl aliquot was diluted with 990 μl of deionised nuclease free water (1.0 mL) and absorbance reading obtained at 260 nm.

5. Purification of Oligomers (a) HPLC Purification

The crude oligomers were first analyzed by HPLC (Dionex PA 100). The buffer system was: A=20 mM phosphate pH 11, B=20 mM phosphate, 1.8 M NaBr, pH 11, flow rate 1.0 mL/min, and wavelength 260-280 nm. Inject 5-15 μl of the each sample. The unconjugated samples were purified by HPLC on a TSK-Gel SuperQ-5PW (20) column packed in house (17.3×5 cm). The buffer system was: A=20 mM phosphate in 10% ACN, pH 8.5 and B=20 mM phosphate, 1.0 M NaBr in 10% ACN, pH 8.5, with a flow rate of 50.0 mL/min, and wavelength 260 and 294. The 5'-cholesterol conjugated sequences were HPLC purified using a reverse-phase column. The buffer system was: A=20 mM TEAA in 10% ACN and B=20 mM TEAA in 70% ACN. The fractions containing the full length oligonucleotides were then pooled together, evaporated and reconstituted to 100 mL with deionised water.

6. Desalting of Purified Oligomer

The purified oligonucleotides were desalted using AKTA Explorer (Amersham Biosciences) using Sephadex G-25 column. First column was washed with water at a flow rate of 25 mL/min for 20-30 min. The sample was then applied in 25 mL fractions. The eluted salt-free fractions were combined together, dried down and reconstituted in 50 mL of RNase free water.

7. Capillary Gel Electrophoresis (CGE) and Electrospray LC/MS

Approximately 0.15 OD of desalted oligonucleotides were diluted in water to 150 μl and then pipetted into vials for CGE and LC/MS analysis.

Table 5 lists some of the oligonucleotides synthesized.

TABLE 5

Factor VII siRNA and the corresponding scrambled control modified with 2'-F and with or without cholesterol conjugation at the 5'-end of sense sequences.

| Sequence NAME | Sequence* | Cal Mass | Found Mass | CGE (%) |
|---|---|---|---|---|
| AL-2918 | Q11GGAfUfCAfUfCfUfC AAGfUfCfUfUAfCdT*dT (SEQ ID NO: 37) | 7332.93 | 7333.61 | 99.91 |
| AL-2919 | Q11GGAfCfUAfCfUfCfU AAGfUfCfUfUAfCdT*dT (SEQ ID NO: 38) | 7332.93 | 7333.62 | 99.59 |
| AL-2920 | GGAfCfUAfCfUfCfUAA GfUfUfCfUAfCdT*dT (SEQ ID NO: 39) | 6628.93 | 6628.45 | 99.61 |

TABLE 5-continued

Factor VII siRNA and the corresponding scrambled control modified with 2'-F and with or without cholesterol conjugation at the 5'-end of sense sequences.

| Sequence NAME | Sequence* | Cal Mass | Found Mass | CGE (%) |
|---|---|---|---|---|
| AL-2921 | GfUAGAAfCfUfUAGA GfUAGfUfCfCdT*dT (SEQ ID NO: 40) | 6726.04 | 6725.78 | 96.01 |
| AL-4723 | GGAfUfCAfUfCfUfCAA GfUfCfUfUAfCdT*dT (SEQ ID NO: 41) | 6628.93 | 6628.47 | 98.94 |
| AL-4724 | GfUAAGAfCfUfUGAG AfUGAfUfCfCdT*dT (SEQ ID NO: 42) | 6726.04 | 6725.56 | 96.29 |

Q11 = cholesterol,
fN = 2'-fluro and
* = thioate linkage

TABLE 6

Listing of some Factor VII siRNA sequences conjugated with endosomolytic agents and targeting ligands.

| Target | Seq. ID NO | Strand (S/AS) | Sequence (5' to 3') |
|---|---|---|---|
| FVII | 43 | S | GGAufcfAufcfufcfAAGufcfufufAcfdTdT sL8 |
| FVII | 44 | S | GGAufcfAufcfufcfAAGufcfufufAcfdTdTsL99 |
| FVII | 45 | S | GGAufcfAufcfufcfAAGufcfufufAcfdTdTsQ8L99 |
| FVII | 46 | S | GGAufcfAufcfufcfAAGufcfufufAcfdTdTsQ8L8 |
| FVII | 47 | S | GGAufcfAufcfufcfAAGufcfufufAcfdTdTsQ8L99 |
| FVII | 48 | S | GGAufcfAufcfufcfAAGufcfufufAcfdTdTsQ96L8 |
| FVII | 49 | S | GGAufcfAufcfufcfAAGufcfufufAcfdTdTsQ11L8 |
| FVII | 50 | S | GGAufcfAufcfufcfAAGufcfufufAcfdTdTsQ11L99 |
| FVII | 51 | S | GGAufcfAufcfufcfAAGufcfufufAcfdTdTsQ8L10 |
| FVII | 52 | S | GGAufcfAufcfufcfAAGufcfufufAcfdTdTsQ96L10 |
| FVII | 53 | S | GGAufcfAufcfufcfAAGufcfufufAcfdTdTsQ8L50 |
| FVII | 54 | S | GGAufcfAufcfufcfAAGufcfufufAcfdTdTsQ96L8 |
| FVII | 55 | S | GGAufcfAufcfufcfAAGufcfufufAcfdTdTsL50 |
| FVII | 56 | S | GGAufcfAufcfufcfAAGufcfufufAcfdTdTsQ8Q11L50 |
| FVII | 57 | S | GGAufcfAufcfufcfAAGufcfufufAcfdTdTsQ96Q11L8 |
| FVII | 58 | S | GGAufcfAufcfufcfAAGufcfufufAcfdTdTsQ8L110 |
| FVII | 59 | S | GGAufcfAufcfufcfAAGufcfufufAcfdTdTsQ96L110 |
| FVII | 60 | S | GGAufcfAufcfufcfAAGufcfufufAcfdTdTsQ8Q11L110 |
| FVII | 61 | S | GGAufcfAufcfufcfAAGufcfufufAcfdTdTsQ96Q8L110 |
| FVII | 62 | S | GGAufcfAufcfufcfAAGufcfufufAcfdTdTsQ11Q8L110 |
| FVII | 63 | S | GGAufcfAufcfufcfAAGufcfufufAcfdTdTsQ11Q96L110 |
| FVII | 64 | S | GGAufcfAufcfufcfAAGufcfufufAcfdTdTsQ8L80 |
| FVII | 65 | S | GGAufcfAufcfufcfAAGufcfufufAcfdTdTsQ96L80 |
| FVII | 66 | S | GGAufcfAufcfufcfAAGufcfufufAcfdTdTsQ8Q11L80 |
| FVII | 67 | S | GGAufcfAufcfufcfAAGufcfufufAcfdTdTsQ96Q8L80 |
| FVII | 68 | S | GGAufcfAufcfufcfAAGufcfufufAcfdTdTsQ11Q8L80 |
| FVII | 69 | S | GGAufcfAufcfufcfAAGufcfufufAcfdTdTsQ11Q96L80 |
| FVII | 70 | S | GGAufcfAufcfufcfAAGufcfufufAcfdTdTsQ8L90 |
| FVII | 71 | S | GGAufcfAufcfufcfAAGufcfufufAcfdTdTsQ96L90 |
| FVII | 72 | S | GGAufcfAufcfufcfAAGufcfufufAcfdTdTsQ8Q11L90 |
| FVII | 73 | S | GGAufcfAufcfufcfAAGufcfufufAcfdTdTsQ96Q8L90 |
| FVII | 74 | S | GGAufcfAufcfufcfAAGufcfufufAcfdTdTsQ11Q8L90 |
| FVII | 75 | S | GGAufcfAufcfufcfAAGufcfufufAcfdTdTsQ11Q96L90 |
| FVII | 76 | S | GGAufcfAufcfufcfAAGufcfufufAcfdTdTs(n x Q94)L50, where n = 1 to 10 |
| FVII | 77 | S | GGAufcfAufcfufcfAAGufcfufufAcfdTdTsQ96(n x Q94)L135, where n = 0 to 10 |
| FVII | 78 | S | GGAufcfAufcfufcfAAGufcfufufAcfdTdTs(n x Q94)Q11L50, where n = 1 to 10 |
| FVII | 79 | S | GGAufcfAufcfufcfAAGufcfufufAcfdTdTsQ11(n x Q94)L50; where n = 1 to 10 |
| FVII | 80 | S | GGAufcfAufcfufcfAAGufcfufufAcfdTdTs(n x Q94)Q96L10; where n = 1 to 10 |
| FVII | 81 | S | GGAufcfAufcfufcfAAGufcfufufAcfdTdTsQ96(n x Q94)L10; where n = 0 to 10 |
| FVII | 82 | S | GGAufcfAufcfufcfAAGufcfufufAcfdTdTsQ96Q11(n x Q94)L135; where n = 1 to 10 |
| FVII | 83 | S | GGAufcfAufcfufcfAAGufcfufufAcfdTdTsQ11(n x Q94)L50; where n = 0 to 10 |
| FVII | 84 | S | GGAufcfAufcfufcfAAGufcfufufAcfdTdTs(n x Q94)Q11(n x Q94)L50, where n = 1 to 10 |

US 8,575,123 B2
// 113 114

TABLE 6-continued

Listing of some Factor VII siRNA sequences conjugated with endosomolytic agents and targeting ligands.

| Target | Seq. ID NO | Strand (S/AS) | Sequence (5' to 3') |
|---|---|---|---|
| FVII | 85 | S | GGAufcfAufcfufcfAAGufcfufufufAcfdTdTs(n x Q94)Q11(n x Q94)L50; where n = 1 to 10 |
| FVII | 86 | S | GGAufcfAufcfufcfAAGufcfufufufAcfdTdTs(n x Q94)Q96(n x Q94)L10; where n = 1 to 10 |
| FVII | 87 | S | GGAufcfAufcfufcfAAGufcfufufufAcfdTdTs(n x Q94)Q96(n x Q94)L10; where n = 0 to 10 |
| FVII | 88 | S | GGAufcfAufcfufcfAAGufcfufufufAcfdTdTsQ96(n x Q94)Q11(n x Q94)L135; where n = 1 to 10 |
| FVII | 89 | S | GGAufcfAufcfufcfAAGufcfufufufAcfdTdTs(n x Q94)Q11(n x Q94)L50; where n = 0 to 10 |
| FVII | 90 | S | GGAufcfAufcfufcfAAGufcfufufufAcfdTdTs(n x Q94)L96L110, where n = 1 to 10 |
| FVII | 91 | S | GGAufcfAufcfufcfAAGufcfufufufAcfdTdTsQ96(n x Q94)L110, where n = 0 to 10 |
| FVII | 92 | S | GGAufcfAufcfufcfAAGufcfufufufAcfdTdTs(n x Q94)Q11L110, where n = 1 to 10 |
| FVII | 93 | S | GGAufcfAufcfufcfAAGufcfufufufAcfdTdTsQ11(n x Q94)L110; where n = 1 to 10 |
| FVII | 94 | S | GGAufcfAufcfufcfAAGufcfufufufAcfdTdTs(n x Q94)Q96L110; where n = 1 to 10 |
| FVII | 95 | S | GGAufcfAufcfufcfAAGufcfufufufAcfdTdTs(n x Q94)Q96Q11L110; where n = 1 to 10 |
| FVII | 96 | S | GGAufcfAufcfufcfAAGufcfufufufAcfdTdTs(n x Q94)Q11Q96L110; where n = 1 to 10 |
| FVII | 97 | S | GGAufcfAufcfufcfAAGufcfufufufAcfdTdTs(n x Q94)Q11Q96(n x Q94)L110; where n = 1 to 10 |
| FVII | 98 | S | GGAufcfAufcfufcfAAGufcfufufufAcfdTdTs(n x Q94)Q96L110; where n = 1 to 10 |
| FVII | 99 | S | GGAufcfAufcfufcfAAGufcfufufufAcfdTdTsQ96(n x Q94)L110; where n = 0 to 10 |
| FVII | 100 | S | GGAufcfAufcfufcfAAGufcfufufufAcfdTdTsQ96Q11(n x Q94)L110; where n = 1 to 10 |
| FVII | 101 | S | GGAufcfAufcfufcfAAGufcfufufufAcfdTdTsQ11(n x Q94)L110; where n = 0 to 10 |
| FVII | 102 | S | GGAufcfAufcfufcfAAGufcfufufufAcfdTdTs(n x Q94)Q11(n x Q94)Q96L110, where n = 1 to 10 |
| FVII | 103 | S | GGAufcfAufcfufcfAAGufcfufufufAcfdTdTs(n x Q94)Q11(n x Q94)L110; where n = 1 to 10 |
| FYII | 104 | S | GGAufcfAufcfufcfAAGufcfufufufAcfdTdTs(n x Q94)Q11(n x Q94)Q11L110; where n = 1 to 10 |
| FVII | 105 | S | GGAufcfAufcfufcfAAGufcfufufufAcfdTdTs(n x Q94)Q96(n x Q94)Q11L110; where n = 1 to 10 |
| FVII | 106 | S | GGAufcfAufcfufcfAAGufcfufufufAcfdTdTs(n x Q94)Q96(n x Q94)Q11L110; where n = 0 to 10 |
| FVII | 107 | S | GGAufcfAufcfufcfAAGufcfufufufAcfdTdTsQ96(n x Q94)Q11(n x Q94)L110; where n = 1 to 10 |
| FVII | 108 | S | GGAufcfAufcfufcfAAGufcfufufufAcfdTdTs(n x Q94)Q11(n x Q94)Q96L110; where n = 0 to 10 |
| FVII | 109 | S | GGAufcfAufcfufcfAAGufcfufufufAcfdTdTs(n x Q94)L96L80, where n = 1 to 10 |
| FVII | 110 | S | GGAufcfAufcfufcfAAGufcfufufufAcfdTdTsQ96(n x Q94)L80, where n = 0 to 10 |
| FVII | 111 | S | GGAufcfAufcfufcfAAGufcfufufufAcfdTdTs(n x Q94)Q11L80, where n = 1 to 10 |
| FVII | 112 | S | GGAufcfAufcfufcfAAGufcfufufufAcfdTdTsQ11(n x Q94)L80; where n = 1 to 10 |
| FVII | 113 | S | GGAufcfAufcfufcfAAGufcfufufufAcfdTdTs(n x Q94)Q96L80; where n = 1 to 10 |
| FVII | 114 | S | GGAufcfAufcfufcfAAGufcfufufufAcfdTdTs(n x Q94)Q96Q11L80; where n = 1 to 10 |
| FVII | 115 | S | GGAufcfAufcfufcfAAGufcfufufufAcfdTdTs(n x Q94)Q11Q96L80; where n = 1 to 10 |
| FVII | 116 | S | GGAufcfAufcfufcfAAGufcfufufufAcfdTdTs(n x Q94)Q11Q96(n x Q94)L80; where n = 1 to 10 |
| FVII | 117 | S | GGAufcfAufcfufcfAAGufcfufufufAcfdTdTs(n x Q94)Q11 (n x Q94)Q96L80; where n = 1 to 10 |
| FVII | 118 | S | GGAufcfAufcfufcfAAGufcfufufufAcfdTdTsQ96(n x Q94)L80; where n = 0 to 10 |
| FVII | 119 | S | GGAufcfAufcfufcfAAGufcfufufufAcfdTdTsQ96Q11(n x Q94)L80; where n = 1 to 10 |
| FVII | 120 | S | GGAufcfAufcfufcfAAGufcfufufufAcfdTdTsQ11(n x Q94)L80; where n = 0 to 10 |
| FVII | 121 | S | GGAufcfAufcfufcfAAGufcfufufufAcfdTdTs(n x Q94)Q11(n x Q94)Q96L80, where n = 1 to 10 |

TABLE 6-continued

Listing of some Factor VII siRNA sequences conjugated with endosomolytic agents and targeting ligands.

| Target | Seq. ID NO | Strand (S/AS) | Sequence (5' to 3') |
|---|---|---|---|
| FVII | 122 | S | GGAufcfAufcfufcfAAGufcfufufAc TABLE 6-continued Listing of some Factor VII siRNA sequencesconjugated with endosomolytic agents and targeting ligands.

| Target | Seq. ID NO | Strand (S/AS) | Sequence (5' to 3') |
|---|---|---|---|
| FVII | 167 | S | GGAufcfAufcfufcfAAGufcfufufAcfdTdTs(n × Q94)Q7L110; where n = 1 to 10 |
| FVII | 168 | S | GGAufcfAufcfufcfAAGufcfufufAcfdTdTsQ7(n × Q94)L110; where n = 0 to 10 |
| FVII | 169 | S | GGAufcfAufcfufcfAAGufcfufufAcfdTdTsQ7Q11(n × Q94)L110; where n = 1 to 10 |
| FVII | 170 | S | GGAufcfAufcfufcfAAGufcfufufAcfdTdTs(n × Q94)Q7(n × Q94)L110, where n = 1 to 10 |
| FVII | 171 | S | GGAufcfAufcfufcfAAGufcfufufAcfdTdTs(n × Q94)Q11(n × Q94)Q7L110; where n = 0 to 10 |
| FVII | 172 | S | GGAufcfAufcfufcfAAGufcfufufAcfdTdTs(n × Q94)Q7L80, where n = 1 to 10 |
| FVII | 173 | S | GGAufcfAufcfufcfAAGufcfufufAcfdTdTsQ7(n × Q94)L80; where n = 1 to 10 |
| FVII | 174 | S | GGAufcfAufcfufcfAAGufcfufufAcfdTdTs(n × Q94)Q7L80; where n = 1 to 10 |
| FVII | 175 | S | GGAufcfAufcfufcfAAGufcfufufAcfdTdTsQ7(n × Q94)L80; where n = 0 to 10 |
| FVII | 176 | S | GGAufcfAufcfufcfAAGufcfufufAcfdTdTsQ7Q11(n × Q94)L80; where n = 1 to 10 |
| FVII | 177 | S | GGAufcfAufcfufcfAAGufcfufufAcfdTdTs(n × Q94)Q7(n × Q94)L80, where n = 1 to 10 |
| FVII | 178 | S | GGAufcfAufcfufcfAAGufcfufufAcfdTdTs(n × Q94)Q11(n × Q94)Q7L80; where n = 0 to 10 |
| FVII | 179 | S | GGAufcfAufcfufcfAAGufcfufufAcfdTdTs(n × Q94)Q7L90, where n = 1 to 10 |
| FVII | 180 | S | GGAufcfAufcfufcfAAGufcfufufAcfdTdTsQ7(n × Q94)L90; where n = 1 to 10 |
| FVII | 181 | S | GGAufcfAufcfufcfAAGufcfufufAcfdTdTs(n × Q94)Q7L90; where n = 1 to 10 |
| FVII | 182 | S | GGAufcfAufcfufcfAAGufcfufufAcfdTdTsQ7(n × Q94)L80; where n = 0 to 10 |
| FVII | 183 | S | GGAufcfAufcfufcfAAGufcfufufAcfdTdTsQ7Q11(n × Q94)L90; where n = 1 to 10 |
| FVII | 184 | S | GGAufcfAufcfufcfAAGufcfufufAcfdTdTs(n × Q94)Q7(n × Q94)L90, where n = 1 to 10 |
| FVII | 185 | S | GGAufcfAufcfufcfAAGufcfufufAcfdTdTs(n × Q94)Q11(n × Q94)Q7L90; where n = 0 to 10 |
| FVII | 186 | AS | GufAAGAcfufufGAGAufGAufcfcfdTsdT |

Note:
nf is 2'-fluoro modified nucleotide, s is phosophorothioate linkage, other symbols are as shown below.

L132:

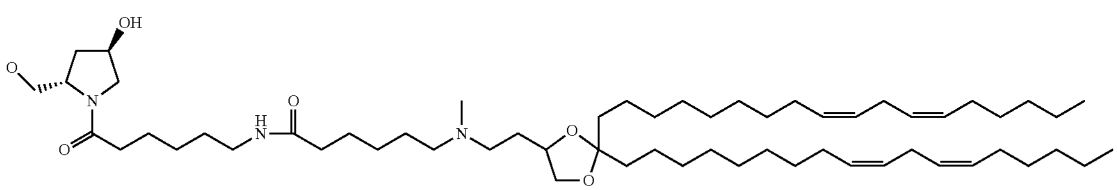

Chemical Formula: $C_{59}H_{106}N_3O_6$
Exact Mass: 952.8082
Molecular Weight: 953.4894

L133:

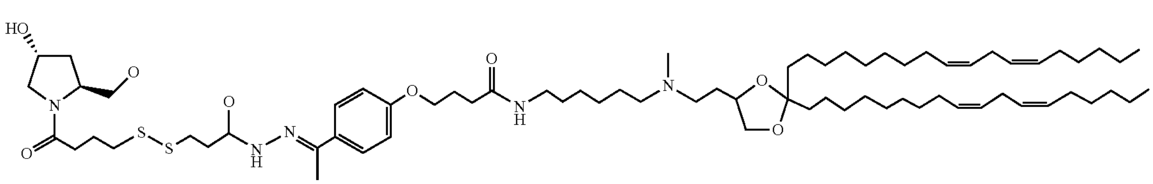

Chemical Formula: $C_{72}H_{132}N_5O_6S_2$
Exact Mass: 1248.87
Molecular Weight: 1249.8978

TABLE 6-continued

Listing of some Factor VII siRNA sequencesconjugated with endosomolytic agents and targeting ligands.

| Target | Seq. ID NO | Strand (S/AS) | Sequence (5' to 3') |
|---|---|---|---|

L134:

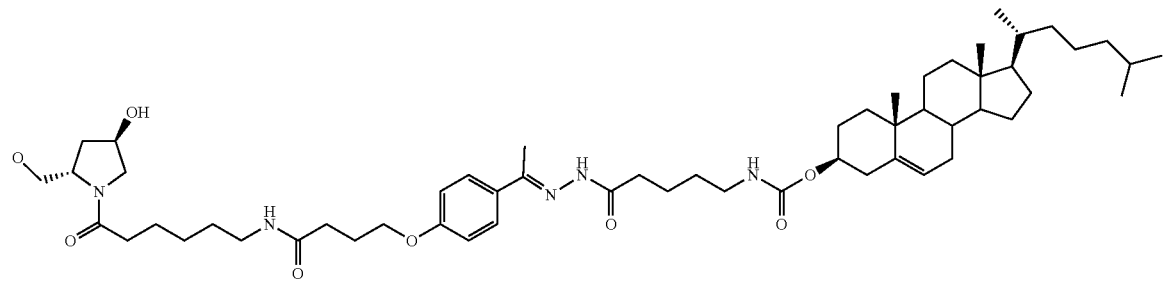

Chemical Formula: $C_{56}H_{65}N_5O_6$
Exact Mass: 958.6633
Molecular Weight: 959.3266

L135:

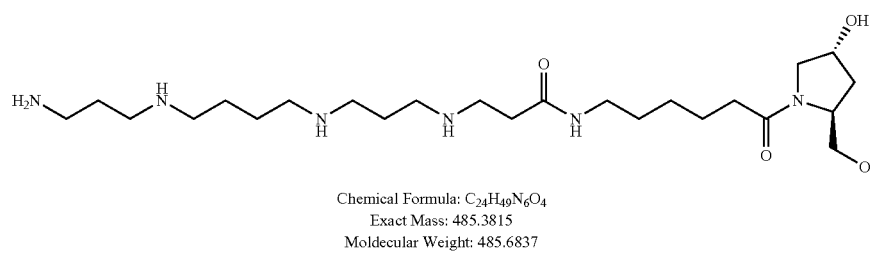

Chemical Formula: $C_{24}H_{49}N_6O_4$
Exact Mass: 485.3815
Moldecular Weight: 485.6837

L136:

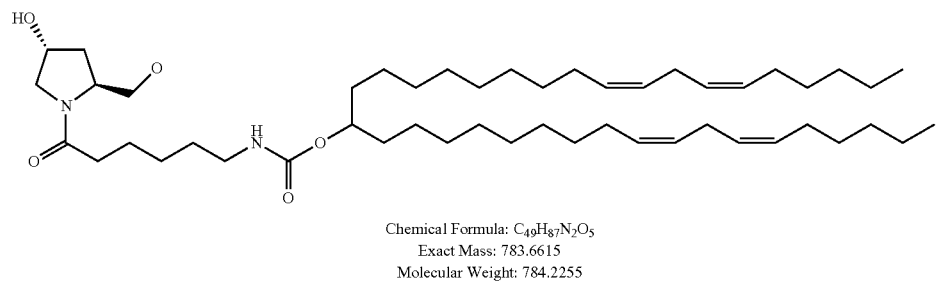

Chemical Formula: $C_{49}H_{87}N_2O_5$
Exact Mass: 783.6615
Molecular Weight: 784.2255

Q7:

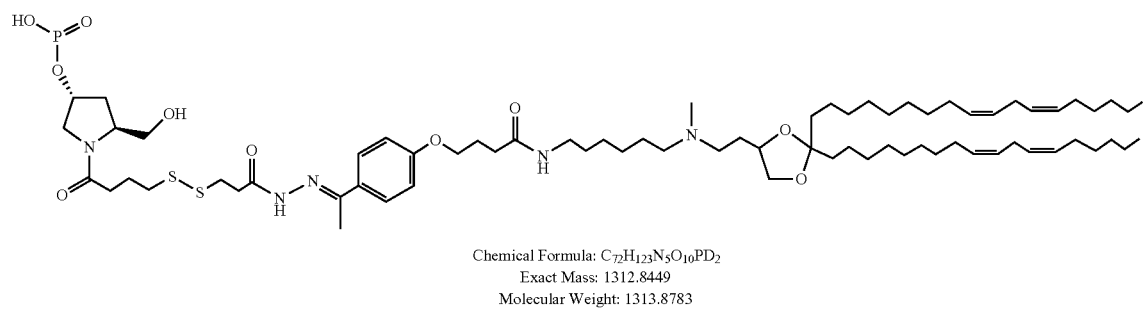

Chemical Formula: $C_{72}H_{123}N_5O_{10}PD_2$
Exact Mass: 1312.8449
Molecular Weight: 1313.8783

TABLE 6-continued

Listing of some Factor VII siRNA sequences conjugated with endosomolytic agents and targeting ligands.

| Target | Seq. ID NO | Strand (S/AS) | Sequence (5' to 3') |
|---|---|---|---|

Q94:

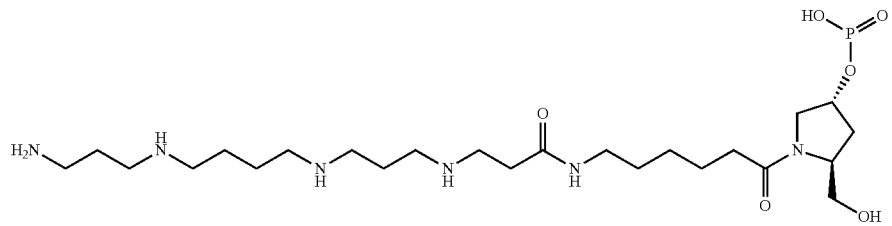

Chemical Formula: $C_{24}H_{50}N_6O_8P$
Exact Mass: 549.3529
Moldecular Weight: 549.6642

Q95:

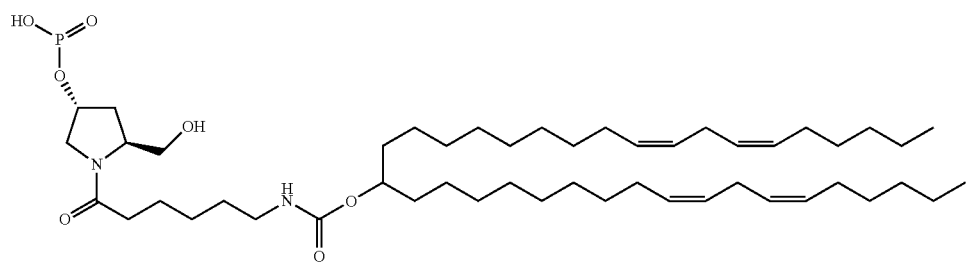

Chemical Formula: $C_{49}H_{88}N_2O_7P$
Exact Mass: 847.6329
Molecular Weight: 848.2060

Q96:

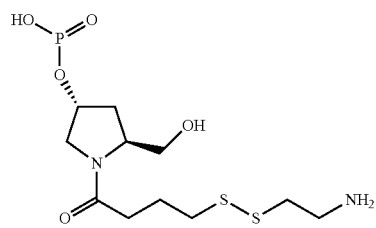

Chemical Formula: $C_{11}H_{22}N_2O_5PS_2$
Exact Mass: 357.0708
Molecular Weight: 357.4065

L99:

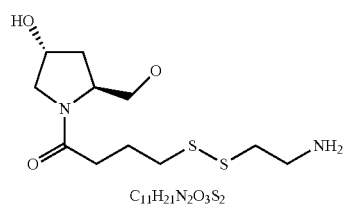

$C_{11}H_{21}N_2O_3S_2$
Exact Mass: 293.0994
Mol. Wt.: 293.4260

TABLE 6-continued
Listing of some Factor VII siRNA sequences conjugated with endosomolytic agents and targeting ligands.
| Target | Seq. ID NO | Strand (S/AS) | Sequence (5' to 3') |
|---|---|---|---|
L8:
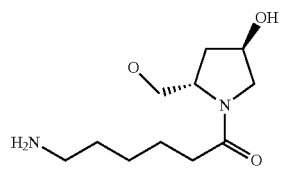
$C_{11}H_{21}N_2O_3$
Exact Mass: 229.1552
Mol.r Wt.: 229.2960
Q8:
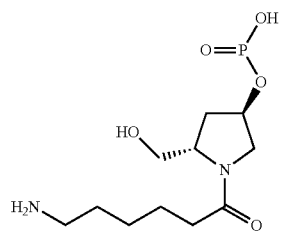
$C_{11}H_{22}N_2O_5P$
Exact Mass: 293.1266
Mol. Wt.: 293.2765
Q11:
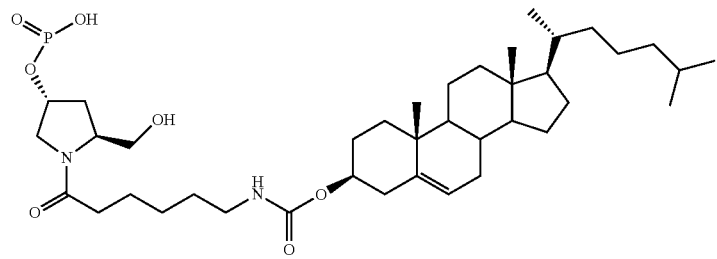
$C_{39}H_{66}N_2O_7P$
Exact Mass: 705.4608
Mol. Wt.: 705.9243
L10:
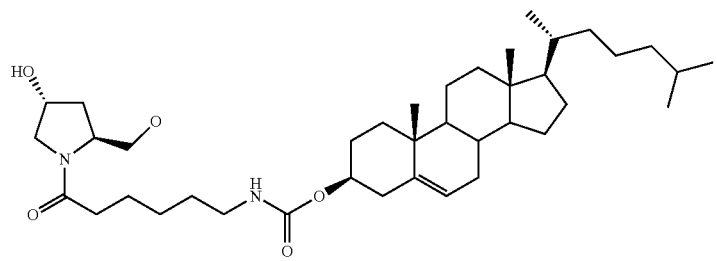
$C_{39}H_{65}N_2O_5$
Exact Mass: 641.4893
Mol. Wt.: 641.9438

TABLE 6-continued
Listing of some Factor VII siRNA sequences conjugated with endosomolytic agents and targeting ligands.
| Target | Seq. ID NO | Strand (S/AS) | Sequence (5' to 3') |
|---|---|---|---|
L80:
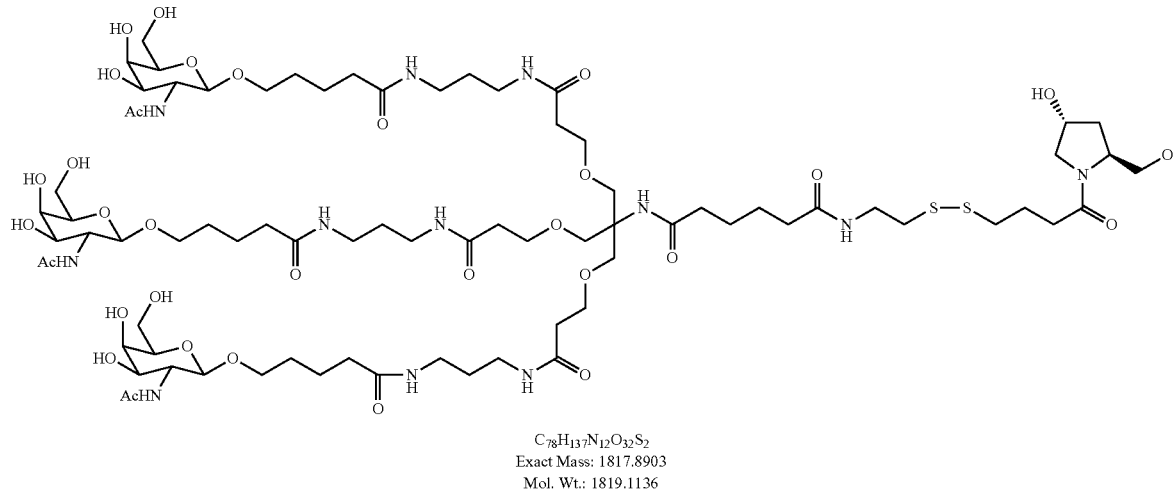
C₇₈H₁₃₇N₁₂O₃₂S₂
Exact Mass: 1817.8903
Mol. Wt.: 1819.1136
L90:
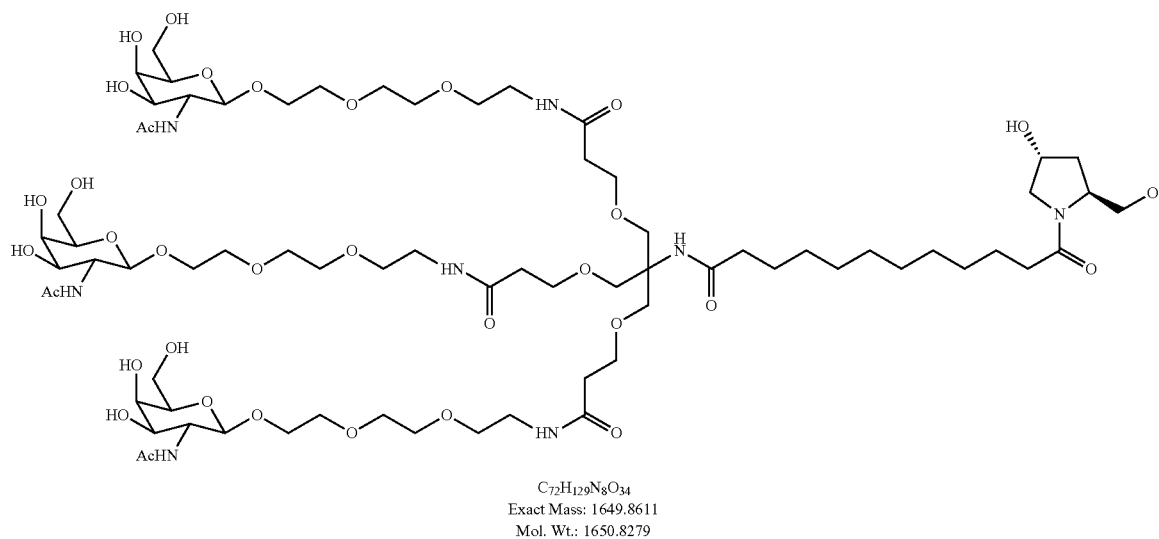
C₇₂H₁₂₉N₈O₃₄
Exact Mass: 1649.8611
Mol. Wt.: 1650.8279
L50:
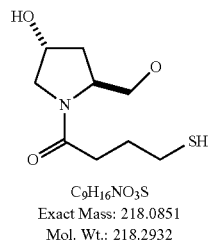
C₉H₁₆NO₃S
Exact Mass: 218.0851
Mol. Wt.: 218.2932

TABLE 6-continued

Listing of some Factor VII siRNA sequences conjugated with endosomolytic agents and targeting ligands.

| Target | Seq. ID NO | Strand (S/AS) | Sequence (5' to 3') |
|---|---|---|---|

L110
C$_{49}$H$_{86}$N$_{7}$O$_{19}$
Exact Mass: 1076.5979
Mol. Wt.: 1077.2426

Q67
C$_{25}$H$_{31}$N$_{8}$O$_{8}$P
Exact Mass: 602.2002
Mol. Wt.: 602.5362

Q17
C$_{30}$H$_{39}$N$_{9}$O$_{10}$P
Exact Mass: 716.2558
Mol. Wt.: 716.6587

While this invention has been particularly shown and described with reference to certain embodiments thereof, it will be understood by those skilled in the art that various changes in form and details may be made therein without departing from the scope of the invention encompassed by the appended claims. For example, the compositions and methods described herein may be useful when used in combination with any number of oligonucleotide modifications, targeting ligands, or membrane active agents, and methods related thereto, as well as other compositions and methods known in the art.

In particular, non-limiting examples of such compositions and methods, which may be used with the instant invention, may be found in the following co-owned applications, all of which are expressly incorporated by reference in their entirety: U.S. Ser. No. 11/115,989, filed Apr. 27, 2005; U.S. Ser. No. 11/119,533, filed Apr. 29, 2005; U.S. Ser. No. 11/186,915, filed Jul. 21, 2005; U.S. Ser. No. 11/834,140, filed Aug. 26, 2007; U.S. Ser. No. 11/197,753, filed Aug. 4, 2005; U.S. Ser. No. 11/099,430, filed Apr. 5, 2005; U.S. Ser. No. 11/170,798, filed Jun. 29, 2005; and U.S. Ser. No. 11/560,336, filed Jun. 14, 2004.

Example 3

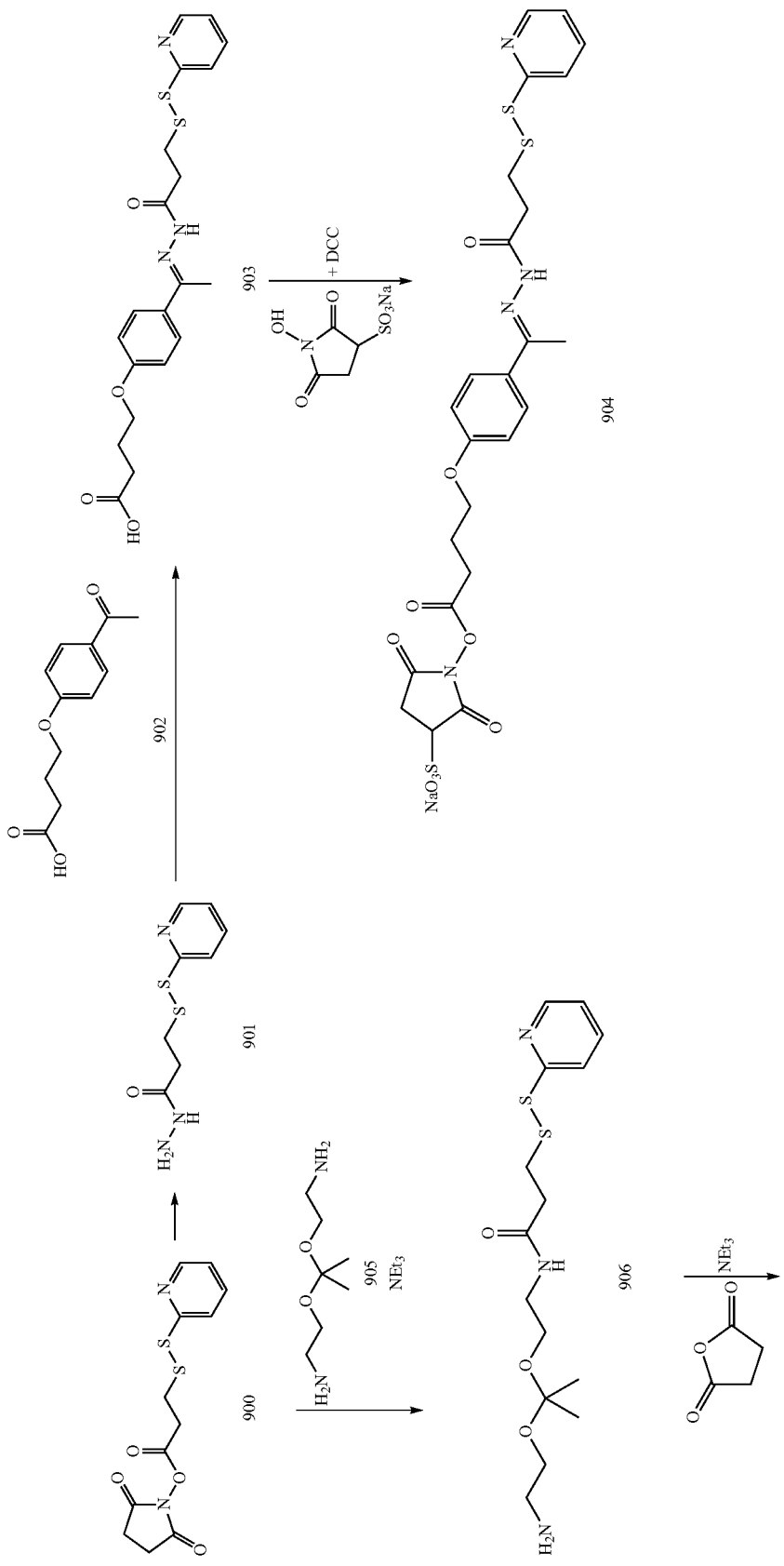

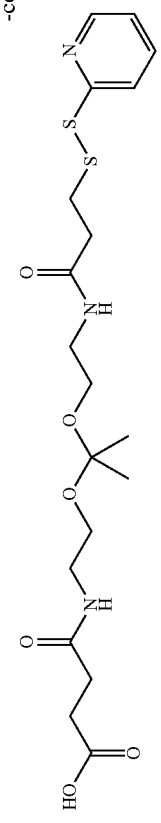
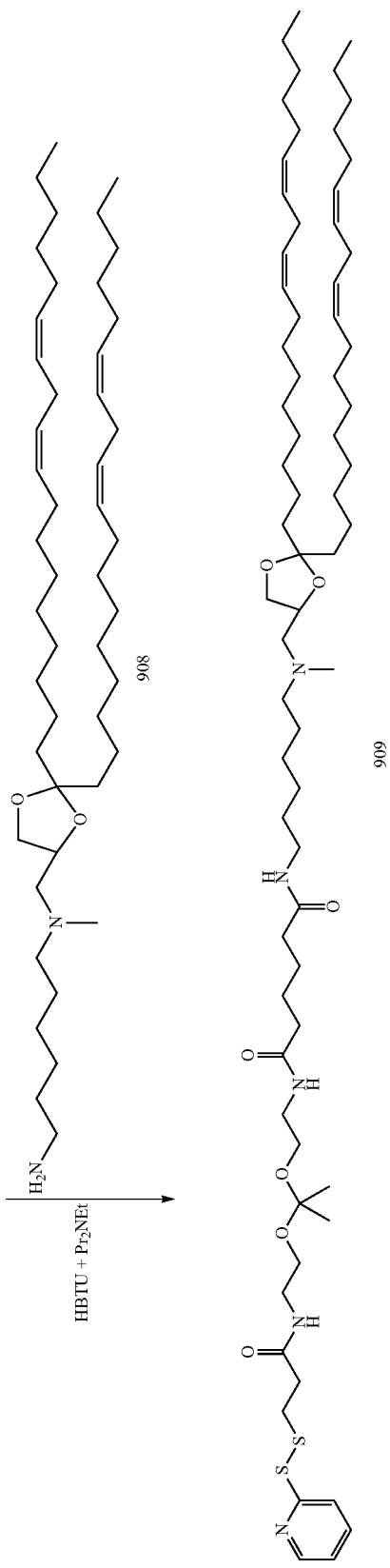

Synthesis of Compound 901: Hydrazone monohydrate (0.80 g, 16 mmol) was added to a solution of commercially available compound 900 (2.00 g, 6.40 mmol) in THF (30 mL) and the mixture was stirred for 1 h at room temperature. Filtration to remove NHS, removal of solvent then column chromatography gave pure compound 901, 0.89 g, 61%. $^1$H NMR (400 MHz, DMSO-d$_6$) δ 9.06 (s, 1H), 8.43 (d, J=4.1, 1H), 7.81 (td, J=7.9, 1.8, 1H), 7.73 (d, J=8.1, 1H), 7.26-7.18 (m, 1H), 2.99 (t, J=7.1, 2H), 2.51-2.45 (m, 2H), 2.42 (t, J=7.1, 2H). $^{13}$C NMR (101 MHz, DMSO-d$_6$) δ 170.16, 160.01, 150.56, 138.80, 122.15, 120.11, 34.85, 33.70. Electrospray/APCI dual mode MS (+ve): Molecular weight for $C_8H_{12}N_3O_8S_2$ (MH)$^+$ Calc. 230.0. Found 229.9

Synthesis of compound 903: Compound 902 was prepared as previously described (Bioconjugate Chem. 2002, 13, 47-58). An ethanolic solution (40 mL) of compound 902 (0.85 g, 3.84 mmol), compound 901 (0.88 g, 3.84 mmol) and AcOH (2 mL) was heated for 6 h at 45° C. On cooling to room temperature, the resulting colorless precipitate was collected by filtration and dried under suction. Yield of pure compound 903w as 1.49 g, 90%. $^1$H NMR (400 MHz, DMSO run at 80° C.) δ 11.82 (s, 1H), 10.18 (s, 1H), 8.48 (d, J=4.1, 1H), 7.81 (d, J=4.0, 2H), 7.69 (s, 2H), 7.24 (d, J=3.9, 1H), 6.96 (d, J=8.6, 2H), 4.10 (t, J=6.5, 2H), 3.20 (t, J=6.8, 2H), 3.07 (s, 2H), 2.43 (t, J=7.3, 2H), 2.24 (s, 3H), 2.02 (p, J=6.9, 2H). $^{13}$C NMR (101 MHz, DMSO-d$_6$, run at 80° C.) δ 174.16, 160.00, 159.90, 149.95, 137.96, 131.38, 127.97, 121.57, 120.16, 114.94, 67.57, 34.67, 30.74, 24.89. Electrospray/APCI dual mode MS (+ve): Molecular weight for $C_{20}H_{24}N_3O_4S_2$ (MH)$^+$ Calc. 434.1. Found 434.1

Synthesis of compound 904: A DMF solution (4 mL) of DCC (181 mg, 0.878 mmol) was added to a DMF solution (1 mL) of NaSO$_3$NHS (173 mg, 0.798 mmol), DMAP (5 mg, 0.04 mmol) and compound 903 (346 mg, 0.798 mmol) and stirred at room temperature for 18 h. The mixture was cooled on an ice bath for 2 h, the dicyclohexylurea was removed by filtration and the product was precipitated by addition of EtOAc (100 mL) to the filtrate with stirring. The pale cream solid, compound 904 (426 mg, 84%) was collected by filtration and dried in vacuo. The material was found to contain 10 mol % of NaSO$_3$NHS and 30 mol % water by elemental analysis. $^1$H NMR shows an E/Z mixture of isomers in 3:1 ratio which resolves to a single compound on heating. $^1$H NMR (400 MHz, DMSO-d$_6$) δ 10.41 (2×s, 1H), 8.43 (2×d, J=4.6, 1H), 7.85-7.75 (m, 2H), 7.65 (2×d, J=8.8, 2H), 7.32-7.12 (m, 1H), 6.94 (2×d, J=8.9, 2H), 4.07 (t, J=6.2, 2H), 3.94 (s, 1H), 3.15-3.01 (m, 4H), 2.91-2.78 (m, 3H), 2.74 (2×d, 5.4, 1H), 2.18 (2×s, 3H), 2.13-2.00 (m, 2H). Elemental Analysis Calculated for $(C_{24}H_{25}N_4NaO_9S_3)$ $(C_4H_4NNaO_6S)_{0.1}(H_2O)_{0.3}$: C: 44.42; H: 3.98; N: 8.71, S: 15.04. Found: C: 44.32; H: 4.01; N: 8.68, S: 15.26.

Synthesis of compound 906: Compound 905 was prepared as previously described (Paramonov, Sergey E.; Bachelder, Eric M.; Beaudette, Tristan T.; Standley, Stephany M.; Lee, Cameron C.; Dashe, Jesse; Frechet, Jean M. J. *Bioconjugate Chemistry* (2008), 19(4), 911-919)

A DCM solution (10 mL) of compound 900 (1.76 g, 5.6 mmol) was added to a cooled (−78° C.) methanolic solution (30 mL) of compound 905 (1.00 g, 6.16 mmol) and NEt$_3$ (1.4 g, 14 mmol). The mixture was warmed to room temperature over 2 h. The solvent was removed and the residue was subjected to column chromatography (0-10% of 7N methanolic NH$_3$ in DCM) to give compound 906 (1.38 g, 69%) as an unstable colorless oil which was used without delay in the next step of the reaction. Electrospray/APCI dual mode MS (+ve): Molecular weight for $C_{15}H_{26}N_3O_3S_2$ (MH)$^+$ Calc. 360.1. Found 360.1

Synthesis of compound 907: Succinic anhydride (578 mg, 5.77 mmol) was added to a DCM solution (50 mL) of freshly prepared compound 906 (1.38 g, 3.84 mmol) and NEt$_3$ (1.6 g, 15.4 mmol) and stirred at room temperature for 1 h. The mixture was subjected to column chromatographic purification to give compound 907 (1.83 g, 95%) as a partial triethylammonium salt. $^1$H NMR (400 MHz, DMSO-d$_6$) δ 11.99 (s, 1H), 8.44 (dd, J=4.8, 0.8, 1H), 8.04 (d, J=5.4, 1H), 7.92 (d, J=5.5, 1H), 7.86-7.79 (m, 1H), 7.75 (d, J=8.1, 1H), 7.23 (ddd, J=7.3, 4.8, 1.0, 1H), 3.32 (q, J=5.9, 6H), 3.14 (dq, J=11.8, 5.9, 4H), 2.99 (t, J=7.1, 2H), 2.37 (t, J=6.6, 2H), 2.28 (t, J=6.6, 2H), 1.24 (s, 6H). Electrospray/APCI dual mode MS (+ve): Molecular weight for $C_{19}H_{28}N_3O_6S_2$ (M−H)$^+$ Calc. 458.2. Found 458.0

Synthesis of compound 909: A DCM solution (8 mL) of compound 908 (385 mg, 0.54 mmol) was added all at once to a DMF solution (8 mL) of compound 907 (248 mg, 0.54 mmol), $^i$Pr$_2$NEt (0.17 g, 1.35 mmol) and HBTU (205 mg, 0.54 mmol) and the mixture was stirred at room temperature for 1 h. Aqueous workup then column chromatography gave pure 909 (488 mg, 78%) as a colorless oil. $^1$H NMR (400 MHz, CDCl$_3$) δ 8.58-8.41 (m, 1H), 7.77-7.59 (m, 2H), 7.12 (ddd, J=6.7, 4.9, 1.8, 1H), 7.05 (s, 1H), 6.31 (s, 1H), 6.20 (s, 1H), 5.45-5.21 (m, 8H), 4.27-4.15 (m, 1H), 4.13-4.03 (m, 1H), 3.60-3.34 (m, 9H), 3.22 (dd, J=13.1, 6.9, 2H), 3.09 (t, J=6.8, 2H), 2.78 (t, J=6.5, 4H), 2.66 (t, J=6.8, 2H), 2.59-2.47 (m, 5H), 2.47-2.31 (m, 3H), 2.27 (s, 3H), 2.13-1.98 (m, 8H), 1.68-1.54 (m, 8H), 1.54-1.42 (m, 4H), 1.42-1.1.9 (m, 42H), 0.90 (t, J=6.9, 6H). Electrospray/APCI dual mode MS (+ve): Molecular weight for: $C_{66}H_{116}N_5O_7S_2$ (MH)$^+$ Calc. 1154.8. Found 1154.8

Example 4

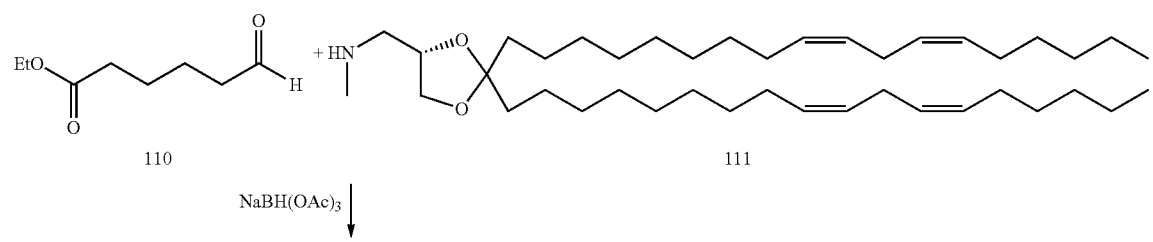

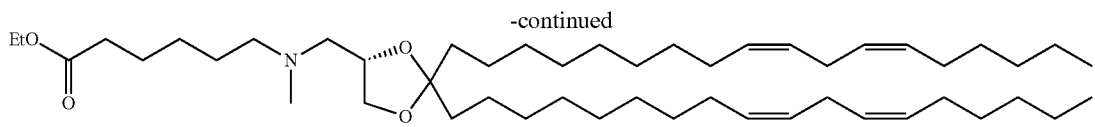

112

LiOH

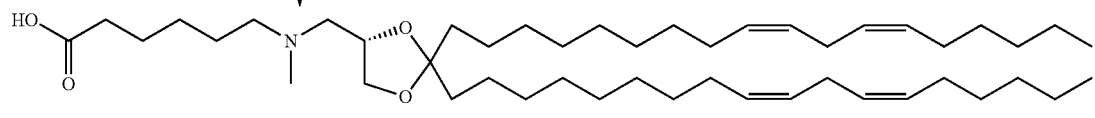

113

NHS, DCC, DMAP
DCM, rt, overnight

114

Synthesis of Compound 112: To the suspension of compound III (1.0 g, 1.629 mmol, 1.0 eq) and NaBH(OAc)$_3$ (0.46 g, 2.1 mmol, 1.3 eq) in DCM (12.0 ml) at 0° C. was added a solution of compound 110 (0.28 g, 1.79 mmol, 1.1 eq) in DCM (3.0 ml) at 0° C. under argon and the reaction was continued at room temperature for 1 hour. After completion of the starting material the reaction was quenched with 1N MaHCO$_3$, diluted with DCM, separated the two layers and the combined organics were washed with brine, dried over MgSO$_4$, concentrated and purified by column chromatography using DCM:MeOH (5%):triethylamine (0.5%) as a gradients to get pure 0.87 g (70%) of the ester compound 112. MS: Calc. mass for C$_{49}$H$_{89}$N$_2$O$_4$: 756.68. found: 757.7 (MH)$^+$.

Synthesis of compound 114: To a solution of compound 113 (3.0 g, 4.12 mmol, 1.0 eq) in dichloromethane (40.0 ml) was added solid N-hydroxysuccinimide (NHS) (0.52 g, 4.53 mmol, 1.1 eq) followed by DCC (0.93 g, 4.53 mmol, 1.1 eq), DMAP (0.05 g, 0.45 mmol, 0.1 eq) and the reaction was continued at room temperature under argon atmosphere. A white precipitate of urea derivative appears slowly in the reaction, continued the reaction for overnight, after complete consumption of the staring material, dichloromoethane was evaporated. Dissolved the reaction mixture in the ethylacetate (25.0 ml), cooled to ice bath temperature to complete precipitate out the DCC urea derivative. Filtered the solid and washed the solid with cold ethylacetate (2×6.0 ml), evaporated the solvent and dried on vacuum to give 3.4 g of the pure NHS ester of the compound 114 in quantitative yields, this was directly used in the next step without further purification. $^1$H NMR (400 MHz, CDCl$_3$): δ 5.50-5.16 (m, 8H), 4.52 (brs, 1H), 4.25-4.05 (m, 1H), 3.52 (t, J=7.9, 1H), 2.95-2.52 (m, 16H), 2.11-1.97 (m, 8H), 1.82-1.76 (m, 3H), 1.64-1.42 (m, 6H), 1.40-1.11 (m, 38H), 0.88 (t, J=6.8, 6H); MS: Calc. mass for C$_{51}$H$_{88}$N$_2$O$_6$: 824.6. found: 825.5 (MH)$^+$.

Example 5

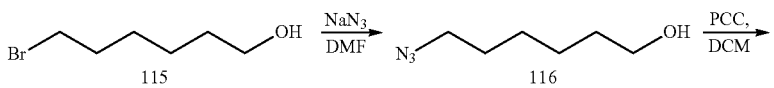

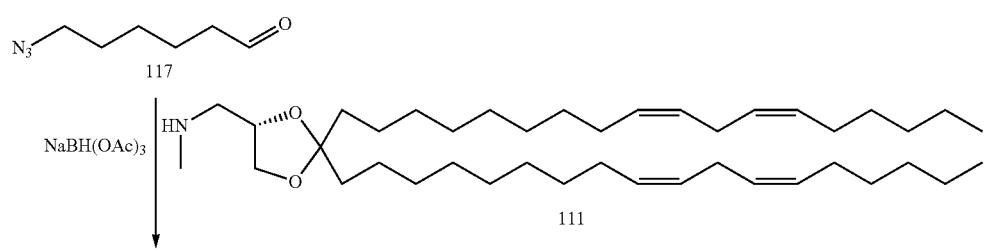

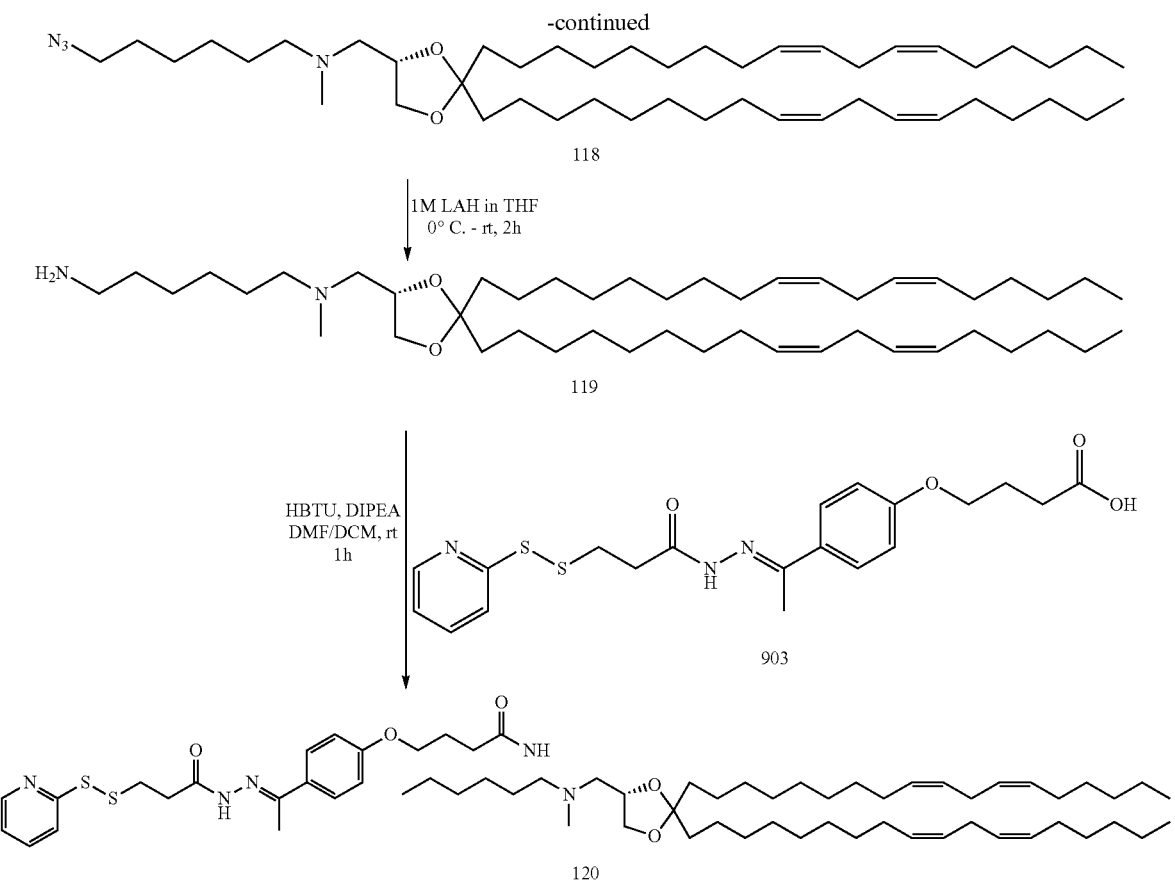

Synthesis of compound 116: A suspension of 6-bromo-1-hexanol 115 (55.2 mmol, 10 g), sodium azide (132 mmol, 8.6 g) in DMF (200 mL) was heated to 100° C. in an autoclave for 15 hours (TLC). The reaction mixture was then cooled to room temperature, diluted with diethyl ether (500 ml), washed with water (4×100 ml) followed by brine (1×100 ml), dried over sodium sulfate and evaporated at reduced pressure to obtain the desired product. The crude product was taken to the next stage without further purification. Yield (7.5 g, 94.5% as pale yellow oil). $^1$H NMR (400 MHz, CDCl$_3$): δ 1.41 (t, 4H, J=3.6 Hz), 1.61 (m, 4H), 3.28 (t, 2H, J=6.8 Hz), 3.66 (t, 2H, J=6.8 Hz).

Synthesis of compound 117: PCC (17 g, 78.6 mol) adsorbed on silica gel (17 g) was added portion wise over a period of 5 minutes to a solution of 116 (7.5 g, 52.4 mmol) product in dichloromethane (75 mL) at RT. After addition, the reaction mixture was stirred for 40 minutes (TLC). Reaction mass was filtered through celite bed, the filtrate was dried over sodium sulfate and evaporated at reduced pressure to obtain the required product as a pale yellow oil. The crude product was taken as such to the next stage without further purification (Yield, 6.60 g, 90%) $^1$H NMR (400 MHz, CDCl$_3$): δ 1.42 (m, 2H), 1.65 (m, 4H), 2.47 (t, 2H, J=7.2 Hz), 3.29 (t, 2H, J=6.8 Hz), 9.78 (s, 1H).

Synthesis of compound 118: Sodium triacetoxyborohydride (5.36 g, 24.36) was added portion-wise during 5 minutes to a solution of 111 (12 g, 19.50 mmol) in DCM (180 ml) at 0° C. To this suspension, was added 117 (3.03 g, 21.48 mmol) product drop-wise at 0° C. After complete addition, the reaction mixture was warmed to room temperature and stirred for another half an hour (TLC). Reaction mixture quenched with 1N NaHCO$_3$ (1×50 ml and, diluted with DCM (200 ml). Organic layer was separated, washed with water (2×100 ml), brine (1×100 ml), dried over sodium sulfate, filtered and evaporated at reduced pressure to obtained crude product, which was purified by flash silica gel chromatography. The required product was eluted with 7% EtOAc/Hexane (12.20 g, 84% as pale green oil). $^1$H NMR (400 MHz, CDCl$_3$): δ 0.89 (s, 6H), 1.27 (s, 40H), 1.47 (t, 2H, J=6.8 Hz), 1.58 (t, 6H, J=4.4 Hz), 2.05 (d, 8H, J=6 Hz), 2.27 (s, 3H), 2.43 (m, 3H), 2.56 (m, 1H), 2.77 (t, 4H, J=5.6 Hz), 3.26 (t, 2H, J=6.8 Hz), 3.53 (t, 1H, J=7.6 Hz), 4.08 (t, 1H, J=7.6 Hz), 4.2 (t, 1H, J=5.6 Hz), 5.33 m, 8H). $^{13}$C NMR (100 MHz, CDCl$_3$): δ 14.1, 22.6, 23.7, 25.6, 27.0, 27.1, 27.2, 28.8, 29.2, 29.3, 29.32, 29.5, 29.6, 29.7, 29.9, 31.5, 37.3, 37.7, 43.1, 51.4, 58.3, 60.1, 69.1, 74.4, 76.7, 77.0, 77.7. MS: Calc. mass for C$_{47}$H$_{86}$N$_4$O$_2$: 738.68. Found; 739.65 (MH)$^+$.

Synthesis of compound 119: To a solution of azido compound 118 (1.0 g, 1.35 mmol, 1.0 eq) in anhydrous THF (12.0 ml) was added 1M solution of LAH (2.03 ml, 2.03 mmol, 1.5 eq) in THF drop wise at 0° C. under argon. Reaction temperature was slowly increased and continued the reaction at room temperature for 2 hours. After complete consumption of the staring material, reaction was quenched with drop wise addition of saturated Na$_2$SO$_4$ solution at 0° C. Separated the solution form the solid and extracted into ethylacetate (25.0 ml), aqueous was extracted with ethylacetate until there is no product appears. Dried the combined organics over Na$_2$SO$_4$, filtered, evaporated the solvent and further dried under vacuum gave 0.82 g (86%) of the neat product 119, which was directly used in the next step without further purification. $^1$H NMR (400 MHz, CDCl$_3$) δ 5.46-5.22 (m, 8H), 4.24-4.14 (m, 1H), 4.08-4.05 (m, 1H), 3.52 (t, J=7.7, 1H), 2.77 (t, J=6.4, 4H), 2.67 (t, J=6.9, 2H), 2.54 (dd, J=12.8, 6.2, 1H), 2.46-2.30 (m, 3H), 2.26 (s, 3H), 2.10-1.96 (m, 8H), 1.57-1.52 (m, 4H), 1.45-1.40 (m, 4H), 1.39-1.16 (m, 42H), 0.88 (t, J=6.8, 6H); Calc. mass for $C_{47}H_{88}N_2O_2$: 712.6, abs. mass: 713.7 $(MH)^+$.

Synthesis of compound 120: Compound 903 (0.26 g, 0.6 mmol, 1.0 eq) was dissolved in 2.5 ml of DMF and added HBTU (0.27 g, 0.72 mmol, 1.2 eq), followed by DIPEA (0.33 ml, 1.8 mmol, 3.0 eq) at room temperature and stirred for 10 minutes under argon atmosphere. A solution of compound 119 (0.42 g, 0.6 mmol, 1.0 eq) in DMF:DCM (1:2, 3.0 ml) was added slowly to the above mixture at room temperature and continued the reaction until there is no starting material. After 2 hours, reaction mixture was poured onto ice and extracted with the DCM, the organic layer was washed with excess amount of water to remove all DMF present in the organic solution, further washed with $NaHCO_3$, dried on $MgOS_4$, concentrated and purified by column chromatography using DCM:MeOH (5%):triethylamine (0.5%) as a gradients to get 0.57 g (85%) of the pure compound 120. $^1$H NMR (400 MHz, $CDCl_3$) δ 8.63 (s, 1H), 8.43 (dd, J=4.8, 0.8, 1H), 7.76 (d, J=8.1, 1H), 7.64-7.59 (m, 2H), 7.07-7.00 (m, 1H), 6.87 (d, J=8.9, 2H), 5.52 (s, 1H), 5.43-5.19 (m, 8H), 4.27-4.12 (m, 1H), 4.05 (dd, J=13.2, 7.0, 3H), 3.52 (t, J=7.7, 1H), 3.30-3.11 (m, 6H), 2.76 (t, J=6.4, 4H), 2.53 (dd, J=12.7, 6.2, 1H), 2.45-2.31 (m, 5H), 2.25 (s, 3H), 2.19-2.10 (m, 5H), 2.04 (q, J=6.7, 8H), 1.64-1.40 (m, 9H), 1.37-1.18 (m, 40H), 0.88 (t, J=6.8, 6H); Calc. mass for $C_6H_{109}N_5O_5S_2$: 1127.7, abs. mass: 1128.5 $(MH)^+$.

Example 6

Synthesis of compound 6b: To a flame dried 500 mL RB flask, freshly activated Mg turnings (2.4 g, 100 mmol) were added and the flask was equipped with a magnetic stir bar, an addition funnel and a reflux condenser. This set-up was degassed and flushed with argon and 10 mL of anhydrous ether was added to the flask via syringe. The bromide 3 (26.5 g, 80.47 mmol) was dissolved in anhydrous ether (50 mL) and added to the addition funnel. About 5 mL of this ether solution was added to the Mg turnings while stirring vigorously. An exothermic reaction was noticed (to confirm/accelerate the Grignard reagent formation, 5 mg of iodine was added and immediate decolorization was observed confirming the formation of the Grignard reagent) and the ether started refluxing. The rest of the solution of the bromide was added dropwise while keeping the reaction under gentle reflux by cooling the flask in water. After the completion of the addition the reaction mixture was kept at 35° C. for 1 h and then cooled in ice bath. Ethyl formate (2.68 g, 36.2 mmol) was dissolved in anhydrous ether (40 mL) and transferred to the addition funnel and added dropwise to the reaction mixture with stirring. An exothermic reaction was observed and the reaction mixture started refluxing. After the initiation of the reaction the rest of the ethereal solution of formate was quickly added as a stream and the reaction mixture was stirred for a further period of 1 h at ambient temperature. The reaction was quenched by adding 10 mL of acetone dropwise followed by ice cold water (60 mL). The reaction mixture was treated with aq. $H_2SO_4$ (10% by volume, 300 mL) until the solution became homogeneous and the layers were separated. The aq. phase was extracted with ether (2×100 mL). The combined ether layers were dried ($Na_2SO_4$) and concentrated to get the

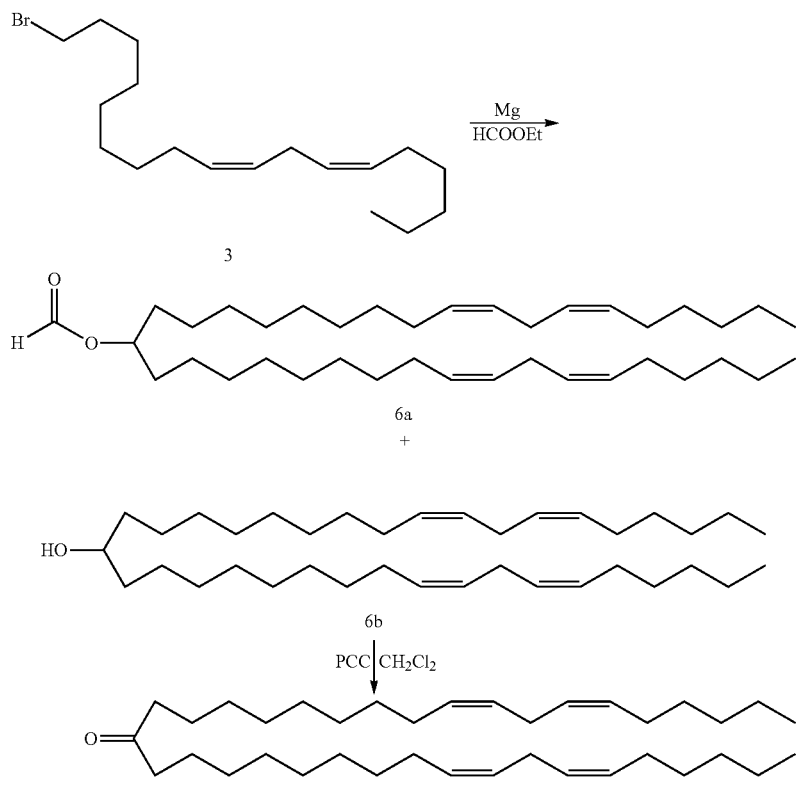

crude product which was purified by column (silica gel, 0-10% ether in hexanes) chromatography. The slightly less polar fractions were concentrated to get the formate 6a (1.9 g) and the pure product fractions were evaporated to provide the pure product 6b as a colorless oil (14.6 g, 78%).

Synthesis of compound 7: To a solution of the alcohol 6b (3 g, 5.68 mmol) in $CH_2Cl_2$ (60 mL), freshly activated 4 Å molecular sieves (50 g) were added and to this solution powdered PCC (4.9 g, 22.7 mmol) was added portion wise over a period of 20 minutes and the mixture was further stirred for 1 hour (Note: careful monitoring of the reaction is necessary in order to get good yields since prolonged reaction times leads to lower yields) and the TLC of the reaction mixture was followed every 10 minutes (5% ether in hexanes) After completion of the reaction, the reaction mixture was filtered through a pad of silica gel and the residue was washed with $CH_2Cl_2$ (400 mL). The filtrate was concentrated and the thus obtained crude product was further purified by column chromatography (silica gel, 1% $Et_2O$ in hexanes) to isolate the pure product 7 (2.9 g, 97%) as a colorless oil. $^1$H NMR ($CDCl_3$, 400 MHz) δ=5.33-5.21 (m, 8H), 2.69 (t, 4H), 2.30 (t, 4H), 2.05-1.95 (m, 8H), 1.55-1.45 (m, 2H), 1.35-1.15 (m, 18H), 0.82 (t, 3H). $^{13}$C NMR ($CDCl_3$) δ=211.90, 130.63, 130.54, 128.47, 128.41, 43.27, 33.04, 32.01, 30.93, 29.89, 29.86, 29.75, 29.74, 27.69, 26.11, 24.35, 23.06, 14.05. MS. Molecular weight calculated for $C_{37}H_{66}O$, Cal. 526.92. Found 528.02 $(MH)^+$.

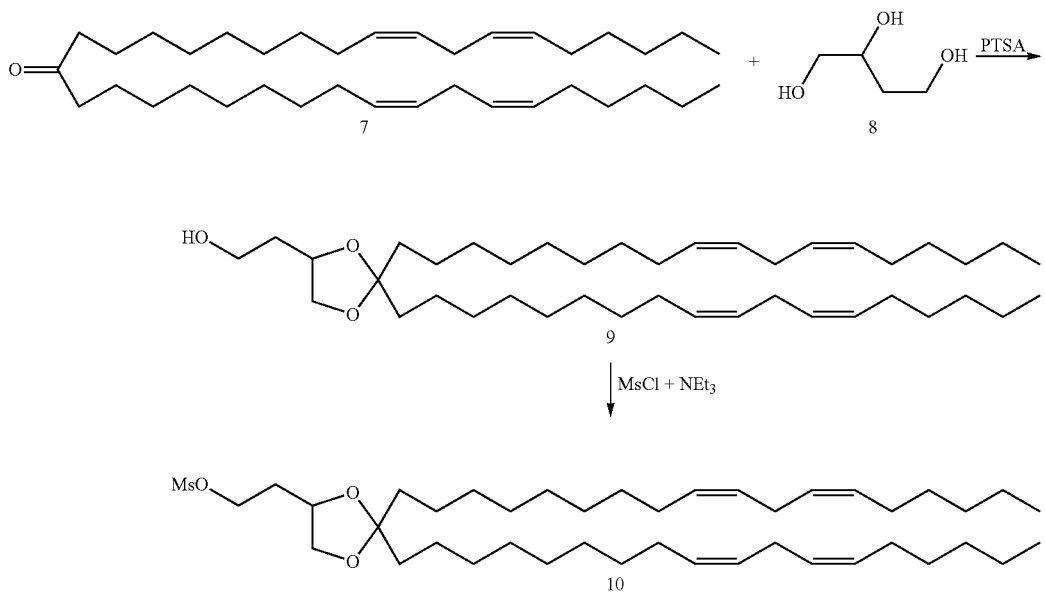

Synthesis of Compound 9: A mixture of compound 8 (10.6 g, 100 mmol), compound 7 (10.54 g, 20 mmol) and PTSA (0.1 eq) was heated under toluene reflux with Soxhlet extractor containing activated 4 Å molecular sieves for 3 h. Removal of solvent then column purification (silica gel, 0-30% EtOAc in hexanes) gave compound 9 (11 g, 90%) as a colorless oil. $^1$H NMR (400 MHz, $CDCl_3$) δ 5.45-5.24 (m, 8H), 4.30-4.17 (m, 1H), 4.08 (dd, J=7.8, 6.1, 1H), 3.80 (dd, J=10.6, 5.0, 3H), 3.53 (t, J=8.0, 1H), 2.77 (t, J=6.4, 5H), 2.29-2.18 (m, 1H), 2.05 (q, J=6.7, 9H), 1.86-1.74 (m, 2H), 1.59 (dd, J=18.3, 9.7, 5H), 1.42-1.18 (m, 43H), 0.89 (t, J=6.8, 6H). $^{13}$C NMR (101 MHz, $CDCl_3$) δ 130.39, 130.36, 130.35, 128.14, 112.80, 77.54, 77.22, 76.90, 75.74, 70.14, 61.08, 37.97, 37.50, 35.56, 31.74, 30.14, 30.13, 29.88, 29.80, 29.73, 29.57, 29.53, 27.45, 27.41, 25.84, 24.20, 24.00, 22.79, 14.30.

Synthesis of Compound 10: To an ice-cold solution of compound 9 (10.5 g, 17 mmol) and $NEt_3$ (5 mL) in DCM (100 mL) a solution of MsCl (2.96 g, 20.5 mmol) in DCM (20 mL) was added dropwise with stirring. After 1 h at r.t., aqueous workup gave a pale yellow oil of 10 which was column purified (silica gel, 0-30% EtOAc in hexanes) to provide the pure mesylate (11.1 g, 94%) as a colorless oil. $^1$H NMR (400 MHz, $CDCl_3$) δ 5.44-5.26 (m, 8H), 4.37 (m, 2H), 4.26-4.13 (m, 1H), 4.10 (m, 1H), 3.53 (m, 1H), 3.02 (s, 3H), 2.76 (d, J=6.4, 4H), 2.05 (d, J=6.9, 10H), 1.55 (s, 4H), 1.29 (d, J=9.8, 34H), 0.88 (t, J=6.9, 6H). Electrospray MS (+ve): Molecular weight for $C42H76O5S$ $(MH)^+$ Calc. 693.5. Found 693.4.

Example 7

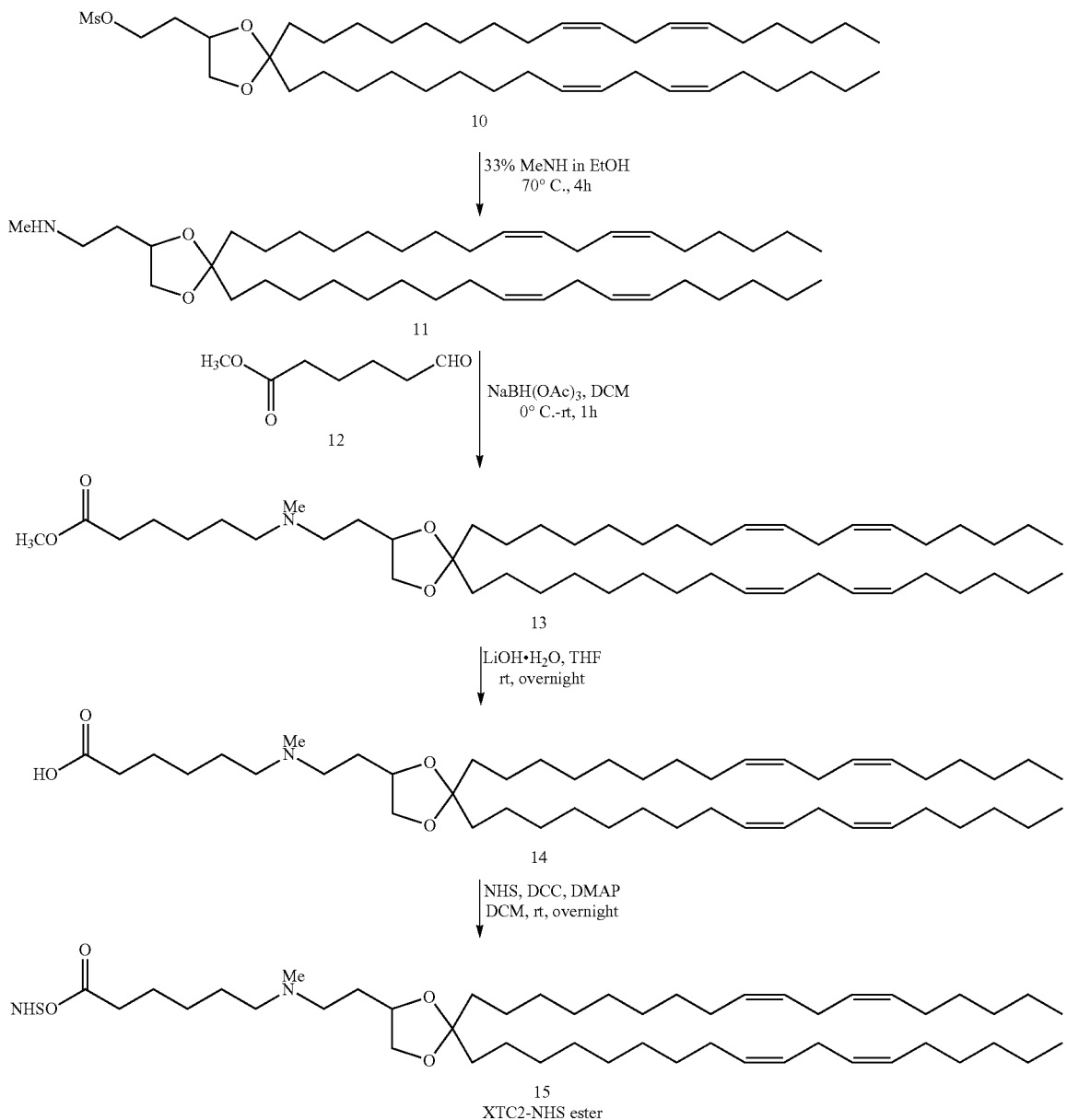

Synthesis of compound 11: To a solution of methanesulfonyl derivative of compound 10 (12.0 g, 17.31 mmol, 1.0 eq) in ethanol (20.0 ml) was added excess amount of 33% methylamine in ethanol (200 ml) in the Parr reactor and continued the reaction at 70° C. for 4 h hours, after complete consumption of the starting material, cooled the reaction, transferred into a round bottom flask, concentrated. Dissolved the reaction product in the ethylacetate and washed with water, dried on $Na_2SO_4$, evaporated and further dried on vacuum gave 10.3 g (95%) of the pure product 11, this was used for the next step without further purification. $^1$H NMR (400 MHz, $CDCl_3$) δ 5.47-5.21 (m, 8H), 4.14-4.04 (m, 2H), 3.49 (t, J=7.6, 1H), 3.00-2.83 (m, 1H), 2.80-2.74 (m, 5H), 2.60 (s, 3H), 2.04 (q, J=6.8, 8H), 1.94-1.81 (m, 2H), 1.60-1.52 (m, 4H), 1.41-1.15 (m, 37H), 0.88 (t, J=6.8, 6H); Calc. mass for $C_{42}H_{77}NO_2$: 627.6, abs. mass: 628.5 $(MH)^+$.

Compound 13: To the suspension of compound II (1.0 g, 1.59 mmol, 1.0 eq) and $NaBH(OAc)_3$ (0.44 g, 2.0 mmol, 1.3 eq) in DCM (12.0 ml) at 0° C. was added a solution of compound 12 (0.25 g, 1.75 mmol, 1.1 eq) in DCM (3.0 ml) at 0° C. under argon and the reaction was continued at room temperature for 1 hour. After completion of the starting material the reaction was quenched with 1N $MaHCO_3$, diluted with DCM, separated the two layers and the combined organics were washed with brine, dried over $MgSO_4$, concentrated and purified by column chromatography using DCM:MeOH (5%):triethylamine (0.5%) as a gradients to get pure 0.86 g (72%) of the ester compound 13. $^1$H NMR (400 MHz, $CDCl_3$) δ 5.47-5.24 (m, 8H), 4.09-4.02 (m, 2H), 3.66 (s, 3H), 3.47 (t, J=7.0, 1H), 2.77 (t, J=6.4, 4H), 2.44-2.41 (m, 1H), 2.31 (t, J=7.5, 4H), 2.19 (s, 3H), 2.04 (q, J=6.7, 8H), 1.88-1.74 (m, 1H), 1.71-1.52 (m, 7H), 1.49-1.45 (m, 2H), 1.40-1.16 (m, 39H), 0.89 (t, J=6.8, 6H); Calc. mass for $C_{49}H_{89}NO_4$: 755.6, abs. mass: 756.5 (MH)$^+$.

Synthesis of compound 14: To a solution of compound 13 (0.86 g, 1.12 mmol, 1.0 eq) in THF (4.0 ml) was added a aqueous solution of LiOH.H$_2$O (0.14 g, 3.36 mmol, 3.0 eq) in water (2.0 ml) drop wise at 0° C. and continued the reaction at room temperature until there is no starting material. After complete consumption of the staring material, THF was evaporated and the aqueous reaction mixture was acidified to pH 6.0 by drop wise addition of acetic acid. Extracted the reaction product into ethyl acetate, organic layer was washed with water, brine, dried over Na$_2$SO$_4$, evaporated the solvent and further dried on vacuum to get 0.73 g (89%) of the clean product 14, this was used directly without further purification. $^1$H NMR (400 MHz, CDCl$_3$) δ 5.46-5.24 (m, 8H), 4.08 (dd, J=8.2, 4.3, 2H), 3.53 (s, 1H), 3.23-2.93 (m, 4H), 2.77-2.71 (m, 7H), 2.37-2.14 (m, 3H), 2.04 (q, J=6.8, 8H), 1.97-1.77 (m, 3H), 1.70-1.47 (m, 6H), 1.44-1.14 (m, 38H), 0.88 (t, J=6.8, 6H); Calc. mass for $C_{48}H_{87}NO_4$: 741.6, abs. mass: 742.5 (MH)$^+$.

Synthesis of compound 15: To a solution of compound 14 (0.73 g, 0.98 mmol, 1.0 eq) in dichloromethane (8.0 ml) was added solid N-hydroxysuccinimide (NHS) (0.12 g, 1.08 mmol, 1.1 eq) followed by DCC (0.22 g, 1.08 mmol, 1.1 eq), DMAP (0.012 g, 0.098 mmol, 0.1 eq) and the reaction was continued at room temperature under argon atmosphere. A white precipitate of urea derivative appears slowly in the reaction, continued the reaction for overnight. After complete consumption of the staring material, dichloromoethane was evaporated, dissolved the reaction mixture in the ethylacetate (6.0 ml), cooled to ice bath temperature to complete precipitate out the DCC urea derivative. Filtered the solid and washed the solid with cold ethylacetate (2×2.0 ml), evaporated the solvent and dried on vacuum to give 0.82 g of the pure NHS ester of the compound 15 in quantitative yields, this was directly used in the next step without further purification. $^1$H NMR (400 MHz, CDCl$_3$) δ 5.45-5.22 (m, 8H), 4.13-3.99 (m, 2H), 3.56-3.44 (m, 1H), 2.95-2.79 (m, 6H), 2.76 (t, J=6.4, 4H), 2.62 (t, J=7.1, 2H), 2.57 (s, 2H), 2.03 (q, J=6.8, 8H), 1.95-1.86 (m, 2H), 1.83-1.63 (m, 5H), 1.61-1.40 (m, 6H), 1.39-1.15 (m, 38H), 0.87 (t, J=6.8, 6H); Calc. mass for $C_{52}H_{90}N_2O_6$: 838.6, abs. Mass: 839.5 (MH)$^+$.

Example 8

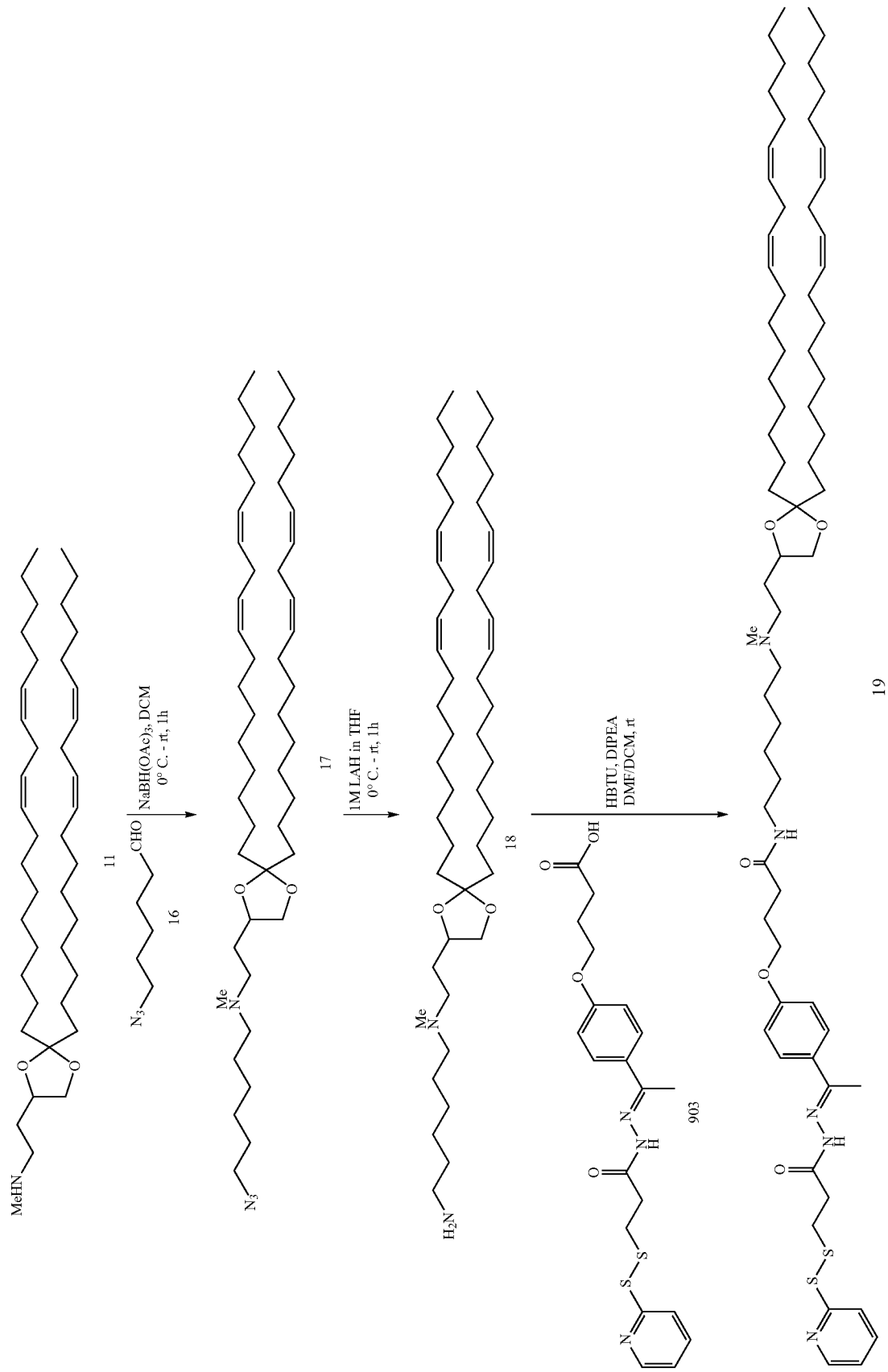

Synthesis of Compound 17: To the suspension of compound II (2.0 g, 3.18 mmol, 1.0 eq) and NaBH(OAc)$_3$ (0.87 g, 4.13 mmol, 1.3 eq) in DCM (15.0 ml) at 0° C. was added a solution of compound 16 (0.49 g, 3.5 mmol, 1.1 eq) in DCM (5.0 ml) at 0° C. under argon and the reaction was continued at room temperature for 1 hour. After completion of the reaction was quenched with 1N MaHCO$_3$, diluted with DCM, separated the two layers and the combined organics were washed with brine, dried over MgSO$_4$, concentrated and purified by column chromatography using DCM:MeOH (5%): triethylamine (0.5%) as a gradients to get 1.85 g (77%) of the pure ester compound 17. $^1$H NMR (400 MHz, CDCl$_3$) δ 5.44-5.25 (m, 8H), 4.14-3.95 (m, 2H), 3.47 (t, J=7.1, 1H), 3.26 (t, J=6.9, 2H), 2.77 (t, J=6.4, 3H), 2.49-2.25 (m, 3H), 2.20 (s, 3H), 2.05 (q, J=6.7, 8H), 1.86-1.76 (m, 1H), 1.71-1.51 (m, 7H), 1.49-1.13 (m, 44H), 0.89 (t, J=6.8, 6H); Calc. mass for C$_{48}$H$_{88}$N$_4$O$_2$: 752.7, abs. mass: 753.5 (MH)$^+$.

Synthesis of compound 18: To a solution of azido derivative 17 (1.5 g, 2.0 mmol, 1.0 eq) in anhydrous THF (12.0 ml) was added 1M solution of LAH (3.0 ml, 3.0 mmol, 1.5 eq) in THF drop wise at 0° C. under argon. Reaction temperature was slowly increased and continued the reaction at room temperature for 2 hours. After complete consumption of the staring material, reaction was quenched with drop wise addition of saturated Na$_2$SO$_4$ solution at 0° C. Separated the solution form the solid and extracted into ethylacetate (25.0 ml), aqueous was extracted with ethylacetate until there is no product appears. Dried the combined organics over Na$_2$SO$_4$, filtered, evaporated the solvent and further dried under vacuum gave 1.31 g (90%) of the neat product 18, which was directly used in the step without further purification. $^1$H NMR (400 MHz, CDCl$_3$) δ 5.45-5.24 (m, 8H), 4.13-3.96 (m, 2H), 3.47 (t, J=7.1, 1H), 2.77 (t, J=6.4, 4H), 2.68 (t, J=6.9, 2H), 2.49-2.26 (m, 4H), 2.20 (s, 3H), 2.04 (q, J=6.7, 8H), 1.88-1.73 (m, 1H), 1.70-1.51 (m, 5H), 1.50-1.40 (m, 4H), 1.39-1.19 (m, 40H), 0.89 (t, J=6.8, 6H); Calc. mass for C$_{48}$H$_{90}$N$_2$O$_2$: 726.7, abs. mass: 727.8 (MH)$^+$.

Synthesis of compound 19: Compound 903 (0.6 g, 0.82 mmol, 1.0 eq) was dissolved in 3.0 ml of DMF and added HBTU (0.37 g, 0.99 mmol, 1.2 eq), followed by DIPEA (0.45 ml, 2.47 mmol, 3.0 eq) at room temperature and stirred for 10 minutes under argon atmosphere. A solution of compound 18 (0.35 g, 0.82 mmol, 1.0 eq) in DMF:DCM (1:2, 3.0 ml) was added slowly to the above mixture at room temperature and continued the reaction until there is no starting material. After 2 hours, reaction mixture was poured onto ice and extracted with the DCM, the organic layer was washed with excess amount of water to remove all DMF present in the organic layer, further washed with NaHCO$_3$, dried on MgSO$_4$, concentrated and purified by column chromatography using DCM:MeOH (5%):triethylamine (0.5%) as a gradients to get 0.81 g (86%) of the pure compound 19. $^1$H NMR (400 MHz, CDCl$_3$) δ 8.63 (s, 1H), 8.47-8.36 (m, 1H), 7.76 (d, J=8.1, 1H), 7.61 (d, J=8.8, 2H), 7.07-6.99 (m, 1H), 6.87 (d, J=8.9, 2H), 5.52 (s, 1H), 5.43-5.25 (m, 8H), 4.13-3.95 (m, 4H), 3.46 (t, J=6.9; 1H), 3.28-3.13 (m, 6H), 2.80-2.75 (m, 4H), 2.42-2.28 (m, 6H), 2.16 (dd, J=19.3, 9.6, 8H), 2.04 (q, J=6.7, 8H), 1.86-1.74 (m, 1H), 1.70-1.40 (m, 8H), 1.39-1.18 (m, 42H), 0.88 (t, J=6.8, 6H); Calc. mass for C$_{68}$H$_{111}$N$_5$O$_5$S$_2$: 1141.8, abs. mass: 1142.7 (MH)$^+$.

Example 9

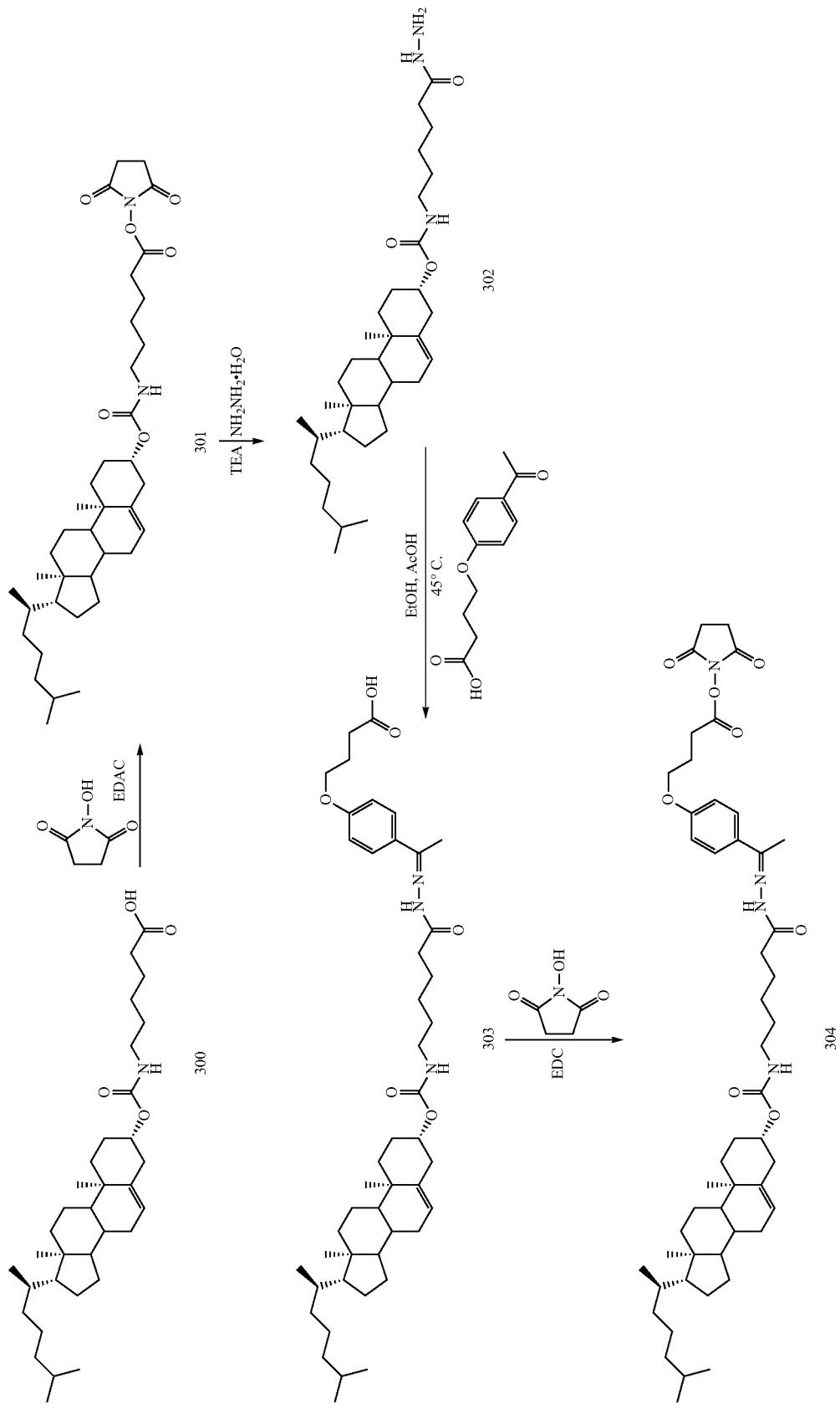

Synthesis of compound 301: Cholesterol acid 300 (4.10 g, 7.53 mmol), N-hydroxy succinimide (1.29 g, 11.29 mmol) and EDAC (2.16 g, 11.26 mol) were taken in a mixture of DCM/DMF. To that DMAP (0.183 g) was added to that and stirred the mixture overnight at ambient temperature. Solvents were removed and the residue dissolved in DCM and washed with water couple of times. TLC showed complete conversion of the starting material. This was used for the next reaction without further purification (white solid, 4.40 g, 92%). MS Cal. for $C_{38}H_{60}N_2O_6$ 640.45. Found. 641.40 (MH)$^+$ Synthesis of compound 302: Compound 301 (2.00 g, 3.12 mmol) was dissolved in THF to that hydrazine hydrate (0.200 mL, 1.2 eq) and TEA (1 mL, excess) were added and stirred overnight. TLC checked and removed the solvent. The residue washed with a mixture of EtOAc/Hexane and dried overnight to get the compound as a white solid (2.10 g, 95%). MS Cal. for $C_{34}H_{59}N_3O_3$ 557.46. Found. 558.44 (MH$^+$)

Synthesis of compound 303: Compound 302 (1.81 g, 3.24 mmol) and ketone (0.722 g, 3.24 mmol) were taken in ethanol (20 mL). To that AcOH (2 mL) was added and stirred the mixture at 50 C for 6 h. Cooled the reaction mixture and kept in the freezer overnight. Filtered and washed with EtOAc and anhydrous ether. Dried under vacuum to get the compound as a white solid (1.68 g, 71%). This compound used for the next reaction without further purification. MS Cal. for $C_{46}H_{71}N_3O_6$ 761.53. Found: 760.52 (M−H). $^1$H NMR (400 MHz, DMSO) δ 11.95 (bs, 1H), 9.73 (m, 1H), 7.93-7.48 (m, 5H), 7.09-6.80 (m, 8H), 5.29 (s, 2H), 4.26 (s, 2H), 4.09-3.87 (m, 6H), 3.48-2.02 (m, 20), 2.02-0.55 (m, 20H).

Synthesis of Compound 304: Compound 303 (0.500 g, 0.656 mmol), N-hydroxy succinimide (0.113 g, 1.5 eq.) and EDAC (0.188 g, 1.5 eq.) were taken in DCM. To that DMAP (20 mg) was added to that and stirred the mixture overnight at ambient temperature. The reaction mixture diluted with DCM, washed with water couple of times and dried. TLC showed complete conversion of the starting material. Solvents were removed and the residue dried overnight to get a white solid (480 mg, 92%). MS Cal. For $C_{50}H_{74}N_4O_8$ 858.55. Found: 859.53 (MH)$^+$.

Example 10

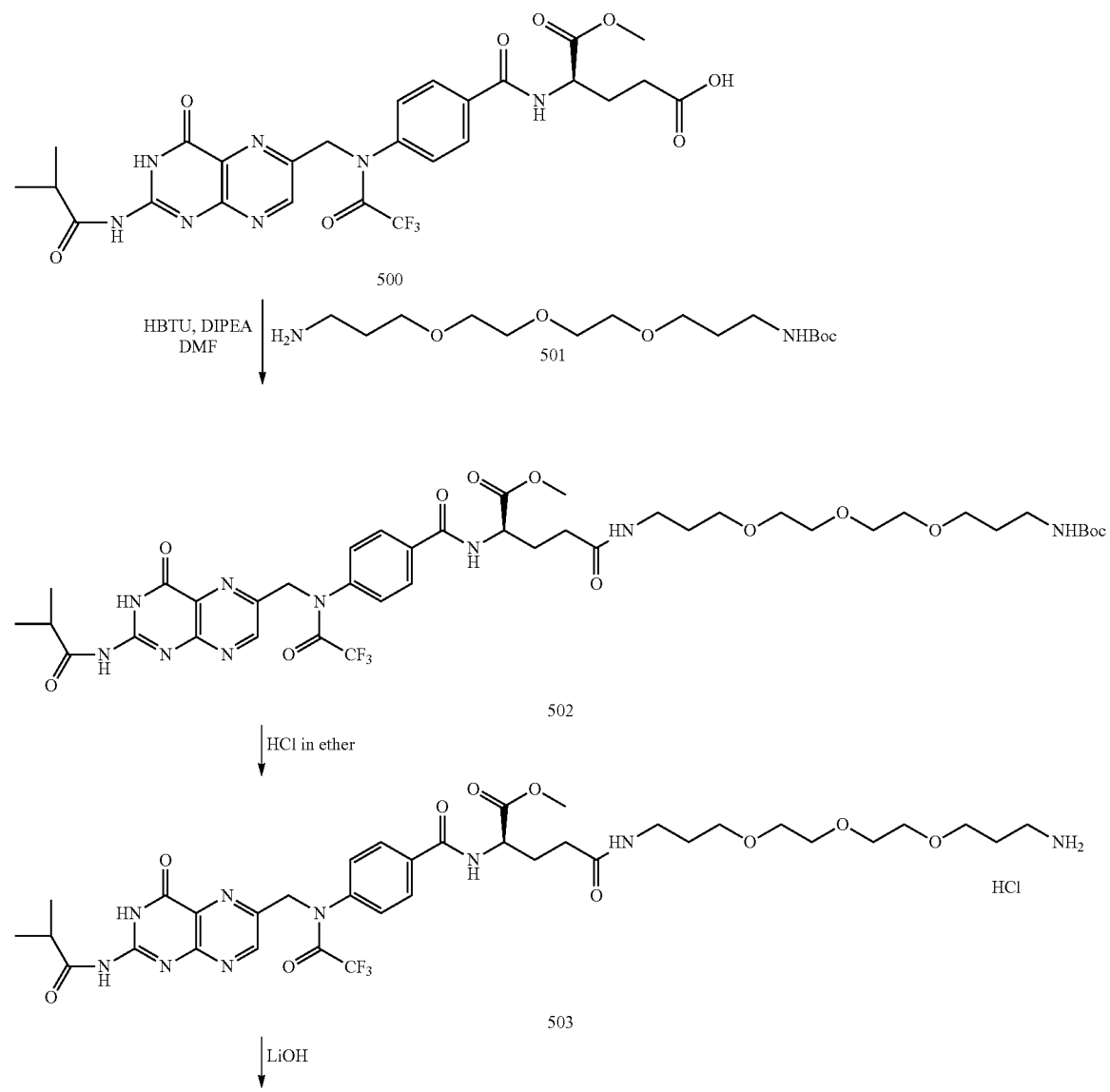

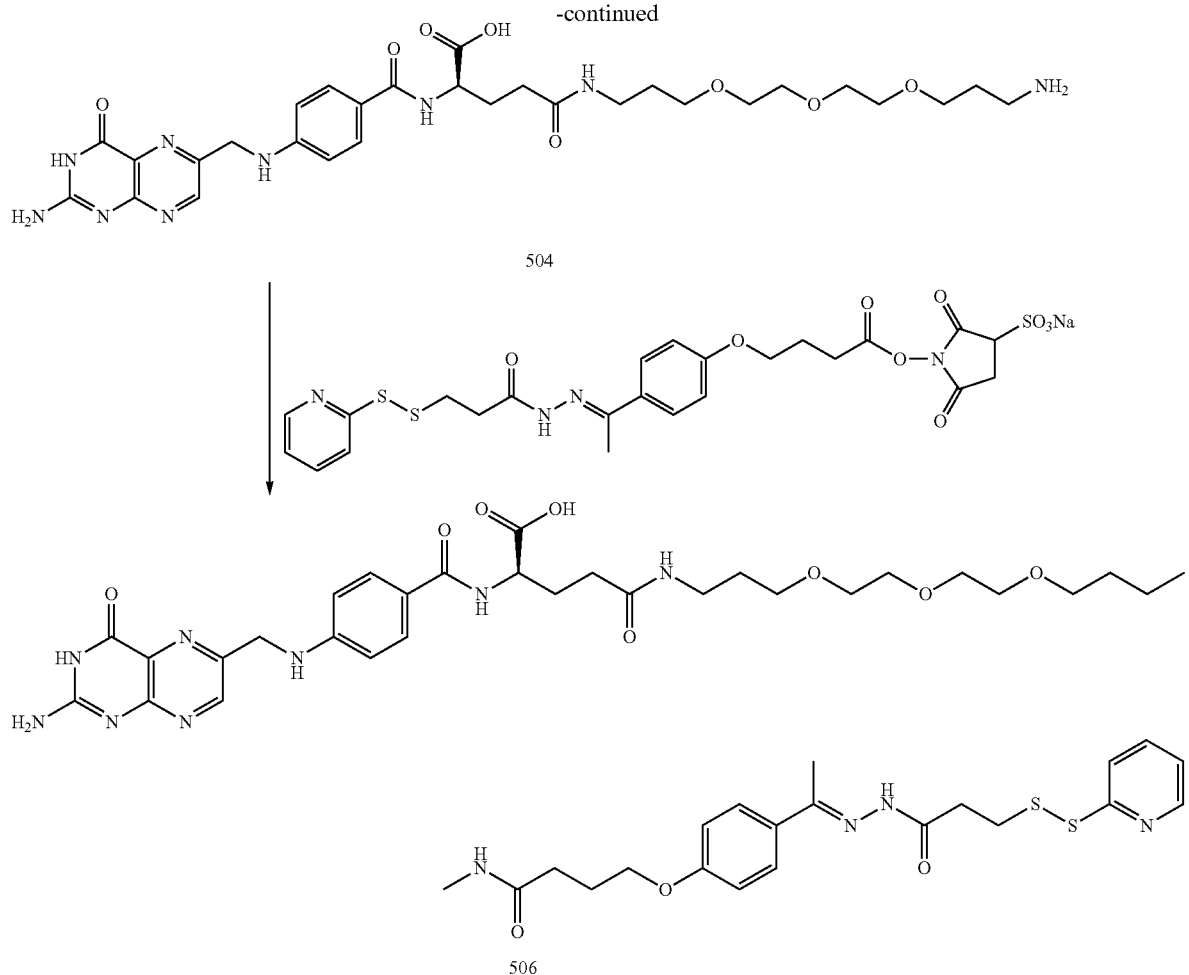

Synthesis of 502: The pteroic acid precursor 500 (1.88 g, 3 mmol) was dissolved in anhydrous DMF (20 mL), HBTU (1.14 g, 1 eq.) followed by DIEA (1.3 g, 3 eq.) were added and stirred for 20 minutes. To this reaction mixture the amine 501 (0.961 g, 3 mmol) was added as a solution in DMF (20 mL). Reaction was monitored by TLC (10% MeOH/DCM, PMA stain). TLC of the reaction mixture showed completion of the reaction after 1 h. The reaction mixture was slowly poured in ice with vigorous stirring. The mixture was extracted with ethyl acetate and the combined organic layers were dried ($Na_2SO_4$) and concentrated to give the crude product. The thus obtained crude product was further purified by column chromatography (silica gel, 0-10% MeOH in DCM) to obtain 502 as a white foam (Yield=2.4 g, 87%). MS. Molecular weight calculated for $C_{41}H_{56}F_3N_9O_{12}$, Cal. 923.40. Found 924.5 $(MH)^+$.

Synthesis of 503: The Boc protected pteroic acid 502 (2.3 g) was treated with 2M HCl in ether (100 mL) and the solution was stirred overnight until all the starting material had disappeared. The reaction mixture was concentrated and dried to isolate the amine hydrochloride salt as a waxy solid (1.9 g 100%). MS. Molecular weight calculated for $C_{36}H_{48}F_3N_9O_{10}$, Cal. 823.35. Found 824.35 $(MH)^+$.

Synthesis of 504: The amine hydrochloride salt 503 (1.8 g) was dissolved in 100 mL THF/MeOH (1:1) and to it an aqueous solution of LiOH (0.4 g in 10 mL of water) was added and the mixture was stirred at room temperature for 2 h. The MS of the reaction mixture showed the complete disappearance of the starting material and only product peak was seen. The reaction mixture was concentrated to remove the organic solvents and the remaining aqueous solution was neutralized to pH 6.8 by adding acetic acid. The thus obtained aqueous solution was freeze dried and triturated with ethyl acetate to get 504 (2.1 g along with inorganic impurities) as an orange crystalline solid. The LC trace showed that the amine is 91% pure and the MS showed the correct mass. This was used as such in the next step. MS. Molecular weight calculated for $C_{29}H_{41}N_9O_8$, Cal. 643.31. Found 624.35 $(MH)^+$.

Synthesis of 505: To a solution of the amine 504 (64 mg, 0.1 mmol) in anhydrouos DMF (20 mL) Hunig's base (0.3 mL) was added followed by the activated ester 904 (63 mg, 0.1 mmol). The reaction mixture was stirred at room temperature for 2 h after which the MS showed the complete disappearance of the starting materials. The reaction mixture was concentrated and the residue was triturated with ethyl acetate to obtain the product as yellow solid (67 mg, 52%). MS. Molecular weight calculated for $C_{49}H_{62}N_{12}O_{11}S_2$, Cal. 1058.41. Found 1057.4 $(M-H^-)$.

Example 11

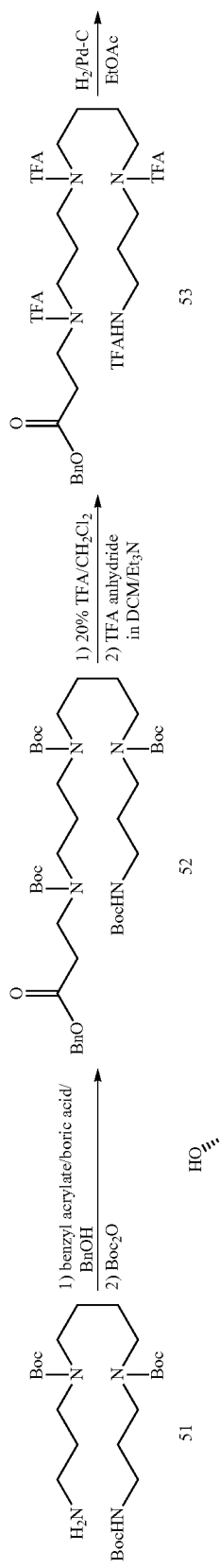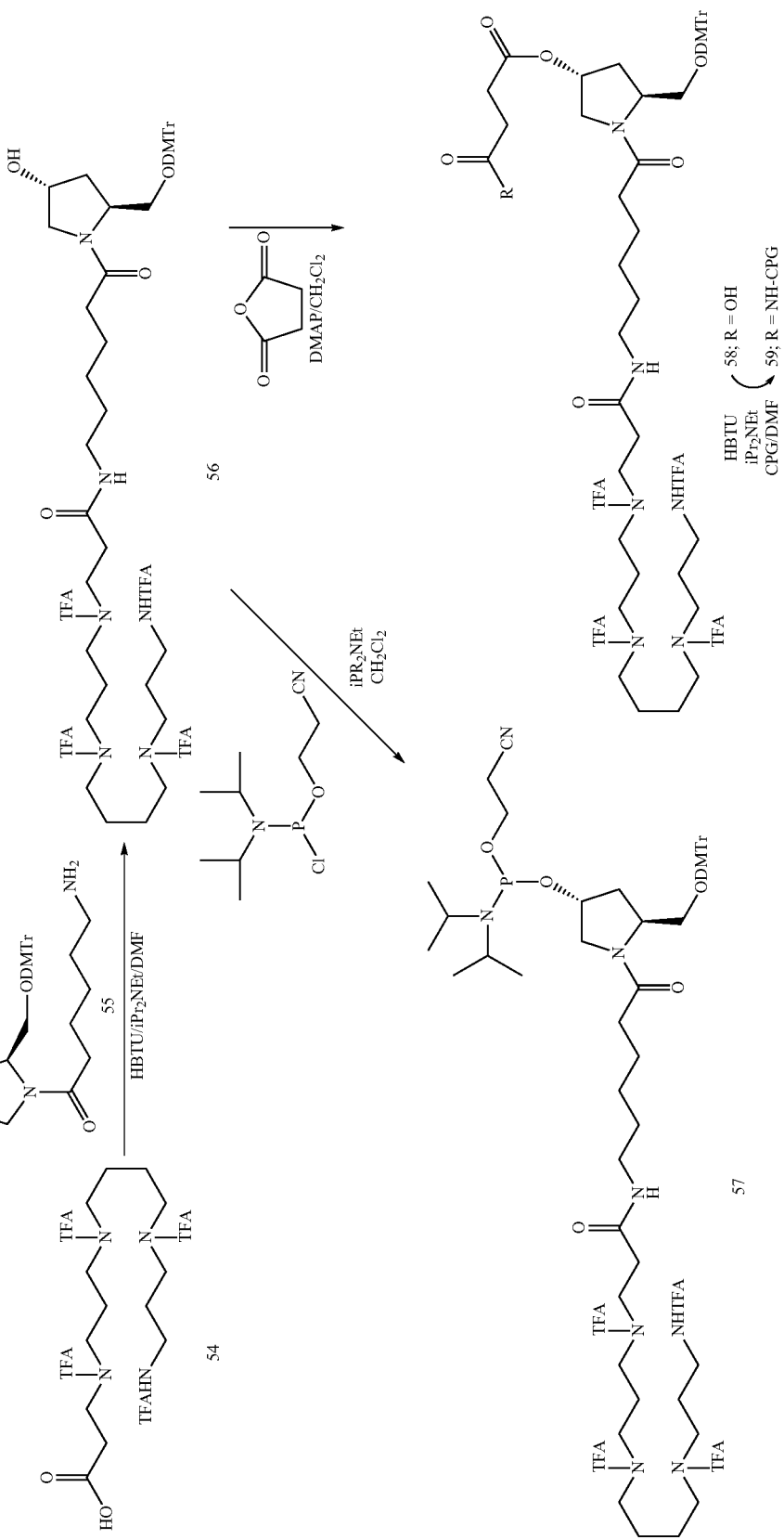

Synthesis of Compound 52: To a solution of compound 51[1] (3.78 g, 7.52 mmol) in benzylalcohol (24 mL), benzyl acrylate (1.22 g, 7.52 mmol) and saturated boric acid aq. (0.5 mL) were dropwisely added. The reaction mixture was stirred for 5 h at room temperature. Then, di-tert-butyl dicarbonate (2.46 g, 11.3 mmol) was added to the mixture. Stirring was continued overnight and the reaction mixture was directly purified by silica gel column chromatography (hexane:ethyl acetate=4:1 to 2:1) to give 52 (4.45 g, 5.82 mmol, 77%, $R_f$=0.26 developed with hexane:ethyl acetate=2:1). $^1$H NMR (400 MHz, DMSO-$d_6$) δ 7.34-7.36 (m, 5H), 6.76 (brs, 1H), 5.08 (s, 2H), 3.39 (t, J=7.0 Hz, 2H), 3.09 (brs, 10H), 2.88 (dd, J=12.4 Hz, 6.0 Hz, 2H), 2.54-2.61 (m, 2H), 1.37-1.62 (m, 44H). $^{13}$C NMR (DMSO-$d_6$, 100 MHz) δ 171.1, 155.4, 154.5, 154.4, 154.3, 135.9, 128.3, 127.9, 127.8, 78.6, 78.2, 78.1, 77.3, 65.5, 44.3, 44.2, 42.7, 37.5, 28.1, 27.9. Molecular weight for $C_{40}H_{68}N_4NaO_{10}$ (M+Na)$^+$ Calc. 787.48. Found 787.4.

(1) (a) Geall, A. J., Blagbrough, I. S. Tetrahedron Letters (1998), 39, 443-446. (b) Geall, A. J., Taylor, R. J., Earll, M. E., Eaton, M. A. W., Blagbrough, I. S. Bioconjugate Chem. (2000), 11, 314-326.

Synthesis of Compound 53: To a solution of 52 (4.20 g, 5.49 mmol) in $CH_2Cl_2$ (120 mL), trifluoroacetic acid (30 mL) was slowly added with cooling in ice bath. The reaction mixture was kept stirring for 15 min, then for 2 h at room temperature. The solvent was removed, coevaporated with toluene, and dried in vacuo to give a crude material. The crude was resuspended in $CH_2Cl_2$ with cooling in ice bath, then trifluoroacetic anhydride (6.87 mL, 49.4 mmol) and triethylamine (9.18 mL, 65.9 mmol) were slowly added. The reaction mixture was stirred for 15 min in ice bath and for 16 h at room temperature. The reaction mixture was extracted with $CH_2Cl_2$ (300 mL) and saturated $NaHCO_3$ aq. (150 mL), dried over anhydrous $Na_2SO_4$, and purified by silica gel column chromatography (hexane:ethyl acetate=4:1 to 1:1.) to give 53 (3.61 g, 4.82 mmol, 88%, $R_f$=0.36 developed with hexane:ethyl acetate=1:1). $^1$H NMR (400 MHz, DMSO-$d_6$) δ 9.45-9.52 (m, 1H), 7.33-7.37 (m, 5 H), 5.11 (d, J=7.6 Hz, 2H), 3.61-3.69 (m, 2H), 3.34-3.39 (m, 10H), 3.21-3.22 (m, 2H), 2.79 (t, J=7.4 Hz, 1H), 2.71 (t, J=7.2 Hz, 1H), 1.75-1.91 (m, 4H), 1.51-1.54 (m, 4H). $^{19}$F NMR (376 MHz, DMSO-$d_6$) δ −68.15, −68.19, −68.21, −68.26, −68.29, −68.31, −68.33, −68.38, −68.40, −68.41, −68.48, −68.49, −74.47, −74.49, −74.50, −74.61. $^{13}$C NMR (DMSO-$d_6$, 100 MHz) δ 170.7, 170.3, 156.8, 156.5, 156.4, 156.1, 156.0, 155.9, 155.8, 155.7, 155.6, 155.5, 155.3, 155.2, 154.9, 154.8, 135.8, 135.7, 129.2, 128.8, 128.4, 128.1, 127.6, 127.3, 120.6, 120.4, 120.1, 117.7, 117.6, 117.5, 117.3, 114.8, 114.7, 114.6, 112.0, 111.8, 111.6, 66.6, 66.4, 65.8, 65.7, 64.9, 64.8, 64.2, 61.2, 61.1, 59.8, 59.7, 58.3, 54.9, 46.8, 46.7, 46.6, 46.0, 45.9, 45.8, 45.7, 45.5, 45.4, 45.3, 45.2, 45.0, 44.9, 44.7, 44.6, 44.5, 44.4, 44.2, 44.1, 44.0, 43.9, 43.7, 43.6, 42.8, 42.7, 42.6, 40.5, 40.3, 40.2, 36.8, 36.4, 32.7, 32.6, 31.6, 31.5, 31.2, 31.1, 31.0, 30.0, 29.6, 27.7, 27.4, 26.5, 26.4, 26.2, 25.8, 25.4, 25.3, 25.1, 25.0, 24.6, 23.9, 23.5, 23.4, 23.3, 20.2, 19.8, 18.9, 14.6, 14.0, 13.4, 12.2. Molecular weight for $C_{28}H_{32}F_{12}N_4NaO_6$ (M+Na)$^+$ Calc. 771.20. Found 771.0.

Synthesis of Compound 54: To a solution of 53 (3.57 g, 4.77 mmol) in EtOAc (50 mL), Palladium on carbon (10 wt. %, Degussa type E101 NE/W: 600 mg) was added. The reaction mixture was stirred under $H_2$ atmosphere for 16 h. After filtration through Celite, the filtrate was removed in vacuo to give 54 (3.04 g, 4.62 mmol, 97%). $^1$H NMR (400 MHz, DMSO-$d_6$) δ 9.45-9.55 (m, 1H), 3.54-3.63 (m, 2H), 3.36-3.39 (m, 10H), 3.19-3.24 (m, 2 H), 2.62 (t, J=7.2 Hz, 1H), 2.56 (t, J=9.0 Hz, 1H), 1.75-1.91 (m, 4H), 1.52-1.55 (m, 4H). $^{19}$F NMR (376 MHz, DMSO-$d_6$) δ −68.19, −68.22, −68.23, −68.24, −68.33, −68.35, −68.38, −68.41, −68.44, −68.48, −68.50, −68.51, −74.50, −74.52, −74.53, −74.64. $^{13}$C NMR (DMSO-$d_6$, 100 MHz) δ 172.4, 172.0, 156.5, 156.4, 156.2, 156.1, 155.9, 155.8, 155.6, 155.5, 155.4, 155.3, 155.2, 154.9, 120.6, 120.5, 120.2, 117.7, 117.6, 117.3, 114.9, 114.8, 114.5, 112.0, 111.6, 46.7, 46.1, 46.0, 45.9, 45.8, 45.0, 44.6, 44.2, 44.0, 43.7, 42.9, 40.1, 39.9, 39:7, 39.5, 39.3, 39.1, 38.9, 36.9, 36.4, 33.1, 31.2, 27.7, 27.5, 25.8, 25.4, 25.1, 24.0, 23.6, 23.3. Molecular weight for $C_{21}H_{25}F_{12}N_4O_6$ (M−H)$^−$ Calc. 657.16. Found 657.0.

Synthesis of Compound 56: A solution of compound 54 (3.0 g, 4.57 mmol) and HBTU (1.91 g, 5.03 mmol) in DMF (50 mL) was treated successively with $iPr_2NEt$ (3.98 mL, 22.9 mmol) and compound 55 (2.68 g, 5.03 mmol) then allowed to stir for 14 h at room temperature. Extraction with $Et_2O$ and sat. $NaHCO_3$ aq. and then column chromatography (0-5% in $CH_2Cl_2$) gave compound 56 (3.70 g, 3.15 mmol, 69%, $R_f$=0.59 developed with 10% MeOH in $CH_2Cl_2$). $^1$H NMR (400 MHz, DMSO-$d_6$) δ 9.44-9.52 (m, 1H), 7.92-7.98 (m, 1H), 7.16-7.32 (m, 9H), 6.86-6.89 (m, 4H), 4.88-4.98 (m, 1H), 4.28-4.40 (m, 1H), 4.09-4.15 (m, 1H), 3.72 (s, 6H), 3.54-3.62 (m, 3H), 3.29-3.36 (m, 10H), 3.13-3.23 (m, 3H), 2.99-3.02 (m, 3H), 2.36-2.44 (m, 2H), 1.74-2.21 (m, 9H), 1.23-1.53 (m, 10H). $^{19}$F NMR (376 MHz, DMSO-$d_6$) δ −68.17, −68.19, −68.22, −68.23, −68.26, −68.29, −68.32, −68.34, −68.40, −68.42, −68.49, −68.51, −74.49, −74.51, −74.52, −74.63. $^{13}$C NMR (DMSO-$d_6$, 100 MHz) δ 170.9, 170.8, 169.4, 169.0, 158.1, 158.0, 156.5, 156.2, 155.6, 155.3, 145.1, 144.7, 135.9, 135.7, 135.5, 135.4, 129.6, 129.5, 127.9, 127.8, 127.6, 126.7, 126.6, 117.7, 117.3, 114.9, 114.5, 113.2, 113.1, 85.8, 85.1, 68.6, 67.4, 65.2, 63.3, 55.9, 53.4, 46.7, 46.0, 45.9, 45.8, 45.1, 44.7, 44.2, 44.1, 43.9, 43.7, 43.6, 38.4, 38.0, 36.9, 36.4, 36.3, 34.5, 34.1, 32.6, 32.5, 28.9, 27.7, 27.5, 26.2, 25.9, 25.8, 25.4, 25.1, 24.5, 24.1, 23.9, 23.6, 23.3. Molecular weight for $C_{53}H_{64}F_{12}N_6NaO_{10}$ (M+Na)$^+$ Calc. 1195.44. Found 1195.2.

Synthesis of Compound 57: To a solution of compound 56 (1.00 g, 0.852 mmol) in $CH_2Cl_2$ (14 mL), diisopropylethylamine (0.742 mL, 4.26 mmol) and 2-cyanoethyl N,N-diisopropylchlorophosphoramidite (0.248 mL, 1.11 mmol) were added at 0° C. The reaction mixture was stirred for 30 min at 0° C. then for 30 min at room temperature under argon atmosphere. The reaction mixture was diluted with $CH_2Cl_2$ (100 mL) and washed with saturated $NaHCO_3$ aq. (50 mL). The organic layer was separated and dried over anhydrous $Na_2SO_4$. The filtrate was concentrated and the resulting crude material was purified by silica gel column chromatography (hexane:EtOAc=1:4 to 100% EtOAc) to give 57 (892 mg, 0.650 mmol, 76%, $R_f$=0.18 developed with EtOAc). $^1$H NMR (400 MHz, DMSO-$d_6$) δ 9.34-9.52 (m, 1H), 7.92-7.95 (m, 1H), 7.16-7.31 (m, 9H), 6.83-6.87 (m, 4H), 4.62-4.64 (m, 1H), 4.11-4.17 (m, 1H), 3.65-3.72 (m, 9H), 3.49-3.56 (m, 5H), 3.30-3.42 (m, 9H), 3.15-3.21 (m, 3H), 2.95-3.02 (m, 3H), 2.72-2.76 (m, 2H), 2.37-2.40 (m, 2H), 2.10-2.20 (4H), 1.75-1.87 (m, 5H), 1.07-1.54 (m, 22H). $^{31}$P NMR (DMSO-$d_6$, 162 MHz) δ 146.93, 146.71, 146.51, 146.20. Molecular weight for $C_{62}H_{81}F_{12}N_8NaO_{11}P$ (M+Na)$^+$ Calc. 1395.55. Found 1395.2.

Synthesis of Compound 58: Compound 56 (1.01 g, 0.861 mmol) in $CH_2Cl_2$ (30 mL) was treated with DMAP (314 mg, 2.57 mmol) and succinic anhydride (171 mg, 1.71 mmol) then stirred for 16 h at room temperature. Column chromatography (4% MeOH/4% $Et_3N$ in $CH_2Cl_2$) of the crude mixture without aqueous work-up gave the compound 58 as the corresponding triethylammonium salt (1.18 g, 99.8%, $R_f$=0.21 developed with 4% MeOH/4% $Et_3N$ in $CH_2Cl_2$). $^1$H NMR (400 MHz, DMSO-$d_6$) δ 9.51-9.58 (m, 1H), 8.01-8.10 (m, 1H), 7.17-7.32 (m, 9H), 6.84-6.88 (m, 4H), 5.22-5.33 (m, 1H), 4.18-4.19 (m, 1H), 3.72 (s, 6H), 3.54-3.62 (m, 3H), 3.35-3.37 (m, 10H), 3.18-3.22 (m, 3H), 2.99-3.06 (m, 3 H), 2.34-2.44 (m, 6H), 1.74-2.22 (m, 9H), 1.10-1.53 (m, 10H). $^{13}$C NMR (100 MHz, DMSO-$d_6$) δ 173.9, 172.3, 170.7, 170.6, 169.3, 168.9, 158.0, 157.9, 156.5, 156.1, 156.0, 155.9, 155.8, 155.5, 155.4, 155.3, 155.2, 155.1, 144.9, 144.6, 135.7, 135.5, 135.3, 129.6, 129.5, 129.4, 127.8, 127.7, 127.5, 126.7, 126.5, 120.5, 117.7, 117.6, 117.3, 114.8, 114.7, 114.4, 113.1, 113.0, 111.9, 85.9, 85.2, 72.6, 63.2, 54.9, 54.8, 52.1, 51.9, 46.7, 46.6, 46.5, 45.4, 43.6, 38.3, 36.8, 36.4, 34.4, 33.9, 33.0, 32.5, 32.4, 29.8, 29.7, 29.4, 28.9, 28.8, 27.7, 26.0, 25.9, 25.8, 25.7, 25.3, 25.1, 25.0, 24.4, 24.0, 23.5, 23.3, 7.11. Molecular weight for $C_{57}H_{67}F_{12}N_6O_{13}$ (M−H)$^-$ Calc. 1271.46. Found 1271.2.

Synthesis of Compound 59: Compound 58 (1.15 g, 0.837 mmol) was dissolved in DMF (80 mL). HBTU (350 mg, 0.921 mmol) then iPr$_2$NEt (0.730 mL, 4.19 mmol) and finally CPG-NH$_2$ (Prime Synthesis CPG-500, NH$_2$ loading=147 μmol/g) (6.27 g, 0.921 mmol) were added in succession. The mixture was shaken for 2.5 h at room temperature, then the solid was collected by filtration, washed with CH$_2$Cl$_2$ (100 mL), then 50% MeOH/CH$_2$Cl$_2$ (300 mL) and dried in vacuo. The residual amino groups were capped by shaking for 1 h with Ac$_2$O/Pyridine/Et$_3$N (25 mL/75 mL/5 mL). Filtration and washing with CH$_2$Cl$_2$ (100 mL), then 50% MeOH/CH$_2$Cl$_2$ (300 mL) then drying overnight in vacuo gave compound 59 (6.56 g, 53 μmol/g).

Example 12

Spermine Azide Derivatives for Post-Synthetic Conjugation

Synthesis of Compound 63: Spermine 60 (11.25 g, 55.6 mmol) was dissolved in acetonitrile (50 mL). Then, copper sulfate pentahydrate (139 mg, 0.556 mmol) and triethylamine (15.5 mL, 111.2 mmol) were added to the solution while stirring. The mixture was cooled in an ice bath, then, a solution of triflic azide 61 in acetonitrile (0.55 M, 100 mL) prepared by the method previously reported[2] was added to the mixture slowly. The reaction mixture was allowed to warm to room temperature and run overnight. Di-tert-butyl dicarbonate (60.7 g, 278 mmol) was slowly added to the solution and the reaction mixture was stirred for 2 hours. After evaporation, the crude was extracted with EtOAc and H$_2$O, dried over anhydrous Na$_2$SO$_4$, and purified by silica gel column chromatography (Hexane:EtOAc=2:1, $R_f$=0.46) to give 63 (13.12 g, 24.8 mmol, 45%). $^1$H NMR (400 MHz, DMSO-$d_6$) δ 6.77 (brs, 1H), 3.30-3.34 (m, 2H), 3.11-3.19 (m, 8H), 2.86-2.90 (m, 2H), 1.71-1.72 (m, 2 H), 1.54-1.56 (m, 2 H), 1.37-1.39 (m, 29 H). Molecular weight for $C_{25}H_{48}N_6NaO_6$ (M+Na)$^+$ Calc. 551.35. Found 551.2.

(2) Yan, R. B., Yang, F., Wu, Y., Zhang, L. H., Ye, X. S. Tetrahedron Letters (2005), 46, 8993-8995.

Synthesis of Compound 64: To a solution of compound 63 (1.37 g, 2.59 mmol) in CH$_2$Cl$_2$ (36 mL), TFA (4 mL) was slowly added with cooling in ice bath. The mixture was stirred for 5 hour at room temperature. The reaction mixture was evaporated and then co-evaporated with toluene. The residue was precipitated with ether and the white solid (TFA salt of 64) collected. Yield: 950 mg, 1.67 mmol, 64%. $^1$H NMR (400 MHz, DMSO-$d_6$) δ 3.48 (t, J=6.4 Hz, 2H), 2.93-2.96 (m, 10 H), 1.62-1.93 (m, 8 H). Molecular weight for $C_{10}H_{25}N_6$ (MH)$^+$ Calc. 229.21. Found 229.3.

Synthesis of Compound 65: To a solution of compound 64 (324 mg, 0.568 mmol) in pyridine (5 mL), trifluoroacetic anhydride (0.361 mL, 2.27 mmol) was slowly added with

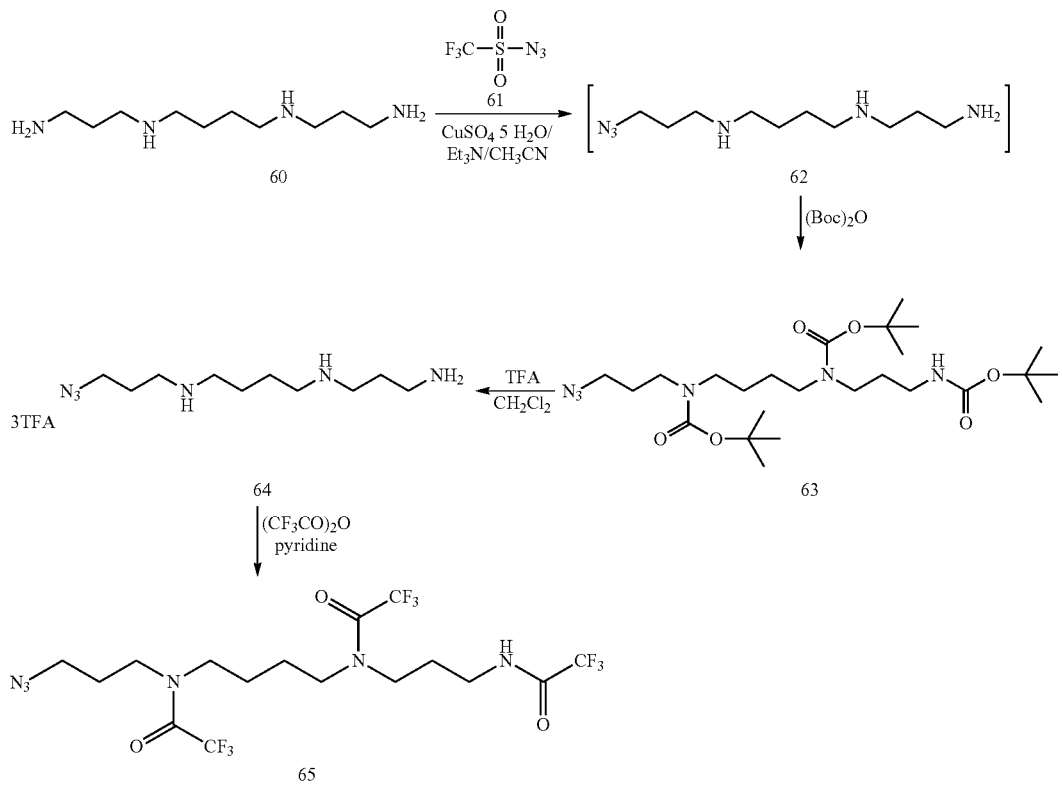

cooling in ice bath. The mixture was stirred for 16 h at room temperature. The reaction mixture was extracted with $CH_2Cl_2$ and sat. $NaHCO_3$ aq., then dried over anhydrous $Na_2SO_4$. The filtrate was concentrated and the resulting crude material was purified by silica gel column chromatography (hexane:EtOAc=4:1 to 1:1) to give 65 (214 mg, 0.414 mmol, 73%, $R_f$=0.33 developed with hexane:EtOAc=1:1). $^1$H NMR (400 MHz, DMSO-$d_6$) δ 9.48-9.53 (m, 1 H), 3.32-3.43 (m, 10 H), 3.18-3.23 (m, 2 H), 1.75-1.84 (m, 4 H), 1.51-1.54 (m, 4 H). $^{19}$F NMR (376 MHz, DMSO-$d_6$) δ −70.92, −70.95, −70.98, −71.02, −71.05, −71.15, −71.18, −77.23, −77.26, −77.38, −77.38. Molecular weight for $C_{10}H_{25}N_6$ (MH)$^+$ Calc. 229.21. Found 229.3.

2.86-2.88 (m, 2 H), 1.36-1.70 (m, 57 H). Molecular weight for $C_{41}H_{78}N_8NaO_{10}$ (M+Na)$^+$ Calc. 865.57. Found 865.5.

(3) Miller, K. A., Suresh Kumar, E. V. K., Wood, S. J., Cromer, J. R., Datta, A., David, S. A. Journal of Medicinal Chemistry (2005), 48, 2589-2599.

Synthesis of Compound 69: Compound 69 was prepared from compound 68 (275 to mg, 0.326 mmol) as described for compound 64. Yield: 235 mg (0.257 mmol, 79%). $^1$H NMR (400 MHz, $D_2O$) δ 3.50 (t, J=6.0 Hz, 2 H), 3.09-3.15 (m, 18 H), 2.06-2.10 (m, 6 H), 1.96 (t, J=6.0 Hz, 2 H), 1.75-1.77 (m, 4 H). Molecular weight for $C_{16}H_{39}N_8$ (MH)$^+$ Calc. 343.33. Found 343.2.

Example 13

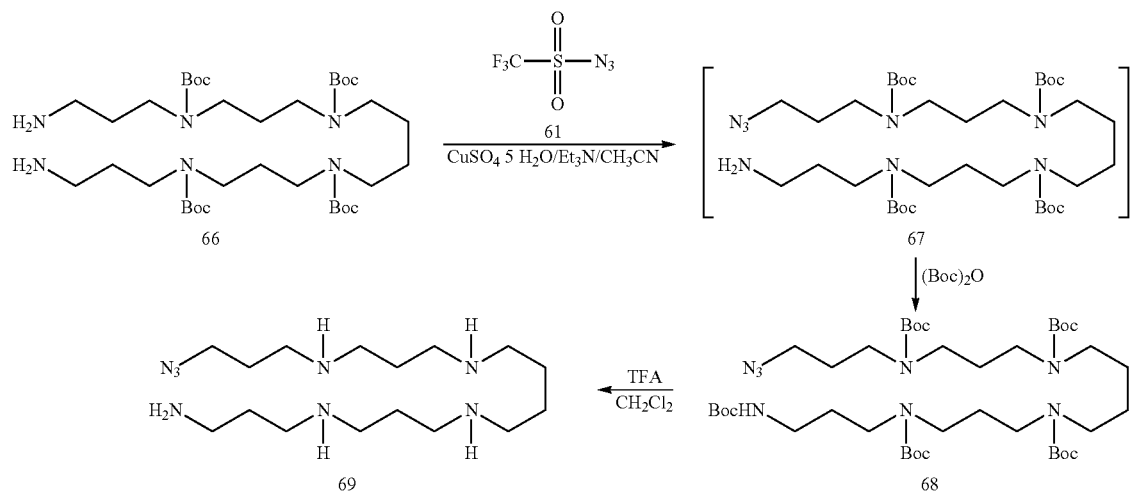

Synthesis of Compound 68: Compound 68 was prepared from compound 66[3] as described for compound 63. $^1$H NMR (400 MHz, DMSO-$d_6$) δ 6.73 (brs, 1 H), 3.05-3.33 (m, 18 H), Example 14

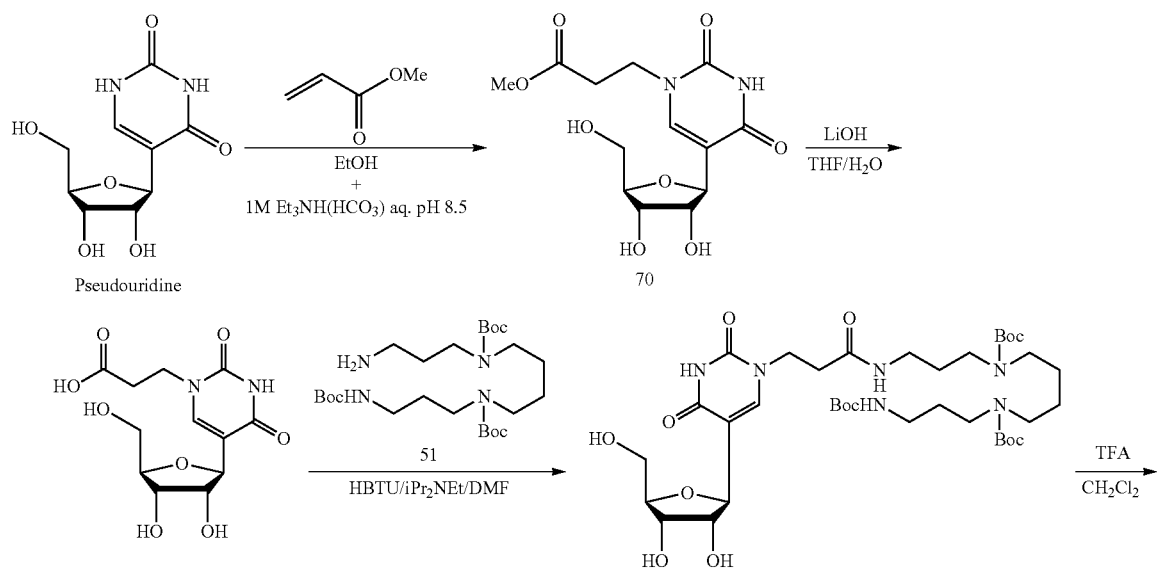

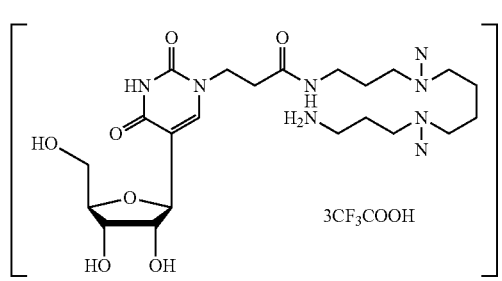
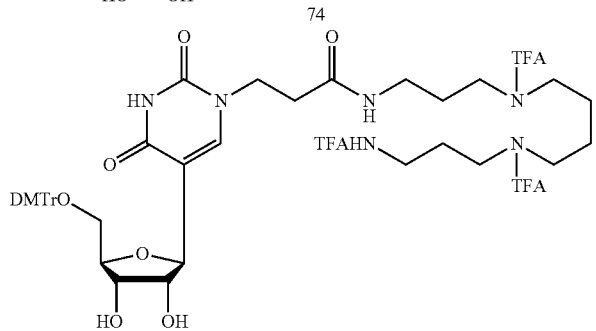

Synthesis of Compound 70: For alkylation at N1 position of pseudouridine, a reported method by Seela et al. for the 2'-deoxypseudouridine analog was used.[4] To a solution of pseudouridine (20 g, 81.9 mmol) in 1M triethylammonium-bicarbonate buffer (pH 8.5, 780 mL) and EtOH (940 mL), methyl acrylate was dropwisely added. The reaction mixture was stirred overnight. After 16 hours, TLC showed a complete reaction. The solvent was removed and dried in vacuo to give a white foam. The crude material was purified by silica gel column chromatography (10% MeOH in $CH_2Cl_2$, $R_f$=0.23) to give 70 (26.6 g, 80.5 mmol, 98%). $^1$H NMR (400 MHz, MeOH-$d_4$) δ 7.77 (d, J=0.8 Hz, 1 H), 4.58 (d, J=4.8 Hz, 1H), 4.15 (t, J=5.2 Hz, 1 H), 4.05 (t, J=5.0 Hz, 1 H ), 3.98-4.02 (m, 2 H), 3.91-3.94 (m, 1 H), 3.80 (dd, J=12.0 Hz, 3.3 Hz, 1 H), 3.67 (s, 3 H), 3.66 (dd, J=12.0 Hz; 3.3 Hz, 1 H), 2.73-2.77 (m, 2 H). $^{13}$C NMR (100 MHz, MeOH-$d_4$) δ 173.1, 165.4, 152.5, 145.8, 112.9, 85.6, 81.5, 75.6, 72.6, 63.3, 52.5, 46.2, 33.7. Molecular weight for $C_{13}H_{19}N_2O_8$ $(MH)^+$ Calc. 330.11. Found 331.0.

(4) Ramzaeva, N.; Rosemeyer, H.; Leonard, P.; Muhlegger, K.; Bergmann, F.; Von der Eltz, H.; Seela, F. *Helvetica Chimica Acta* 2000, 83, 1108-1126.

Synthesis of Compound 71: To a solution of compound 70 (5.00 g, 15.1 mmol) in THF (100 mL) and $H_2O$ (20 mL), lithium hydroxide monohydrate (1.03 g, 25.5 mmol) was added. The reaction mixture was stirred overnight. Additional lithium hydroxide monohydrate (500 mg, 11.9 mmol) was added. After 2 hours, the reaction mixture was treated with Amberlite IR-120 (plus) ion exchange resin. The resin was filtered off and washed with THF/$H_2O$. The filtrate was evaporated to give compound 71 as a white solid (4.78 g, quantitatively). $^1$H NMR (400 MHz, DMSO-$d_6$) δ 11.34 (s, 1 H), 7.75 (s, 1 H), 4.92-4.93 (m, 1 H), 4.70-4.72 (m, 1 H), 4.45 (d, J=4.0 Hz, 1 H), 3.80-3.93 (m, 4 H), 3.68-3.72 (m, 1 H), 3.61 (dd, J=12.0 Hz, 3.2 Hz, 1 H), 3.47 (dd, J=12.0 Hz, 4.0 Hz, 1 H), 3.17 (d, J=3.2 Hz, 1 H), 2.59 (t, J=7.0 Hz, 2 H). $^{13}$C NMR (100 MHz, DMSO-$d_6$) δ 172.1, 163.0, 150.4, 143.6, 111.4, 83.2, 79.0, 73.7, 70.4, 61.3, 44.1, 32.7. Molecular weight for $C_{12}H_{15}N_2O_8$ $(M-H)^-$ Calc. 315.08. Found 315.1.

Synthesis of Compound 72: To a solution of compound 71 (4.78 g, 15.1 mmol) in DMF (150 mL), HBTU (6.89 g, 18.17 mmol) and diisopropylethylamine (13.19 mL, 7.57 mL) were added. After stirring for 10 minute, a solution of compound 51 in $CH_2Cl_2$ (100 mL) was added. The reaction mixture was stirred for 16 h. Aqueous work-up and silica gel column chromatography (0-10% MeOH in $CH_2Cl_2$) gave compound 72 (7.51 g, 9.38 mmol, 62%, $R_f$=0.30 developed with 10% MeOH in $CH_2Cl_2$). $^1$H NMR (400 MHz, DMSO-$d_6$) δ 11.34 (s, 1 H), 7.94 (brs, 1 H), 7.67 (s, 1 H), 6.76 (brs, 1 H), 4.92 (d, J=2.6 Hz, 1 H), 4.72-4.75 (m, 2 H), 4.43 (d, J=2.2 Hz; 1 H), 3.81-3.94 (m, 4 H), 3.68-3.72 (m, 1 H), 3.57-162 (m, 1 H), 3.44-3.49 (m, 1 H), 3.09 (s, 8 H), 2.99 (dd, J=6.0 Hz, 12.4 Hz, 2 H), 2.88 (dd, J=6.4 Hz, 12.4 Hz, 2 H), 2.43 (t, J=6.8 Hz, 2 H), 1.37-1.56 (m, 35 H). $^{13}$C NMR (100 MHz, DMSO-$d_6$) δ 169.5, 163.2, 155.8, 154.9, 150.5, 144.0, 111.4, 83.5, 79.1, 78.6, 77.8, 73.8, 70.7, 61.5, 54.9, 46.7, 46.6, 46.2, 45.0, 44.6, 44.5, 37.6, 36.4, 34.3, 28.4, 28.2, 25.8, 25.7, 25.4, 25.3, 25.2, 22.4. Molecular weight for $C_{37}H_{64}N_6NaO_{13}$ $(M+Na)^+$ Calc. 823.44. Found 823.2.

Synthesis of Compound 74: To a solution of 72 (2.48 g, 3.10 mmol) in $CH_2Cl_2$ (40 mL), trifluoroacetic acid (10 mL) was slowly added with cooling in ice bath. The reaction mixture was kept stirring for 10 min, then for 1 h at room temperature. The solvent was removed, coevaporated with toluene, and dried in vacuo to give a crude material 73 (Molecular weight for $C_{22}H_{41}N_6O_7$ $(M+H)^+$ Calc. 501.30. Found 501.2.) The crude was dissolved in pyridine (30 mL), then trifluoroacetic anhydride (2.15 mL, 15.5 mmol) was slowly added with cooling in ice bath. The reaction mixture was stirred for 16 h then quenched by addition of $H_2O$ (15 mL). After stirring for 1 h, the mixture was evaporated and dried in vacuo. Silica gel column chromatography (0-20% MeOH in $CH_2Cl_2$) gave compound 74 (1.34 g, 1.70 mmol, 55%, $R_f$=0.56 developed with 20% MeOH in $CH_2Cl_2$). $^1$H NMR (400 MHz, DMSO-$d_6$) δ 11.35 (s, 1 H), 9.45-9.53 (m, 1 H), 8.00-8.08 (m, 1 H), 7.66 (s, 1 H), 4.92 (brs, 1 H), 4.74 (brs, 1 H), 4.42 (d, J=4.4 Hz, 1 H), 3.83-4.10 (m, 6 H), 3.58-3.71 (m, 2 H), 3.34-3.48 (m, 10 H), 3.19-3.24 (m, 2 H), 2.44 (t, J=7.0 Hz, 2 H), 1.52-1.82 (m, 8 H). $^{19}$F NMR (376 MHz, DMSO-d$_6$) δ −68.18, −68.19, −68.24, −68.27, −68.31, −68.38, −68.41, −74.47, −74.50, −74.63. $^{13}$C NMR (100 MHz, DMSO-d$_6$) δ 169.4, 169.3, 163.0, 150.4, 146.0, 143.6, 140.9, 125.4, 111.3, 83.3, 78.9, 73.7, 70.5, 61.4, 46.8, 46.7, 46.6, 46.0, 45.8, 45.6, 45.0, 44.7, 44.6, 44.5, 44.2, 36.8, 36.4, 36.1, 35.7, 34.2, 34.1, 28.5, 27.7, 26.5, 25.8, 25.4, 25.1, 23.5, 23.3. Molecular weight for C$_{28}$H$_{37}$F$_9$N$_6$NaO$_{10}$ (M+Na)$^+$ Calc. 811.23. Found 811.2.

Synthesis of Compound 75: To a solution of compound 74 (450 mg, 0.571 mmol) in pyridine (4 mL), DMTrCl (193 mg, 0.571 mmol) was added. The reaction mixture was stirred for 2 h at room temperature and then evaporated all. The crude was extracted with CH$_2$Cl$_2$ and H$_2$O, dried over anhydrous Na$_2$SO$_4$, and purified by silica gel column chromatography (0-10% MeOH in CH$_2$Cl$_2$) to give 75 (300 mg, 0.275 mmol, 48%, R$_1$=0.44 developed with 10% MeOH in CH$_2$Cl$_2$). $^1$H NMR (400 MHz, DMSO-d$_6$) δ 11.33 (s, 1 H), 9.42-9.53 (m, 1 H), 7.91-8.00 (m, 1 H), 7.18-7.43 (m, 10 H), 6.87-6.89 (m, 4 H), 5.02 (dd, J=3.0 Hz, 4.6 Hz, 1 H), 4.76 (t, J=6.0 Hz, 1 H), 4.50-4.51 (m, 1 H), 3.79-3.92 (m, 3 H), 3.73 (s, 6 H), 3.53-3.71 (m, 2 H), 2.98-3.37 (m, 14 H), 2.36 (t, J=6.4 Hz, 2 H), 1.48-1.82 (m, 8 H). $^{19}$F NMR (376 MHz, DMSO-d$_6$) δ −68.17, −68.18, −68.19, −68.24, −68.28, −68.31, −68.34, −68.37, −68.40, −74.45, −74.48, −74.60, −74.61. Molecular weight for C$_{49}$H$_{55}$F$_9$N$_6$NaO$_{12}$ (M+Na)$^+$ Calc. 1113.36. Found 1114.2; C$_{49}$H$_{54}$F$_9$N$_6$O$_{12}$ (M−H)$^-$ Calc. 1089.37. Found 1089.3.

Example 15

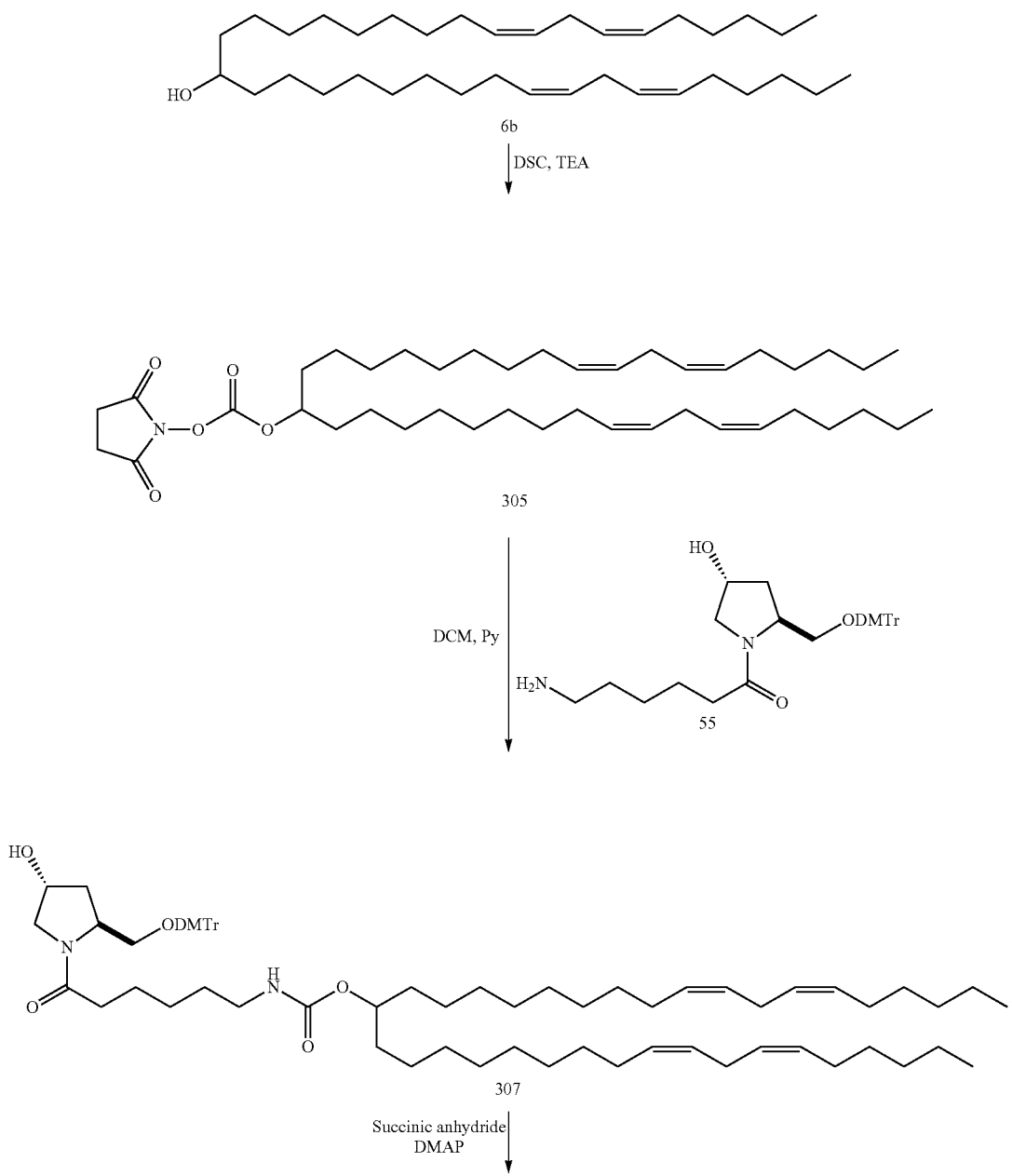

-continued

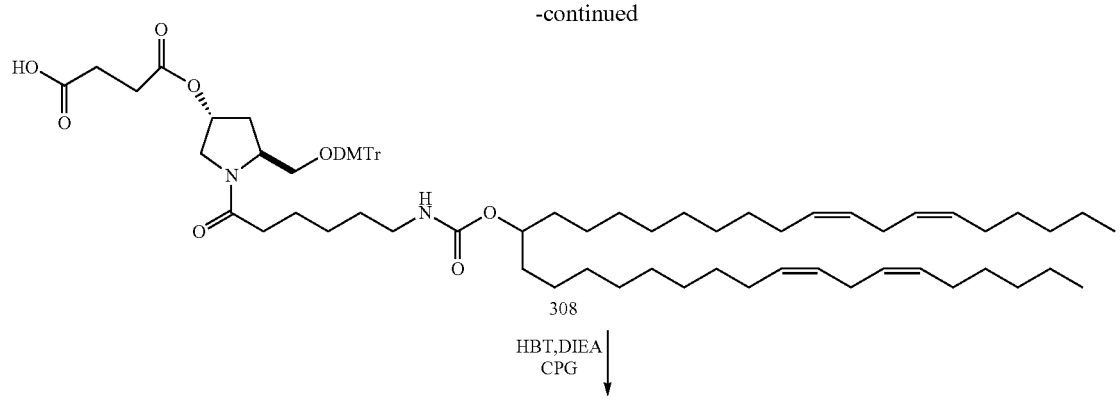

308

HBT,DIEA
CPG

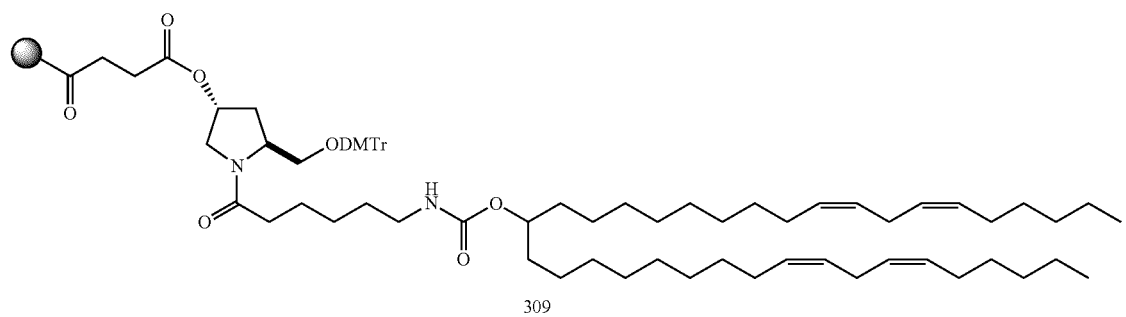

309

Synthesis of Compound 307: Dilinoleyl alcohol 6b (5.60 g, 10.50 mmol) and DSC (4.00 g, 15.87 mmol) were taken in anhydrous DCM (100 mL) and cooled in ice-water mixture. TEA (4.27 ml, 3 eq.) was added and stirred the mixture for two days. Reaction was monitored by TLC. Reaction mixture diluted with DCM and washed with water (two times) dried over sodium sulfate. Solvent was removed and the residue dried overnight. This material was used as such for the next reaction without any purification. To a solution of compound 305 (10.50 mmol) from the above reaction and hydroxyl proline derivative 55 (5.59 g, 10.50 mmol) in DCM (100 mL) pyridine (10 mL) was added and stirred the mixture overnight at ambient temperature. Reaction was monitored by TLC and removed solvent under reduced pressure. Dissolved the residue in DCM and washed with water, sodium bicarbonate solution and brine. Crude product was purified by chromatography 30-80% EtOAc/Hexane) to get the required product (6.64 g, 54%). MS: Molecular weight cal. for $C_{70}H_{106}N_2O_7$ 1086.80. Found: 1109.79 (M+Na).

Synthesis of Compound 308: To a solution of compound 307 (1.42 g, 1.30 mmol) in DCM was added DMAP (0.475 g, 3.90 mmol) followed by succinic anhydride (0.201 g, 2 eq.) and the reaction was continued for overnight at room temperature under argon. After completion of the reaction was cooled under ice cold temperature, cooled reaction mixture was washed with 10% cold citric acid solution followed by cold water. Combined organics were washed with brine, dried over $Na_2SO_4$, evaporated the solvent and purified the mixture through small bed of silica gel using DCM:MeOH (10%): triethylamine (0.5%), as gradients to get pure 308 (1.50 g quantitative yields). MS: Molecular weight cal. for $C_{74}H_{110}N_2O_{10}$ 1186.82. Found: 1185.78 (M−1).

Synthesis of CPG derivative 309: To a solution of compound 308 (1.50 g, 1.30 mmol) in DMF was added DIEA (0.700 ml, 3.0 eq), HBTU (0.740 g, 1.5 eq) followed by long alkylamino CPG (10 g, loading: 124 μmol/g) and continued on shaker for 4 hours. Filtered the resin, washed with DCM (2×), 10% MeOH in DCM (2×), DCM (2×), finally with ether (2×) and dried on vacuum. Capping: Dried resin was capped in a solution of pyridine:acetic anhydride (20%) mixture (100 ml) and continued on shaker for 45 minutes. After completion, the resin was filtered, washed with DCM (2×), 10% MeOH in DCM (2×), DCM (2×), finally with ether (2×) and dried on vacuum (10.35 g, loading: 73 μmol/g).

Example 16

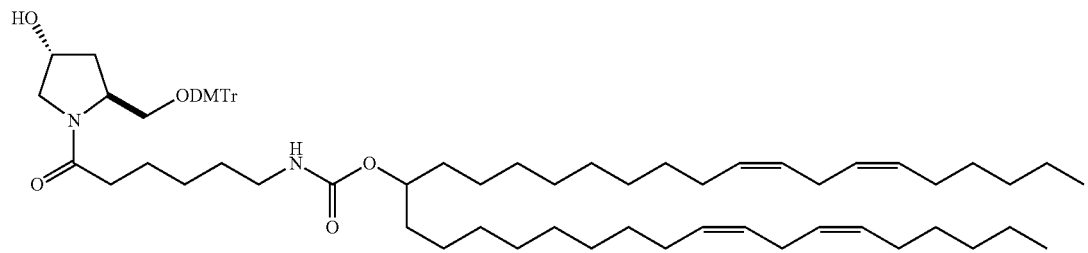

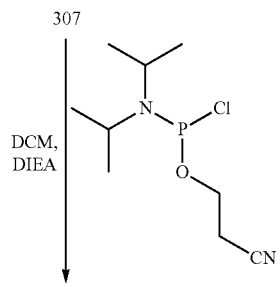

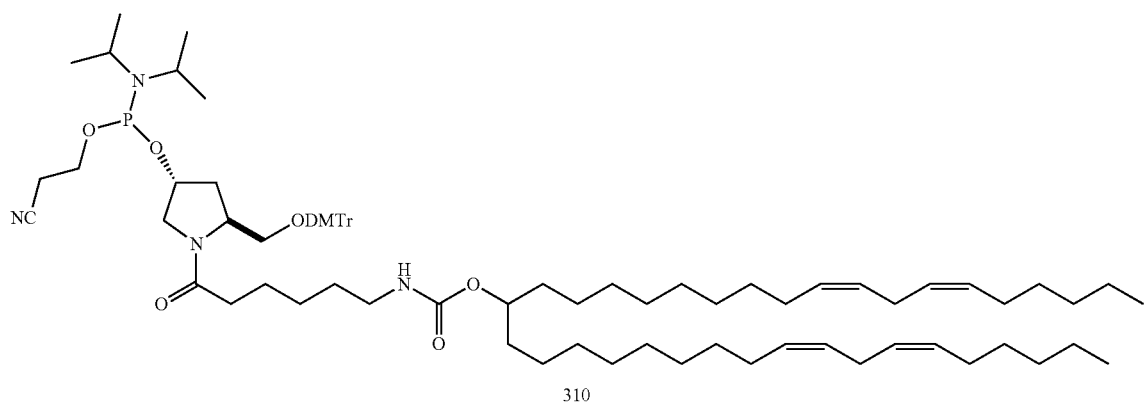

Synthesis of Compound 310: To a solution of compound 307 (3.12 g, 2.86 mmol) in DCM (50 mL). was added DIEA (1.00 mL, 2 eq) followed by choloroamidite reagent (0.850 ml, 1.30 eq). and stirred the mixture under argon. Reaction was monitored by TLC and after 15 minutes the mixture diluted with DCM, washed with sodium bicarbonate solution, water and dried. Crude product was purified by chromatography (40-80% EtOAc/Hexane with 1 TEA) to get the required compound (2.86 g, 78%), $^{31}$P NMR (400 MHz, DMSO-d6) δ 151.87, 151.69, 151.52, 151.20.

Example 17

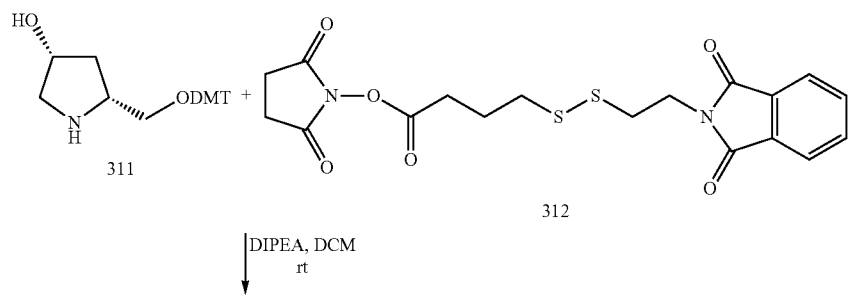

-continued

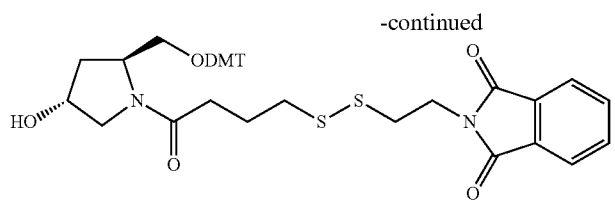

313

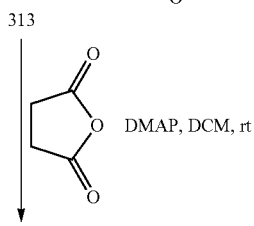

DMAP, DCM, rt

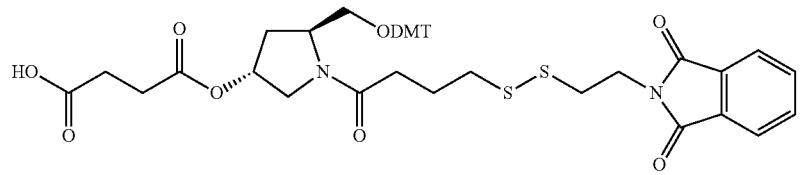

314

CPG-NH2
HBTU, DIPEA, DMF, rt

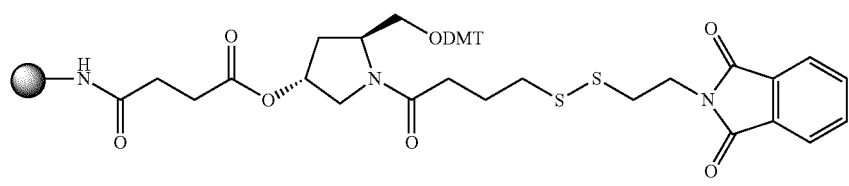

315

Synthesis of compound 313: To a solution of compound 311 (6.28 g, 15.0 mmol, 1.0 eq) and DIPEA (8.3 ml, 45.0 mmol, 3.0 eq) in DCM was added a solution of activated ester of compound 312 (6.33 g, 15.0 mmol, 1.0 eq) in DCM at room temperature and the reaction was continued for 4 hours, after completion of the reaction, solvent was evaporated and purified directly over silica gel using hexane:ethylacetate:triethylamine (0.5%) as gradients to get 9.47 g (87%) of the pure product 313. Ms: Calc. mass for $C_{40}H_{42}N_2O_7S_2$ is 726.2. found: 749.2 (M+Na).

Synthesis of compound 314: To a solution of compound 313 (9.46 g, 13.03 mmol, 1.0 eq) in DCM was added DMAP (4.76 g, 39.09 mmol, 3.0 eq) followed by succinic anhydride (2.6 g, 26.06 g, 2.0 eq) and the reaction was continued for overnight at room temperature under argon. After completion of the reaction was cooled under ice cold temperature, cooled reaction mixture was washed with 10% citric acid solution followed by cold water. Combined organics were washed with brine, dried over $Na_2SO_4$, evaporated the solvent and purified the mixture through small bed of silica gel using DCM:MeOH (10%):triethylamine (0.5%) as gradients to get pure 10.7 g (quantitative yields) of the compound 314. MS: Calc. mass for $C_{44}H_{46}N_2O_{10}S_2$ is 826.2. found 826.2.

Synthesis of Compound 315 (loading on CPG-NH₂): To a solution of compound 314 (10.65 g, 12.9 mmol, 1.0 eq) in DMF was added DIPEA (6.98 ml, 37.92 mmol, 3.0 eq), HBTU (7.19 g, 18.96 mmol, 1.5 eq) followed by CPG-NH₂ (105 g, 13.02 mmol, 1.01 eq, load: 124 µmol/g) and continued on shaker for 4 hours. Filtered the resin, washed with DCM (2×), 10% MeOH in DCM (2×), DCM (2×), finally with ether (2×) and dried on vacuum. Capping: Dried resin was capped in a solution of pyridine:acetic anhydride (20%) mixture (400 ml) and continued on shaker for 45 minutes. After completion, the resin was filtered, washed with DCM (2×), 10% MeOH in DCM (2×), DCM (2×), finally with ether (2×) and dried on vacuum to the resin 315 (110 g. Loading: 66 µmol/g).

Example 18

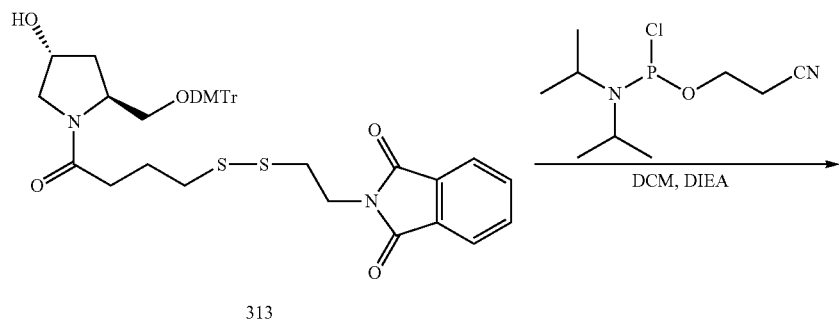

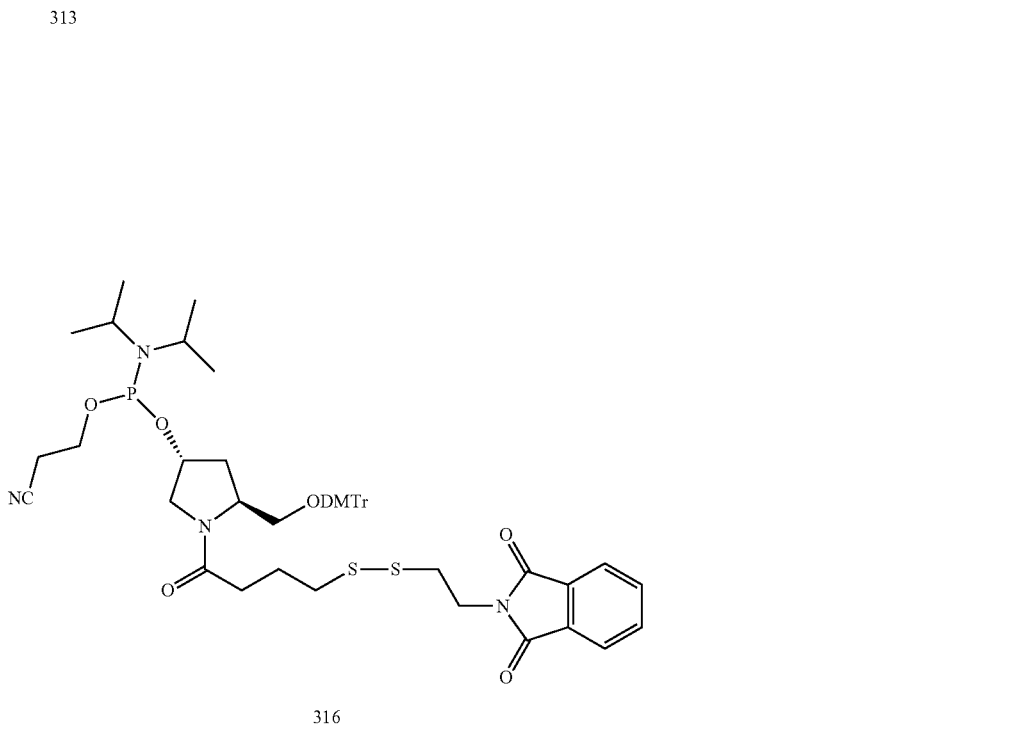

Synthesis of compound 316: To a solution of compound 313 (5.36, 7.37 mmol) in DCM (50 mL) was added DIEA (3.30 mL, 2.5 eq) followed by choloroamidite reagent (2.14 ml, 1.30 eq). and stirred the mixture under argon. Reaction was monitored by TLC and after 15 minutes the mixture diluted with DCM, washed with sodium bicarbonate solution, water and dried. Crude product was purified by chromatography (40-100% EtOAc/Hexane with 1% TEA) to get the required compound (5.63, 82%), $^{31}$P NMR (400 MHz, DMSO-d6) d 151.92, 151.74, 151.53, 151.28.

Example 19

Synthesis of Spermine and Cholesterol Oligonucleotide Conjugate

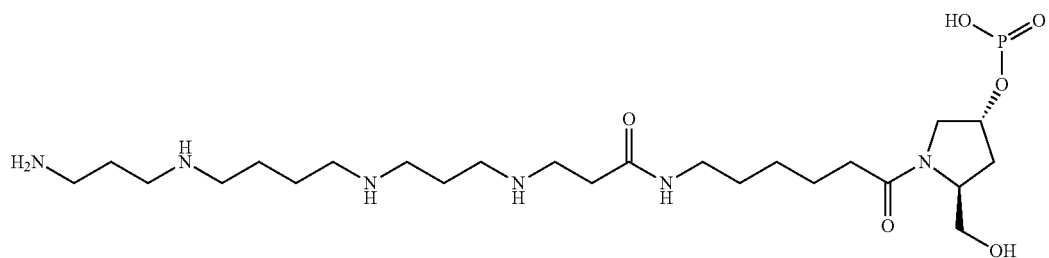

Q94: Spermine

-continued

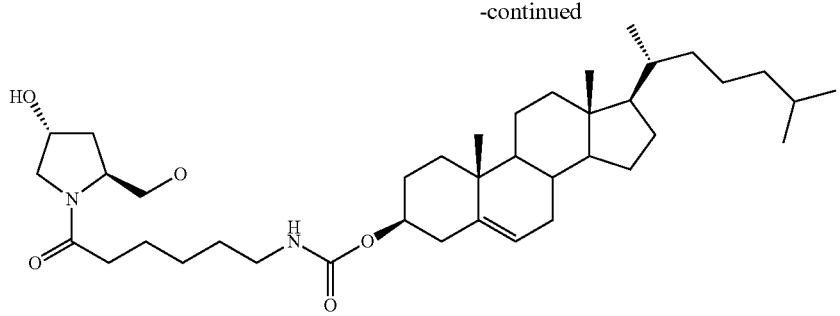

L10: Cholesterol

The oligonucleotide (A-40867: AAUCuuAuAuuuGAUCcAAsQ94L10 (SEQ ID NO: 187) (target ApoB) was synthesized on ABI 392 DNA/RNA Synthesizer at 40umol scale using standard phosphoramidite chemistry as outlined in Example 2. The solid support was then treated with 0.5M piperdine in acetonitrile for 5 to 10mins followed 3 times acetonitrile wash. The cleavage from the solid support and nucleobase deprotection was done with 3:1 mixture of Ammonia/ethanol at 55° C. for 5 hours. Reaction mixture was cooled and filtered, the support was washed the 3x volume of DMSO. Added 1.5x volume TEA3HF into the reaction mixture and heated at 40C for 1.5 hours. The crude product was purified with reverse phase HPLC and desalted with size exclusion column. Calculated MW: 8010.8, observed MW: 8009.1

Example 20

Conjugation of DLink-DMA with Hydrazone Linkage to Oligonucleotide

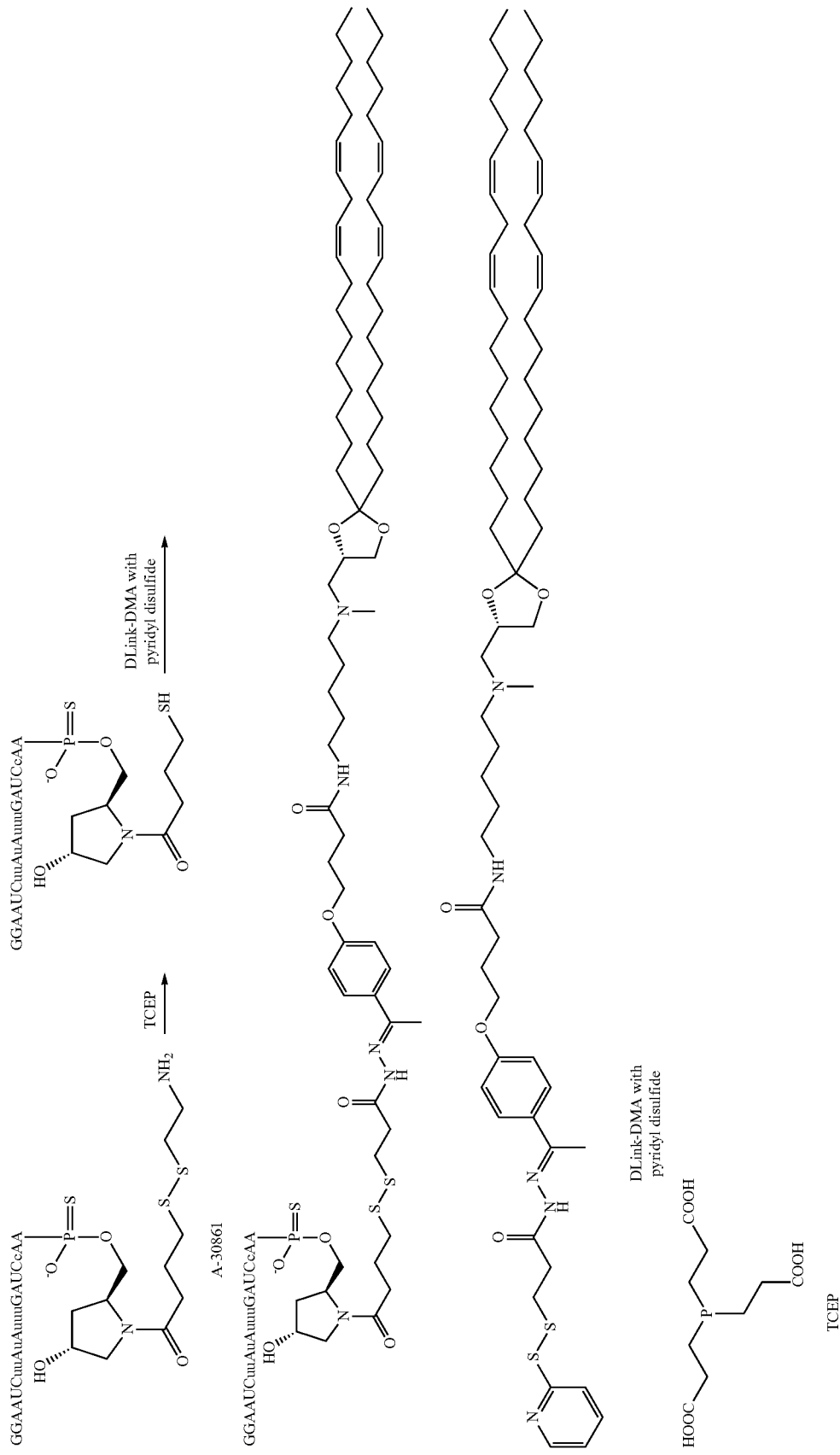

Oligonucleotide (A30861) (SEQ ID NO: 188) was synthesized and purified using standard protocols outlined in example 2. Purified A30861 was dissolved in 50mM TEAA buffer (pH=7) and added 2-3 equivalents of TCEP (0.1M in water). Incubated at 40° C. for 30mins or room temp for overnight. Removed excess TCEP on C18 column and collected the RNA in 50mM TEAA buffer with 25% acetonitrile. Dissolved 2-3 equivalents DLinK-DMA pyridyl disulfide in 1:1 mixture of DMSO and acetonitrile and added into the RNA solution. Coupling reaction was performed at room temperature for 30 minutes. Calculated MW: 8056.1, Observed MW: 8053.8 (major impurity: 8038.6).

Example 21

Post Synthesis Conjugation of Activated DLin-k-DMA with Thiol Modified Oligonucleotides

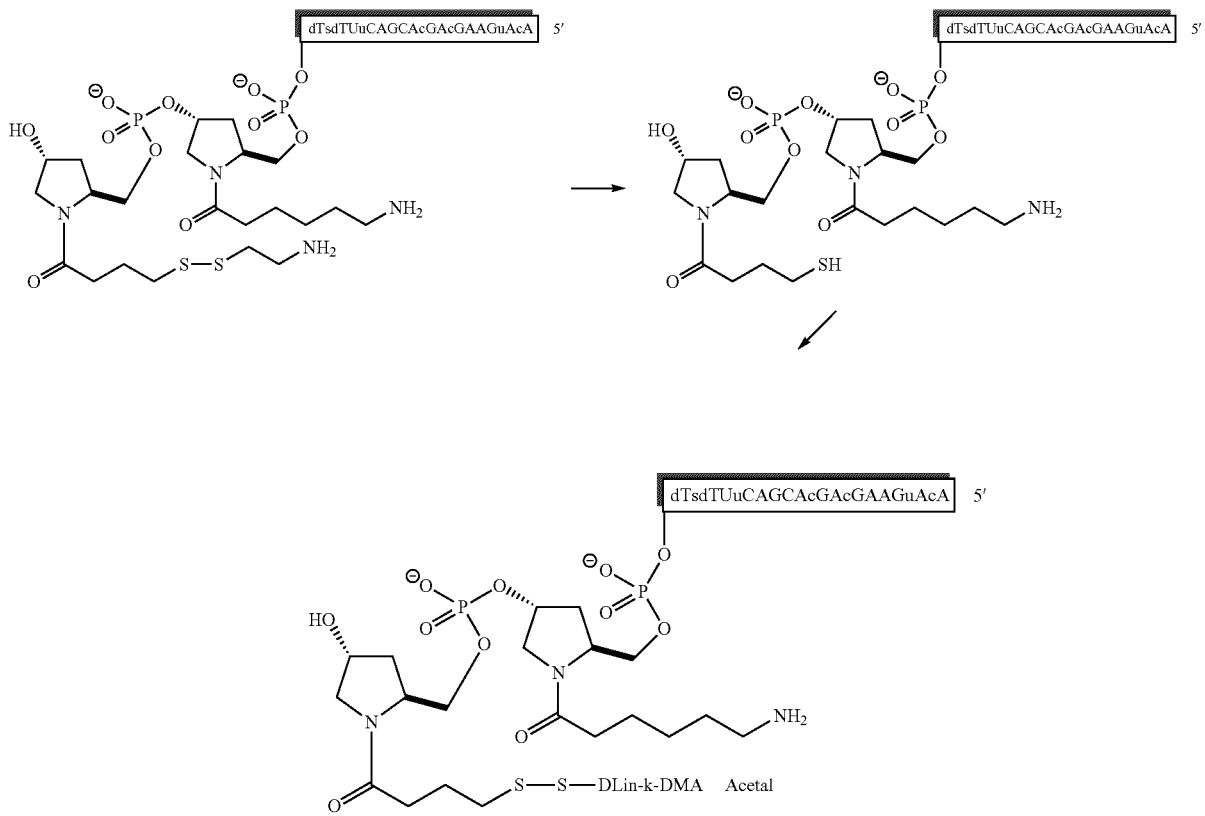

Oligonucleotide (40377.1: AcAuGAAGcAGcACGACuUdTsdTQ8L99(SEQ ID NO: 189), Q8,=Hyp-Amino, L99=Hyp-S-S-amino) was synthesized and purified using standard protocols outlined in example 2. DLin-k-DMA was then conjugated with the oligonucleotide as follow:

Reduction of Disulfide bond: The oligonucleotide (10 mg) was dissolved in 1.0 ml of 0.5 M Ammonium acetate. 0.2 M TCEP solution (280 ul) was added and put at heating block at 45 oC for 90 min. The excess of TCEP was removed by using Sephadex G-25 Nap-25 column. The identity of the compound was confirmed by Ion exchange analysis as well as LC-MS analysis.

Conjugation of thiol modified oligonucleotides with acid-cleavable-DLin-k-DMA. The Thiol containing sample was dissolved in 450 μl of 0.2M Sodium bicarbonate buffer (pH 8.5). To the dissolved oligonucleotide activated acid-cleavable-DLin-k-DMA (10 equiv.) in 50 μl of DMF was added and the reaction mixture was shaken over night at room temperature. Progress of reaction was analyzed by HPLC. LC-MS analysis of conjugated oligonucleotides is in progress.

Example 22

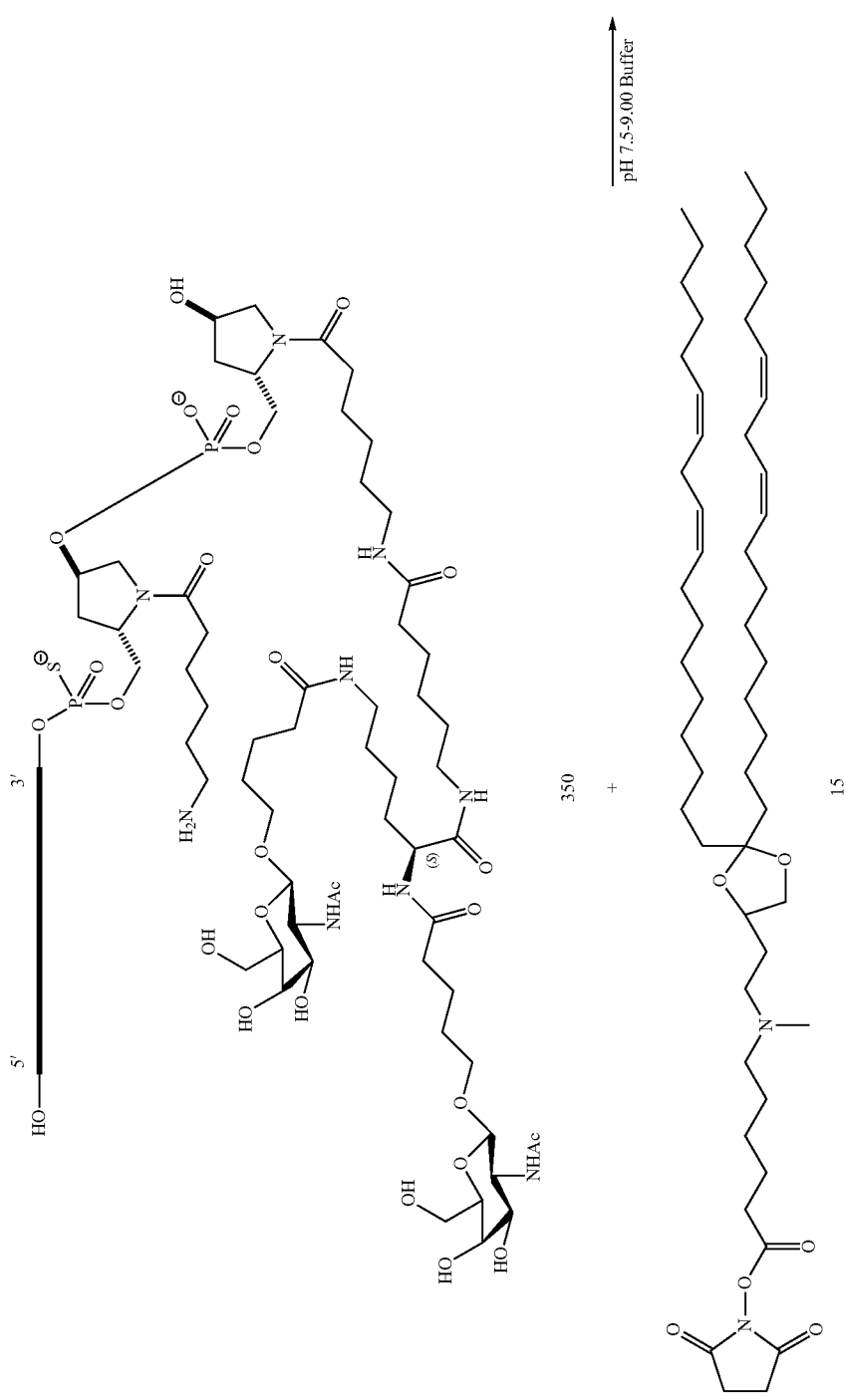

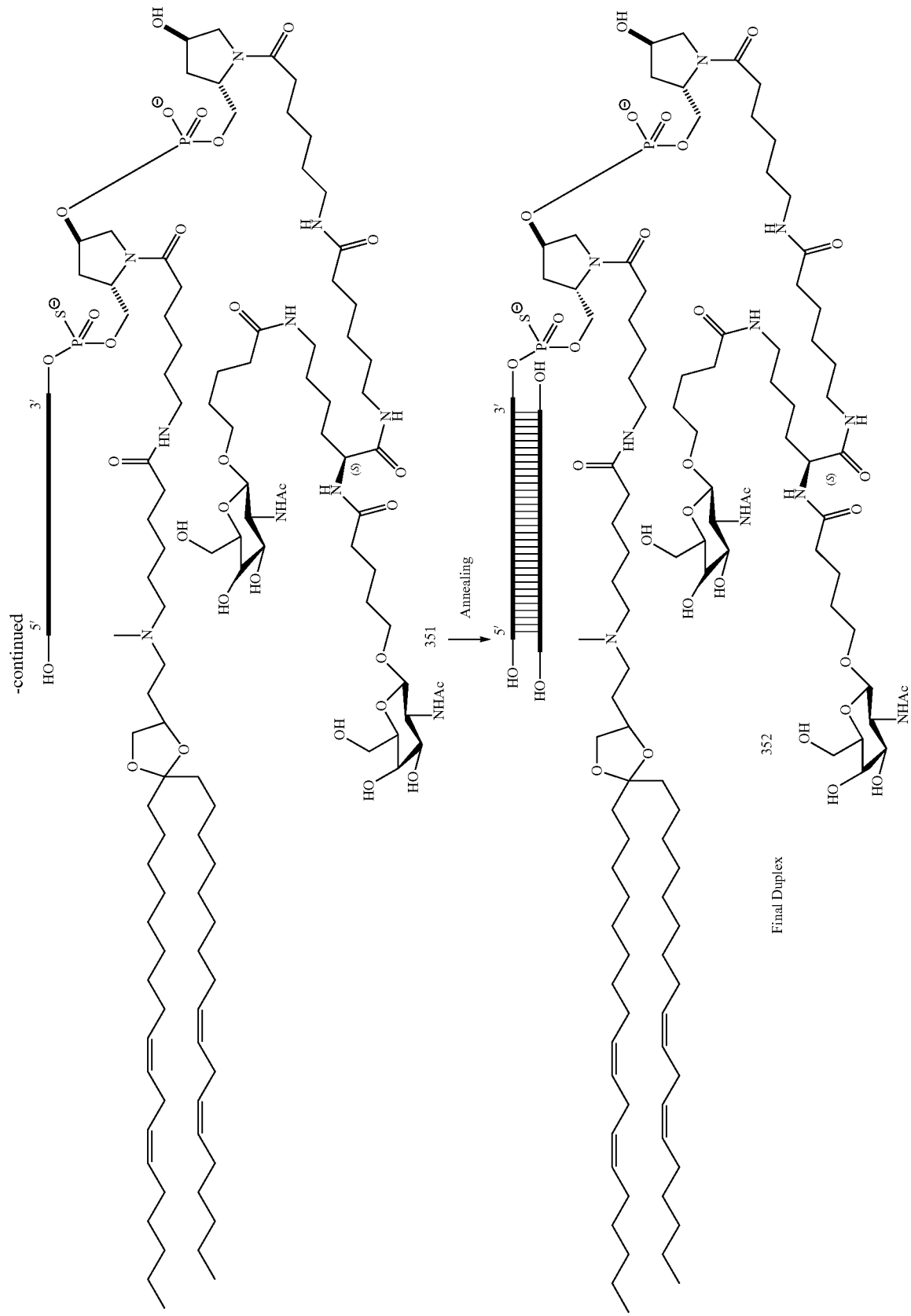

Amino RNA 350 is treated with compound 15 under basic pH to get compound 351. It is purified and anneal with corresponding complementary sequence to get the duplex 352. This compound is used for all biological experiments.

Example 23

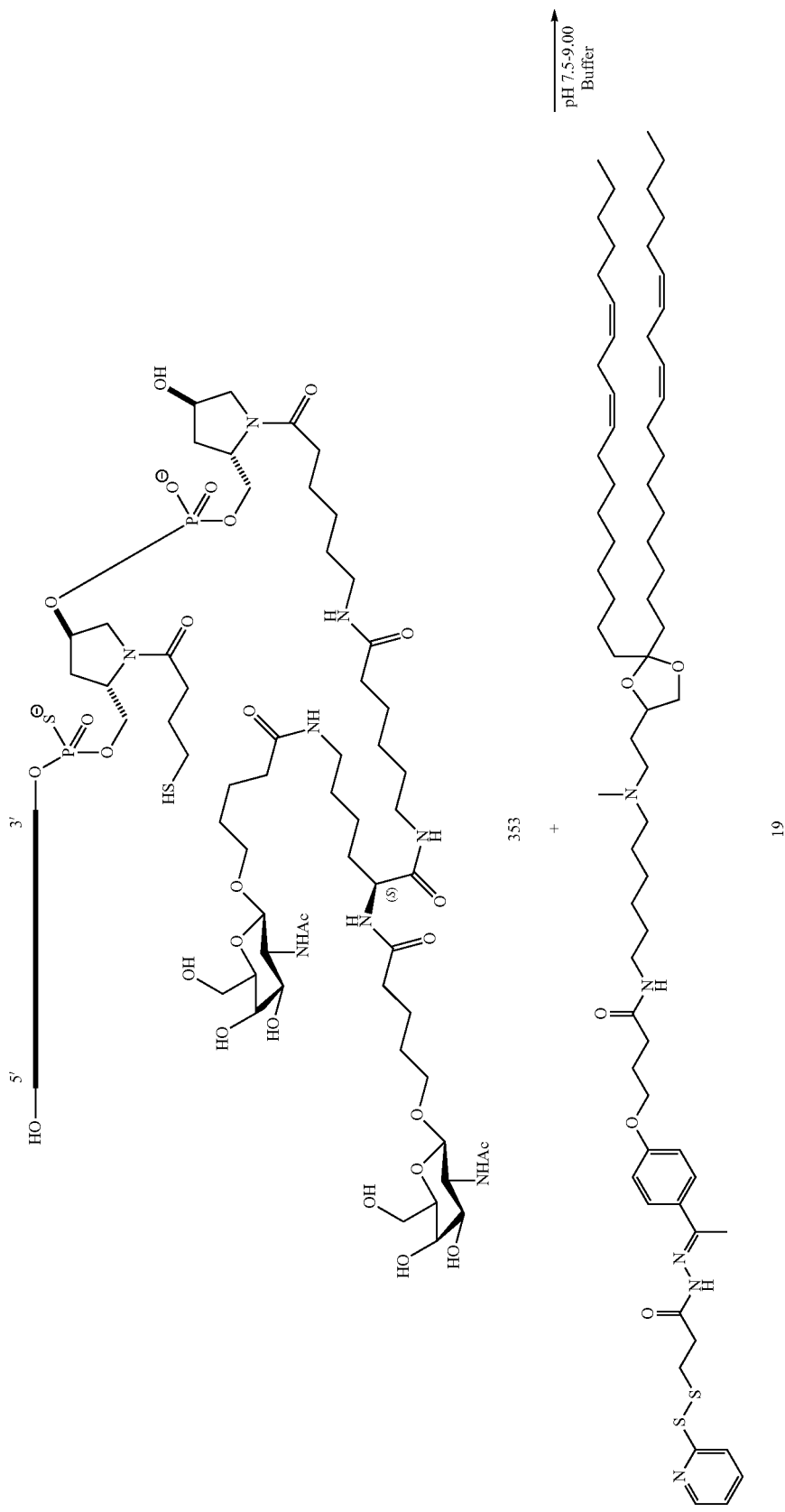

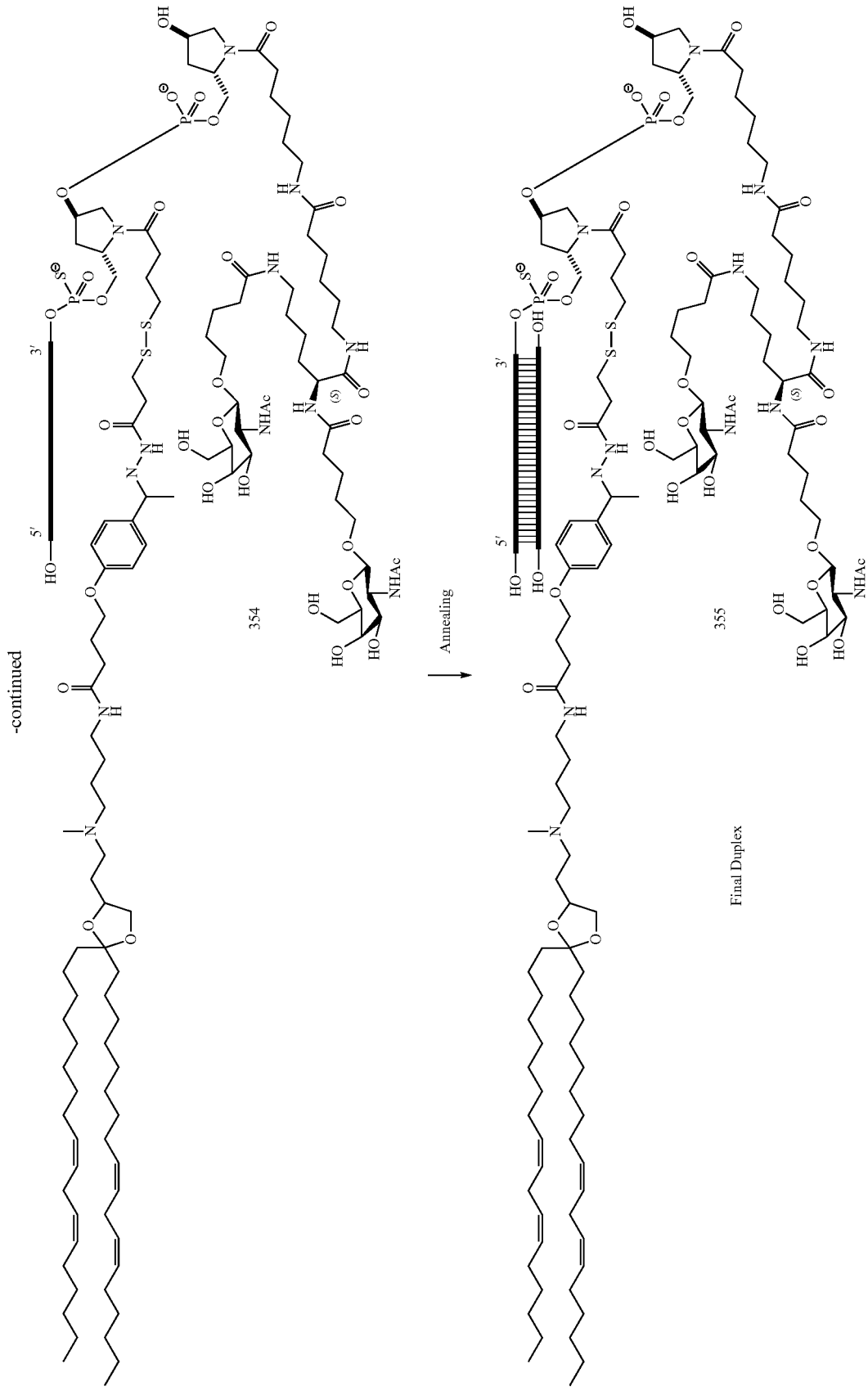

Thiol RNA 353 is treated with compound 19 under basic pH to get compound 354. It is purified and anneal with corresponding complementary sequence to get the duplex 355. This compound is used for all biological experiments.

Example 24

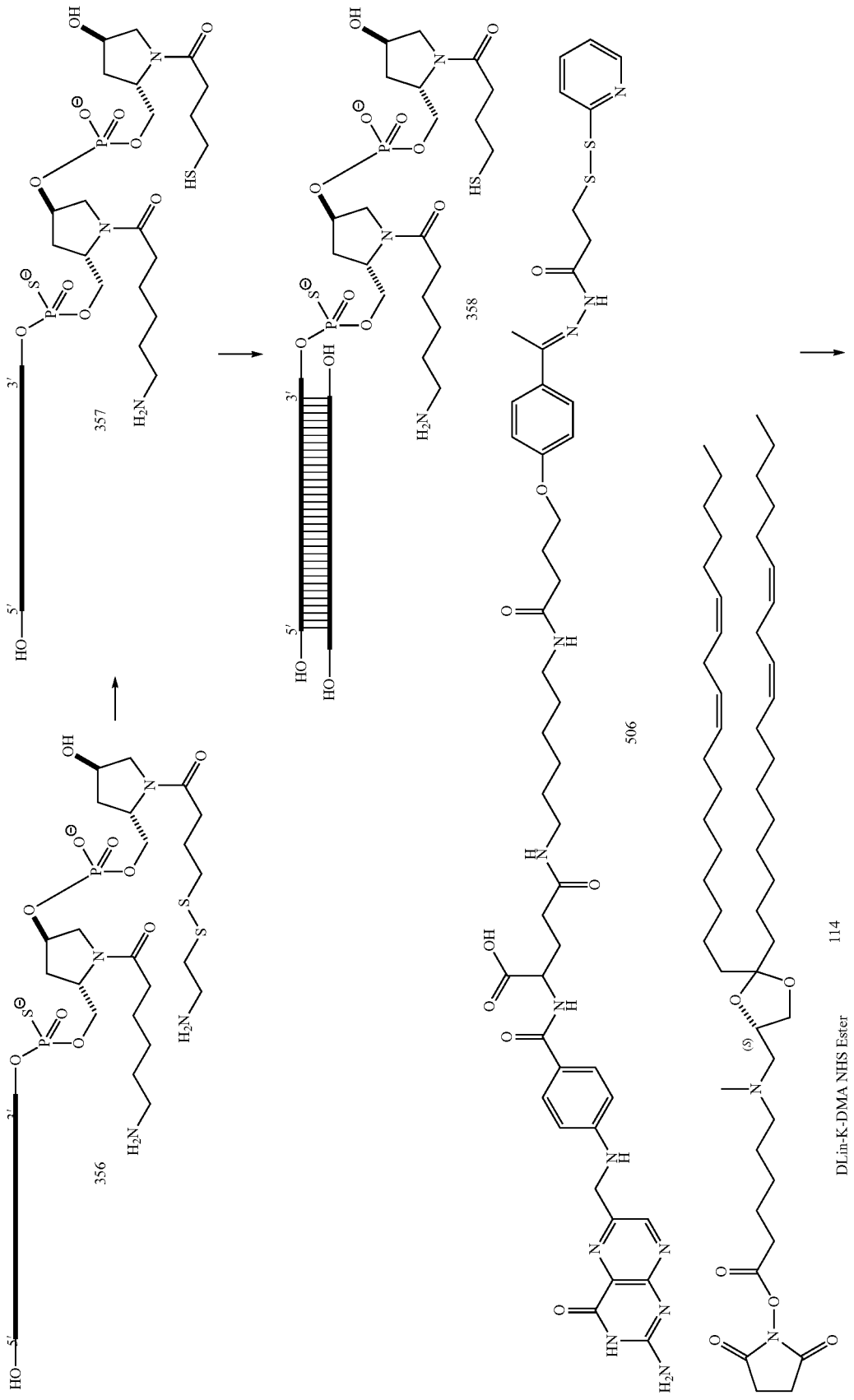

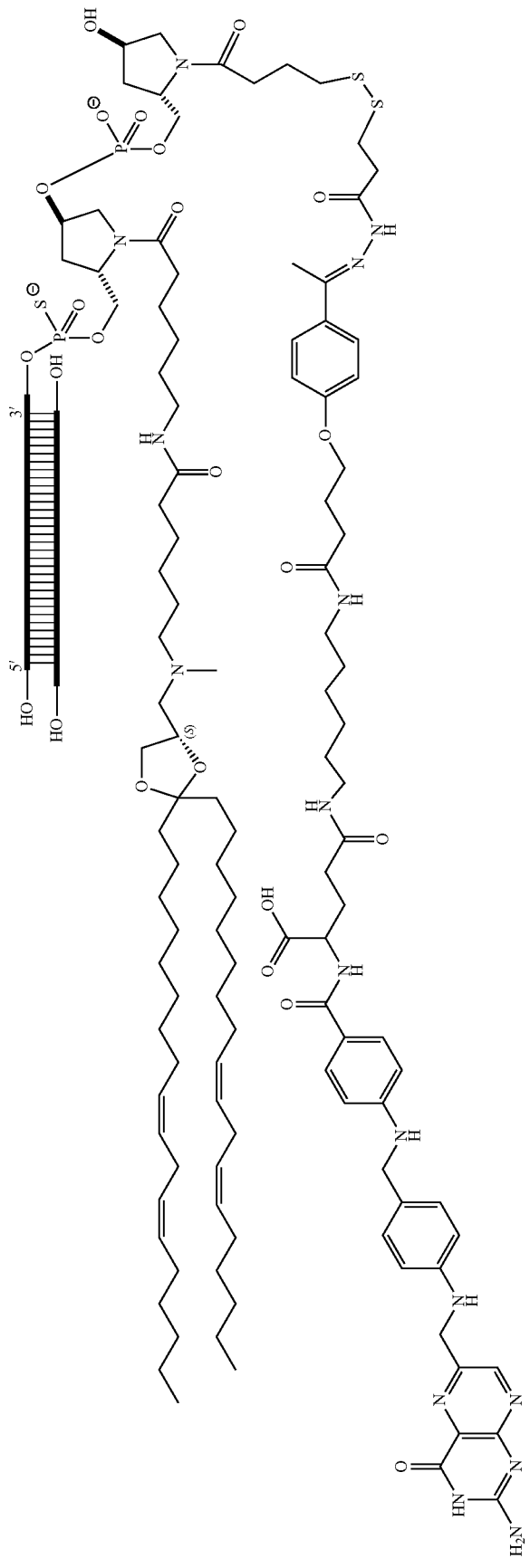
359
-continued

Bifuntional RNA 357 is annealed with corresponding complementary strand to get the duplex 358. This compound is treated with compound 506 under basic pH initially to get the intermediate. The intermediate is then treat with the NHS ester 114 to get the final compound 359. It is purified and is used for all biological experiments.
Example 25
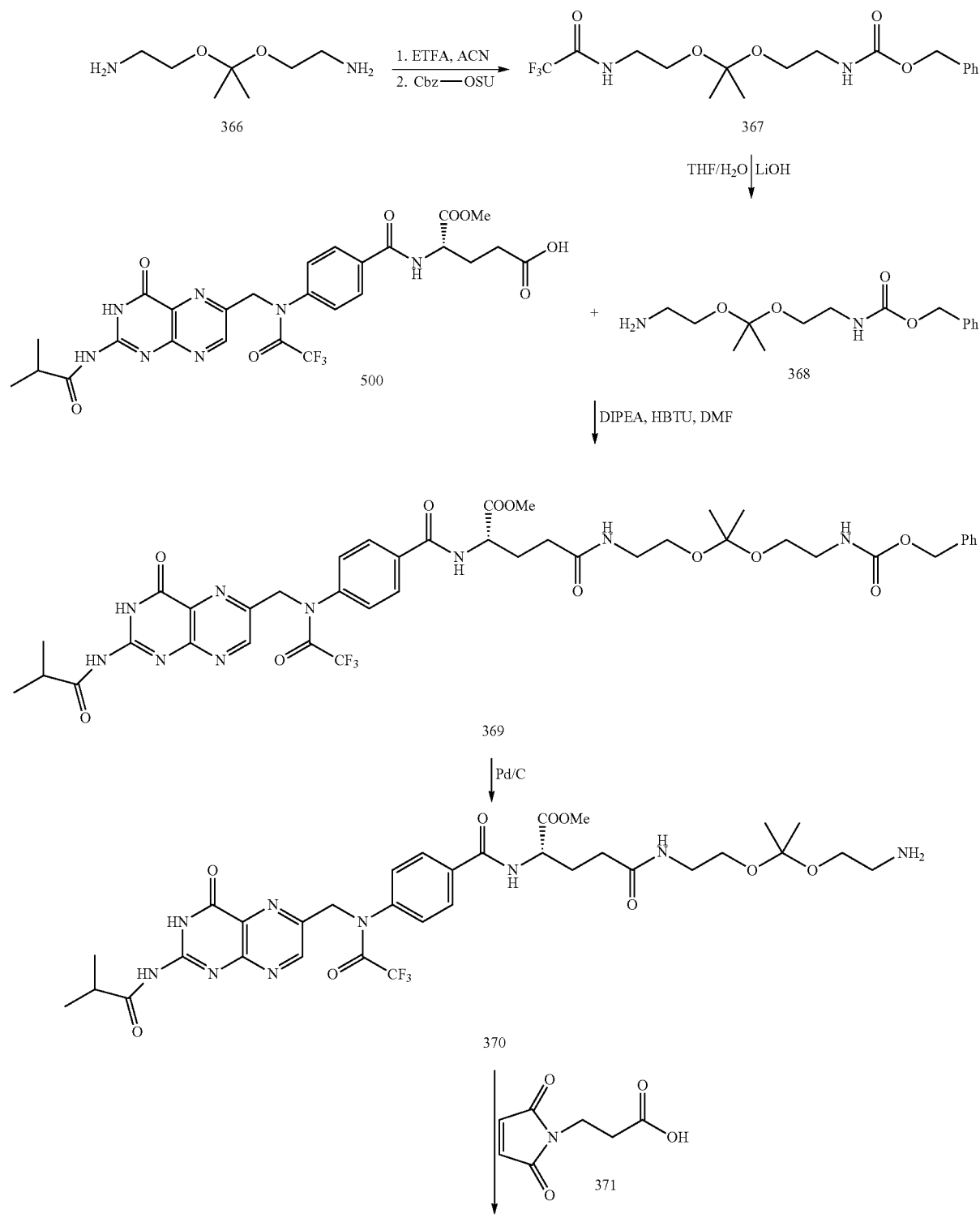

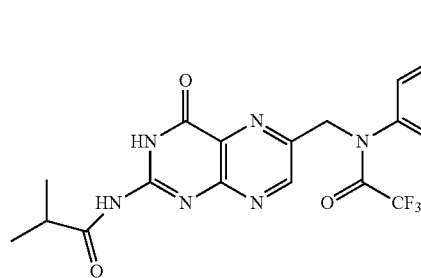
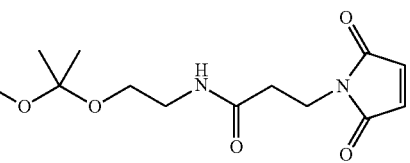

372

↓ LiOH

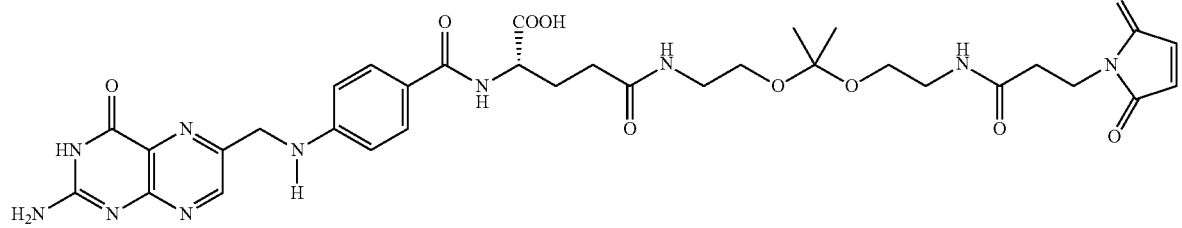

373

The ketal 366 was synthesized using a reported procedure (Paramonov, S. E.; Bachelder, E. M.; Beaudette, T. T.; Standley, S. M.; Lee, C. C.; Dashe, J.; Frechet, Jean M. J. Fully Acid-Degradable Biocompatible Polyacetal Microparticles for Drug Delivery. *Bioconjugate Chemistry* (2008), 19 (4), 911-919). The transient protection of the ketal was carried out in two steps in one pot first by treating the diamine with one equivalent of ethyltrifluoroacetate followed by one equivalent of Cbz-OSu to provide the di protected derivative 367 in 80% yield after column purification. The protected amine 367 on treatment with aqueous LiOH provided the maine 368 in quantitative yield. Coupling of this amine 368 (0.5 g) with the protected folic acid 113 (1 g) provided the coupled product 369 (1.1 g) which on hydrogenation provided the amine 370 in quantitative yield. Coupling of amine 370 was carried out with the maleimidopropionic acid 371 to give the coupled product 372 in good yields. The final deprotection of all the protecting group in 372 is carried out using ice-cold aqueous LiOH in THF to afford the precursor 373 as an orange solid.

Example 26

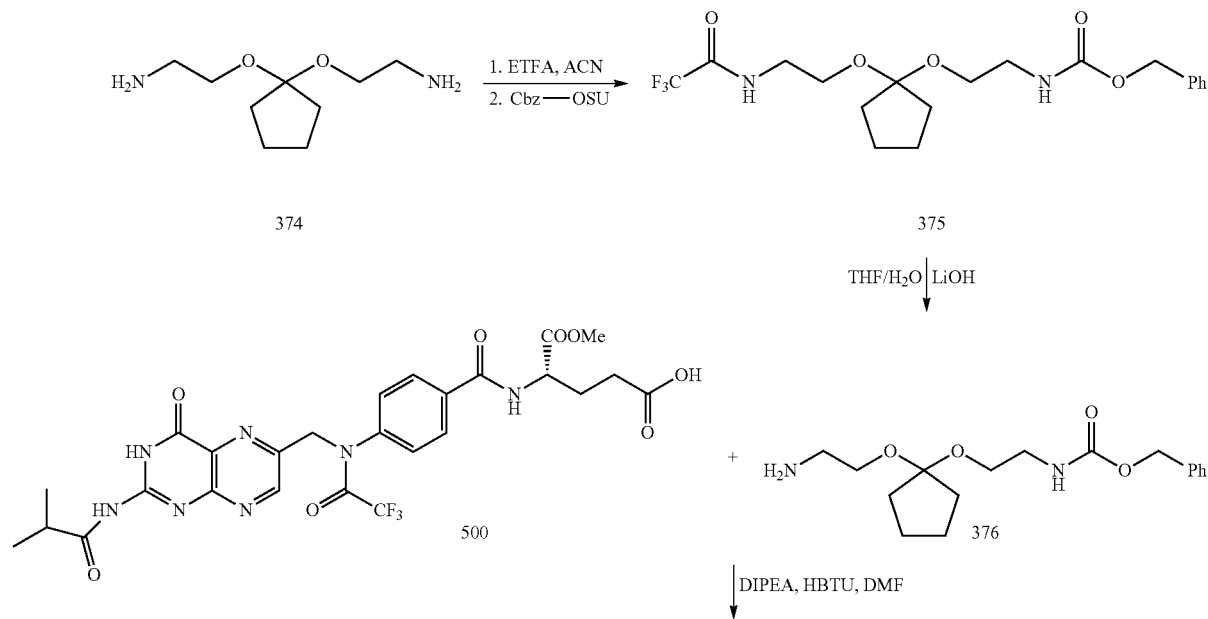

203 204
-continued
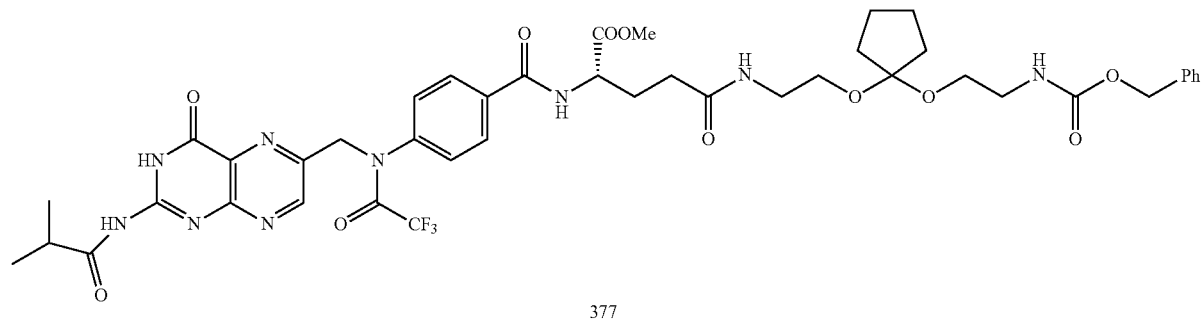
377 ↓ Pd/C
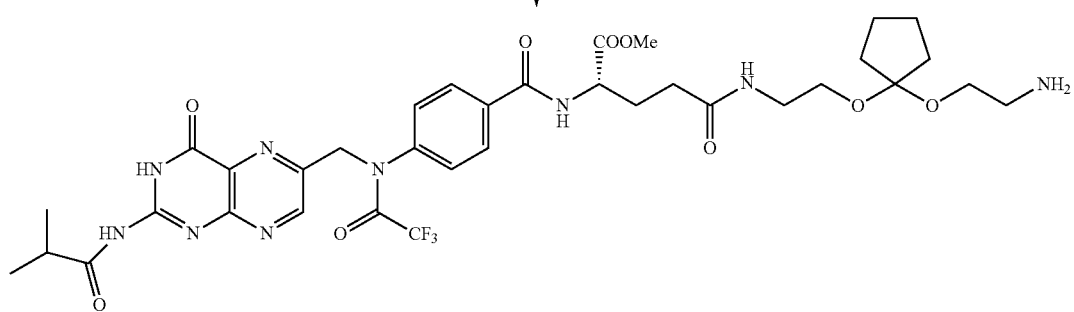
378 ↓ (379)
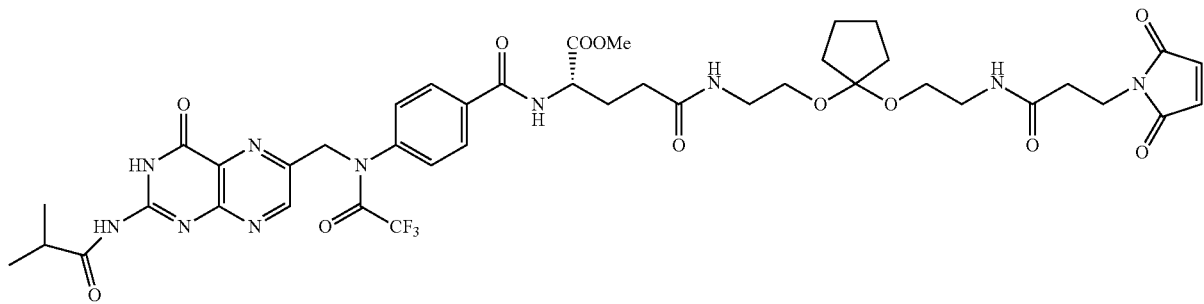
380 ↓ LiOH
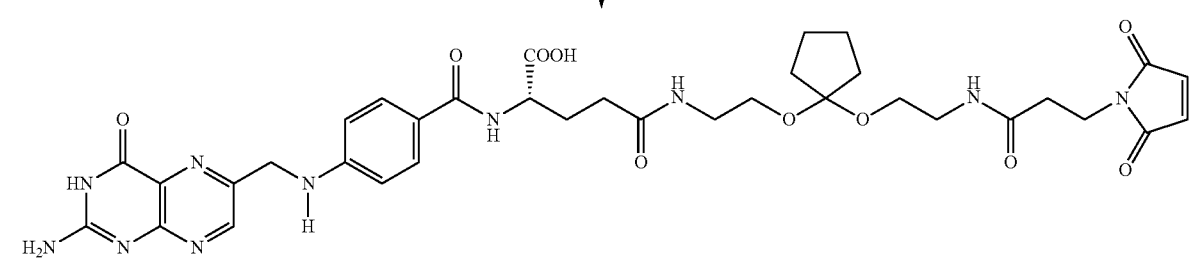
381

In another embodiment, the dimethyl acetal group was replaced by a cyclopentenyl group. The ketal 374 is converted to the monoprotected amine 376 via the TFA derivative 375 as shown in the following Scheme. The amine 376 on treatment with the acid 500 provided the coupled product 377 which is hydrogenated to give the amine 378 which is coupled with the maleimide 379 and deprotected to give the derivative 381.

Example 27

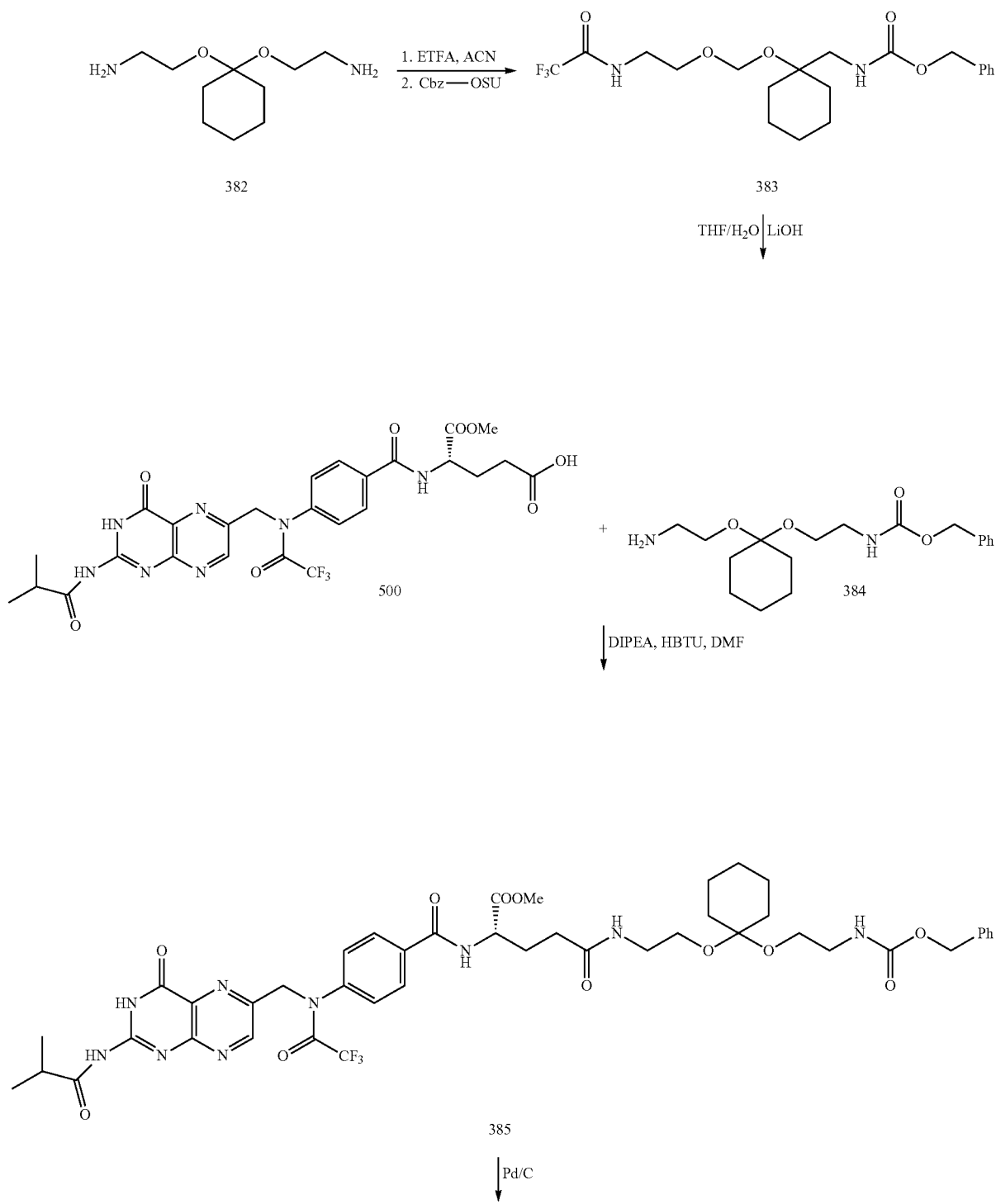

-continued
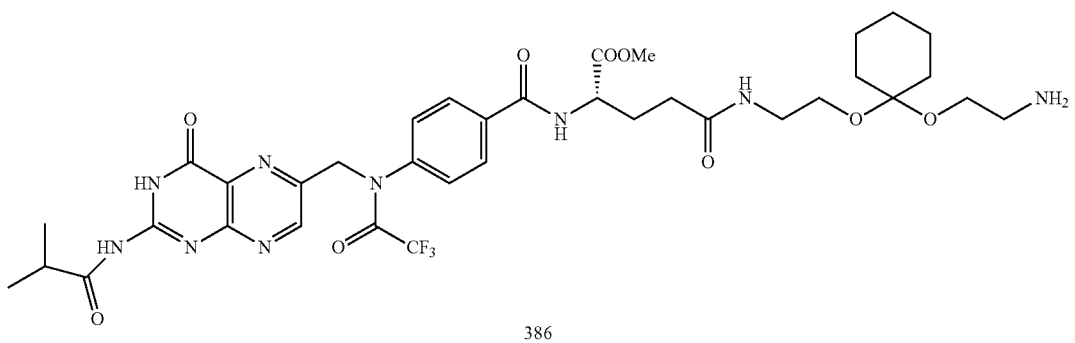
386
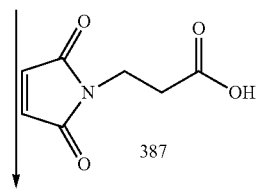
387
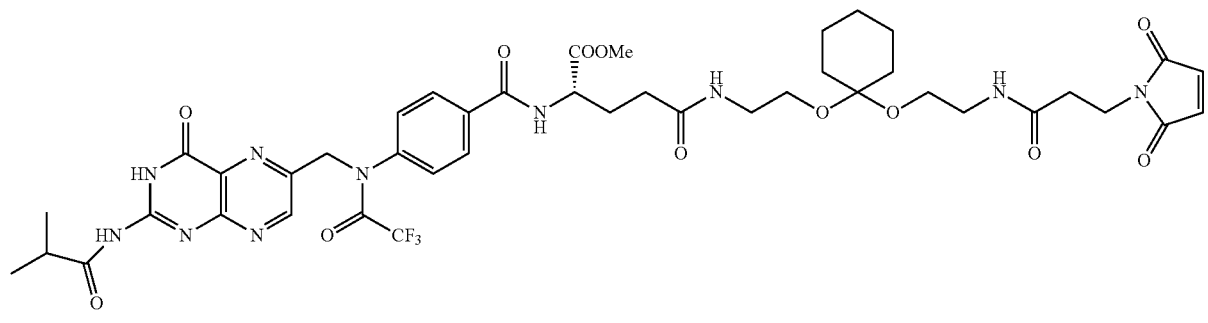
388
 LiOH
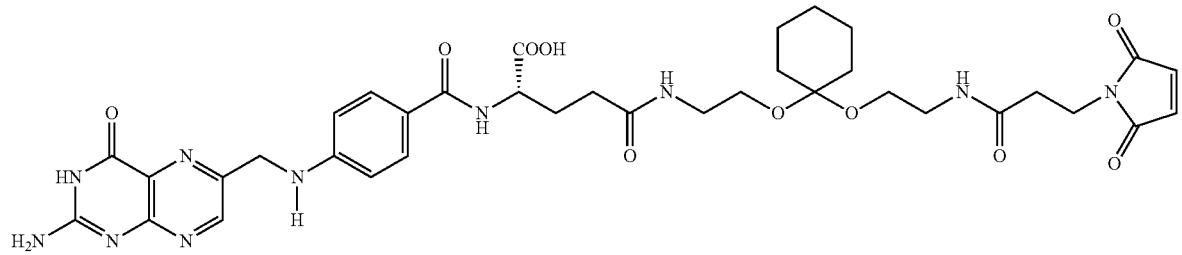
389

In another embodiment, the dimethyl acetal group was replaced by a cyclohexyl group. The ketal 382 is converted to the monoprotected amine 384 via the TFA derivative 383 as shown in the following Scheme. The amine 384 on treatment with the acid 500 provided the coupled product 385 which is hydrogenated to give the amine 386 which is coupled with the maleimide 387 and deprotected to give the derivative 389.

Example 28

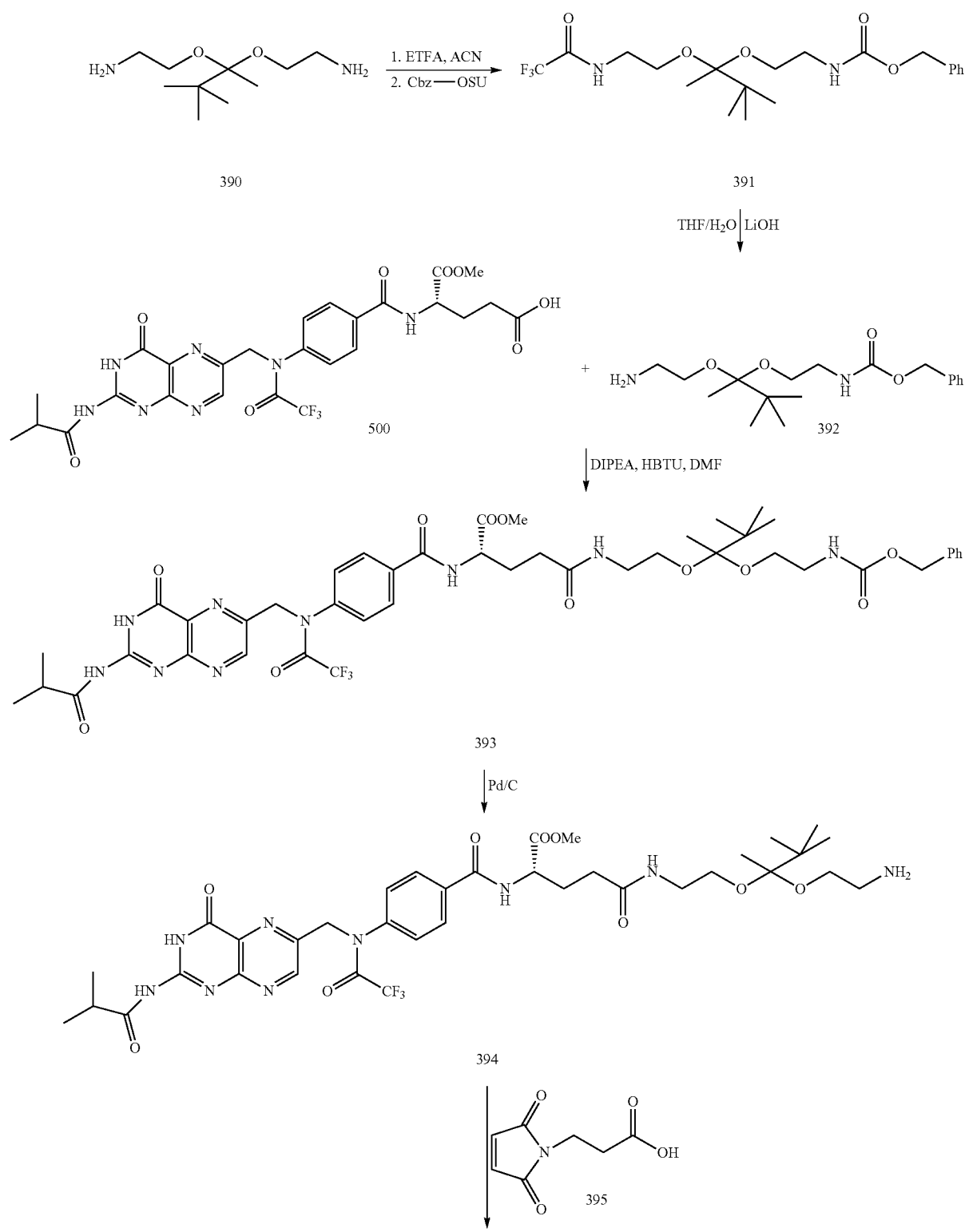

-continued

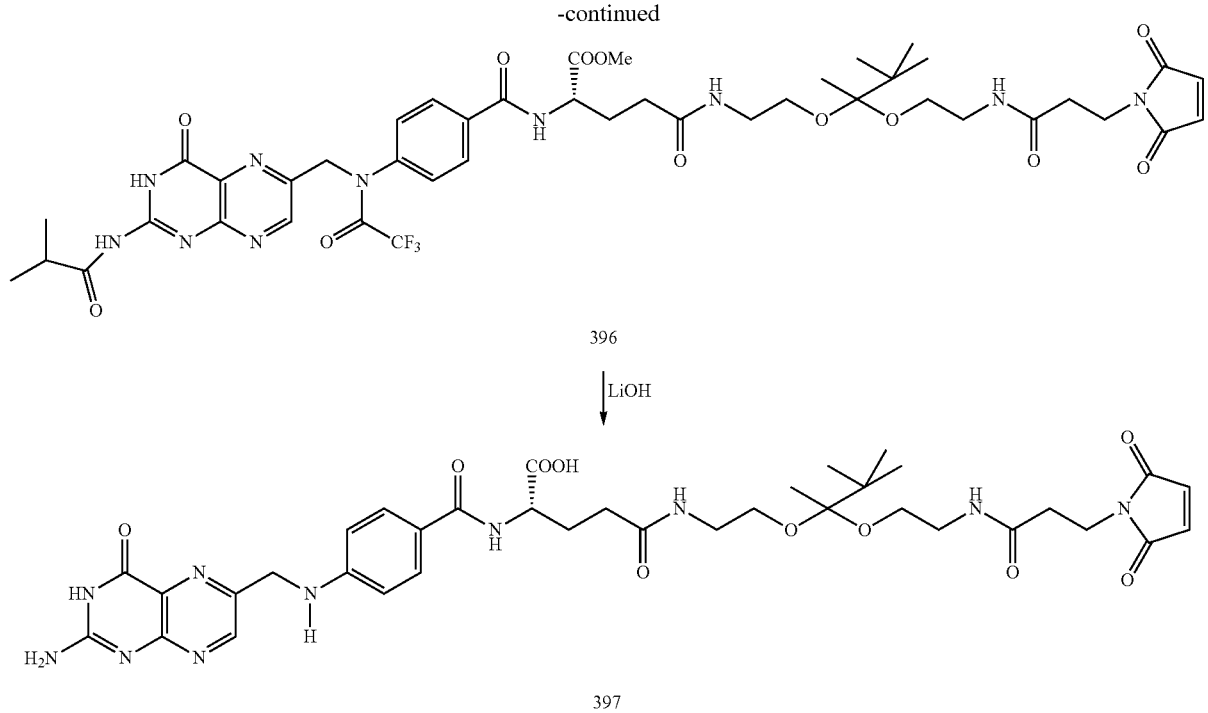

In another embodiment, the dimethyl acetal group was replaced by a methyl t-butyl group. The ketal 390 is converted to the monoprotected amine 392 via the TFA derivative 391 as shown in the following Scheme. The amine 392 on treatment with the acid 500 provided the coupled product 393 which is hydrogenated to give the amine 394 which is coupled with the maleimide 395 and deprotected to give the derivative 397.

Example 29

213 214
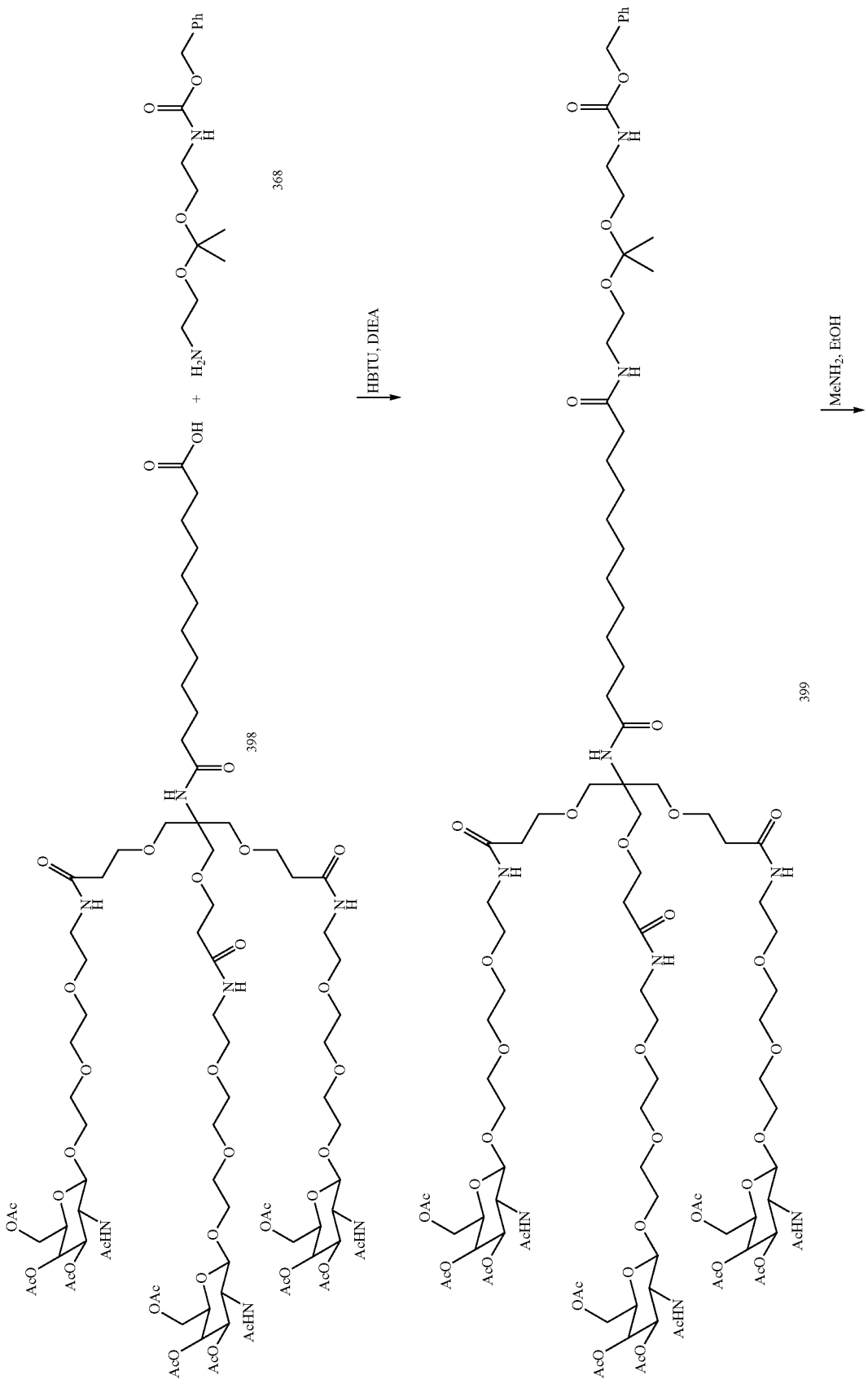

-continued
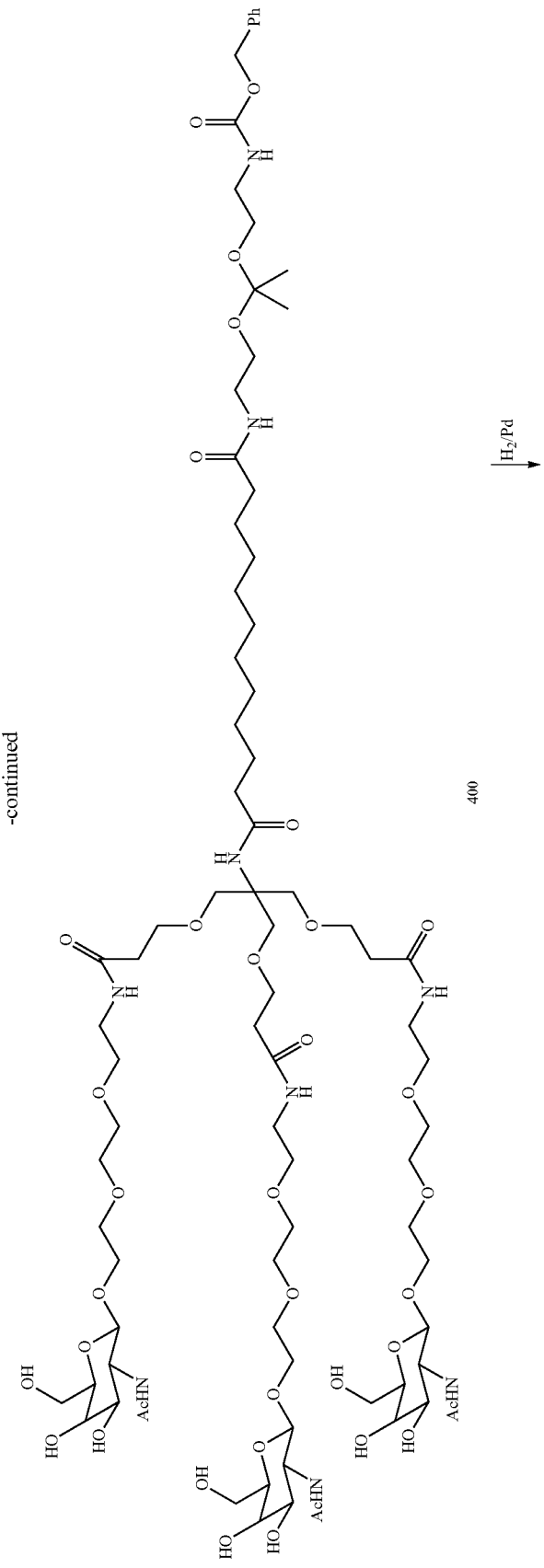
$\xrightarrow{H_2/Pd}$

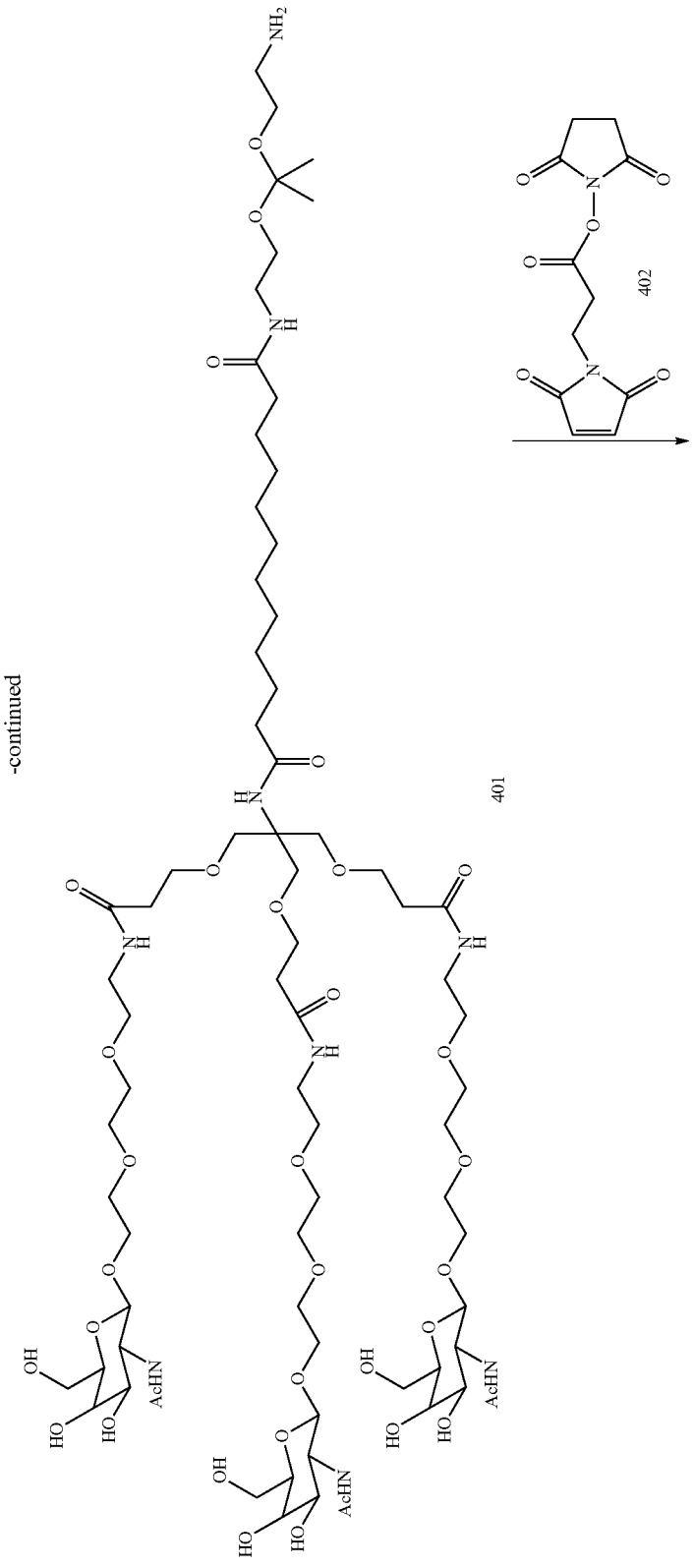

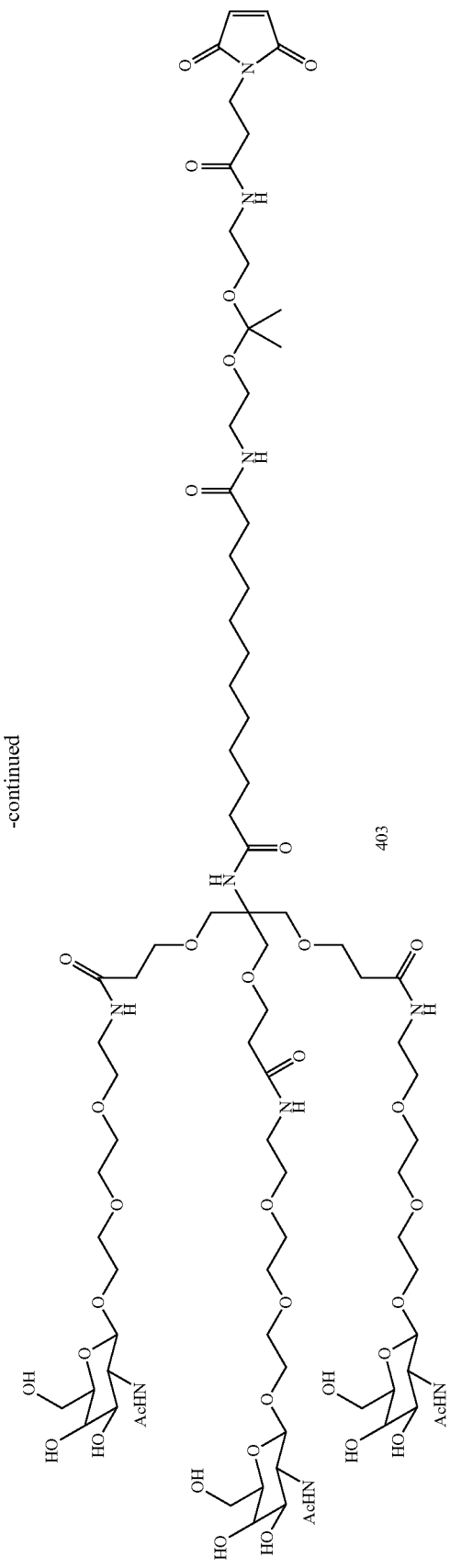

Compound 403 is prepared as outlined above and then conjugated to nucleic acid.

Example 30

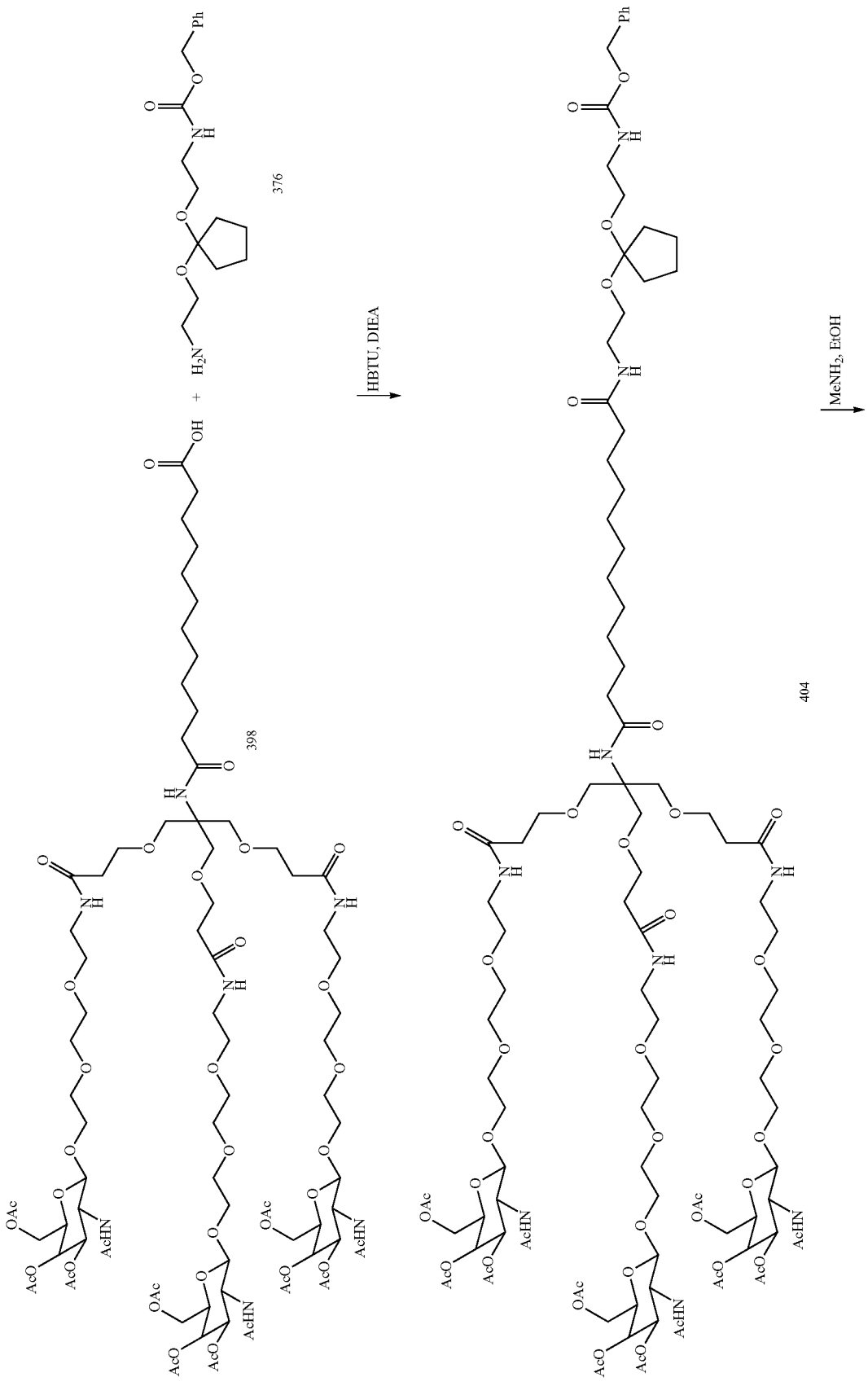

-continued
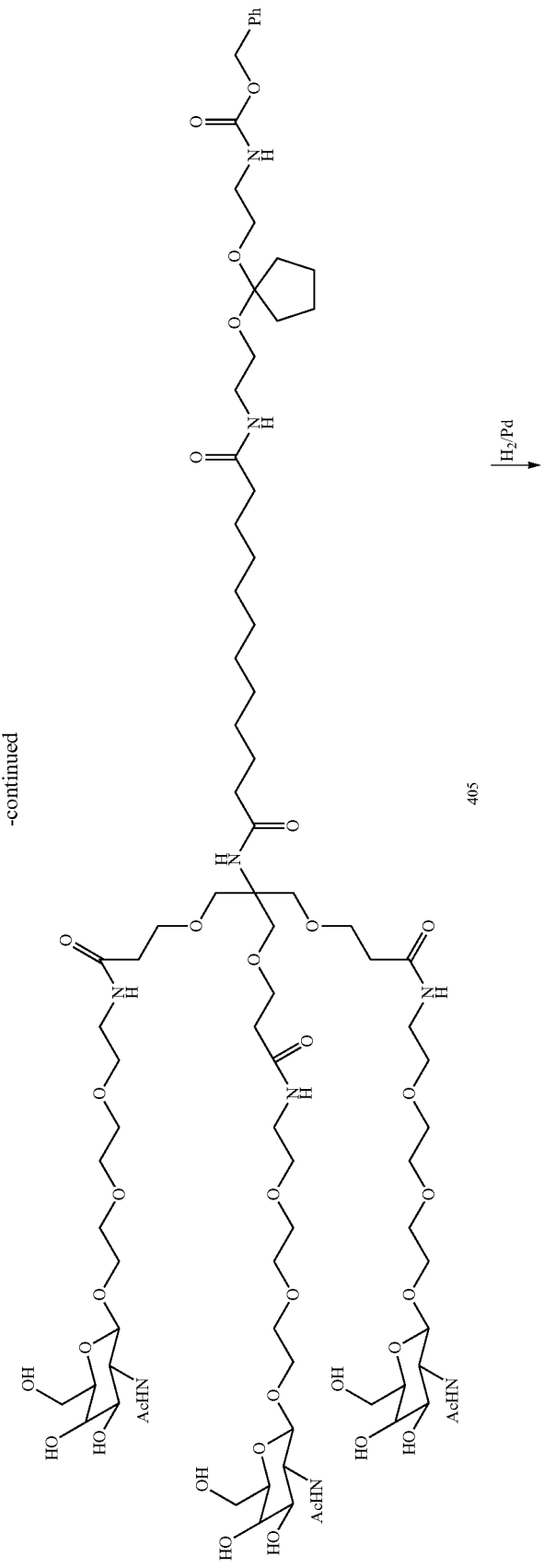
405
H₂/Pd

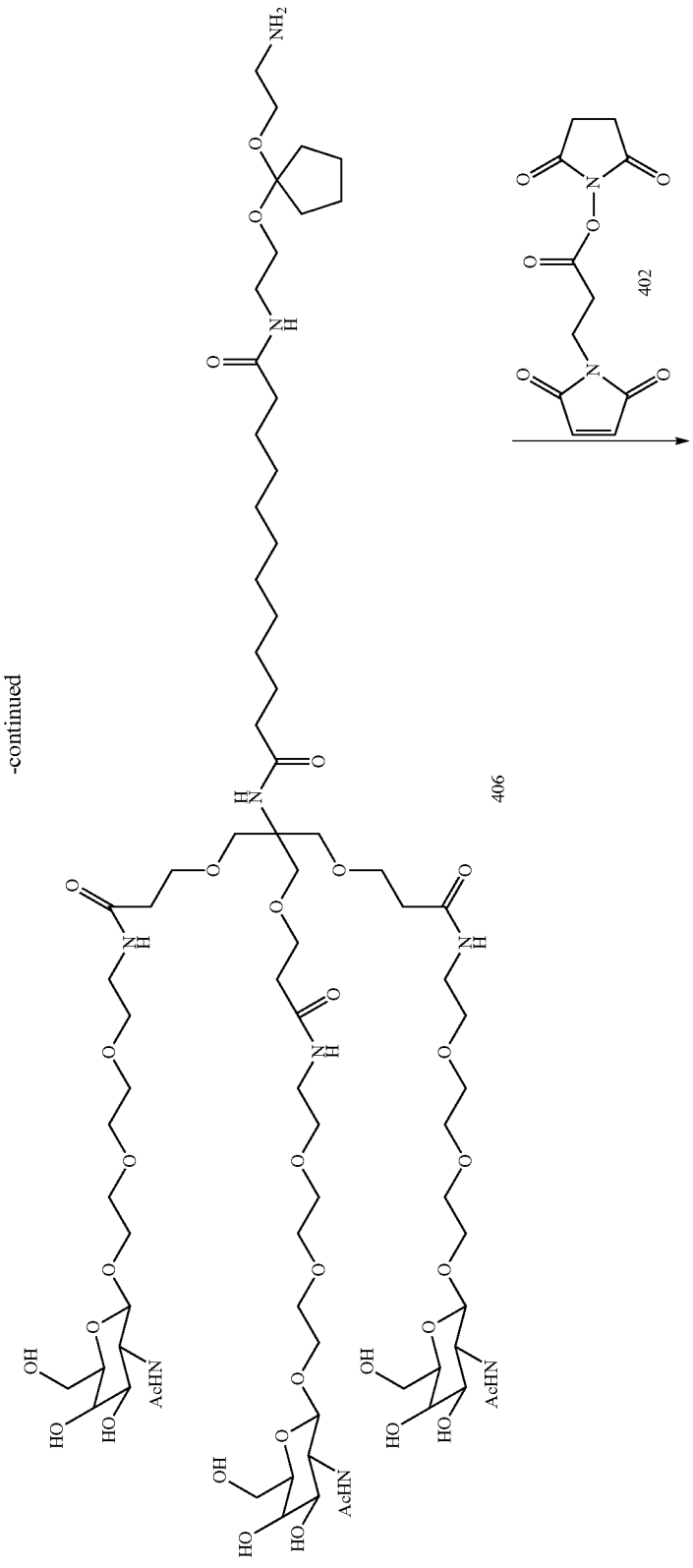

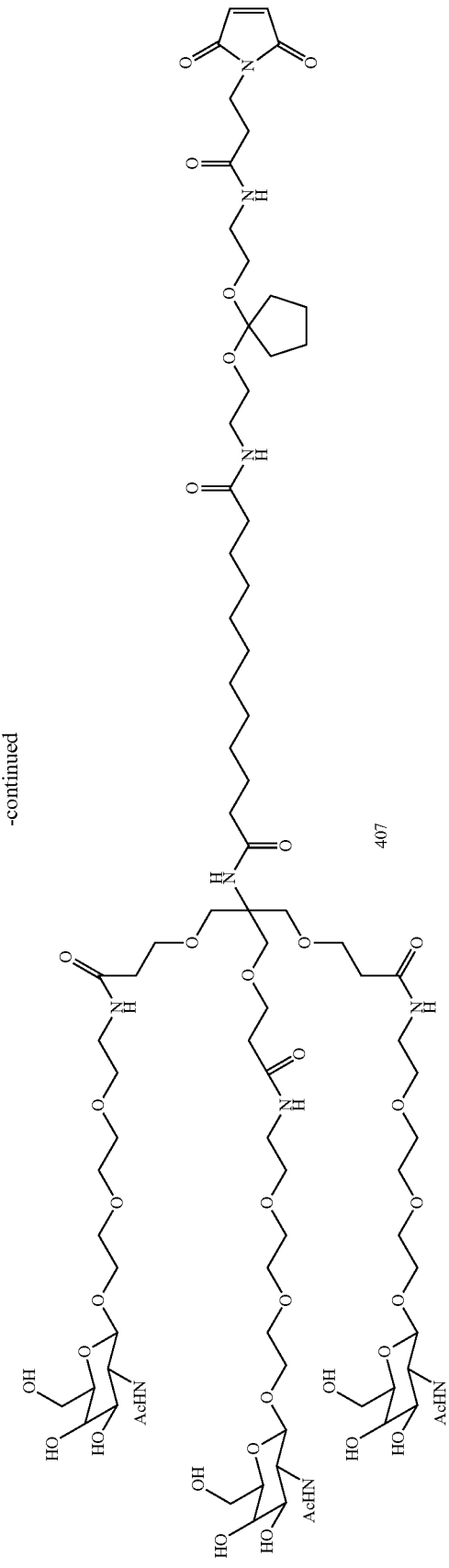

Compound 407 is prepared as outlined above and then conjugated to nucleic acid.

Example 31

233 234
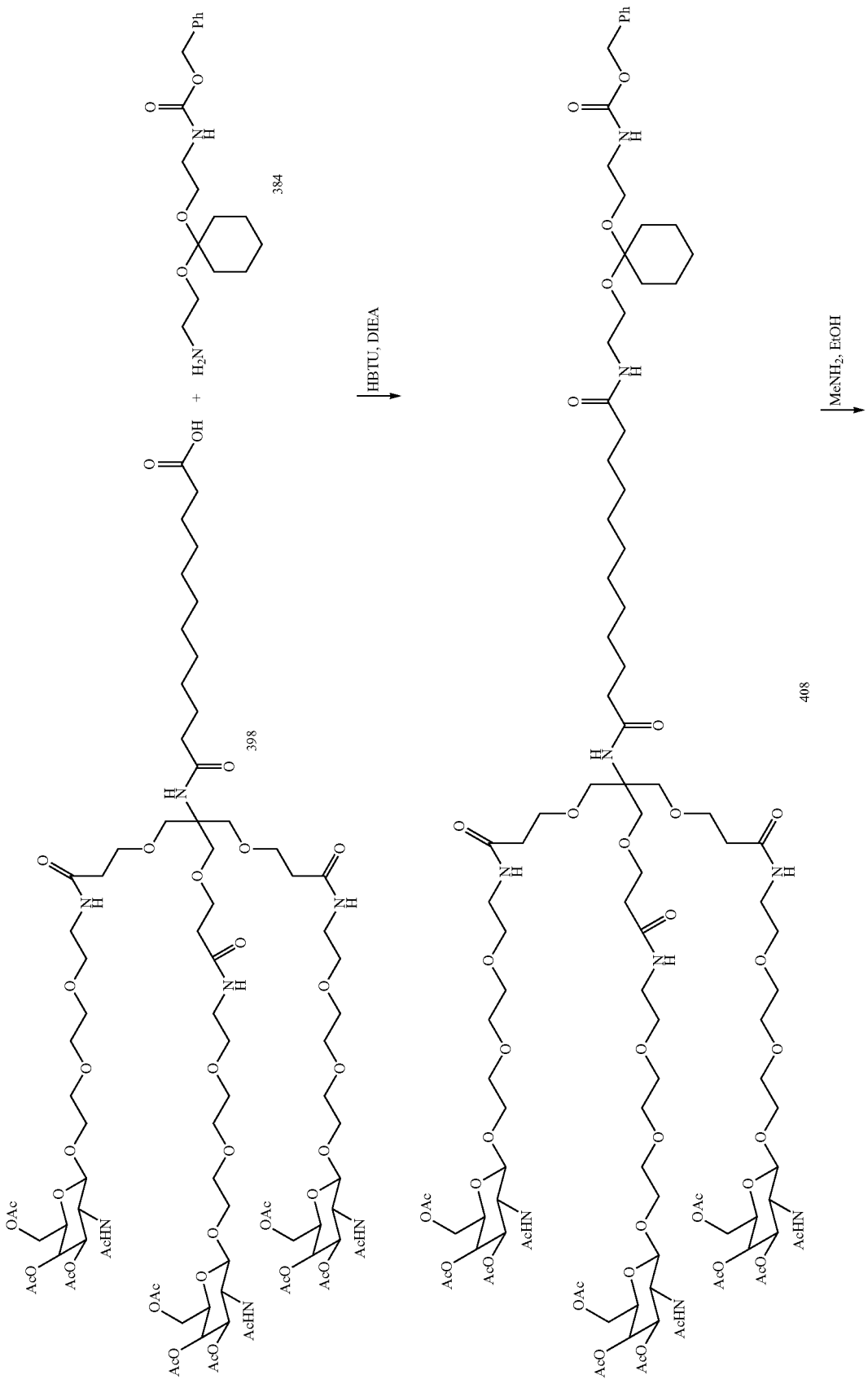

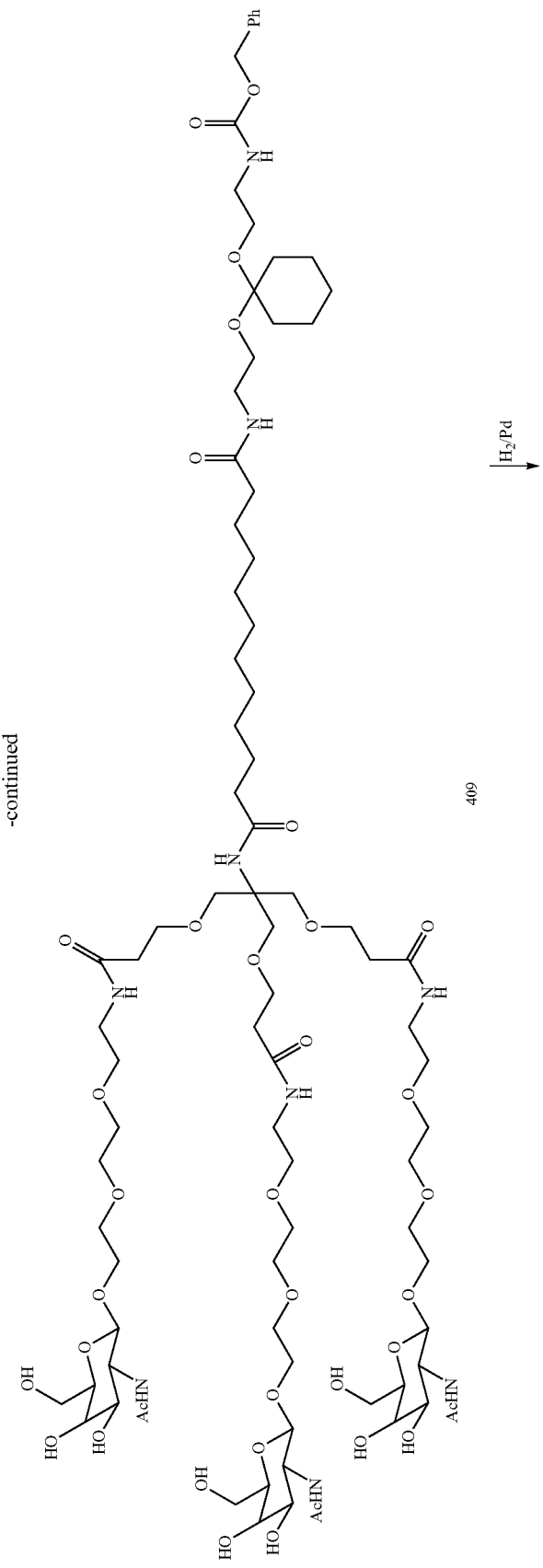

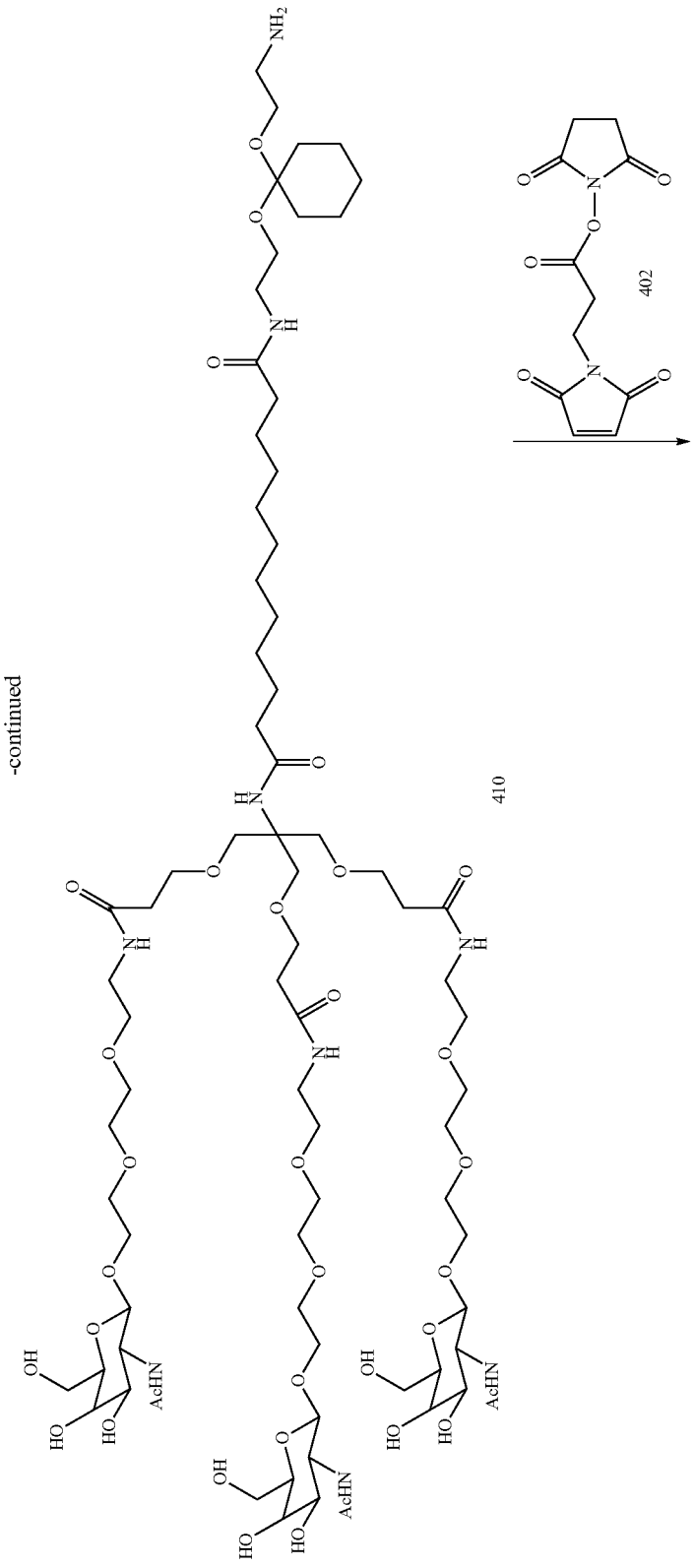

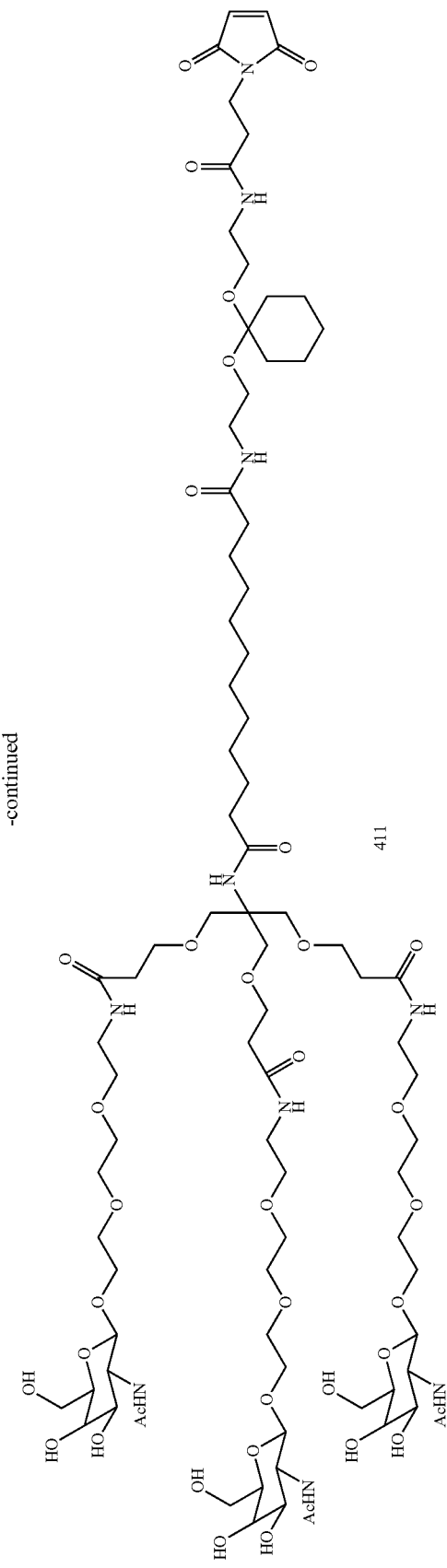

Compound 411 is prepared as outlined above and then conjugated to nucleic acid.

Example 32

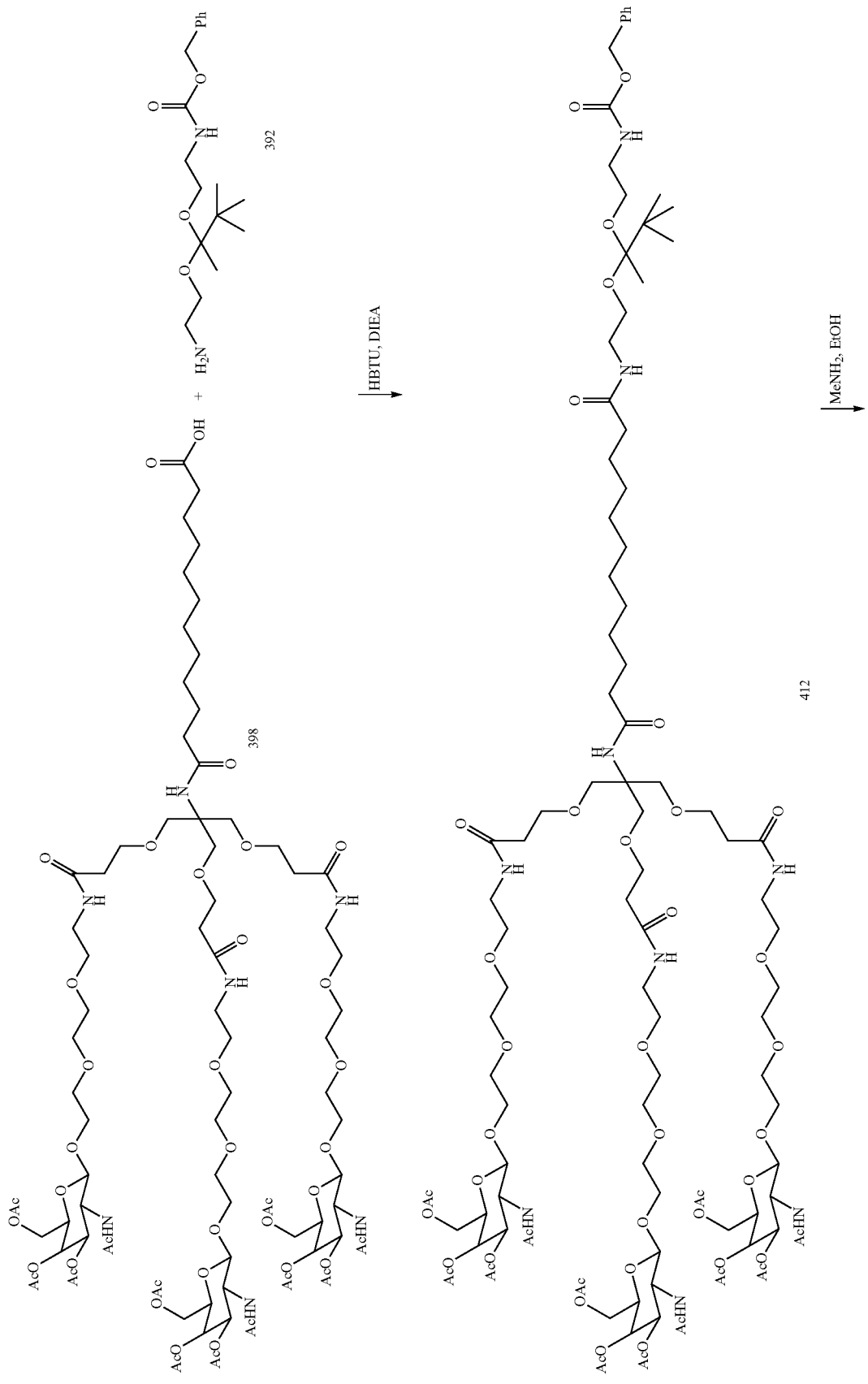

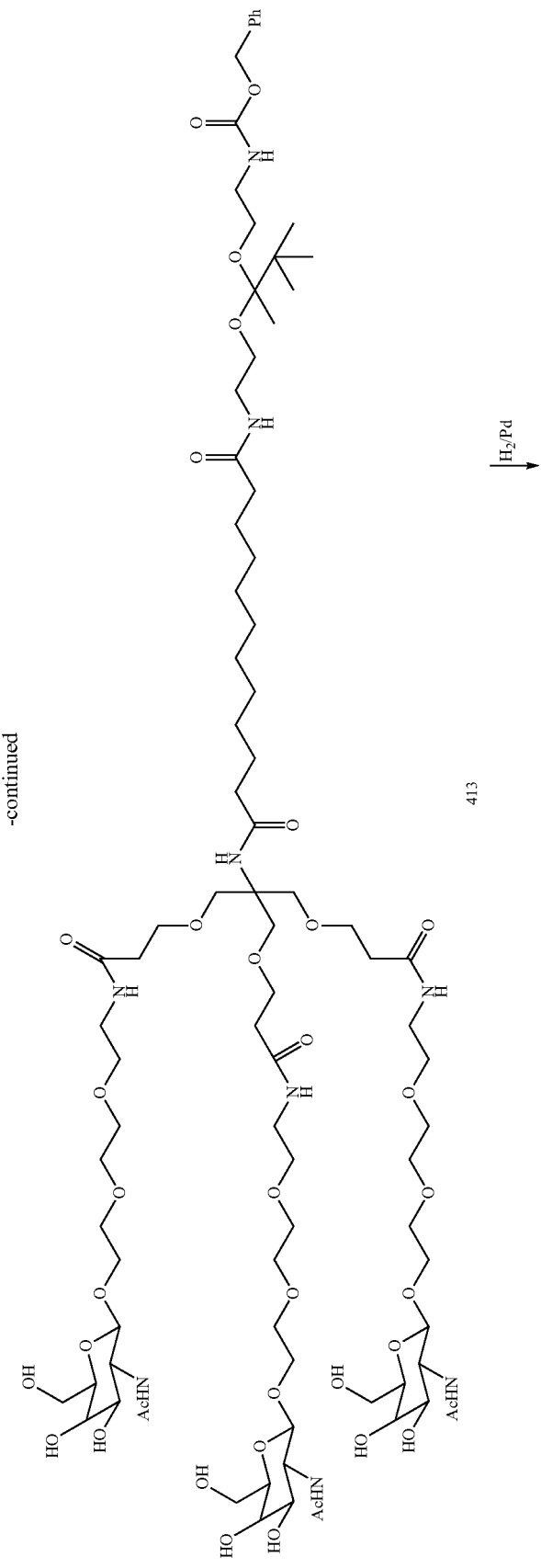
-continued
413
H₂/Pd

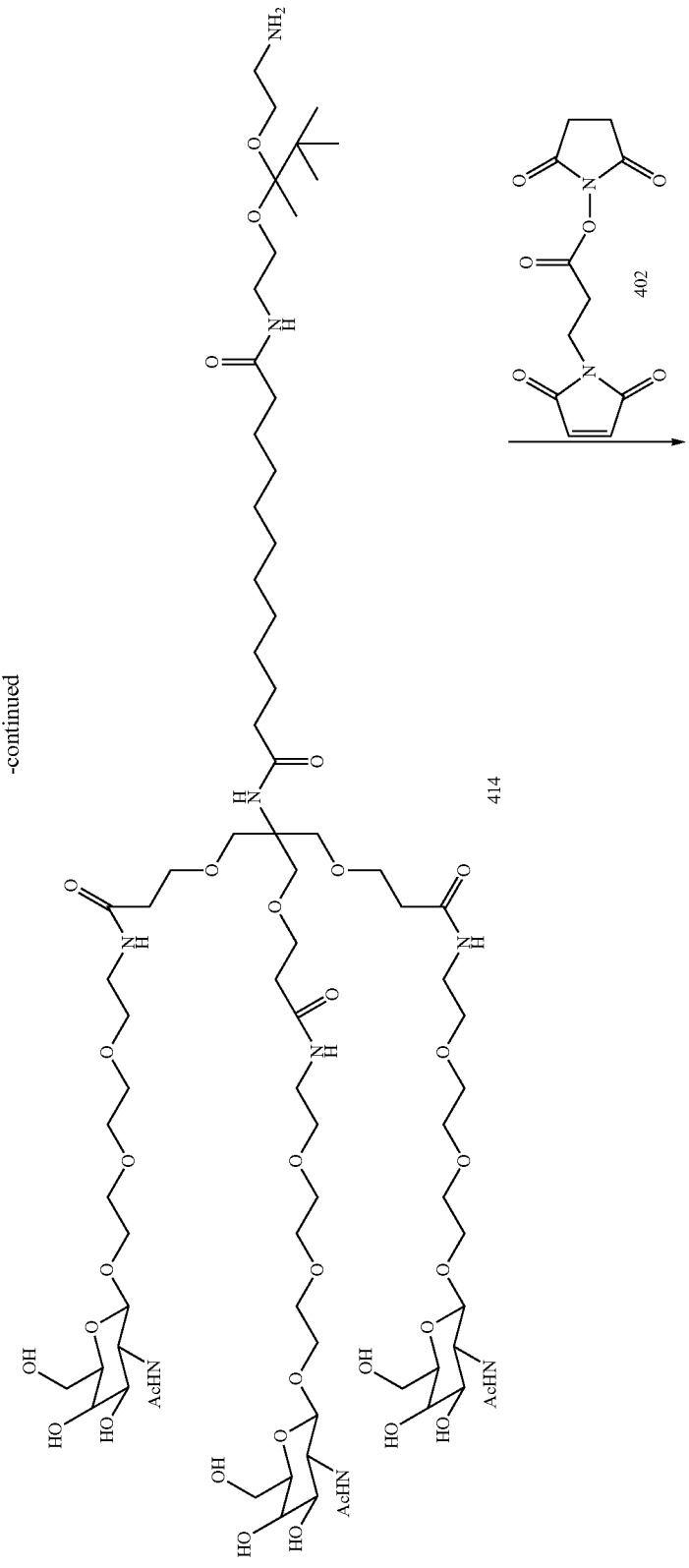

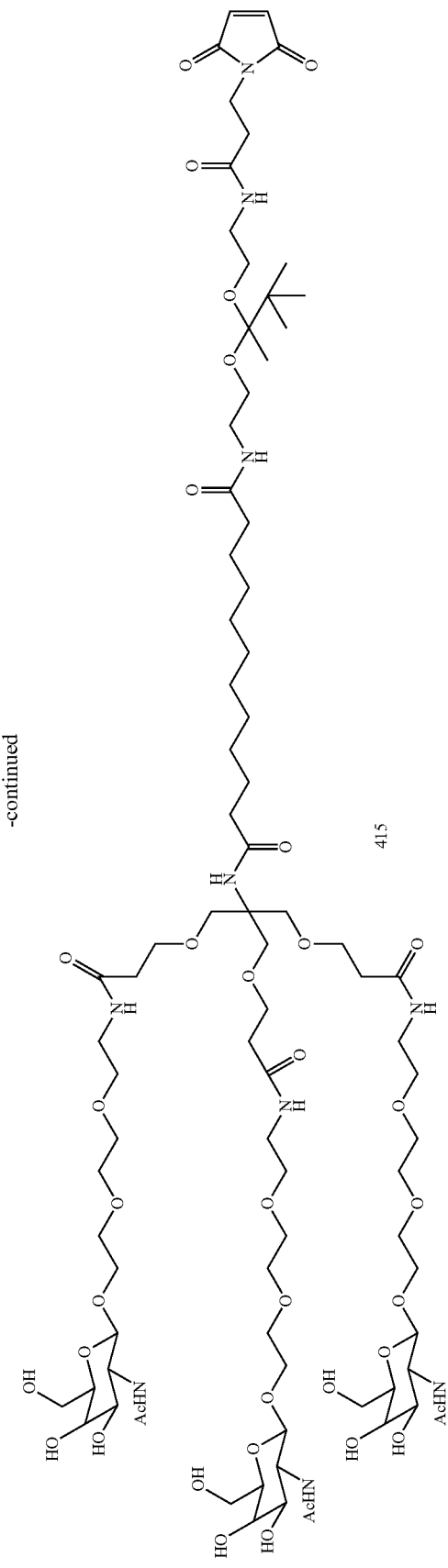

Compound 415 is prepared as outlined above and then conjugated to nucleic acid.
Example 33
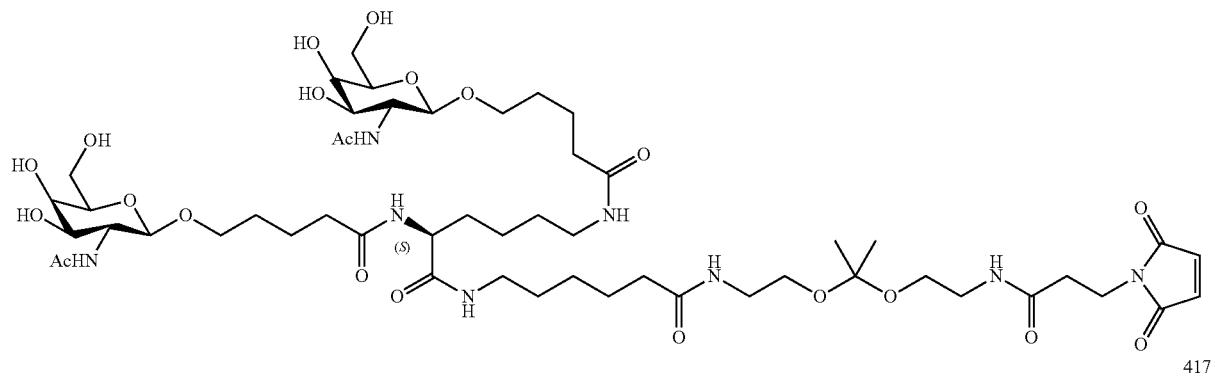
416
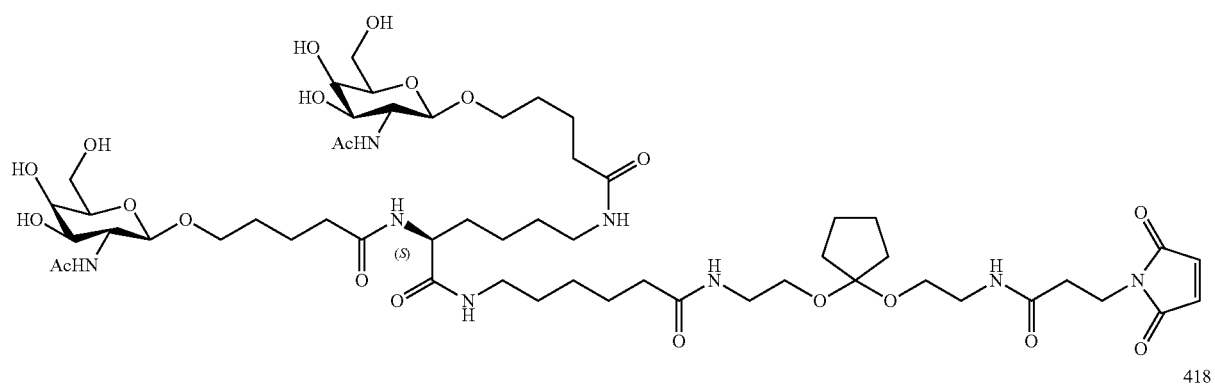
417
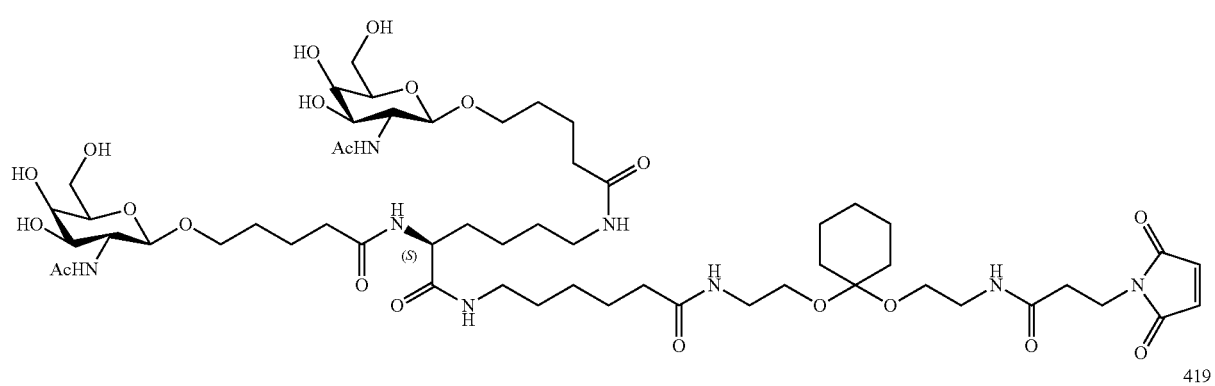
418
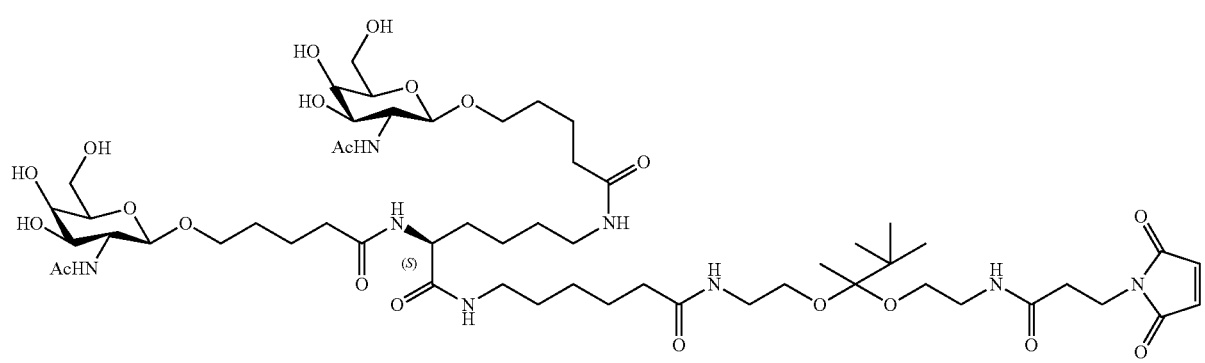
419
Compound 416, 417, 418, 419 are prepared as outlined above and then conjugated to nucleic acid.

What is claimed is:

1. A modular composition, comprising a nucleic acid, at least one endosomolytic component, and at least one targeting ligand, the composition having the formula:

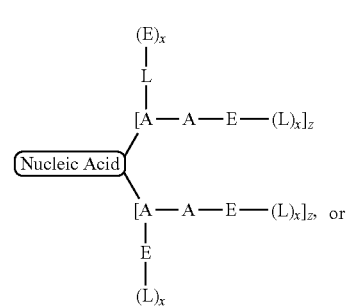
(I)

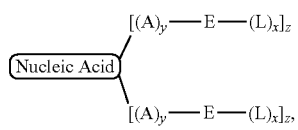
(II)

wherein

Nucleic Acid is the nucleic acid;

E is the endosomolytic component;

L is the targeting ligand;

x represents independently for each occurrence 0 or 1;

y represents independently for each occurrence 1,2,3,4,5, or 6;

z in formula (I) is 1,2,3,4,5, or 6 in one instance, and 0,1,2,3,4,5, or 6 in the other instance; and z in formula (II) represents independently for each occurrence 1,2,3, 4,5, or 6;

A is a linking moiety selected from the group consisting of:

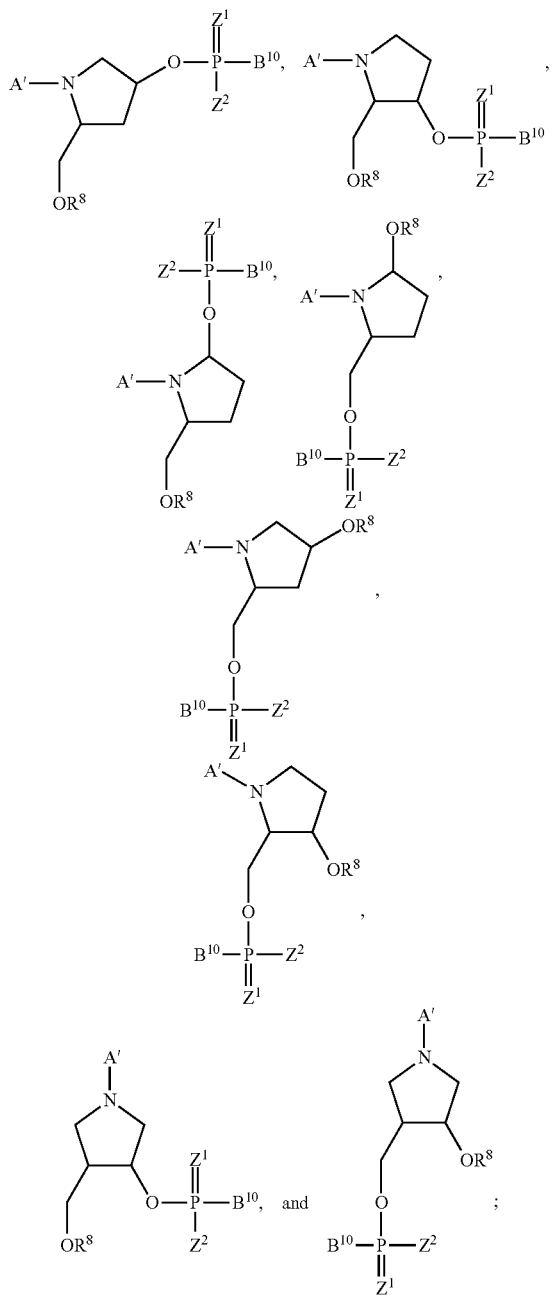

wherein $Z^1$ represents independently for each occurrence O or S;
$Z^2$ represents independently for each occurrence —OH, —OM, -Oalkyl, -Oaryl, -Oaralkyl, —SH, —SM, -Salkyl, -Saryl, -aralkyl, —N($R^3$)$R^4$, —C($R^{11}$)$_2)_m$N($R^{11}$)$_2$, —N($R^{11}$)(C($R^{11}$)$_2)_m$N($R^{11}$)$_2$, or alkyl;
$R^3$ and $R^4$ represent independently H or alkyl; or $R^3$ and $R^4$ taken together form a 3-, 4-, 5-, 6-, or 7-membered ring;
$R_{11}$ represents independently for each occurrence hydrogen or alkyl;

M represents independently for each occurrence an alkali metal or a transition metal with an overall charge of +1;
$R^8$ represents independently for each occurrence hydrogen, alkyl, aryl, aralkyl, acyl, silyl, a bond to the nucleic acid, or, when combined with $B^{10}$, a bond between linking moieties;
$B^{10}$ is a bond between A and the nucleic acid or, when combined with $R^8$, is a bond between linking moieties;
A' is a direct bond or a tether having the formula: —[(P-Q-R)$_q$—X—(P'-Q'-R')$_{q'}$]$_{q''}$-T-, wherein:
P, R, T, P' and R' are each independently absent, CO, NH, O, S, OC(O), NHC(O), $CH_2$, $CH_2NH$, $CH_2O$; NHCH($R^a$)C(O), —C(O)—CH($R^a$)—NH—, C(O)—(optionally substituted alkyl)-NH—, CH═N—O,

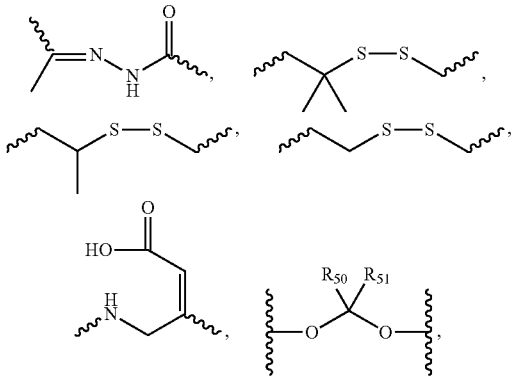

cyclyl, heterocyclyl, aryl or heteroaryl;
$R_{50}$ and $R_{51}$ are independently alkyl, substituted alkyl, or $R_{50}$ and $R_{51}$ taken together form a cyclic ring;
Q and Q' are each independently for each occurrence absent, —(CH$_2$)$_n$—, —C($R^{40}$)($R^{41}$)(CH$_2$)$_n$—, —(CH$_2$)$_n$ C($R^{40}$)($R^{41}$)—, —(CH$_2$CH$_2$O)$_m$CH$_2$CH$_2$—, —(CH$_2$CH$_2$O)$_m$CH$_2$CH$_2$NH—, aryl, heteroaryl, cyclyl, or heterocyclyl;
X is absent or a cleavable linking group;
$R^a$ is H or an amino acid side chain;
$R^{40}$ and $R^{41}$ are each independently H, $CH_3$, OH, SH or N($R^x$)$_2$;
$R^x$ is, for each occurrence, H, methyl, ethyl, propyl, isopropyl, butyl or benzyl;
q, q' and q" are each independently 0-30;
n is, for each occurrence, an integer from 1-20; and
m is, for each occurrence, an integer from 0-50;
provided that E and L are each present at least once.

2. The composition of claim 1, wherein the composition has the formula:

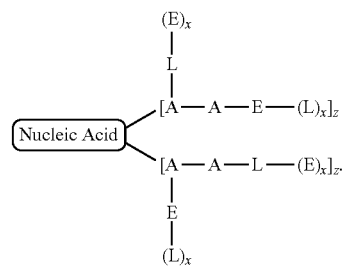

3. The composition of claim 1, wherein the composition has the formula:

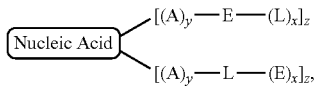

wherein each z is independently 1,2,3,4,5, or 6.

4. The composition of claim 3, wherein the composition has the formula:

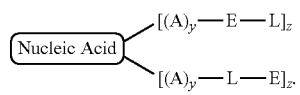

5. The composition of claim 1, wherein the A' tether is an alkyl diradical, heteroalkyl diradical, alkenyl diradical, alkynyl diradical, alkylalkynyl diradical, aminoalkyl diradical, thioether, —C(O)—, —S(O)—, —S(O)$_2$—, —C(R)$_2$—, or has the formula selected from the group consisting of:

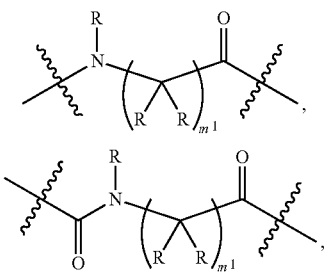

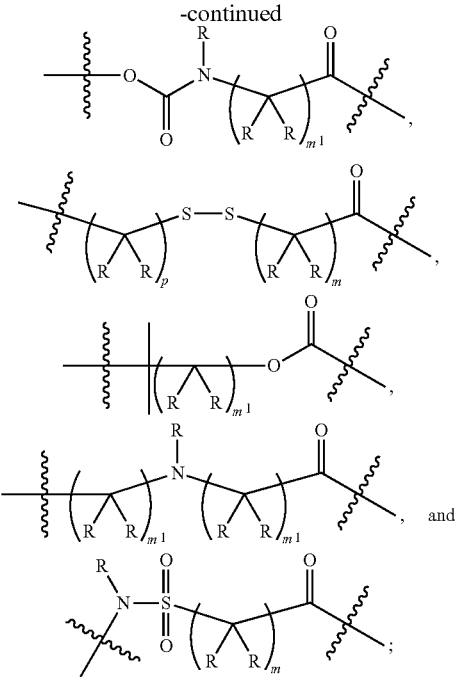

wherein
m represents independently for each occurrence 1,2,3,4,5, 6,7, or 8;
$m^1$ represents independently for each occurrence 0,1,2,3, 4,5,6,7, or 8;
p represents independently for each occurrence 1,2,3, or 4; and
R represents independently for each occurrence hydrogen or alkyl.

6. The composition of claim 1, wherein the A' tether is selected from the group consisting of:

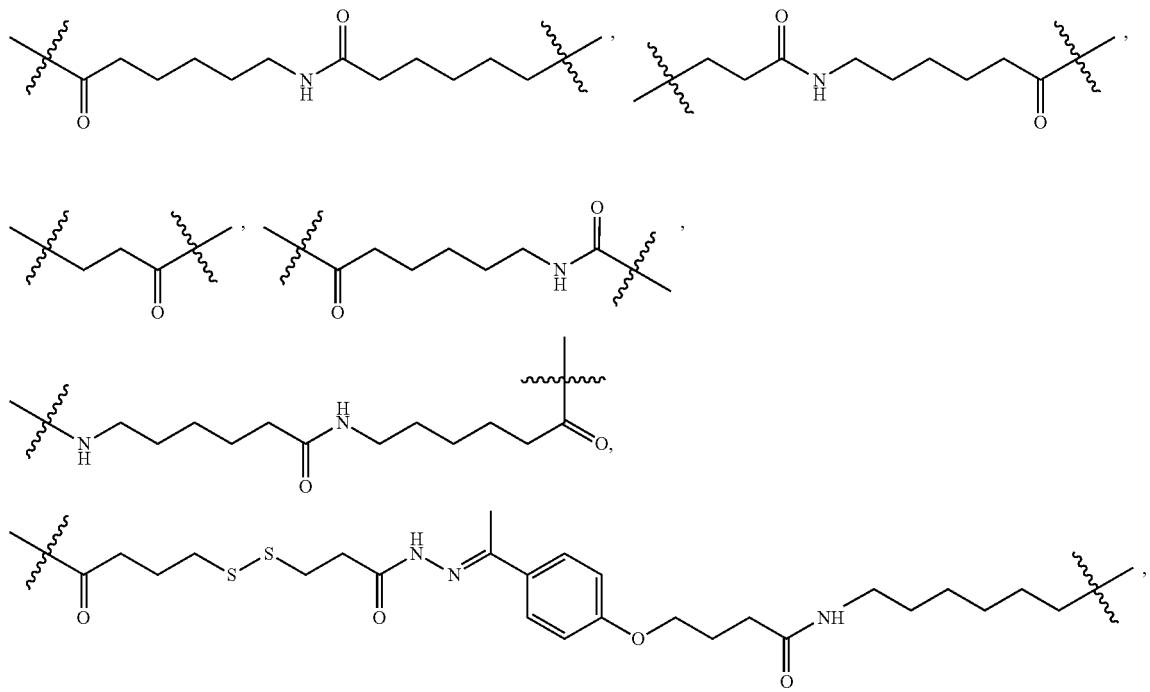

-continued
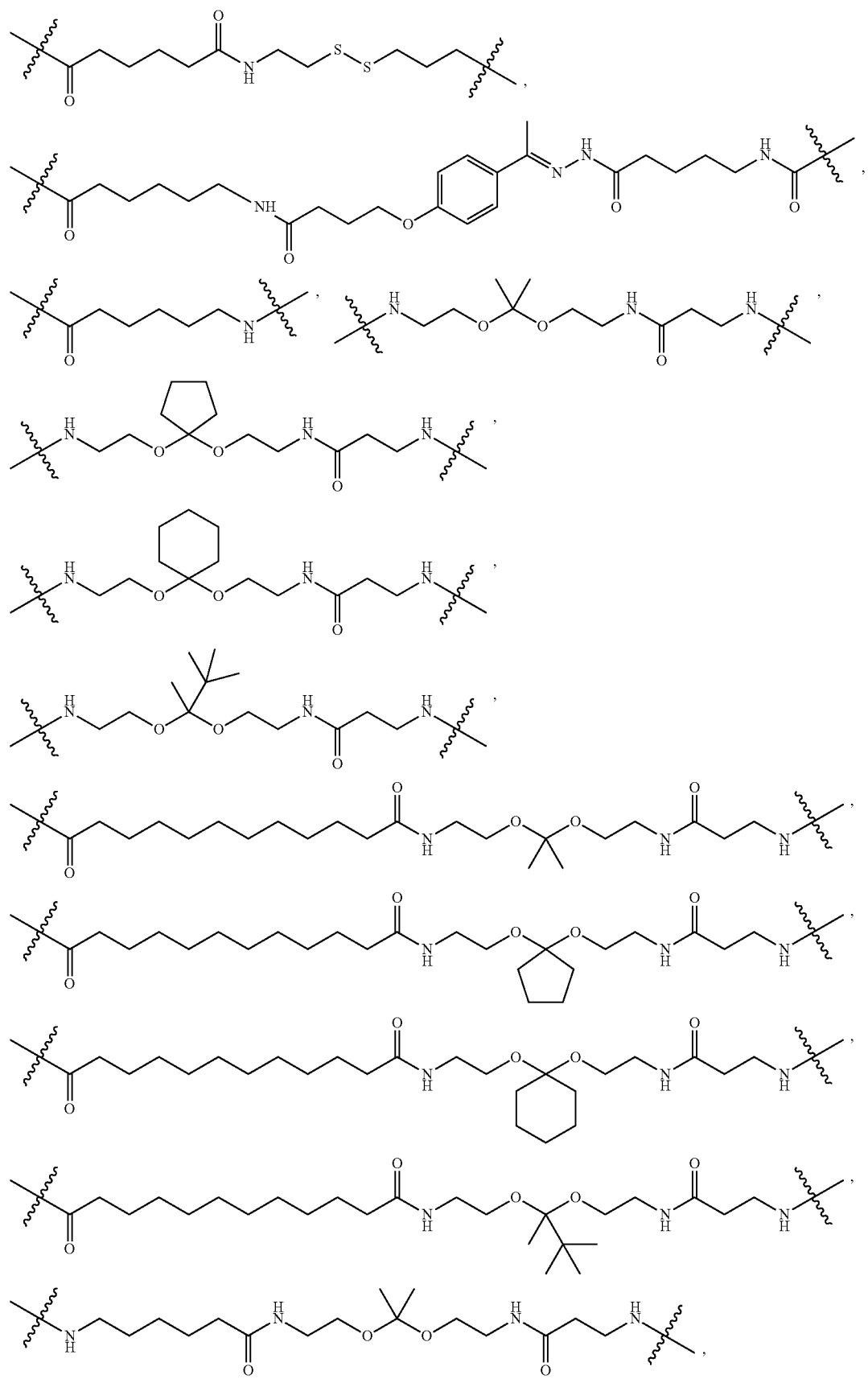

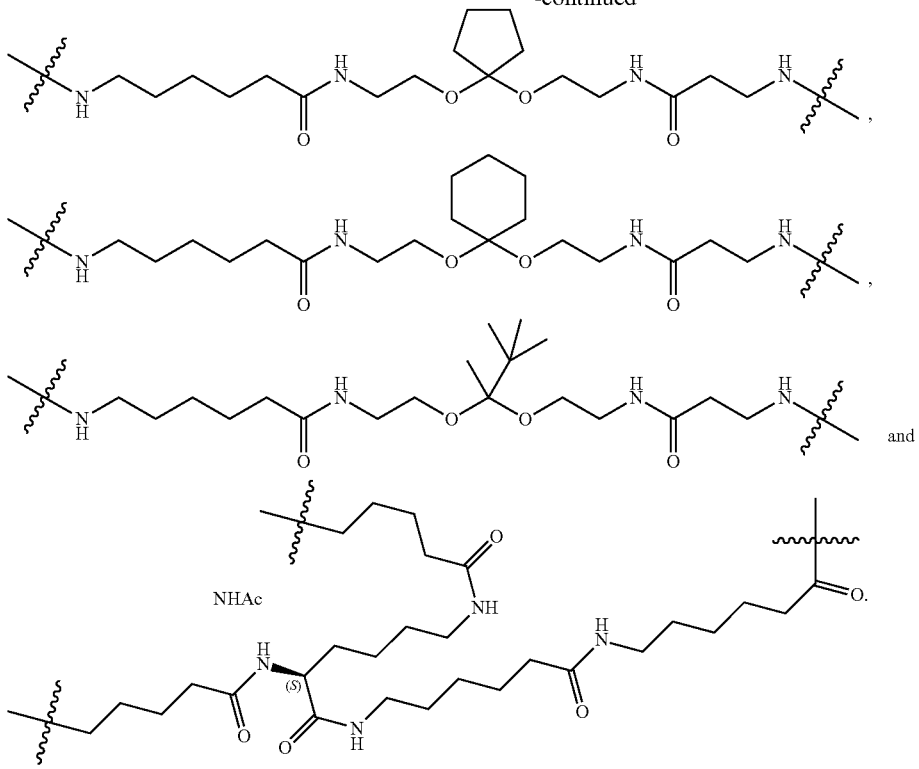

7. The composition of claim 1, wherein the endosomolytic component is selected from the group consisting of imidazoles, poly or oligoimidazoles, linear or brached polyethyleneimines (PEIs), linear and branched polyamines, cationic linear and branched polyamines, polycarboxylates, polycations, masked oligo or poly cations or anions, acetals, polyacetals, ketals, polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, and natural and synthetic fusogenic lipids.

8. The composition of claim 1, wherein the endosomolytic component is a polyanionic peptide or a polyanionic peptidomimetic.

9. The composition of claim 7, wherein the fusogenic lipid is selected from the group consisting of 1,2-dileoyl-sn-3-phosphoethanolamine (DOPE), phosphatidylethanolamine (POPE), palmitoyloleoylphosphatidylcholine (POPC), (6Z, 9Z,28Z,31Z)-heptatriaconta -6,9,28,31-tetraen-19-ol (DiLin), N-methyl(2,2-di((9Z,12Z)-octadeca-9,12-dienyl)-1,3-dioxolan -4-yl)methanamine (DLin-k-DMA) and N-methyl-2-(2,2-di((9Z,12Z)-octadeca-9,12-dienyl)-1,3-dioxolan-4-yl)ethanamine (XTC).

10. The composition of claim 1, wherein the endosomolytic component is selected from a group consisting of GALA, EALA, INF-7, Inf HA-2, diINF-7, diINF3, GLF, GALA -INF3, INF-5, JTS-1, ppTG1, ppTG20, KALA, HA, melittin, and histinde-rich peptide $CHK_6HC$.

11. The composition of claim 1, wherein the targeting ligand is selected from the group consisting of an antibody, a ligand-binding portion of a receptor, a ligand for a receptor, an aptamer, D-galactose, N-acetyl-D-galactose (GalNAc), multivalent N-acetyl-D-galactose, D-mannose, cholesterol, a fatty acid, a lipoprotein, folate, thyrotropin, melanotropin, surfactant protein A, mucin, carbohydrate, multivalent lactose, multivalent galactose, N-acetyl-alactosamine, N-acetyl-gulucosamine, multivalent mannose, multivalent fucose, glycosylated polyaminoacids, transferrin, bisphosphonate, polyglutamate, polyaspartate, a lipophilic moiety that enhance plasma protein binding, a steroid, bile acid, vitamin $B_{12}$, biotin, an RGD peptide, an RGD peptide mimetic, ibuprofen, naproxen, aspirin, folate, and analogs and derivatives thereof.

12. The composition of claim 11, wherein the targeting ligand is selected from the group consisting of D-galactose, N-acetyl-D-galactose (GalNAc), GalNAc2, and GalNAc3, cholesterol, folate, and analogs and derivates thereof 13. The composition of claim 1, wherein the nucleic acid is selected from a group consisting of an iRNA agent, an antisense oligonucleotide, an antagomir, an activating RNA, a decoy oligonucleotide, an aptamer, a microRNA (miRNA), miRNA mimics, antimir, activating RNA (RNAa), a supermir, a U1 adaptor and a ribozyme.

14. The composition of claim 1, wherein the nucleic acid contains at least one sugar modification.

15. The composition of claim 14,wherein said sugar modification is a 2'-modification.

16. The composition of claim 15, wherein said 2'-modificaiton is selected from the group consisting of 2'-O-Me(2'-O-methyl), 2'-O-MOE(2'-O- methoxyethyl), 2'-F, 2'-O-[2-(methylamino)-2-oxoethyl](2'-O-NMA), 2'-O-amine, 2'-SH, 2'-S-alkyl, 2'-O—CH$_2$-(4'-C)(LNA), 2'-O—CH$_2$CH$_2$-(4'-C)(ENA), 2'-O-aminopropyl (2'-O-AP), 2'-O-dimethylaminoethyl (2'-O-DMAOE), 2'-O-dimethylaminopropyl (2'-O-DMAP), and 2'-O -dimethylaminoethyloxyethyl (2'-O-DMAEOE).

17. The composition of claim 1, wherein the nucleic acid contains at least one backbone modification.

18. The composition of claim 17, wherein said backbone modification is selected from the group consisting of phosophorothioate, phosphorodithioate, phosphoramidate, phosphonate, alkylphosphonate, siloxane, carbonate, carboxymethyl, carbamate, amide, thioether, ethylene oxide linker, sulfonate, sulfonamide, thioformacetal, formacetal, oxime, methyleneimino, methyleneaminocarbonyl, methylenemethylimino (MMI), methylenehydrazo, methylenedimethylhydrazo (MDH), and methyleneoxymethylimino.

19. The composition of claim 1, where in the nucleic acid comprises at least one nucleobase modification.

20. The composition of claim 19, wherein the nucleobase modification is selected from the group consisting of difluorotolyl, 5-nitroindole, 3-nitropyrrole, 2-(amino)purine, 2,6-(diamino)purine, 5-substituted pyrimidines, $N^2$-substituted purines, $N^6$-substituted purines and $O^6$-substituted purines.

21. The composition of claim 1, wherein the nucleic acid is a single-stranded oligonucleotide.

22. The composition of claim 1, wherein the nucleic acid is a hairpin oligonucleotide.

23. The composition of claim 1, wherein the nucleic acid is a double-stranded oligonucleotide.

24. The composition of claim 1, wherein the endosomolytic agent and the targeting ligand are on the same terminal end of the nucleic acid.

25. The composition of claim 1, wherein the endosomolytic agent and the targeting ligands are on the opposite terminal ends of the nucleic acid.

26. The composition of claim 1, wherein one of the endosomolytic agent and the targeting ligand is at the terminal end of the nucleic acid and the other is at an internal, non-terminal position on the nucleic acid.

27. The composition of claim 1, wherein both the endosomolytic agent and the targeting ligand are located at internal, non-terminal positions on the nucleic acid.

28. The composition of claim 23, wherein the endosomolytic agent and the targeting ligand are both on the same strand.

29. The composition of claim 23, wherein the endosomolytic agent and the targeting ligand are on different strands.

30. The composition of claim 29, wherein the endosomolytic agent and the targeting ligand are located on the same end of the double-stranded oligonucleotide.

31. The composition of claim 29, wherein the endosomolytic agent and the targeting ligand are located on the opposite ends of the double-stranded oligonucleotide.

32. The composition of claim 1, wherein the tether comprises at least one redox cleavable linking group.

33. The composition of claim 1, wherein the tether comprises at least one pH sensitive component.

34. A method of delivering a modular composition to a cell, the method comprising (a) contacting a cell with a modular composition of claim 1; and (b) allowing the cell to internalize the modular composition so as to deliver the modular composition to the cell.

35. The method of claim 34, wherein the targeting ligand provides sufficient permeability and retention to allow the nucleic acid to accumulate in the cell.

36. The method of claim 34, wherein the method is performed in vitro.

37. The method of claim 34, wherein the method is performed in vivo.

38. The method of claim 34, wherein the method is performed ex vivo.

39. A method of inhibiting the expression of one or more genes, comprising contacting one or more cells with an effective amount of the modular composition of claim 1 so as to inhibit the expression of one or more genes in the one or more cells, wherein the effective amount is an amount that suppresses the expression of the one or more genes.

* * * * *

SEQUENCE LISTING

<160> NUMBER OF SEQ ID NOS: 189

<210> SEQ ID NO 1
<211> LENGTH: 29
<212> TYPE: PRT
<213> ORGANISM: Artificial Sequence
<220> FEATURE:
<223> OTHER INFORMATION: Endosomolytic Component: GALA

<400> SEQUENCE: 1

Ala Ala Leu Glu Ala Leu Ala Glu Ala Leu Glu Ala Leu Glu Ala
1               5                   10                  15

Leu Glu Ala Leu Ala Glu Ala Ala Ala Ala Gly Gly Cys
            20                  25

<210> SEQ ID NO 2
<211> LENGTH: 30
<212> TYPE: PRT
<213> ORGANISM: Artificial Sequence
<220> FEATURE:
<223> OTHER INFORMATION: Endosomolytic Component: EALA

<400> SEQUENCE: 2

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 3
<211> LENGTH: 15
<212> TYPE: PRT
<213> ORGANISM: Artificial Sequence
<220> FEATURE:
<223> OTHER INFORMATION: Endosomolytic Component.

<400> SEQUENCE: 3

Ala Leu Glu Ala Leu Ala Glu Ala Leu Glu Ala Leu Ala Glu Ala
1               5                   10                  15

<210> SEQ ID NO 4
<211> LENGTH: 22
<212> TYPE: PRT
<213> ORGANISM: Artificial Sequence
<220> FEATURE:
<223> OTHER INFORMATION: Endosomolytic Component: INF-7

<400> SEQUENCE: 4

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 5
<211> LENGTH: 23
<212> TYPE: PRT
<213> ORGANISM: Artificial Sequence
<220> FEATURE:
<223> OTHER INFORMATION: Endosomolytic Component: INF HA-2

<400> SEQUENCE: 5

Gly Leu Phe Gly Ala Ile Ala Gly Phe Ile Glu Asn Gly Trp Glu Gly
1               5                   10                  15

Met Ile Asp Gly Trp Tyr Gly
            20

```
<210> SEQ ID NO 6
<211> LENGTH: 48
<212> TYPE: PRT
<213> ORGANISM: Artificial Sequence
<220> FEATURE:
<223> OTHER INFORMATION: Endosomolytic Component: diINF-7

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: Endosomolytic Component: diINF3

<400> SEQUENCE: 7

Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40

<210> SEQ ID NO 8
<211> LENGTH: 35
<212> TYPE: PRT
<213> ORGANISM: Artificial Sequence
<220> FEATURE:
<223> OTHER INFORMATION: Endosomolytic Component: GLF

<400> SEQUENCE: 8

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 9
<211> LENGTH: 34
<212> TYPE: PRT
<213> ORGANISM: Artificial Sequence
<220> FEATURE:
<223> OTHER INFORMATION: Endosomolytic Component: GALA-INF3

<400> SEQUENCE: 9

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 10
<211> LENGTH: 41
<212> TYPE: PRT
```

```
<213> ORGANISM: Artificial Sequence
<220> FEATURE:
<223> OTHER INFORMATION: Endosomolytic Component: INF-5
<220> FEATURE:
<221> NAME/KEY: MOD_RES
<222> LOCATION: (17)..(17)
<223> OTHER INFORMATION: Nle
<220> FEATURE:
<221> NAME/KEY: MOD_RES
<222> LOCATION: (38)..(38)
<223> OTHER INFORMATION: Nle

<400> SEQUENCE: 10

Gly Leu Phe Glu Ala Ile Glu Gly Phe Ile Glu Asn Gly Trp Glu Gly
1               5                   10                  15

Leu Ile Asp Gly Lys Gly Leu Phe Glu Ala Ile Glu Gly Phe Ile Glu
            20                  25                  30

Asn Gly Trp Glu Gly Leu Ile Asp Gly
        35                  40

<210> SEQ ID NO 11
<211> LENGTH: 20
<212> TYPE: PRT
<213> ORGANISM: Artificial Sequence
<220> FEATURE:
<223> OTHER INFORMATION: Endosomolytic Component: JTS-1

<400> SEQUENCE: 11

Gly Leu Phe Glu Ala Leu Leu Glu Leu Leu Glu Ser Leu Trp Glu Leu
1               5                   10                  15

Leu Leu Glu Ala
            20

<210> SEQ ID NO 12
<211> LENGTH: 20
<212> TYPE: PRT
<213> ORGANISM: Artificial Sequence
<220> FEATURE:
<223> OTHER INFORMATION: Endosomolytic Component: ppTG1

<400> SEQUENCE: 12

Gly Leu Phe Lys Ala Leu Leu Lys Leu Leu Lys Ser Leu Trp Lys Leu
1               5                   10                  15

Leu Leu Lys Ala
            20

<210> SEQ ID NO 13
<211> LENGTH: 20
<212> TYPE: PRT
<213> ORGANISM: Artificial Sequence
<220> FEATURE:
<223> OTHER INFORMATION: Endosomolytic Component: ppTG20

<400> SEQUENCE: 13

Gly Leu Phe Arg Ala Leu Leu Arg Leu Leu Arg Ser Leu Trp Arg Leu
1               5                   10                  15

Leu Leu Arg Ala
            20

<210> SEQ ID NO 14
<211> LENGTH: 30
<212> TYPE: PRT
<213> ORGANISM: Artificial Sequence
<220> FEATURE:
<223> OTHER INFORMATION: Endosomolytic Component: KALA

<400> SEQUENCE: 14
```

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 15
<211> LENGTH: 22
<212> TYPE: PRT
<213> ORGANISM: Artificial Sequence
<220> FEATURE:
<223> OTHER INFORMATION: Endosomolytic Component: HA

<400> SEQUENCE: 15

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 16
<211> LENGTH: 26
<212> TYPE: PRT
<213> ORGANISM: Artificial Sequence
<220> FEATURE:
<223> OTHER INFORMATION: Endosomolytic Component: Melittin

<400> SEQUENCE: 16

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 17
<211> LENGTH: 10
<212> TYPE: PRT
<213> ORGANISM: Artificial Sequence
<220> FEATURE:
<223> OTHER INFORMATION: Endosomolytic Component: Histidine rich

<400> SEQUENCE: 17

Cys His Lys Lys Lys Lys Lys Lys His Cys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Derivative of the N-terminal sequence of the
      HA-2 subunit of the influenza virus hemagglutinin

<400> SEQUENCE: 18

His His His His His Trp Tyr Gly
1               5

<210> SEQ ID NO 19
<211> LENGTH: 16
<212> TYPE: PRT
<213> ORGANISM: Artificial Sequence
<220> FEATURE:
<223> OTHER INFORMATION: Hydrophobic MTS-containing peptide: RFGF

<400> SEQUENCE: 19

Ala Ala Val Ala Leu Leu Pro Ala Val Leu Leu Ala Leu Leu Ala Pro
1               5                   10                  15
```

```
<210> SEQ ID NO 20
<211> LENGTH: 11
<212> TYPE: PRT
<213> ORGANISM: Artificial Sequence
<220> FEATURE:
<223> OTHER INFORMATION: RFGF analogue

<400> SEQUENCE: 20

Ala Ala Leu Leu Pro Val Leu Leu Ala Ala Pro
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Cell Permeation Peptide: Penetratin

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Cell Permeation Peptide: Tat fragment (48-60)

<400> SEQUENCE: 22

Gly Arg Lys Lys Arg Arg Gln Arg Arg Arg Pro Pro Gln Cys
1               5                   10

<210> SEQ ID NO 23
<211> LENGTH: 27
<212> TYPE: PRT
<213> ORGANISM: Artificial Sequence
<220> FEATURE:
<223> OTHER INFORMATION: Cell Permeation Peptide: Signal Sequence-based
      peptide

<400> SEQUENCE: 23

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 18
<212> TYPE: PRT
<213> ORGANISM: Artificial Sequence
<220> FEATURE:
<223> OTHER INFORMATION: Cell Permeation Peptide: PVEC

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
<211> LENGTH: 26
<212> TYPE: PRT
<213> ORGANISM: Artificial Sequence
<220> FEATURE:
<223> OTHER INFORMATION: Cell Permeation Peptide: Transportan

<400> SEQUENCE: 25
```

```
Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 26
<211> LENGTH: 18
<212> TYPE: PRT
<213> ORGANISM: Artificial Sequence
<220> FEATURE:
<223> OTHER INFORMATION: Cell Permeation Peptide: Amphiphilic model
      peptide

<400> SEQUENCE: 26

Lys Leu Ala Leu Lys Leu Ala Leu Lys Ala Leu Lys Ala Ala Leu Lys
1               5                   10                  15

Leu Ala

<210> SEQ ID NO 27
<211> LENGTH: 9
<212> TYPE: PRT
<213> ORGANISM: Artificial Sequence
<220> FEATURE:
<223> OTHER INFORMATION: Cell Permeation Peptide: Arg9

<400> SEQUENCE: 27

Arg Arg Arg Arg Arg Arg Arg Arg Arg
1               5

<210> SEQ ID NO 28
<211> LENGTH: 10
<212> TYPE: PRT
<213> ORGANISM: Artificial Sequence
<220> FEATURE:
<223> OTHER INFORMATION: Cell Permeation Peptide: Bacterial cell wall
      permeating

<400> SEQUENCE: 28

Lys Phe Phe Lys Phe Phe Lys Phe Phe Lys
1               5                   10

<210> SEQ ID NO 29
<211> LENGTH: 37
<212> TYPE: PRT
<213> ORGANISM: Artificial Sequence
<220> FEATURE:
<223> OTHER INFORMATION: Cell Permeation Peptide: LL-37

<400> SEQUENCE: 29

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 30
<211> LENGTH: 31
<212> TYPE: PRT
<213> ORGANISM: Artificial Sequence
<220> FEATURE:
<223> OTHER INFORMATION: Cell Permeation Peptide: Cecropin P1

<400> SEQUENCE: 30

Ser Trp Leu Ser Lys Thr Ala Lys Lys Leu Glu Asn Ser Ala Lys Lys
1               5                   10                  15
```

Arg Ile Ser Glu Gly Ile Ala Ile Ala Ile Gln Gly Gly Pro Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Cell Permeation Peptide: Alpha-defensin

<400> SEQUENCE: 31

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 32
<211> LENGTH: 36
<212> TYPE: PRT
<213> ORGANISM: Artificial Sequence
<220> FEATURE:
<223> OTHER INFORMATION: Cell Permeation Peptide: b-defensin

<400> SEQUENCE: 32

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
            35

<210> SEQ ID NO 33
<211> LENGTH: 12
<212> TYPE: PRT
<213> ORGANISM: Artificial Sequence
<220> FEATURE:
<223> OTHER INFORMATION: Cell Permeation Peptide: Bactenecin

<400> SEQUENCE: 33

Arg Lys Cys Arg Ile Val Val Ile Arg Val Cys Arg
1               5                   10

<210> SEQ ID NO 34
<211> LENGTH: 42
<212> TYPE: PRT
<213> ORGANISM: Artificial Sequence
<220> FEATURE:
<223> OTHER INFORMATION: Cell Permeation Peptide: PR-3
<220> FEATURE:
<221> NAME/KEY: MISC_FEATURE
<222> LOCATION: (42)..(42)
<223> OTHER INFORMATION: NH2 modification of C-terminus

<400> SEQUENCE: 34

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
            35                  40

<210> SEQ ID NO 35
<211> LENGTH: 13
<212> TYPE: PRT
<213> ORGANISM: Artificial Sequence

```
<220> FEATURE:
<223> OTHER INFORMATION: Cell Permeation Peptide: Indolicidin
<220> FEATURE:
<221> NAME/KEY: MISC_FEATURE
<222> LOCATION: (13)..(13)
<223> OTHER INFORMATION: NH2 modification to C-terminus

<400> SEQUENCE: 35

Ile Leu Pro Trp Lys Trp Pro Trp Trp Pro Trp Arg Arg
1               5                   10

<210> SEQ ID NO 36
<211> LENGTH: 23
<212> TYPE: DNA
<213> ORGANISM: Artificial Sequence
<220> FEATURE:
<223> OTHER INFORMATION: Conserved sequence between mouse lamin B1,
      lamin B2, keratin complex 2-gene 1 and lamin A/C

<400> SEQUENCE: 36
aagctggccc tggacatgga gat                                           23

<210> SEQ ID NO 37
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (1)..(1)
<223> OTHER INFORMATION: Conjugation of Cholesterol to 5' end
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage

<400> SEQUENCE: 37
ggaucaucuc aagucuuact t                                             21

<210> SEQ ID NO 38
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (1)..(1)
<223> OTHER INFORMATION: Conjugation of Cholesterol to 5' end
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
```

```
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage

<400> SEQUENCE: 38
ggacuacucu aaguucuact t                                              21

<210> SEQ ID NO 39
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage

<400> SEQUENCE: 39
ggacuacucu aaguucuact t                                              21

<210> SEQ ID NO 40
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (2)..(2)
<223> OTHER INFORMATION: 2'-fluro modification
<220> FEATURE:
<221> NAME/KEY: misc_feature
<222> LOCATION: (7)..(9)
<223> OTHER INFORMATION: 2'-fluro modification
<220> FEATURE:
<221> NAME/KEY: misc_feature
<222> LOCATION: (14)..(14)
<223> OTHER INFORMATION: 2'-fluro modification
<220> FEATURE:
<221> NAME/KEY: misc_feature
<222> LOCATION: (17)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage
```

-continued

```
<400> SEQUENCE: 40
guagaacuua gaguagucct t                                               21

<210> SEQ ID NO 41
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage

<400> SEQUENCE: 41
ggaucaucuc aagucuuact t                                               21

<210> SEQ ID NO 42
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (2)..(2)
<223> OTHER INFORMATION: 2'-fluro modification
<220> FEATURE:
<221> NAME/KEY: misc_feature
<222> LOCATION: (7)..(9)
<223> OTHER INFORMATION: 2'-fluro modification
<220> FEATURE:
<221> NAME/KEY: misc_feature
<222> LOCATION: (14)..(14)
<223> OTHER INFORMATION: 2'-fluro modification
<220> FEATURE:
<221> NAME/KEY: misc_feature
<222> LOCATION: (17)..(19)
<223> OTHER INFORMATION: 2'-fluro modification
<220> FEATURE:
<221> NAME/KEY: misc_feature
<222> LOCATION: (20)..(21)
<223> OTHER INFORMATION: Thioate linkage

<400> SEQUENCE: 42
guaagacuug agaugaucct t                                               21

<210> SEQ ID NO 43
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
```

```
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L8 through
      phosphorothioate linkage

<400> SEQUENCE: 43
ggaucaucuc aagucuuact t                                           21

<210> SEQ ID NO 44
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L99 through
      phosphorothioate linkage

<400> SEQUENCE: 44
ggaucaucuc aagucuuact t                                           21

<210> SEQ ID NO 45
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
```

```
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L99

<400> SEQUENCE: 45
ggaucaucuc aagucuuact t                                            21

<210> SEQ ID NO 46
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L8

<400> SEQUENCE: 46
ggaucaucuc aagucuuact t                                            21

<210> SEQ ID NO 47
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L99

<400> SEQUENCE: 47
ggaucaucuc aagucuuact t                                            21
```

-continued

```
<210> SEQ ID NO 48
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L8

<400> SEQUENCE: 48
ggaucaucuc aagucuuact t                                              21

<210> SEQ ID NO 49
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to L8

<400> SEQUENCE: 49
ggaucaucuc aagucuuact t                                              21

<210> SEQ ID NO 50
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
```

-continued

```
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to L99

<400> SEQUENCE: 50
ggaucaucuc aagucuuact t                                             21

<210> SEQ ID NO 51
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and link to L10

<400> SEQUENCE: 51
ggaucaucuc aagucuuact t                                             21

<210> SEQ ID NO 52
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
```

-continued

```
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L10

<400> SEQUENCE: 52
ggaucaucuc aagucuuact t                                              21

<210> SEQ ID NO 53
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L50

<400> SEQUENCE: 53
ggaucaucuc aagucuuact t                                              21

<210> SEQ ID NO 54
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L8

<400> SEQUENCE: 54
ggaucaucuc aagucuuact t                                              21
```

```
<210> SEQ ID NO 55
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L50 through
      phosphorothioate linkage

<400> SEQUENCE: 55
ggaucaucuc aagucuuact t                                         21

<210> SEQ ID NO 56
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to Q11 and L50

<400> SEQUENCE: 56
ggaucaucuc aagucuuact t                                         21

<210> SEQ ID NO 57
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
```

```
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q11 and L8

<400> SEQUENCE: 57
ggaucaucuc aagucuuact t                                              21

<210> SEQ ID NO 58
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L110

<400> SEQUENCE: 58
ggaucaucuc aagucuuact t                                              21

<210> SEQ ID NO 59
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
```

```
<221> NAME/KEY: misc_feature
<222> LOCATION: (21)..(21)
<223> OTHER INFORMATION: Conjugate the 3' end to Q96 through
      phosphorothioate linkage, and then link to L110

<400> SEQUENCE: 59
ggaucaucuc aagucuuact t                                                  21

<210> SEQ ID NO 60
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to Q11 and L110

<400> SEQUENCE: 60
ggaucaucuc aagucuuact t                                                  21

<210> SEQ ID NO 61
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q8 and L110

<400> SEQUENCE: 61
ggaucaucuc aagucuuact t                                                  21

<210> SEQ ID NO 62
<211> LENGTH: 21
```

```
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q8 and L110

<400> SEQUENCE: 62
ggaucaucuc aagucuuact t                                         21

<210> SEQ ID NO 63
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q96 and L110

<400> SEQUENCE: 63
ggaucaucuc aagucuuact t                                         21

<210> SEQ ID NO 64
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
```

```
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L80

<400> SEQUENCE: 64
ggaucaucuc aagucuuact t                                                  21

<210> SEQ ID NO 65
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L80

<400> SEQUENCE: 65
ggaucaucuc aagucuuact t                                                  21

<210> SEQ ID NO 66
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
```

```
<223> OTHER INFORMATION: Conjugate the 3' end to Q8 through
      phosphorothioate linkage, and then link to Q11 and L80

<400> SEQUENCE: 66
ggaucaucuc aagucuuact t                                              21

<210> SEQ ID NO 67
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q8 and L80

<400> SEQUENCE: 67
ggaucaucuc aagucuuact t                                              21

<210> SEQ ID NO 68
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q8 and L80

<400> SEQUENCE: 68
ggaucaucuc aagucuuact t                                              21

<210> SEQ ID NO 69
<211> LENGTH: 21
<212> TYPE: DNA
<213> ORGANISM: Artificial Sequence
```

```
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q96 and L80

<400> SEQUENCE: 69
ggaucaucuc aagucuuact t                                          21

<210> SEQ ID NO 70
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to L90

<400> SEQUENCE: 70
ggaucaucuc aagucuuact t                                          21

<210> SEQ ID NO 71
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
```

```
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to L90

<400> SEQUENCE: 71
ggaucaucuc aagucuuact t                                           21

<210> SEQ ID NO 72
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q8 through
      phosphorothioate linkage, and then link to Q11 and L90

<400> SEQUENCE: 72
ggaucaucuc aagucuuact t                                           21

<210> SEQ ID NO 73
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q8 and L90
```

```
<400> SEQUENCE: 73
ggaucaucuc aagucuuact t                                              21

<210> SEQ ID NO 74
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q8 and L90

<400> SEQUENCE: 74
ggaucaucuc aagucuuact t                                              21

<210> SEQ ID NO 75
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to Q96 and L90

<400> SEQUENCE: 75
ggaucaucuc aagucuuact t                                              21

<210> SEQ ID NO 76
<211> LENGTH: 21
<212> TYPE: DNA
<213> ORGANISM: Artificial Sequence
<220> FEATURE:
<223> OTHER INFORMATION: Combined DNA/RNA Molecule, Synthetic
```

```
            Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94) and L50, where n = 1 to 10

<400> SEQUENCE: 76
ggaucaucuc aagucuuact t                                             21

<210> SEQ ID NO 77
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L135,
      where n = 0 to 10

<400> SEQUENCE: 77
ggaucaucuc aagucuuact t                                             21

<210> SEQ ID NO 78
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
```

```
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11 and L50, where n = 1 to 10

<400> SEQUENCE: 78
ggaucaucuc aagucuuact t                                             21

<210> SEQ ID NO 79
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L50,
      where n = 1 to 10

<400> SEQUENCE: 79
ggaucaucuc aagucuuact t                                             21

<210> SEQ ID NO 80
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96 and L10, where n = 1 to 10
```

```
<400> SEQUENCE: 80
ggaucaucuc aagucuuact t                                              21

<210> SEQ ID NO 81
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L10,
      where n = 0 to 10

<400> SEQUENCE: 81
ggaucaucuc aagucuuact t                                              21

<210> SEQ ID NO 82
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q11, (n x Q94) and
      L135, where n = 1 to 10

<400> SEQUENCE: 82
ggaucaucuc aagucuuact t                                              21

<210> SEQ ID NO 83
<211> LENGTH: 21
<212> TYPE: DNA
<213> ORGANISM: Artificial Sequence
```

```
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L50,
      where n = 0 to 10

<400> SEQUENCE: 83
ggaucaucuc aagucuuact t                                              21

<210> SEQ ID NO 84
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L50, where n = 1 to
      10

<400> SEQUENCE: 84
ggaucaucuc aagucuuact t                                              21

<210> SEQ ID NO 85
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
```

```
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L50, where n = 1 to
      10

<400> SEQUENCE: 85
ggaucaucuc aagucuuact t                                               21

<210> SEQ ID NO 86
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94) and L10, where n = 1 to
      10

<400> SEQUENCE: 86
ggaucaucuc aagucuuact t                                               21

<210> SEQ ID NO 87
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
```

```
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94) and L10, where n = 0 to
      10

<400> SEQUENCE: 87
ggaucaucuc aagucuuact t                                              21

<210> SEQ ID NO 88
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94), Q11,
      (n x Q94) and L135, where n = 1 to 10

<400> SEQUENCE: 88
ggaucaucuc aagucuuact t                                              21

<210> SEQ ID NO 89
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L50, where n = 0 to
      10

<400> SEQUENCE: 89
ggaucaucuc aagucuuact t                                              21
```

```
<210> SEQ ID NO 90
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), L96 and L110, where n = 1 to 10

<400> SEQUENCE: 90
ggaucaucuc aagucuuact t                                               21

<210> SEQ ID NO 91
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L110,
      where n = 0 to 10

<400> SEQUENCE: 91
ggaucaucuc aagucuuact t                                               21

<210> SEQ ID NO 92
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
```

```
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11 and L110, where n = 1 to 10

<400> SEQUENCE: 92
ggaucaucuc aagucuuact t                                             21

<210> SEQ ID NO 93
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L110,
      where n = 1 to 10

<400> SEQUENCE: 93
ggaucaucuc aagucuuact t                                             21

<210> SEQ ID NO 94
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
```

```
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, and L110, where n = 1 to 10

<400> SEQUENCE: 94
ggaucaucuc aagucuuact t                                              21

<210> SEQ ID NO 95
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, Q11 and L110, where n = 1 to 10

<400> SEQUENCE: 95
ggaucaucuc aagucuuact t                                              21

<210> SEQ ID NO 96
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96 and L110, where n = 1 to 10

<400> SEQUENCE: 96
ggaucaucuc aagucuuact t                                              21
```

-continued

```
<210> SEQ ID NO 97
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96, (n x Q94) and L110, where
      n = 1 to 10

<400> SEQUENCE: 97
ggaucaucuc aagucuuact t                                             21

<210> SEQ ID NO 98
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L110, where
      n = 1 to 10

<400> SEQUENCE: 98
ggaucaucuc aagucuuact t                                             21

<210> SEQ ID NO 99
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
```

```
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L110,
      where n = 0 to 10

<400> SEQUENCE: 99
ggaucaucuc aagucuuact t                                              21

<210> SEQ ID NO 100
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q11, (n x Q94) and
      L110, where n = 1 to 10

<400> SEQUENCE: 100
ggaucaucuc aagucuuact t                                              21

<210> SEQ ID NO 101
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
```

```
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L110,
      where n = 0 to 10

<400> SEQUENCE: 101
ggaucaucuc aagucuuact t                                              21

<210> SEQ ID NO 102
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L110, where
      n = 1 to 10

<400> SEQUENCE: 102
ggaucaucuc aagucuuact t                                              21

<210> SEQ ID NO 103
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L110, where n = 1
      to 10
```

<400> SEQUENCE: 103
ggaucaucuc aagucuuact t                                              21

<210> SEQ ID NO 104
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q11 and L110, where
      n = 1 to 10

<400> SEQUENCE: 104
ggaucaucuc aagucuuact t                                              21

<210> SEQ ID NO 105
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94), Q11 and L110, where
      n = 1 to 10

<400> SEQUENCE: 105
ggaucaucuc aagucuuact t                                              21

<210> SEQ ID NO 106
<211> LENGTH: 21
<212> TYPE: DNA
<213> ORGANISM: Artificial Sequence

```
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94), Q11 and L110, where
      n = 0 to 10

<400> SEQUENCE: 106
ggaucaucuc aagucuuact t                                            21

<210> SEQ ID NO 107
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94), Q11,
      (n x Q94) and L110, where n = 1 to 10

<400> SEQUENCE: 107
ggaucaucuc aagucuuact t                                            21

<210> SEQ ID NO 108
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
```

```
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L110, where
      n = 0 to 10

<400> SEQUENCE: 108
ggaucaucuc aagucuuact t                                              21

<210> SEQ ID NO 109
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), L96 and L80, where n = 1 to 10

<400> SEQUENCE: 109
ggaucaucuc aagucuuact t                                              21

<210> SEQ ID NO 110
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
```

```
<222> LOCATION: (21)..(21)
<223> OTHER INFORMATION: Conjugate the 3' end to Q96 through
      phosphorothioate linkage, and then link to (n x Q94) and L80,
      where n = 0 to 10

<400> SEQUENCE: 110
ggaucaucuc aagucuuact t                                              21

<210> SEQ ID NO 111
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11 and L80, where n = 1 to 10

<400> SEQUENCE: 111
ggaucaucuc aagucuuact t                                              21

<210> SEQ ID NO 112
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L80,
      where n = 1 to 10

<400> SEQUENCE: 112
ggaucaucuc aagucuuact t                                              21

<210> SEQ ID NO 113
```

-continued

```
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96 and L80, where n = 1 to 10

<400> SEQUENCE: 113
ggaucaucuc aagucuuact t                                              21

<210> SEQ ID NO 114
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, Q11 and L80, where n = 1 to 10

<400> SEQUENCE: 114
ggaucaucuc aagucuuact t                                              21

<210> SEQ ID NO 115
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
```

```
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96 and L80, where n = 1 to 10

<400> SEQUENCE: 115
ggaucaucuc aagucuuact t                                              21

<210> SEQ ID NO 116
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96, (n x Q94) and L80, where
      n = 1 to 10

<400> SEQUENCE: 116
ggaucaucuc aagucuuact t                                              21

<210> SEQ ID NO 117
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
```

```
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L80, where
      n = 1 to 10

<400> SEQUENCE: 117
ggaucaucuc aagucuuact t                                              21

<210> SEQ ID NO 118
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L80,
      where n = 0 to 10

<400> SEQUENCE: 118
ggaucaucuc aagucuuact t                                              21

<210> SEQ ID NO 119
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q11, (n x Q94) and
      L80, where n = 1 to 10

<400> SEQUENCE: 119
ggaucaucuc aagucuuact t                                              21
```

```
<210> SEQ ID NO 120
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L80,
      where n = 0 to 10

<400> SEQUENCE: 120
ggaucaucuc aagucuuact t                                              21

<210> SEQ ID NO 121
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L80, where
      n = 1 to 10

<400> SEQUENCE: 121
ggaucaucuc aagucuuact t                                              21

<210> SEQ ID NO 122
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
```

```
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L80, where n = 1 to
      10

<400> SEQUENCE: 122
ggaucaucuc aagucuuact t                                            21

<210> SEQ ID NO 123
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q11 and L80, where
      n = 1 to 10

<400> SEQUENCE: 123
ggaucaucuc aagucuuact t                                            21

<210> SEQ ID NO 124
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
```

```
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94), Q11 and L80, where
      n = 1 to 10

<400> SEQUENCE: 124
ggaucaucuc aagucuuact t                                                   21

<210> SEQ ID NO 125
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94), Q11 and L80, where
      n = 0 to 10

<400> SEQUENCE: 125
ggaucaucuc aagucuuact t                                                   21

<210> SEQ ID NO 126
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94), Q11,
      (n x Q94) and L80, where n = 1 to 10
```

```
<400> SEQUENCE: 126
ggaucaucuc aagucuuact t                                              21

<210> SEQ ID NO 127
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L80, where
      n = 0 to 10

<400> SEQUENCE: 127
ggaucaucuc aagucuuact t                                              21

<210> SEQ ID NO 128
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), L96 and L90, where n = 1 to 10

<400> SEQUENCE: 128
ggaucaucuc aagucuuact t                                              21

<210> SEQ ID NO 129
<211> LENGTH: 21
<212> TYPE: DNA
<213> ORGANISM: Artificial Sequence
<220> FEATURE:
```

-continued

```
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L90,
      where n = 0 to 10

<400> SEQUENCE: 129
ggaucaucuc aagucuuact t                                            21

<210> SEQ ID NO 130
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11 and L90, where n = 1 to 10

<400> SEQUENCE: 130
ggaucaucuc aagucuuact t                                            21

<210> SEQ ID NO 131
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
```

```
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L90,
      where n = 1 to 10

<400> SEQUENCE: 131
ggaucaucuc aagucuuact t                                              21

<210> SEQ ID NO 132
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96 and L90, where n = 1 to 10

<400> SEQUENCE: 132
ggaucaucuc aagucuuact t                                              21

<210> SEQ ID NO 133
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
```

-continued and then link to (n x Q94), Q96, Q11 and L90, where n = 1 to 10

<400> SEQUENCE: 133
ggaucaucuc aagucuuact t                                              21

<210> SEQ ID NO 134
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96 and L90, where n = 1 to 10

<400> SEQUENCE: 134
ggaucaucuc aagucuuact t                                              21

<210> SEQ ID NO 135
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, Q96, (n x Q94) and L90, where
      n = 1 to 10

<400> SEQUENCE: 135
ggaucaucuc aagucuuact t                                              21

<210> SEQ ID NO 136
<211> LENGTH: 21
<212> TYPE: DNA
<213> ORGANISM: Artificial Sequence

```
-continued

<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L90, where
      n = 1 to 10

<400> SEQUENCE: 136
ggaucaucuc aagucuuact t                                              21

<210> SEQ ID NO 137
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94) and L90,
      where n = 0 to 10

<400> SEQUENCE: 137
ggaucaucuc aagucuuact t                                              21

<210> SEQ ID NO 138
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
```

-continued

```
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to Q11, (n x Q94) and
      L90, where n = 1 to 10

<400> SEQUENCE: 138
ggaucaucuc aagucuuact t                                               21

<210> SEQ ID NO 139
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q11 through
      phosphorothioate linkage, and then link to (n x Q94) and L90,
      where n = 0 to 10

<400> SEQUENCE: 139
ggaucaucuc aagucuuact t                                               21

<210> SEQ ID NO 140
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
```

```
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q96 and L90, where
      n = 1 to 10

<400> SEQUENCE: 140
ggaucaucuc aagucuuact t                                              21

<210> SEQ ID NO 141
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) and L90, where
      n = 1 to 10

<400> SEQUENCE: 141
ggaucaucuc aagucuuact t                                              21

<210> SEQ ID NO 142
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(1)
<223> OTHER INFORMATION: Link the 3' end to phosphorothioate linkage,
      and then link to (n x Q94), Q11, (n x Q94), Q11 and L90, where
      n = 1 to 10

<400> SEQUENCE: 142
ggaucaucuc aagucuuact t                                              21
```

```
<210> SEQ ID NO 143
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94) Q11 and L90, where
      n = 1 to 10

<400> SEQUENCE: 143
ggaucaucuc aagucuuact t                                         21

<210> SEQ ID NO 144
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q96, (n x Q94), Q11 and L90, where
      n = 0 to 10

<400> SEQUENCE: 144
ggaucaucuc aagucuuact t                                         21

<210> SEQ ID NO 145
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
```

-continued

```
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q96 through
      phosphorothioate linkage, and then link to (n x Q94), Q11,
      (n x Q94) and L90, where n = 1 to 10

<400> SEQUENCE: 145
ggaucaucuc aagucuuact t                                              21

<210> SEQ ID NO 146
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94) Q96 and L90, where
      n = 0 to 10

<400> SEQUENCE: 146
ggaucaucuc aagucuuact t                                              21

<210> SEQ ID NO 147
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
```

```
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L132 through
      phosphorothioate linkage

<400> SEQUENCE: 147
ggaucaucuc aagucuuact t                                             21

<210> SEQ ID NO 148
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L133 through
      phosphorothioate linkage

<400> SEQUENCE: 148
ggaucaucuc aagucuuact t                                             21

<210> SEQ ID NO 149
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L134 through
      phosphorothioate linkage

<400> SEQUENCE: 149
```

```
ggaucaucuc aagucuuact t                                              21

<210> SEQ ID NO 150
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to L136 through
      phosphorothioate linkage

<400> SEQUENCE: 150
ggaucaucuc aagucuuact t                                              21

<210> SEQ ID NO 151
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L99

<400> SEQUENCE: 151
ggaucaucuc aagucuuact t                                              21

<210> SEQ ID NO 152
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
```

```
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L50

<400> SEQUENCE: 152
ggaucaucuc aagucuuact t                                                 21

<210> SEQ ID NO 153
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L8

<400> SEQUENCE: 153
ggaucaucuc aagucuuact t                                                 21

<210> SEQ ID NO 154
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
```

```
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q96 and L110

<400> SEQUENCE: 154
ggaucaucuc aagucuuact t                                              21

<210> SEQ ID NO 155
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q8 and L110

<400> SEQUENCE: 155
ggaucaucuc aagucuuact t                                              21

<210> SEQ ID NO 156
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L110

<400> SEQUENCE: 156
ggaucaucuc aagucuuact t                                              21
```

```
<210> SEQ ID NO 157
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q96 and L80

<400> SEQUENCE: 157
ggaucaucuc aagucuuact t                                              21

<210> SEQ ID NO 158
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q8 and L80

<400> SEQUENCE: 158
ggaucaucuc aagucuuact t                                              21

<210> SEQ ID NO 159
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
```

-continued

```
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L80

<400> SEQUENCE: 159
ggaucaucuc aagucuuact t                                             21

<210> SEQ ID NO 160
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q96 and L90

<400> SEQUENCE: 160
ggaucaucuc aagucuuact t                                             21

<210> SEQ ID NO 161
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
```

```
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to Q8 and L90

<400> SEQUENCE: 161
ggaucaucuc aagucuuact t                                              21

<210> SEQ ID NO 162
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q95 through
      phosphorothioate linkage, and then link to L90

<400> SEQUENCE: 162
ggaucaucuc aagucuuact t                                              21

<210> SEQ ID NO 163
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94) and L133, where n = 1 to 10

<400> SEQUENCE: 163
ggaucaucuc aagucuuact t                                              21

<210> SEQ ID NO 164
```

```
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94) and L133, where n = 0 to 10

<400> SEQUENCE: 164
ggaucaucuc aagucuuact t                                               21

<210> SEQ ID NO 165
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L110, where n = 1 to 10

<400> SEQUENCE: 165
ggaucaucuc aagucuuact t                                               21

<210> SEQ ID NO 166
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
```

```
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L110,
      where n = 1 to 10

<400> SEQUENCE: 166
ggaucaucuc aagucuuact t                                          21

<210> SEQ ID NO 167
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L110, where n = 1 to 10

<400> SEQUENCE: 167
ggaucaucuc aagucuuact t                                          21

<210> SEQ ID NO 168
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
```

```
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L110,
      where n = 0 to 10

<400> SEQUENCE: 168
ggaucaucuc aagucuuact t                                              21

<210> SEQ ID NO 169
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to Q11, (n x Q94) and
      L110, where n = 1 to 10

<400> SEQUENCE: 169
ggaucaucuc aagucuuact t                                              21

<210> SEQ ID NO 170
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7, (n x Q94) and L110, where n = 1
      to 10

<400> SEQUENCE: 170
ggaucaucuc aagucuuact t                                              21
```

```
<210> SEQ ID NO 171
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q7 and L110, where
      n = 0 to 10

<400> SEQUENCE: 171
ggaucaucuc aagucuuact t                                           21

<210> SEQ ID NO 172
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L80, where n = 1 to 10

<400> SEQUENCE: 172
ggaucaucuc aagucuuact t                                           21

<210> SEQ ID NO 173
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
```

-continued

```
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L80,
      where n = 1 to 10

<400> SEQUENCE: 173
ggaucaucuc aagucuuact t                                             21

<210> SEQ ID NO 174
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L80, where n = 1 to 10

<400> SEQUENCE: 174
ggaucaucuc aagucuuact t                                             21

<210> SEQ ID NO 175
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
```

```
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L80,
      where n = 0 to 10

<400> SEQUENCE: 175
ggaucaucuc aagucuuact t                                              21

<210> SEQ ID NO 176
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to Q11, (n x Q94) and
      L80, where n = 1 to 10

<400> SEQUENCE: 176
ggaucaucuc aagucuuact t                                              21

<210> SEQ ID NO 177
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7, (n x Q94) and L80, where n = 1 to
      10

<400> SEQUENCE: 177
```
ggaucaucuc aagucuuact t                                        21

<210> SEQ ID NO 178
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q7 and L80, where
      n = 0 to 10

<400> SEQUENCE: 178
ggaucaucuc aagucuuact t                                        21

<210> SEQ ID NO 179
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L90, where n = 1 to 10

<400> SEQUENCE: 179
ggaucaucuc aagucuuact t                                        21

<210> SEQ ID NO 180
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide

```
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L90,
      where n = 1 to 10

<400> SEQUENCE: 180
ggaucaucuc aagucuuact t                                              21

<210> SEQ ID NO 181
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7 and L90, where n = 1 to 10

<400> SEQUENCE: 181
ggaucaucuc aagucuuact t                                              21

<210> SEQ ID NO 182
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
```

-continued

<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to (n x Q94) and L80,
      where n = 0 to 10

<400> SEQUENCE: 182
ggaucaucuc aagucuuact t                                              21

<210> SEQ ID NO 183
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Conjugate the 3' end to Q7 through
      phosphorothioate linkage, and then link to Q11, (n x Q94) and
      L90, where n = 1 to 10

<400> SEQUENCE: 183
ggaucaucuc aagucuuact t                                              21

<210> SEQ ID NO 184
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q7, (n x Q94) and L90, where n = 1 to

10

<400> SEQUENCE: 184
ggaucaucuc aagucuuact t                                              21

<210> SEQ ID NO 185
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (4)..(5)
<223> OTHER INFORMATION: 2'-fluro modification
<220> FEATURE:
<221> NAME/KEY: misc_feature
<222> LOCATION: (7)..(10)
<223> OTHER INFORMATION: 2'-fluro modification
<220> FEATURE:
<221> NAME/KEY: misc_feature
<222> LOCATION: (14)..(17)
<223> OTHER INFORMATION: 2'-fluro modification
<220> FEATURE:
<221> NAME/KEY: misc_feature
<222> LOCATION: (19)..(19)
<223> OTHER INFORMATION: 2'-fluro modification
<220> FEATURE:
<221> NAME/KEY: misc_feature
<222> LOCATION: (21)..(21)
<223> OTHER INFORMATION: Link the 3' end to phosphorothioate linkage,
      and then link to (n x Q94), Q11, (n x Q94), Q7 and L90, where
      n = 0 to 10

<400> SEQUENCE: 185
ggaucaucuc aagucuuact t                                              21

<210> SEQ ID NO 186
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (2)..(2)
<223> OTHER INFORMATION: 2'-fluro modification
<220> FEATURE:
<221> NAME/KEY: misc_feature
<222> LOCATION: (7)..(9)
<223> OTHER INFORMATION: 2'-fluro modification
<220> FEATURE:
<221> NAME/KEY: misc_feature
<222> LOCATION: (14)..(14)
<223> OTHER INFORMATION: 2'-fluro modification
<220> FEATURE:
<221> NAME/KEY: misc_feature
<222> LOCATION: (17)..(19)
<223> OTHER INFORMATION: 2'-fluro modification
<220> FEATURE:
<221> NAME/KEY: misc_feature
<222> LOCATION: (20)..(21)
<223> OTHER INFORMATION: Phosphorothioate linkage

<400> SEQUENCE: 186
guaagacuug agaugaucct t                                              21

<210> SEQ ID NO 187
<211> LENGTH: 19
<212> TYPE: DNA
<213> ORGANISM: Artificial Sequence
<220> FEATURE:

```
<223> OTHER INFORMATION: Combined DNA/RNA Molecule, Synthetic
      Oligonucleotide: A-40867
<220> FEATURE:
<221> NAME/KEY: misc_feature
<222> LOCATION: (21)..(21)
<223> OTHER INFORMATION: Link the 3' end to Q94 through phosphorothioate
      linkage, and then link to L10

<400> SEQUENCE: 187
aaucuuauau uugauccaa                                                   19

<210> SEQ ID NO 188
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide: A30861
<220> FEATURE:
<221> NAME/KEY: misc_feature
<222> LOCATION: (21)..(21)
<223> OTHER INFORMATION: Link the 3' end to DLink-DMA with hydrazone
      linkage

<400> SEQUENCE: 188
ggaaucuuau auuugaucca a                                                21

<210> SEQ ID NO 189
<211> LENGTH: 21
<212> TYPE: DNA
<213> ORGANISM: Artificial Sequence
<220> FEATURE:
<223> OTHER INFORMATION: Combined DNA/RNA Molecule, Synthetic
      Oligonucleotide
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(21)
<223> OTHER INFORMATION: Link the 3' end to Q8 and L99, and then
      conjugate to DLin-k-DMA

<400> SEQUENCE: 189
acaugaagca gcacgacuuu t                                                21
```